US012692238B2

(12) United States Patent
Mccann et al.

(10) Patent No.: US 12,692,238 B2
(45) Date of Patent: Jul. 28, 2026

(54) SUBSTITUTED PYRIDAZINONE HERBICIDES

(71) Applicant: FMC CORPORATION, Philadelphia, PA (US)

(72) Inventors: Stephen Frederick Mccann, Newark, DE (US); Thomas Paul Selby, Hockessin, DE (US); Thomas Martin Stevenson, Newark, DE (US); Alison Mary Levens, Wilmington, DE (US)

(73) Assignee: FMC CORPORATION, Philadelphia, PA (US)

( * ) Notice: Subject to any disclaimer, the term of this patent is extended or adjusted under 35 U.S.C. 154(b) by 617 days.

(21) Appl. No.: 18/267,645

(22) PCT Filed: Dec. 20, 2021

(86) PCT No.: PCT/US2021/064466
§ 371 (c)(1),
(2) Date: Jun. 15, 2023

(87) PCT Pub. No.: WO2022/140309
PCT Pub. Date: Jun. 30, 2022

(65) Prior Publication Data

US 2024/0101519 A1 Mar. 28, 2024

Related U.S. Application Data

(60) Provisional application No. 63/129,431, filed on Dec. 22, 2020, provisional application No. 63/146,827, filed on Feb. 8, 2021.

(51) Int. Cl.
*C07D 237/16* (2006.01)
*A01N 43/58* (2006.01)
(Continued)

(52) U.S. Cl.
CPC ........... *C07D 237/16* (2013.01); *A01N 43/58* (2013.01); *A01N 47/06* (2013.01); *A01P 13/02* (2021.08); *C07D 409/04* (2013.01)

(58) Field of Classification Search
CPC ............................ C07D 237/16; C07D 409/04
See application file for complete search history.

(56) References Cited

U.S. PATENT DOCUMENTS 8,962,625 B2 2/2015 Kiji et al.
2023/0085307 A1 * 3/2023 Tanaka ................ C07D 409/14 504/236

FOREIGN PATENT DOCUMENTS

EP 2 204 366 A1 7/2010
WO 2010/104217 A1 9/2010

(Continued)

OTHER PUBLICATIONS

International Search Report of Corresponding PCT/US2021/064466 patent application.

*Primary Examiner* — John Pak
(74) *Attorney, Agent, or Firm* — FMC CORPORATION; D. Andrew Travis

(57) ABSTRACT

Disclosed are compounds of Formula 1, including all stereoisomers, N-oxides, and salts thereof, agricultural compositions containing them and their use as herbicides

1

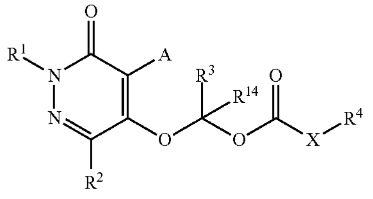

wherein $R^1$, $R^2$, $R^3$, $R^4$, $R^{14}$, and X are as defined in the disclosure, A is selected from

A-1

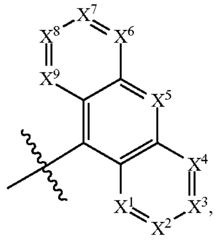

A-2

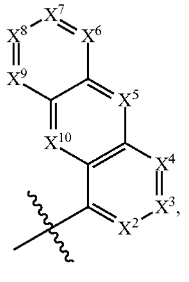

A-3

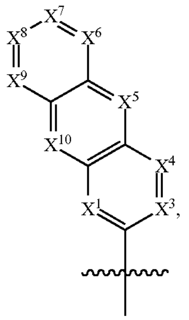

(Continued)

-continued

A-4

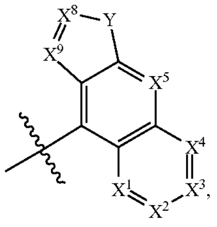

A-5

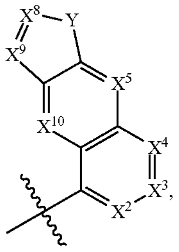

A-6

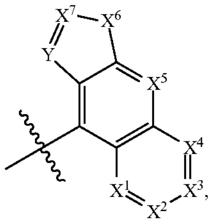

A-7

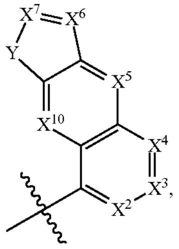

A-8

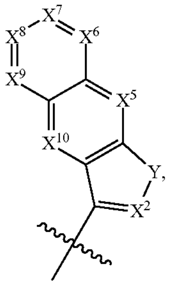

-continued

A-9

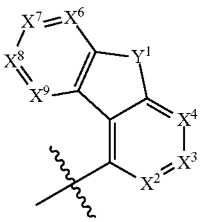

and

A-10

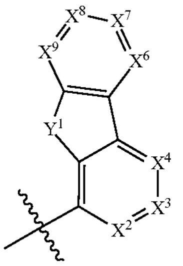

and

A-11

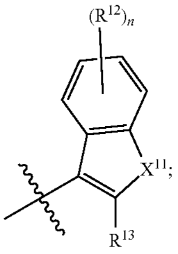

and $R^{12}$, $R^{13}$, n, $X^1$, $X^2$, $X^3$, $X^4$, $X^5$, $X^6$, $X^7$, $X^8$, $X^9$, $X^{10}$, $X^{11}$, Y and $Y^1$ are as defined in the disclosure.

18 Claims, No Drawings

(51) Int. Cl.

| | |
|---|---|
| ***A01N 47/06*** | (2006.01) |
| ***A01P 13/02*** | (2006.01) |
| ***C07D 409/04*** | (2006.01) |

(56) References Cited

FOREIGN PATENT DOCUMENTS

| | | | |
|---|---|---|---|
| WO | 2015/168010 | A1 | 11/2015 |
| WO | 2016/174072 | A1 | 11/2016 |
| WO | 2017/074988 | A1 | 5/2017 |
| WO | 2017/074992 | A1 | 5/2017 |
| WO | 2018/183432 | A1 | 10/2018 |

* cited by examiner

SUBSTITUTED PYRIDAZINONE HERBICIDES

FIELD OF THE INVENTION

This invention relates to certain pyridazinone herbicides, their N-oxides, salts and compositions, and methods of their use for controlling undesirable vegetation.

BACKGROUND OF THE INVENTION

The control of undesired vegetation is extremely important in achieving high crop efficiency. Achievement of selective control of the growth of weeds especially in such useful crops as rice, soybean, sugar beet, maize, potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds that are more effective, less costly, less toxic, environmentally safer or have different sites of action.

SUMMARY OF THE INVENTION

This invention is directed to compounds of Formula 1, all stereoisomers, N-oxides, and salts thereof, agricultural compositions containing them and their use as herbicides:

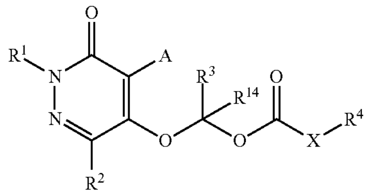

1 wherein

- $R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy; or a 5- or 6-membered saturated or partially saturated heterocyclic ring containing ring members selected from carbon and up to 1 O and 1 S, said ring optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;
- $R^2$ is H, halogen, cyano, formyl, $C_1$-$C_7$ alkyl, $C_3$-$C_8$ alkylcarbonylalkyl, $C_3$-$C_8$ alkoxycarbonylalkyl, $C_2$-$C_4$ alkylcarbonyl, $C_2$-$C_7$ alkylcarbonyloxy, $C_4$-$C_7$ alkylcycloalkyl, $C_3$-$C_7$ alkenyl, $C_3$-$C_7$ alkynyl, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_1$-$C_7$ alkoxy, $C_1$-$C_5$ alkylthio or $C_2$-$C_3$ alkoxycarbonyl; or phenyl optionally substituted by halogen, $C_1$-$C_4$ alkyl or $C_1$-$C_4$ haloalkyl;
- $R^3$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy; or a 5- or 6-membered saturated or partially saturated heterocyclic ring containing ring members selected from carbon and up to 1 O and 1 S, said ring optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;
- $R^4$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy, $(CH_2CH_2O)_tR^5$; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy; or a 5- or 6-membered saturated or partially saturated heterocyclic ring containing ring members selected from carbon and up to 1 O and 1 S, said ring optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;
- $R^5$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy; or a 5- or 6-membered saturated or partially saturated heterocyclic ring containing ring members selected from carbon and up to 1 O and 1 S, said ring optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;
- t is an integer from 1 to 10;
- X is a direct bond, O, S or $NR^6$;
- $R^6$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy; or a 5- or 6-membered saturated or partially saturated heterocyclic ring containing ring members selected from carbon and up to 1 O and 1 S, said ring optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy; or $R^4$ and $R^6$ can be taken together with the nitrogen atom to which they are attached to form a 3 to 7 membered ring, containing carbon atoms and optionally 1 to 3 oxygen, sulfur or nitrogen atoms as ring members, wherein up to 2 carbon atom ring members are independently selected from C(=O) and C(=S), and the sulfur atom ring member is selected from S, S(O) or $S(O)_2$, said ring being optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

A is selected from

A-1

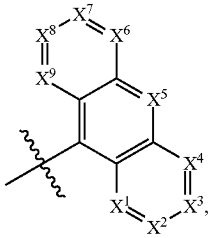

A-2

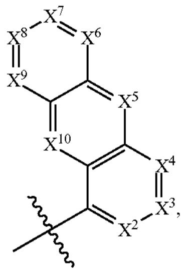

A-3

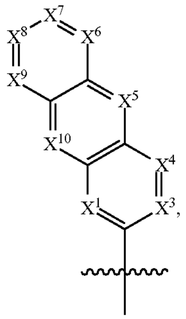

-continued

A-4

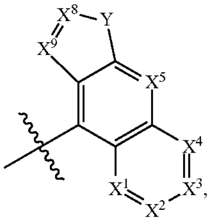

A-5

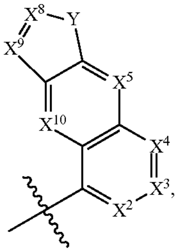

A-6

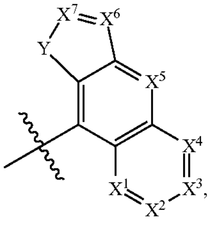

A-7

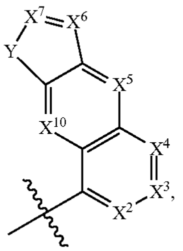

A-8

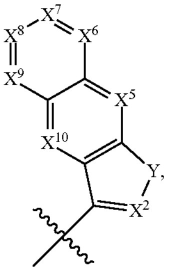

A-9

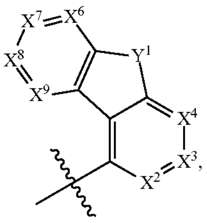

-continued

A-10

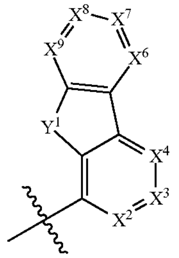

and

A-11

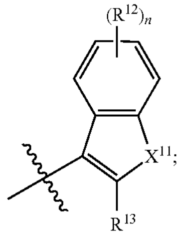

;

$X^1$, $X^2$, $X^3$, $X^4$, $X^5$, $X^6$, $X^7$, $X^8$, $X^9$ and $X^{10}$ are each independently N or $CR^7$; provided that no more than 4 of $X^1$, $X^2$, $X^3$, $X^4$, $X^5$, $X^6$, $X^7$, $X^8$, $X^9$ and $X^{10}$ are N;

$X^{11}$ is O, S or $NR^9$; or $X^{11}$ is —$C(R^{10})$=$C(R^{11})$—, wherein the carbon atom bonded to $R^{10}$ is also bonded to the carbon atom bonded to $R^{13}$, and the carbon atom bonded to $R^{11}$ is also bonded to the phenyl ring moiety in Formula 1;

Y is O, S or $NR^8$;

$Y^1$ is O, S, $NR^8$ or $CR^{7a}R^{7b}$;

each $R^7$ is independently H, halogen, cyano, nitro, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl;

$R^{7a}$ is H, halogen, —CN, nitro, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl;

$R^{7b}$ is H, halogen, —CN, nitro, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl; or $R^{7a}$ and $R^{7b}$ are taken together as =O; or $R^{7a}$ and $R^{7b}$ are taken together with the carbon atom to which they are bonded to form an optionally substituted 3- to 7-membered carbocyclic ring;

$R^8$ is H, $C_1$-$C_3$ alkyl or $C_1$-$C_3$ haloalkyl;

$R^9$ is H, $C_1$-$C_3$ alkyl or $C_1$-$C_3$ haloalkyl;

$R^{10}$ and $R^{11}$ are independently H, halogen, nitro, —CN, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl;

each $R^{12}$ is independently halogen, —CN, nitro, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_5$ haloalkylthio or $C_2$-$C_5$ alkoxycarbonyl;

$R^{13}$ is H, halogen, nitro, —CN, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl;

$R^{14}$ is H; and n is 0, 1, 2, 3 or 4.

More particularly, this invention pertains to a compound of Formula 1 (including all stereoisomers), an N-oxide or a salt thereof. This invention also relates to a herbicidal composition comprising a compound of the invention (i.e. in a herbicidally effective amount) and at least one component selected from the group consisting of surfactants, solid diluents and liquid diluents. This invention further relates to a method for controlling the growth of undesired vegetation comprising contacting the vegetation or its environment with a herbicidally effective amount of a compound of the invention (e.g., as a composition described herein).

This invention also includes a herbicidal mixture comprising (a) a compound selected from Formula 1, N-oxides, and salts thereof, and (b) at least one additional active ingredient selected from (b1) through (b16), and salts of compounds of (b1) through (b16), as described below.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling", used either alone or in a combination of words means a young plant developing from the embryo of a seed.

As referred to herein, the term "broadleaf" used either alone or in words such as "broadleaf weed" means dicot or dicotyledon, a term used to describe a group of angiosperms characterized by embryos having two cotyledons.

As used herein, the term "alkylating" refers reaction in which nucleophile displaces a leaving group such as halide or sulfonate from a carbon-containing radical. Unless otherwise indicated, the term "alkylating" does not limit the carbon-containing radical to alkyl.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. "Alkylthio" includes branched or straight-chain alkylthio moieties such as methylthio, ethylthio, and the different propylthio, butylthio, pentylthio and hexylthio isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Alkylsulfinyl" includes both enantiomers of an alkylsulfinyl group. Examples of "alkylsulfinyl" include $CH_3S(O)—$, $CH_3CH_2S(O)—$, $CH_3CH_2CH_2S(O)—$, $(CH_3)_2CHS(O)—$ and the different butylsulfinyl, pentylsulfinyl and hexylsulfinyl isomers. Examples of "alkylsulfonyl" include $CH_3S(O)_2—$, $CH_3CH_2S(O)_2—$, $CH_3CH_2CH_2S(O)_2—$, $(CH_3)_2CHS(O)_2—$, and the different butylsulfonyl, pentylsulfonyl and hexylsulfonyl isomers. "Cyanoalkyl" denotes an alkyl group substituted with one cyano group. Examples of "cyanoalkyl" include $NCCH_2$ and $NCCH_2CH_2$ (alternatively identified as $CH_2CH_2CN$). "Nitroalkyl" denotes an alkyl group substituted with one nitro group. Examples of "nitroalkyl" include $NO_2NCH_2$ and $NO_2NCH_2CH_2$ (alternatively identified as $CH_2CH_2NO_2$). "Cyano" means NC—, and "formyl" means HC(═O)—. "Alkylamino" includes an NH radical substituted with straight-chain or branched alkyl. Examples of "alkylamino" include $CH_3CH_2NH$, $CH_3CH_2CH_2NH$, and $(CH_3)_2CHCH_2NH$. Examples of "dialkylamino" include $(CH_3)_2N$, $(CH_3CH_2CH_2)_2N$ and $CH_3CH_2(CH_3)N$.

"Cycloalkyl" includes, for example, cyclopropyl, cyclobutyl, cyclopentyl and cyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. The term "alkylcycloalkyl" donotes an alkyl group bonded to a cycloalkyl moiety.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$. The terms "haloalkoxy", "haloalkoxyalkyl", "haloalkylthio", "haloalkenyl", "haloalkynyl", and the like, are as defined analogously to the term "haloalkyl". Examples of "haloalkoxy" include $CF_3O—$, $CCl_3CH_2O—$, $HCF_2CH_2CH_2O—$ and $CF_3CH_2O—$. Examples of "haloalkoxyalkyl" include $CF_3OCH_2—$, $CCl_3CH_2OCH_2—$, $HCF_2CH_2CH_2OCH_2—$ and $CF_3CH_2OCH_2—$. Examples of "haloalkylthio" include $CCl_3S—$, $CF_3S—$, $CCl_3CH_2S—$ and $ClCH_2CH_2CH_2S—$. Examples of "haloalkenyl" include $(Cl)_2C═CHCH_2—$ and $CF_3CH_2CH═CHCH_2—$. Examples of "haloalkynyl" include $HC≡CCHCl—$, $CF_3C≡C—$, $CCl_3C≡C—$ and $FCH_2C≡CCH_2—$.

"Alkylcarbonyl" denotes a straight-chain or branched alkyl moiety bonded to a C(═O) moiety. Examples of "alkylcarbonyl" include $CH_3C(═O)—$, $CH_3CH_2C(═O)—$, $CH_3CH_2CH_2C(═O)—$, $(CH_3)_2CHC(═O)—$ and the different butoxy- or pentoxycarbonyl isomers. "Alkoxycarbonyl" denotes a straight-chain or branched alkoxy moieties bonded to a C(═O) moiety. Examples of "alkoxycarbonyl" include $CH_3OC(═O)—$, $CH_3CH_2OC(═O)—$, $CH_3CH_2CH_2OC(═O)—$, $(CH_3)_2CHOC(═O)—$ and the different butoxy- or pentoxycarbonyl isomers. C(═O) or C(O) designates carbonyl. The term "alkoxycarbonylalkyl" denotes a straight-chain or branched alkoxycarbonyl moiety bonded through an alkyl moiety. The term "alkylcarbonylalkyl" denotes a straight or branched alkylcarbonyl moiety bonded through an alkyl moiety. The term "alkylcarbonyloxy" donates an alkylcarbony moiety bonded through oxygen. Examples of alkylcarbonyloxy include $CH_3C(═O)O—$, $CH_3CH_2C(═O)O—$, $CH_3CH_2CH_2C(═O)O—$ and $(CH_3)_2CHC(═O)—$. The term alkanediyl or alkenediyl refers to a linear or branched alkane or alkene linking chain respectively. Examples of alkanediyl include $—CH_2—$, $—CH_2CH(CH_3)—$ or $—CH_2CH_2CH_2—$. Examples of alkenediyl include $—CH═CH—$, $—CH_2C═CH—$ or $—CH═C(CH_3)—$. The term "adjacent" in the context of locating a substituent means "next to" or "immediately next to".

The total number of carbon atoms in a substituent group is indicated by the "$C_i$-$C_j$" prefix where i and j are numbers from 1 to 8. For example, $C_1$-$C_4$ alkylsulfonyl designates methylsulfonyl through butylsulfonyl; $C_3$-$C_8$ alkylcarbonylalkyl can be, for example, $CH_3COCH_2—$, $CH_3COCH_2CH_2—$ or $CH_3CH_2CH_2COCH_2CH_2CH_2CH_2—$; $C_4$-$C_7$ alkylcycloalkyl can be, for example, methylcyclopropyl, methylcyclobutyl, ethylcyclopropyl, or propylcyclobutyl; $C_2$ alkoxyalkyl designates $CH_3OCH_2$—; $C_3$ alkoxyalkyl designates, for example, $CH_3CH(OCH_3)$—, $CH_3OCH_2CH_2$— or $CH_3CH_2OCH_2$—; and $C_4$ alkoxyalkyl designates the various isomers of an alkyl group substituted with an alkoxy group containing a total of four carbon atoms, examples including $CH_3CH_2CH_2OCH_2$— and $CH_3CH_2OCH_2CH_2$—.

When a group contains a substituent which can be hydrogen, for example $R^3$ or $R^v$, then when this substituent is taken as hydrogen, it is recognized that this is equivalent to said group being unsubstituted. When one or more positions on a group are said to be "not substituted" or "unsubstituted", then hydrogen atoms are attached to take up any free valency. Unless otherwise indicated as being optionally substituted, the term "phenyl" means unsubstituted phenyl. Unless otherwise indicated as being optionally substituted, the term "benzyl" means unsubstituted benzyl.

When a compound is substituted with a substituent bearing a subscript that indicates the number of said substituents can exceed 1, said substituents (when they exceed 1) are independently selected from the group of defined substituents, e.g., $(R^{12})_n$, wherein n is 0, 1, 2, 3 or 4. When n is 0, then hydrogen may be at the position even if not recited in the substituent definition. When a functional group or a compound is shown to be optionally substituted with a substituent, the said functional group or compound may be unsubstituted or substituted. When one or more positions on a group are said to be "not substituted" or "unsubstituted", then hydrogen atoms are attached to take up any free valency.

When A is A-11, the attachment point of $(R^{12})_n$ is illustrated as floating. Each $R^{12}$ can be attached to any of the 5 available aromatic carbons by replacement of a hydrogen atom.

The term "ring system" denotes two or more fused rings. The term "bicyclic ring system" denotes a ring system consisting of two fused rings.

Compounds of this invention can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

Compounds of Formula 1 typically exist in more than one form, and Formula 1 thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due to the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations, improved biological performance) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus, a wide variety of salts of a compound of Formula 1 are useful for control of undesired vegetation (i.e. are agriculturally suitable). The salts of a compound of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

When $R^1$, $R^3$, $R^4$, $R^5$, or $R^6$ is a 5- or 6-membered nitrogen-containing heterocyclic ring, it may be attached to the remainder of Formula 1 though any available carbon or nitrogen ring atom, unless otherwise described. As noted above, $R^1$, $R^2$, $R^3$, $R^4$, $R^5$, or $R^6$ can be (among others) phenyl optionally substituted with one or more substituents selected from a group of substituents as defined in the Summary of the Invention (i.e. halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy). An example of phenyl optionally substituted with one to five substituents is the ring illustrated as U-1 in Exhibit 1, wherein $R^v$ is as a substituent on $R^5$, $R^6$ or $R^7$ as defined in the Summary of the Invention, and r is an integer.

As noted above, $R^1$, $R^3$, $R^4$, $R^5$, or $R^6$ can be (among others) a 5- or 6-membered heterocyclic ring, which may be saturated or unsaturated, optionally substituted with one or more substituents selected from a group of substituents as defined in the Summary of the Invention. Examples of a 5- or 6-membered unsaturated aromatic heterocyclic ring optionally substituted with from one or more substituents include the rings U-2 through U-61 illustrated in Exhibit 1 wherein $R^v$ is independently halogen, $C_1$-$C_4$ alkyl or $C_1$-$C_4$ haloalkyl and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

Exhibit 1

U-1

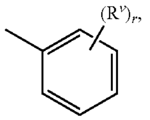

U-2

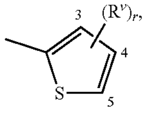

U-3

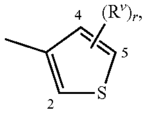

U-4

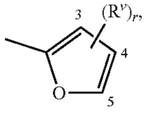

U-5

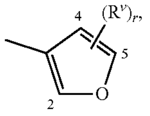

U-6

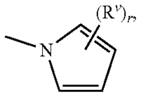

-continued

U-7

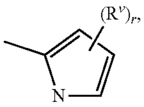

U-8

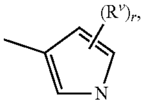

U-9

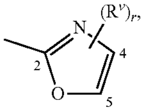

U-10

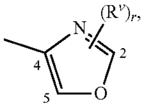

U-11

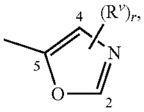

U-12

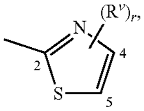

U-13

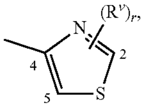

U-14

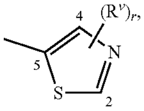

U-15

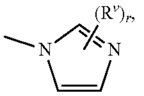

U-16

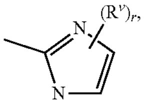

U-17

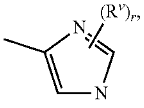

U-18

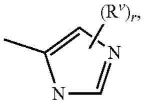

U-19

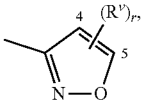

-continued
U-20
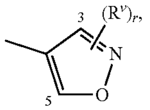
U-21
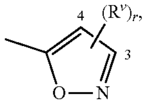
U-22
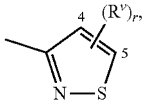
U-23
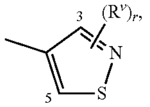
U-24
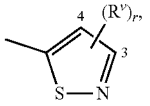
U-25
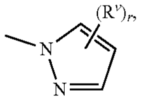
U-26
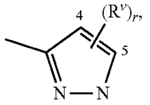
U-27
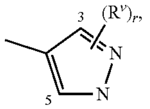
U-28
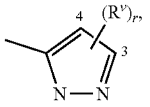
U-29
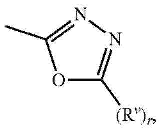
U-30
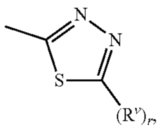
U-31
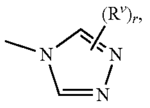
U-32
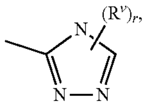
-continued
U-33
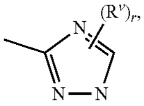
U-34
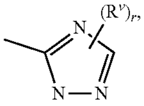
U-35
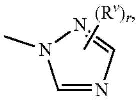
U-36
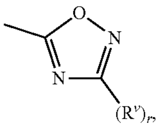
U-37
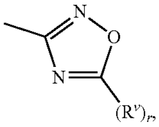
U-38
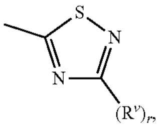
U-39
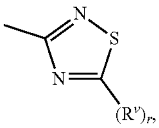
U-40
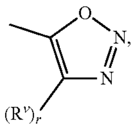
U-41
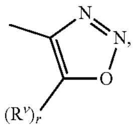
U-42
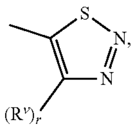
U-43
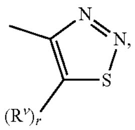
U-44
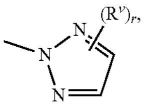

-continued

U-45

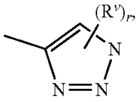

U-46

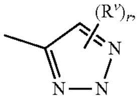

U-47

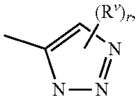

U-48

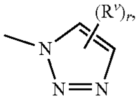

U-49

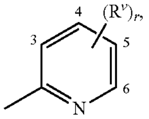

U-50

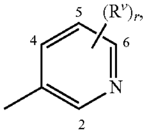

U-51

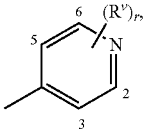

U-52

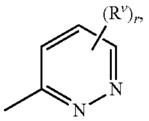

U-53

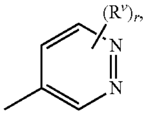

U-54

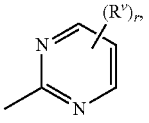

U-55

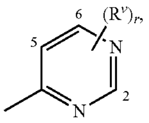

U-56

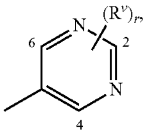

-continued

U-57

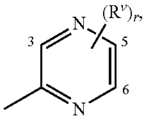

U-58

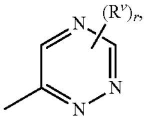

U-59

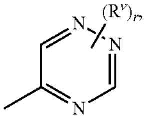

U-60

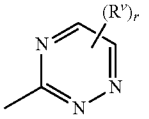

and

U-61

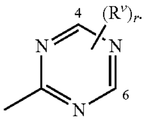

Note that when $R^1$, $R^3$, $R^4$, $R^5$ or $R^6$ is a 5- or 6-membered saturated or unsaturated non-aromatic heterocyclic ring optionally substituted with one or more substituents selected from the group of substituents as defined in the Summary of the Invention for $R^1$, $R^3$, $R^4$, $R^5$ or $R^6$, one or two carbon ring members of the heterocycle can optionally be in the oxidized form of a carbonyl moiety.

Examples of a 5- or 6-membered heterocyclic ring that is saturated or non-aromatic unsaturated heterocyclic ring containing ring members selected from up to two O atoms and up to two S atoms, and optionally substituted on carbon atom ring members with up to four $R^v$ includes the rings T-1 through T-35 as illustrated in Exhibit 2. Note that when the attachment point on the T group is illustrated as floating, the T group can be attached to the remainder of Formula 1 through any available carbon or nitrogen of the T group by replacement of a hydrogen atom. The optional substituents corresponding to $R^v$ can be attached to any available carbon or nitrogen by replacing a hydrogen atom. For these T rings, r is typically an integer from 0 to 4, limited by the number of available positions on each T group. The term "optionally substituted" means "substituted or unsubstituted". Note that when $T^2$ is N, the nitrogen atom can complete its valence by substitution with either H or the substituents corresponding to $R^v$ as defined in the Summary of the Invention on $R^5$, $R^6$ or $R^7$. Exemplary values for $R^1$ include T-1, T-2, T-7 and T-9 (i.e. when when $R^1$ is, among other, a 5- or 6-membered saturated or partially saturated heterocyclic ring containing ring members selected from carbon and up to 1 O and 1 S") and T-28 through T-31 where $T^2$ is O or S.

Exhibit 2
T-1
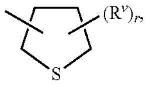
T-2
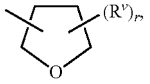
T-3
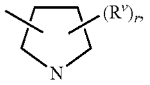
T-4
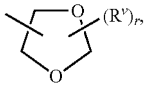
T-5
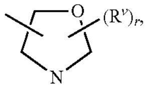
T-6
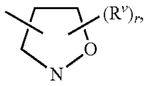
T-7
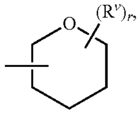
T-8
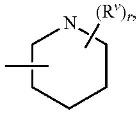
T-9
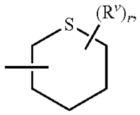
T-10
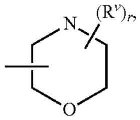
T-11
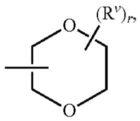
T-12
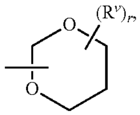
T-13
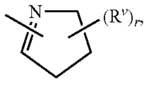
-continued
T-14
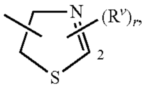
T-15
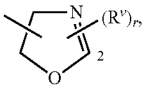
T-16
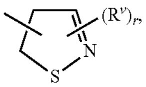
T-17
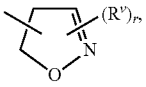
T-18
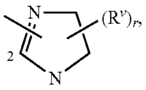
T-19
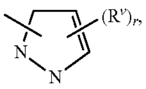
T-20
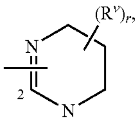
T-21
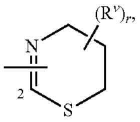
T-22
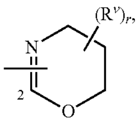
T-23
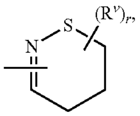
T-24
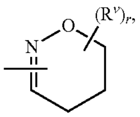
T-25
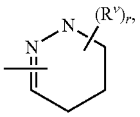
T-26
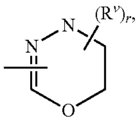

-continued

T-27

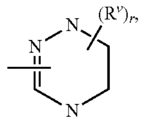

T-28

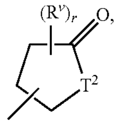

T-29

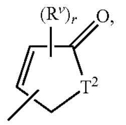

T-30

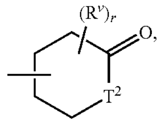

T-31

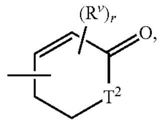

T-32

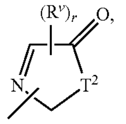

T-33

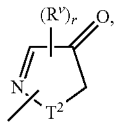

T-34

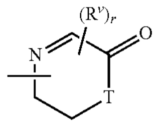

and

T-35

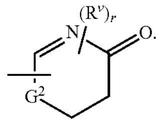

Although $R^v$ groups are shown in the structures U-1 through U-61, it is noted that they do not need to be present since they are optional substituents. Note that when $R^v$ is H when attached to an atom, this is the same as if said atom is unsubstituted. The nitrogen atoms that require substitution to fill their valence are substituted with H or $R^v$. Note that when the attachment point between $(R^v)_r$ and the U group is illustrated as floating, $(R^v)_r$ can be attached to any available carbon atom or nitrogen atom of the U group. Note that when the attachment point on the U group is illustrated as floating, the U group can be attached to the remainder of Formula 1 through any available carbon or nitrogen of the U group by replacement of a hydrogen atom. Note that some U groups can only be substituted with less than 4 $R^v$ groups (e.g., U-2 through U-5, U-7 through U-48, and U-52 through U-61).

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry* II, A. R. Katritzky, C. W. Rees and E. F. V. Scriven editors-in-chief, Pergamon Press, Oxford, 1996.

Embodiments of the present invention as described in the Summary of the Invention include those described below. In the following Embodiments, Formula 1 includes stereoisomers, N-oxides and salts thereof, and reference to "a compound of Formula 1" includes the definitions of substituents specified in the Summary of the Invention unless further defined in the Embodiments.

Embodiment 1. A compound of Formula 1, stereoisomers, N-oxides, and salts thereof, agricultural compositions containing them and their use as herbicides as described in the Summary of the Invention. Embodiment 2a. A compound of Embodiment 1 wherein A is A-11.

Embodiment 2b. A compound of Embodiment 1 wherein A is A-1.

Embodiment 2c. A compound of Embodiment 1 wherein A is A-2.

Embodiment 2d. A compound of Embodiment 1 wherein A is A-3.

Embodiment 2e. A compound of Embodiment 1 wherein A is A-4.

Embodiment 2f. A compound of Embodiment 1 wherein A is A-5.

Embodiment 2g. A compound of Embodiment 1 wherein A is A-6.

Embodiment 2h. A compound of Embodiment 1 wherein A is A-7.

Embodiment 2i. A compound of Embodiment 1 wherein A is A-8.

Embodiment 2j. A compound of Embodiment 1 wherein A is A-9.

Embodiment 2k. A compound of Embodiment 1 wherein A is A-10.

Embodiment 2l. A compound of Embodiment 1 wherein A is selected from A-1, A-4 and A-6.

Embodiment 2m. A compound of Embodiment 1 wherein A is selected from A-9 and A-10.

Embodiment 3a. A compound of any one of the preceding Embodiments wherein $R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy; benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy.

Embodiment 3b. A compound of Embodiment 3a wherein $R^1$ is H, $C_1$-$C_7$ alkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_2$-$C_7$ alkoxyalkyl, $C_3$-$C_7$ alkylthioalkyl, $C_1$-$C_7$ alkoxy or benzyl substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy.

Embodiment 3c. A compound of Embodiment 3b wherein $R^1$ is $C_1$-$C_4$ alkyl, $C_3$-$C_4$ alkenyl, $C_3$-$C_4$ alkynyl, $C_3$-$C_4$ cycloalkyl, $C_2$-$C_3$ cyanoalkyl, $C_1$-$C_3$ haloalkyl or $C_2$-$C_4$ alkoxyalkyl.

Embodiment 3d. A compound of Embodiment 3c wherein $R^1$ is $C_1$-$C_3$ alkyl, allyl, propargyl, $CH_2CH_2CN$, $C_1$-$C_2$ haloalkyl or 2-methoxyethyl.

Embodiment 3e. A compound of Embodiment 3d wherein $R^1$ is methyl, ethyl, n-propyl or 2-methoxyethyl.

Embodiment 3f. A compound of Embodiment 3e wherein $R^1$ is methyl or ethyl.

Embodiment 3g. A compound of Embodiment 3f wherein $R^1$ is methyl.

Embodiment 3h. A compound of Embodiment 3a or 3b wherein $R^1$ is other than H.

Embodiment 3i. A compound of Embodiment 3a wherein $R^1$ is other than phenyl.

Embodiment 4a. A compound of any of the preceeding Embodiments wherein $R^2$ is H, halogen, cyano, formyl, $C_1$-$C_7$ alkyl, $C_3$-$C_8$ alkylcarbonylalkyl, $C_3$-$C_8$ alkoxycarbonylalkyl, $C_2$-$C_4$ alkylcarbonyl, $C_2$-$C_7$ alkylcarbonyloxy, $C_4$-$C_7$ alkylcycloalkyl, $C_3$-$C_7$ alkenyl, $C_3$-$C_7$ alkynyl, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_1$-$C_7$ alkoxy, $C_1$-$C_5$ alkylthio or $C_2$-$C_3$ alkoxycarbonyl.

Embodiment 4b. A compound of Embodiment 4a wherein $R^2$ is H, halogen, —CN, —CHO, $C_1$-$C_7$ alkyl, $C_2$-$C_4$ alkylcarbonyl, $C_2$-$C_7$ alkylcarbonyloxy, $C_4$-$C_7$ alkylcycloalkyl, $C_1$-$C_4$ alkylsulfinyl, $C_1$-$C_4$ alkylsulfonyl, $C_1$-$C_4$ alkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_2$-$C_7$ alkoxyalkyl or $C_1$-$C_7$ alkoxy.

Embodiment 4c. A compound of Embodiment 4b wherein $R^2$ is H, halogen, —CN, $C_1$-$C_4$ alkyl, $C_3$-$C_5$ cycloalkyl, $C_1$-$C_3$ haloalkyl, $C_2$-$C_4$ alkoxyalkyl or $C_1$-$C_3$ alkoxy.

Embodiment 4d. A compound of Embodiment 4c wherein $R^2$ is H, halogen, $C_1$-$C_3$ alkyl, cyclopropyl, $C_1$-$C_2$ haloalkyl, methoxy or ethoxy.

Embodiment 4e. A compound of Embodiment 4d wherein $R^2$ is H, F, Cl, Br, methyl, ethyl, n-propyl, $CF_3$ or methoxy.

Embodiment 4f. A compound of Embodiment 4e wherein $R^2$ is methyl or ethyl.

Embodiment 4g. A compound of Embodiment 4f wherein $R^2$ is methyl.

Embodiment 4h. A compound of Embodiment 4e wherein $R^2$ is F or Cl.

Embodiment 4i. A compound of Embodiment 4h wherein $R^2$ is F.

Embodiment 4h. A compound of Embodiment 4h wherein $R^2$ is Cl.

Embodiment 4i. A compound of Embodiment 4e wherein $R^2$ is Me or Cl.

Embodiment 4j. A compound of Formula 1 wherein $R^2$ is other than phenyl.

Embodiment 4j. A compound of Formula 1 wherein $R^2$ is other than H.

Embodiment 5a. A compound of any of the preceeding Embodiments wherein $R^3$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy.

Embodiment 5b. A compound of Embodiment 5a wherein $R^3$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, or $C_1$-$C_7$ alkoxy.

Embodiment 5c. A compound of Embodiment 5b wherein $R^3$ is H, $C_1$-$C_4$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ cycloalkyl, $C_4$-$C_7$ cycloalkylalkyl, $C_2$-$C_3$ cyanoalkyl, $C_1$-$C_7$ haloalkyl, $C_2$-$C_7$ alkoxyalkyl, or $C_1$-$C_7$ alkoxy.

Embodiment 5d. A compound of Embodiment 5c wherein $R^3$ is H, $C_1$-$C_4$ alkyl, $C_4$-$C_7$ alkylcycloalkyl, $C_3$-$C_7$ cycloalkyl, $C_4$-$C_7$ cycloalkylalkyl, $C_2$-$C_3$ cyanoalkyl, $C_1$-$C_7$ haloalkyl, $C_2$-$C_7$ alkoxyalkyl, or $C_1$-$C_7$ alkoxy.

Embodiment 5e. A compound of Embodiment 5d wherein $R^3$ is H, $C_1$-$C_4$ alkyl, $C_3$-$C_7$ cycloalkyl, $C_4$-$C_7$ cycloalkylalkyl, or $C_1$-$C_7$ alkoxy.

Embodiment 5f. A compound of Embodiment 5e wherein $R^3$ is H, methyl, ethyl, cyclopropyl, cyclopropylmethyl, or Methoxy.

Embodiment 5g. A compound of Embodiment 5f wherein $R^3$ is H, methyl, ethyl, cyclopropyl, or cyclopropylmethyl.

Embodiment 5h. A compound of Embodiment 5g wherein $R^3$ is H, or methyl.

Embodiment 5i. A compound of Embodiment 5h wherein $R^3$ is H.

Embodiment 5j. A compound of Embodiment 5 wherein $R^3$ is benzyl.

Embodiment 6a. A compound of any of the preceeding Embodiments wherein X is a direct bond.

Embodiment 6b. A compound of Embodiments 1 through 5 wherein X is O.

Embodiment 6c. A compound of Embodiments 1 through 5 wherein X is S.

Embodiment 6d. A compound of Embodiments 1 through 5 wherein X is $NR^6$.

Embodiment 6e. A compound of Embodiments 1 through 5 wherein X is a direct bond or O.

Embodiment 7a. A compound of any of the preceeding Embodiments 7 wherein $R^4$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy, $(CH_2CH_2O)_rR^5$; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy.

Embodiment 7b. A compound of any of Embodiments 1 through 6e wherein $R^4$ is a 5-or 6-membered saturated or partially saturated heterocyclic ring containing ring members selected from carbon and up to 1 O and 1 S, said ring being unsubstituted or substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy.

Embodiment 7c. A compound of Embodiment 7a wherein $R^4$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl or $C_1$-$C_7$ alkoxy.

Embodiment 7d. A compound of Embodiment 7c wherein $R^4$ is H, $C_1$-$C_4$ alkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl or $C_1$-$C_7$ alkoxy.

Embodiment 7e. A compound of Embodiment 7d wherein $R^4$ is H, $C_1$-$C_4$ alkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl or $C_1$-$C_7$ alkoxy.

Embodiment 7f. A compound of Embodiment 7e wherein $R^4$ is H, $C_1$-$C_4$ alkyl, $C_4$-$C_7$ cycloalkylalkyl or $C_1$-$C_7$ alkoxy.

Embodiment 7g. A compound of Embodiment 7f wherein $R^4$ is H, methyl, ethyl, i-propyl, t-Bu, cyclopropyl, cyclobutyl, cyclopentyl, cyclohexyl, methoxy or ethoxy.

Embodiment 7h. A compound of Embodiment 7f wherein $R^4$ is H, methyl, ethyl, i-propyl, t-Bu or methoxy.

Embodiment 8a. A compound of any of the preceeding Embodiments wherein $R^5$ is H, $C_1$-$C_7$ alkyl, $C_3$-$C_8$ alkylcarbonylalkyl, $C_3$-$C_8$ alkoxycarbonylalkyl; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy.

Embodiment 8b. A compound of Embodiment 8a wherein $R^5$ is $C_1$-$C_7$ alkyl.

Embodiment 8c. A compound of Embodiment 8a wherein $R^5$ is H.

Embodiment 8d. A compound of Embodiment 8a wherein $R^5$ is $C_3$-$C_8$ alkylcarbonylalkyl.

Embodiment 8e. A compound of Embodiment 8a wherein $R^5$ is benzyl optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy.

Embodiment 9a. A compound of any of the preceeding Embodiments wherein $R^6$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy; or a 5- or 6-membered saturated or partially saturated heterocyclic ring containing ring members selected from carbon and up to 1 O and 1 S, said ring optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy.

Embodiment 9b. A compound of Embodiment 9a wherein $R^6$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy.

Embodiment 9c. A compound of Embodiment 9b wherein $R^6$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ cycloalkyl, $C_4$-$C_7$ cycloalkylalkyl, $C_2$-$C_7$ alkoxyalkyl, $C_3$-$C_7$ alkylthioalkyl or $C_1$-$C_7$ alkoxy.

Embodiment 9d. A compound of Embodiment 9c wherein $R^6$ is H or $C_1$-$C_7$ alkyl.

Embodiment 9e. A compound of Embodiment 9c wherein $R^6$ is $C_1$-$C_3$ alkyl.

Embodiment 9f. A compound of Embodiment 9e wherein $R^6$ is Me.

Embodiment 9g. A compound of any one of Embodiments 1 though 8 wherein $R^4$ and $R^6$ can be taken together with the nitrogen atom to which they are attached to form a 3 to 7 membered ring, containing carbon atoms and optionally 1 to 3 oxygen, sulfur or nitrogen atoms as ring members, wherein up to 2 carbon atom ring members are independently selected from C(=O) and C(=S), and the sulfur atom ring member is selected from S, S(O) or $S(O)_2$, said ring being unsubstituted or substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy.

Embodiment 9h. A compound of Embodiment 9g wherein $R^4$ and $R^6$ can be taken together with the nitrogen atom to form a three membered ring.

Embodiment 9i. A compound of Embodiment 9g wherein $R^4$ and $R^6$ can be taken together with the nitrogen atom to form a four membered ring.

Embodiment 9j. A compound of Embodiment 9g wherein $R^4$ and $R^6$ can be taken together with the nitrogen atom to form a five membered ring.

Embodiment 9k. A compound of Embodiment 9g wherein $R^4$ and $R^6$ can be taken together with the nitrogen atom to form a six membered ring.

Embodiment 9l. A compound of Embodiment 9g wherein $R^4$ and $R^6$ can be taken together with the nitrogen atom to which they are attached to form a pyrrolidine, piperidine or piperazine.

Embodiment 10a. A compound of any one of the preceeding Embodiments wherein each $X^1$, $X^2$, $X^3$, $X^4$, $X^5$, $X^6$, $X^7$, $X^8$, $X^9$ and $X^{10}$ is $CR^7$.

Embodiment 10b. A compound of Formula 1 or any one of the preceding Embodiments wherein A is A-1 and each $X^1$, $X^2$, $X^3$, $X^4$, $X^5$, $X^6$, $X^7$, $X^8$ and $X^9$ is CH.

Embodiment 11a. A compound of any one of the preceeding Embodiments wherein each $R^7$ is independently H, halogen, $C_1$-$C_3$ alkyl, $C_3$-$C_4$ cycloalkyl, $C_1$-$C_3$ haloalkyl or $C_1$-$C_3$ alkoxy.

Embodiment 11b. A compound of Embodiment 11a wherein each $R^7$ is independently H, halogen, $C_1$-$C_2$ alkyl, cyclopropyl or $C_1$-$C_2$ haloalkyl.

Embodiment 11c. A compound of Embodiment 11b wherein each $R^7$ is independently H, halogen, methyl, ethyl or $CF_3$.

Embodiment 11d. A compound of Embodiment 11c wherein each $R^7$ is independently H, F, Cl, Br or methyl.

Embodiment 11e. A compound of Embodiment 11d wherein each $R^7$ is H.

Embodiment 11f. A compound of Embodiment 11d wherein each $R^7$ is Me.

Embodiment 11g. A compound of Embodiment 11d wherein each $R^7$ is F.

Embodiment 11h. A compound of Embodiment 11d wherein each $R^7$ is Cl.

Embodiment 12. A compound of any one of the preceding Embodiments wherein $X^{11}$ is O, S or $NR^9$; or $X^{11}$ is —$C(R^{10})$=$C(R^{11})$—.

Embodiment 12a. A compound of any of the preceeding Embodiments wherein $X^{11}$ is O, S or $NR^9$.

Embodiment 12b. A compound of Embodiment 12a wherein $X^{11}$ is O.

Embodiment 12c. A compound of Embodiment 12a wherein $X^{11}$ is S.

Embodiment 12d. A compound of Embodiment 12a wherein $X^{11}$ is $NR^9$.

Embodiment 12e. A compound of any of Embodiments 1 through 11h wherein $X^{11}$ is —$C(R^{10})$=$C(R^{11})$—.

Embodiment 12f. A compound of any of Embodiments 1 through 11h wherein $X^{11}$ is O, S, —CH=CH—, —$C(CH_3)$=CH—, —CH=CF—, —CH=CCl— or —CH=$C(CH_3)$—.

Embodiment 12g. A compound of Embodiment 12f wherein $X^{11}$ is —CH=CH—, —$C(CH_3)$=CH—, —CH=CF—, —CH=CCl— or —CH=$C(CH_3)$—

Embodiment 12h. A compound of Embodiment 12g wherein $X^{11}$ is —CH=CH—, —CH=CF—, —CH=CCl— or —CH=$C(CH_3)$—.

Embodiment 12i. A compound of Embodiment 12h wherein $X^{11}$ is —CH=CH—.

Embodiment 13a. A compound of any one of the preceding Embodiments wherein $R^9$ is $C_1$-$C_2$ alkyl.

Embodiment 13b. A compound of Embodiment 13 wherein $R^9$ is methyl.

Embodiment 14a. A compound of any one of the preceding Embodiments wherein independently, $R^{10}$ and $R^{11}$ are H, halogen, —CN, $C_1$-$C_3$ alkyl, $C_2$-$C_4$ alkenyl, $C_2$-$C_4$ alkynyl, $C_3$-$C_4$ cycloalkyl, $C_1$-$C_3$ haloalkyl, $C_1$-$C_3$ alkoxy, $C_1$-$C_2$ haloalkoxy, $C_1$-$C_2$ alkylthio or $C_1$-$C_2$ haloalkylthio.

Embodiment 14b. A compound of Embodiment 14a wherein independently, $R^{10}$ and $R^{11}$ are H, halogen, —CN, $C_1$-$C_2$ alkyl, —CH=$CH_2$, —C≡CH, cyclopropyl, $C_1$-$C_2$ haloalkyl or $C_1$-$C_2$ alkoxy.

Embodiment 14c. A compound of Embodiment 14b wherein independently, $R^{10}$ and $R^{11}$ are H, halogen, —CN, methyl, ethyl, —CH=$CH_2$, —C≡CH, cyclopropyl, $CF_3$, methoxy or ethoxy.

Embodiment 14d. A compound of Embodiment 14c wherein independently, $R^{10}$ and $R^{11}$ are H, halogen or $C_1$-$C_2$ alkyl.

Embodiment 14e. A compound of Embodiment 14d wherein independently, $R^{10}$ and $R^{11}$ are H or halogen.

Embodiment 14f. A compound of Embodiment 14d wherein $R^{10}$ is H and $R^{11}$ is halogen.

Embodiment 14g. A compound of Embodiment 14d wherein $R^{10}$ is halogen and $R^{11}$ is H.

Embodiment 14h. A compound of Embodiment 14c wherein independently, $R^{10}$ and $R^{11}$ are H or $C_1$-$C_2$ alkyl.

Embodiment 14i. A compound of Embodiment 14g wherein $R^{10}$ is H or methyl (i.e. $CH_3$).

Embodiment 14j. A compound of Embodiment 14h wherein $R^{10}$ is H and $R^{11}$ is H, or $R^{10}$ is H and $R^{11}$ is $CH_3$, or $R^{10}$ is $CH_3$ and $R^{11}$ is H.

Embodiment 14k. A compound of Embodiment 14i wherein $R^{10}$ is H and $R^{11}$ is H.

Embodiment 15a. A compound of any one of the preceding Embodiments wherein each $R^{12}$ is independently halogen, —CN, $C_1$-$C_3$ alkyl, $C_2$-$C_4$ alkenyl, $C_2$-$C_4$ alkynyl, $C_3$-$C_4$ cycloalkyl, $C_1$-$C_3$ haloalkyl, $C_1$-$C_3$ alkoxy, $C_1$-$C_2$ haloalkoxy, $C_1$-$C_2$ alkylthio or $C_1$-$C_2$ haloalkylthio.

Embodiment 15b. A compound of Embodiment 15a wherein each $R^{12}$ is independently halogen, —CN, $C_1$-$C_2$ alkyl, —CH=$CH_2$, —C≡CH, cyclopropyl, $C_1$-$C_2$ haloalkyl or $C_1$-$C_2$ alkoxy.

Embodiment 15c. A compound of Embodiment 15b wherein each $R^{12}$ is independently halogen, —CN, methyl, ethyl, —CH=$CH_2$, —C≡CH, cyclopropyl, $CF_3$, methoxy or ethoxy.

Embodiment 15d. A compound of Embodiment 15c wherein each $R^{12}$ is independently halogen, —CN, methyl, ethyl, methoxy or ethoxy.

Embodiment 15e. A compound of Embodiment 15d wherein each $R^{12}$ is independently F, Cl, Br, methyl, ethyl or methoxy.

Embodiment 15f. A compound of Embodiment 15e wherein each $R^{12}$ is methyl.

Embodiment 15g. A compound of Embodiment 15e wherein each $R^{12}$ is F.

Embodiment 15h. A compound of Embodiment 15e wherein each $R^{12}$ is Cl.

Embodiment 16a. A compound of Formula 1 or any one of the preceding Embodiments wherein $R^{13}$ is H, halogen, —CN, $C_1$-$C_3$ alkyl, $C_2$-$C_4$ alkenyl, $C_2$-$C_4$ alkynyl, $C_3$-$C_4$ cycloalkyl, $C_1$-$C_3$ haloalkyl, $C_1$-$C_3$ alkoxy, $C_1$-$C_2$ haloalkoxy, $C_1$-$C_2$ alkylthio or $C_1$-$C_2$ haloalkylthio.

Embodiment 16b. A compound of Embodiment 16a wherein $R^{13}$ is halogen, —CN, $C_1$-$C_2$ alkyl, —CH=$CH_2$, —C≡CH, cyclopropyl, $C_1$-$C_2$ haloalkyl or $C_1$-$C_2$ alkoxy.

Embodiment 16c. A compound of Embodiment 16b wherein $R^{13}$ is halogen, —CN, methyl, ethyl, —CH=$CH_2$, —C≡CH, cyclopropyl, $CF_3$, methoxy or ethoxy.

Embodiment 16d. A compound of Embodiment 16c wherein $R^{13}$ is Me or ethyl.

Embodiment 16e. A compound of Embodiment 16d wherein $R^{13}$ is Me or Cl.

Embodiment 16f. A compound of Embodiment 16e wherein $R^{13}$ is Me.

Embodiment 16g. A compound of Embodiment 16e wherein $R^{13}$ is Cl.

Embodiment 16h. A compound of Embodiment 16e wherein $R^{13}$ is F.

Embodiment 17. A compound of Formula 1 or any one of the preceding Embodiments wherein n is 0, 1, 2, 3 or 4.

Embodiment 17a. A compound of Embodiment 17 wherein n is 0, 1 or 2.

Embodiment 17aa. A compound of Embodiment 17 wherein n is 1 or 2.

Embodiment 17b. A compound of Embodiment 17a wherein n is 0.

Embodiment 17c. A compound of Embodiment 17a wherein n is 1.

Embodiment 17d. A compound of Embodiment 17a wherein n is 2.

Embodiments of this invention, including Embodiments 1-17d above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-17d above as well as any other embodiments described herein, and any combination thereof, pertain to the compositions and methods of the present invention.

Combinations of Embodiments 1-17d are illustrated by:

Embodiment A. A compound of Formula 1 as described in the Summary of the Invention wherein A is A-11;

$R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

$R^2$ is H, halogen, cyano, formyl, $C_1$-$C_7$ alkyl, $C_3$-$C_8$ alkylcarbonylalkyl, $C_3$-$C_8$ alkoxycarbonylalkyl, $C_2$-$C_4$ alkylcarbonyl, $C_2$-$C_7$ alkylcarbonyloxy, $C_4$-$C_7$ alkylcycloalkyl, $C_3$-$C_7$ alkenyl, $C_3$-$C_7$ alkynyl, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_1$-$C_7$ alkoxy, $C_1$-$C_5$ alkylthio or $C_2$-$C_3$ alkoxycarbonyl;

$R^3$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

$R^4$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy, $(CH_2CH_2O)_rR^5$; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

each $R^{12}$ is independently halogen, —CN, $C_1$-$C_3$ alkyl, $C_2$-$C_4$ alkenyl, $C_2$-$C_4$ alkynyl, $C_3$-$C_4$ cycloalkyl, $C_1$-$C_3$ haloalkyl, $C_1$-$C_3$ alkoxy, $C_1$-$C_2$ haloalkoxy, $C_1$-$C_2$ alkylthio or $C_1$-$C_2$ haloalkylthio;

$R^{13}$ is halogen, —CN, $C_1$-$C_3$ alkyl, $C_2$-$C_4$ alkenyl, $C_2$-$C_4$ alkynyl, $C_3$-$C_4$ cycloalkyl, $C_1$-$C_3$ haloalkyl, $C_1$-$C_3$ alkoxy, $C_1$-$C_2$ haloalkoxy, $C_1$-$C_2$ alkylthio or $C_1$-$C_2$ haloalkylthio.

Embodiment A1. A compound of Embodiment A wherein $R^1$ is $C_1$-$C_4$ alkyl, $C_3$-$C_4$ alkenyl, $C_3$-$C_4$ alkynyl, $C_3$-$C_4$ cycloalkyl, $C_2$-$C_3$ cyanoalkyl, $C_1$-$C_3$ haloalkyl or $C_2$-$C_4$ alkoxyalkyl;

$R^2$ is H, halogen, —CN, $C_1$-$C_4$ alkyl, $C_3$-$C_5$ cycloalkyl, $C_1$-$C_3$ haloalkyl, $C_2$-$C_4$ alkoxyalkyl or $C_1$-$C_3$ alkoxy;

$R^3$ is H, $C_1$-$C_4$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ cycloalkyl, $C_4$-$C_7$ cycloalkylalkyl, $C_2$-$C_3$ cyanoalkyl, $C_1$-$C_7$ haloalkyl, $C_2$-$C_7$ alkoxyalkyl or $C_1$-$C_7$ alkoxy;

$R^4$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl or $C_1$-$C_7$ alkoxy;

$R^{12}$ is independently halogen, —CN, methyl, ethyl, methoxy or ethoxy; and $R^{13}$ is halogen, —CN, methyl, ethyl, $—CH=CH_2$, —C≡CH, cyclopropyl, $CF_3$, methoxy or ethoxy.

Embodiment A2. A compound of Embodiment A1 wherein $R^1$ is $C_1$-$C_3$ alkyl, allyl, propargyl, $CH_2CH_2CN$, $C_1$-$C_2$ haloalkyl or 2-methoxyethyl;

$R^2$ is H, halogen, $C_1$-$C_3$ alkyl, cyclopropyl, $C_1$-$C_2$ haloalkyl, methoxy or ethoxy;

$R^3$ is H, $C_1$-$C_4$ alkyl, $C_3$-$C_7$ cycloalkyl, $C_4$-$C_7$ cycloalkylalkyl or $C_1$-$C_7$ alkoxy;

$R^4$ is H, $C_1$-$C_4$ alkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl or $C_1$-$C_7$ alkoxy;

each $R^{12}$ is independently F, Cl, Br, methyl, ethyl or methoxy; and n is 0, 1 or 2.

Embodiment A3. A compound of Embodiment A2 wherein $R^1$ is methyl, ethyl, n-propyl or 2-methoxyethyl;

$R^2$ is H, F, Cl, methyl, ethyl, n-propyl, $CF_3$ or methoxy;

$R^3$ is H or methyl;

$R^4$ is H, $C_1$-$C_4$ alkyl, $C_4$-$C_7$ cycloalkylalkyl or $C_1$-$C_7$ alkoxy;

$X^{11}$ is $—C(R^{10})=C(R^{11})—$; and independently, $R^{10}$ and $R^{11}$ are H, halogen or $C_1$-$C_2$ alkyl.

Embodiment A4. A compound of Embodiment A3 wherein $R^1$ is methyl;

$R^2$ is Me or Cl;

$R^3$ is H;

$R^4$ is H, methyl, ethyl, i-propyl, t-Bu, cyclopropyl, cyclobutyl, cyclopentyl, cyclohexyl, methoxy or ethoxy; and $R^{10}$ is H and $R^{11}$ is H, or $R^{10}$ is H and $R^{11}$ is $CH_3$, or $R^{10}$ is $CH_3$ and $R^{11}$ is H.

Embodiment A5. A compound of Embodiment A2 wherein $R^1$ is methyl, ethyl, n-propyl or 2-methoxyethyl;

$R^2$ is H, F, Cl, methyl, ethyl, n-propyl, $CF_3$ or methoxy;

$R^3$ is H or methyl;

$R^4$ is H, $C_1$-$C_4$ alkyl, $C_4$-$C_7$ cycloalkylalkyl or $C_1$-$C_7$ alkoxy;

$X^{11}$ is O.

Embodiment A6. A compound of Embodiment A2 wherein $R^1$ is methyl, ethyl, n-propyl or 2-methoxyethyl;

$R^2$ is H, F, Cl, methyl, ethyl, n-propyl, $CF_3$ or methoxy;

$R^3$ is H or methyl;

$R^4$ is H, $C_1$-$C_4$ alkyl, $C_4$-$C_7$ cycloalkylalkyl or $C_1$-$C_7$ alkoxy;

$X^{11}$ is S.

Embodiment A7. A compound of Embodiment A2 wherein

X is a direct bond or O.

Embodiment B. A compound of Formula 1 as described in the Summary of the Invention wherein A is selected from A-1, A-4 and A-6;

$R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

$R^2$ is H, halogen, cyano, formyl, $C_1$-$C_7$ alkyl, $C_3$-$C_8$ alkylcarbonylalkyl, $C_3$-$C_8$ alkoxycarbonylalkyl, $C_2$-$C_4$ alkylcarbonyl, $C_2$-$C_7$ alkylcarbonyloxy, $C_4$-$C_7$ alkylcycloalkyl, $C_3$-$C_7$ alkenyl, $C_3$-$C_7$ alkynyl, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_1$-$C_7$ alkoxy, $C_1$-$C_5$ alkylthio or $C_2$-$C_3$ alkoxycarbonyl;

$R^3$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

$R^4$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy, $(CH_2CH_2O)_tR^5$; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy.

Embodiment B1. A compound of Embodiment B wherein

A is A-1;

$R^1$ is H, $C_1$-$C_7$ alkyl, $C_3$-$C_8$ alkoxycarbonylalkyl, $C_4$-$C_7$ alkylcycloalkyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_2$-$C_7$ alkoxyalkyl, $C_3$-$C_7$ alkylthioalkyl, $C_1$-$C_7$ alkoxy or benzyl.

$R^2$ is H, halogen, —CN, $C_1$-$C_4$ alkyl, $C_3$-$C_5$ cycloalkyl, $C_1$-$C_3$ haloalkyl, $C_2$-$C_4$ alkoxyalkyl or $C_1$-$C_3$ alkoxy;

$R^3$ is H, $C_1$-$C_4$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ cycloalkyl, $C_4$-$C_7$ cycloalkylalkyl, $C_2$-$C_3$ cyanoalkyl, $C_1$-$C_7$ haloalkyl, $C_2$-$C_7$ alkoxyalkyl or $C_1$-$C_7$ alkoxy;

$R^4$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl or $C_1$-$C_7$ alkoxy;

each $X^1$, $X^2$, $X^3$, $X^4$, $X^5$, $X^6$, $X^7$, $X^8$ and $X^9$ is $CR^7$;

each $R^7$ is independently H, halogen, $C_1$-$C_3$ alkyl, $C_3$-$C_4$ cycloalkyl, $C_1$-$C_3$ haloalkyl or $C_1$-$C_3$ alkoxy;

X is a direct bond or O.

Embodiment B2. A compound of Embodiment B1 wherein $R^1$ is $C_1$-$C_4$ alkyl, $C_3$-$C_4$ alkenyl, $C_3$-$C_4$ alkynyl, $C_3$-$C_4$ cycloalkyl, $C_2$-$C_3$ cyanoalkyl, $C_1$-$C_3$ haloalkyl or $C_2$-$C_4$ alkoxyalkyl;

$R^2$ is H, halogen, $C_1$-$C_3$ alkyl, cyclopropyl, $C_1$-$C_2$ haloalkyl, methoxy or ethoxy;

$R^3$ is H, $C_1$-$C_4$ alkyl, $C_3$-$C_7$ cycloalkyl, $C_4$-$C_7$ cycloalkylalkyl or $C_1$-$C_7$ alkoxy;

each $R^7$ is independently H, halogen, $C_1$-$C_2$ alkyl, cyclopropyl or $C_1$-$C_2$ haloalkyl.

Embodiment B3. A compound of Embodiment B2 wherein $R^1$ is methyl, ethyl, n-propyl or 2-methoxyethyl;

$R^2$ is H, F, Cl, methyl, ethyl, n-propyl, $CF_3$ or methoxy; and each $R^7$ is independently H, halogen, methyl, ethyl or $CF_3$.

Embodiment C1. A compound of Formula 1 as described in the Summary of the Invention or any one of the preceeding Embodiments wherein $R^3$ is H, $R^{14}$ is H, X is direct bond and $R^4$ is H, methyl, ethyl, i-propyl, t-Bu or methoxy, which has improved herbicidal activities on certain weeds.

Embodiment C2. A compound of Embodiment C1 wherein the weeds are *Galium, Ambrosia, Amaranthus, Bassia* or *Erigeron.*

Embodiment C2a. A compound of Embodiment C1 wherein the weeds are *Galium aparine, Ambrosia artemisiifolia, Amaranthus palmeri, Bassia scoparia* or *Erigeron canadensis.*

Embodiment C2b. A compound of Embodiment C1 wherein the weeds are galium, ragweed, pigweed, kochia or horseweed.

Embodiment C3. A compound of Formula 1 as described in the Summary of the Invention wherein $R^3$ is H, $R^{14}$ is H, X is direct bond and $R^4$ is H, methyl, ethyl, i-propyl, t-Bu or methoxy, which has improved tox profiles.

Embodiment C4. A compound of Formula 1 as described in the Summary of the Invention wherein $R^3$ is H, $R^{14}$ is H, X is direct bond and $R^4$ is H, methyl, ethyl, i-propyl, t-Bu or methoxy, which has improved pharmacokinetics properties.

Embodiment D. A compound of Formula 1, stereoisomers, and salts thereof, agricultural compositions containing them and their use as herbicides as described in the Summary of the Invention.

Specific embodiments include a compound of Formula 1 selected from the group consisting of:

5-[(acetyloxy)methoxy]-6-chloro-4-(2,7-dimethyl-1-naphthalenyl)-2-methyl-3(2H)-pyridazinone;

5-[(acetyloxy)methoxy]-4-(2-bromo-5-fluorobenzo[b]thien-3-yl)-2,6-dimethyl-3(2H)-pyridazinone;

[[5-(2-fluoro-7-methyl-9-anthracenyl)-1,6-dihydro-1,3-dimethyl-6-oxo-4-pyridazinyl]oxy]methyl methyl carbonate;

5-[(acetyloxy)methoxy]-6-chloro-2-methyl-4-(2-methyl-1-naphthalenyl)-3(2H)-pyridazinone; and 5-[(acetyloxy)methoxy]-4-(2-fluoro-7-methyl-9-anthracenyl)-2,6-dimethyl-3(2H)-pyridazinone.

This invention also relates to a method for controlling undesired vegetation comprising applying to the locus of the vegetation herbicidally effective amounts of the compounds of the invention (e.g., as a composition described herein). Of note as embodiments relating to methods of use are those involving the compounds of embodiments described above. Compounds of the invention are particularly useful for selective control of weeds in crops such as wheat, barley, maize, soybean, sunflower, cotton, oilseed rape and rice, and specialty crops such as sugarcane, citrus, fruit and nut crops.

Also noteworthy as embodiments are herbicidal compositions of the present invention comprising the compounds of embodiments described above.

This invention also includes a herbicidal mixture comprising (a) a compound selected from Formula 1, N-oxides, and salts thereof, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solanesyltransferase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, hydantocidin, metam, methyldymron, oleic acid, oxaziclomefone, pelargonic acid and pyributicarb, (b16) herbicide safeners, and salts of compounds of (b1) through (b16).

"Photosystem II inhibitors" (b1) are chemical compounds that bind to the D-1 protein at the $Q_B$-binding niche and thus block electron transport from $Q_A$ to $Q_B$ in the chloroplast thylakoid membranes. The electrons blocked from passing through photosystem II are transferred through a series of reactions to form toxic compounds that disrupt cell membranes and cause chloroplast swelling, membrane leakage, and ultimately cellular destruction. The $Q_B$-binding niche has three different binding sites: binding site A binds the triazines such as atrazine, triazinones such as hexazinone, and uracils such as bromacil, binding site B binds the phenylureas such as diuron, and binding site C binds benzothiadiazoles such as bentazon, nitriles such as bromoxynil and phenyl-pyridazines such as pyridate. Examples of photosystem II inhibitors include ametryn, amicarbazone, atrazine, bentazon, bromacil, bromofenoxim, bromoxynil, chlorbromuron, chloridazon, chlorotoluron, chloroxuron, cumyluron, cyanazine, daimuron, desmedipham, desmetryn, dimefuron, dimethametryn, diuron, ethidimuron, fenuron, fluometuron, hexazinone, ioxynil, isoproturon, isouron, lenacil, linuron, metamitron, methabenzthiazuron, metobromuron, metoxuron, metribuzin, monolinuron, neburon, pentanochlor, phenmedipham, prometon, prometryn, propanil, propazine, pyridafol, pyridate, siduron, simazine, simetryn, tebuthiuron, terbacil, terbumeton, terbuthylazine, terbutryn and trietazine.

"AHAS inhibitors" (b2) are chemical compounds that inhibit acetohydroxy acid synthase (AHAS), also known as acetolactate synthase (ALS), and thus kill plants by inhibiting the production of the branched-chain aliphatic amino acids such as valine, leucine and isoleucine, which are required for protein synthesis and cell growth. Examples of AHAS inhibitors include amidosulfuron, azimsulfuron, bensulfuron-methyl, bispyribac-sodium, cloransulam-methyl, chlorimuron-ethyl, chlorsulfuron, cinosulfuron, cyclosulfamuron, diclosulam, ethametsulfuron-methyl, ethoxysulfuron, flazasulfuron, florasulam, flucarbazone-sodium, flumetsulam, flupyrsulfuron-methyl, flupyrsulfuron-sodium, foramsulfuron, halosulfuron-methyl, imazamethabenz-methyl, imazamox, imazapic, imazapyr, imazaquin, imazethapyr, imazosulfuron, iodosulfuron-methyl (including sodium salt), iofensulfuron (2-iodo-N-[[(4-methoxy-6-methyl-1,3,5-triazin-2-yl)amino]carbonyl]benzenesulfonamide), mesosulfuron-methyl, metazosulfuron (3-chloro-4-(5,6-dihydro-5-methyl-1,4,2-dioxazin-3-yl)-N-[[(4,6-dimethoxy-2-pyrimidinyl)amino]carbonyl]-1-methyl-1H-pyrazole-5-sulfonamide), metosulam, metsulfuron-methyl, nicosulfuron, oxasulfuron, penoxsulam, primisulfuron-methyl, propoxycarbazone-sodium, propyrisulfuron (2-chloro-N-[[(4,6-dimethoxy-2-pyrimidinyl)amino]carbonyl]-6-propylimidazo[1,2-b]pyridazine-3-sulfonamide), prosulfuron, pyrazosulfuron-ethyl, pyribenzoxim, pyriftalid, pyriminobac-methyl, pyrithiobac-sodium, rimsulfuron, sulfometuron-methyl, sulfosulfuron, thiencarbazone, thifensulfuron-methyl, triafamone (N-[2-[(4,6-dimethoxy-1,3,5-triazin-2-yl)carbonyl]-6-fluorophenyl]-1,1-difluoro-N-methylmethanesulfonamide), triasulfuron, tribenuron-methyl, trifloxysulfuron (including sodium salt), triflusulfuron-methyl and tritosulfuron.

"ACCase inhibitors" (b3) are chemical compounds that inhibit the acetyl-CoA carboxylase enzyme, which is responsible for catalyzing an early step in lipid and fatty acid synthesis in plants. Lipids are essential components of cell membranes, and without them, new cells cannot be produced. The inhibition of acetyl CoA carboxylase and the subsequent lack of lipid production leads to losses in cell membrane integrity, especially in regions of active growth such as meristems. Eventually shoot and rhizome growth ceases, and shoot meristems and rhizome buds begin to die back. Examples of ACCase inhibitors include alloxydim, butroxydim, clethodim, clodinafop, cycloxydim, cyhalofop, diclofop, fenoxaprop, fluazifop, haloxyfop, pinoxaden, profoxydim, propaquizafop, quizalofop, sethoxydim, tepraloxydim and tralkoxydim, including resolved forms such as fenoxaprop-P, fluazifop-P, haloxyfop-P and quizalofop-P and ester forms such as clodinafop-propargyl, cyhalofop-butyl, diclofop-methyl and fenoxaprop-P-ethyl.

Auxin is a plant hormone that regulates growth in many plant tissues. "Auxin mimics" (b4) are chemical compounds mimicking the plant growth hormone auxin, thus causing uncontrolled and disorganized growth leading to plant death in susceptible species. Examples of auxin mimics include aminocyclopyrachlor (6-amino-5-chloro-2-cyclopropyl-4-pyrimidinecarboxylic acid) and its methyl and ethyl esters and its sodium and potassium salts, aminopyralid, benazolin-ethyl, chloramben, clacyfos, clomeprop, clopyralid, dicamba, 2,4-D, 2,4-DB, dichlorprop, fluroxypyr, halauxifen (4-amino-3-chloro-6-(4-chloro-2-fluoro-3-methoxyphenyl)-2-pyridinecarboxylic acid), halauxifen-methyl (methyl 4-amino-3-chloro-6-(4-chloro-2-fluoro-3-methoxyphenyl)-2-pyridinecarboxylate), MCPA, MCPB, mecoprop, picloram, quinclorac, quinmerac, 2,3,6-TBA, triclopyr, and methyl 4-amino-3-chloro-6-(4-chloro-2-fluoro-3-methoxyphenyl)-5-fluoro-2-pyridinecarboxylate.

"EPSP synthase inhibitors" (b5) are chemical compounds that inhibit the enzyme, 5-enol-pyruvylshikimate-3-phosphate synthase, which is involved in the synthesis of aromatic amino acids such as tyrosine, tryptophan and phenylalanine. EPSP inhibitor herbicides are readily absorbed through plant foliage and translocated in the phloem to the growing points. Glyphosate is a relatively nonselective postemergence herbicide that belongs to this group. Glyphosate includes esters and salts such as ammonium, isopropylammonium, potassium, sodium (including sesquisodium) and trimesium (alternatively named sulfosate).

"Photosystem I electron diverters" (b6) are chemical compounds that accept electrons from Photosystem I, and after several cycles, generate hydroxyl radicals. These radicals are extremely reactive and readily destroy unsaturated lipids, including membrane fatty acids and chlorophyll. This destroys cell membrane integrity, so that cells and organelles "leak", leading to rapid leaf wilting and desiccation, and eventually to plant death. Examples of this second type of photosynthesis inhibitor include diquat and paraquat.

"PPO inhibitors" (b7) are chemical compounds that inhibit the enzyme protoporphyrinogen oxidase, quickly resulting in formation of highly reactive compounds in plants that rupture cell membranes, causing cell fluids to leak out. Examples of PPO inhibitors include acifluorfen-sodium, azafenidin, benzfendizone, bifenox, butafenacil, carfentrazone, carfentrazone-ethyl, chlomethoxyfen, cinidon-ethyl, fluazolate, flufenpyr-ethyl, flumiclorac-pentyl, flumioxazin, fluoroglycofen-ethyl, fluthiacet-methyl, fomesafen, halosafen, lactofen, oxadiargyl, oxadiazon, oxyfluorfen, pentoxazone, profluazol, pyraclonil, pyraflufen-ethyl, saflufenacil, sulfentrazone, thidiazimin, trifludimoxazin (dihydro-1,5-dimethyl-6-thioxo-3-[2,2,7-trifluoro-3,4-dihydro-3-oxo-4-(2-propyn-1-yl)-2H-1,4-benzoxazin-6-yl]-1,3,5-triazine-2,4(1H,3H)-dione) and tiafenacil (methyl N-[2-[[2-chloro-5-[3,6-dihydro-3-methyl-2,6-dioxo-4-(trifluoromethyl)-1(2H)-pyrimidinyl]-4-fluorophenyl]thio]-1-oxopropyl]-β-alaninate).

"GS inhibitors" (b8) are chemical compounds that inhibit the activity of the glutamine synthetase enzyme, which plants use to convert ammonia into glutamine. Consequently, ammonia accumulates and glutamine levels decrease. Plant damage probably occurs due to the combined effects of ammonia toxicity and deficiency of amino acids required for other metabolic processes. The GS inhibitors include glufosinate and its esters and salts such as glufosinate-ammonium and other phosphinothricin derivatives, glufosinate-P ((2s)-2-amino-4-(hydroxymethylphosphinyl)butanoic acid) and bilanaphos.

"VLCFA elongase inhibitors" (b9) are herbicides having a wide variety of chemical structures, which inhibit the elongase. Elongase is one of the enzymes located in or near chloroplasts which are involved in biosynthesis of VLCFAs. In plants, very-long-chain fatty acids are the main constituents of hydrophobic polymers that prevent desiccation at the leaf surface and provide stability to pollen grains. Such herbicides include acetochlor, alachlor, anilofos, butachlor, cafenstrole, dimethachlor, dimethenamid, diphenamid, fenoxasulfone (3-[[(2,5-dichloro-4-ethoxyphenyl)methyl]sulfonyl]-4,5-dihydro-5,5-dimethylisoxazole), fentrazamide, flufenacet, indanofan, mefenacet, metazachlor, metolachlor, naproanilide, napropamide, napropamide-M ((2R)—N,N-diethyl-2-(1-naphthalenyloxy)propanamide), pethoxamid, piperophos, pretilachlor, propachlor, propisochlor, pyroxasulfone, and thenylchlor, including resolved forms such as S-metolachlor and chloroacetamides and oxyacetamides.

"Auxin transport inhibitors" (b10) are chemical substances that inhibit auxin transport in plants, such as by binding with an auxin-carrier protein. Examples of auxin transport inhibitors include diflufenzopyr, naptalam (also known as N-(1-naphthyl)phthalamic acid and 2-[(1-naphthalenylamino)carbonyl]benzoic acid).

"PDS inhibitors" (b11) are chemical compounds that inhibit carotenoid biosynthesis pathway at the phytoene desaturase step. Examples of PDS inhibitors include beflubutamid, diflufenican, fluridone, flurochloridone, flurtamone norflurzon and picolinafen.

"HPPD inhibitors" (b12) are chemical substances that inhibit the biosynthesis of synthesis of 4-hydroxyphenylpyruvate dioxygenase. Examples of HPPD inhibitors include benzobicyclon, benzofenap, bicyclopyrone (4-hydroxy-3-[[2-[(2-methoxyethoxy)methyl]-6-(trifluoromethyl)-3-pyridinyl]carbonyl]bicyclo[3.2.1]oct-3-en-2-one), fenquinotrione (2-[[8-chloro-3,4-dihydro-4-(4-methoxyphenyl)-3-oxo-2-quinoxalinyl]carbonyl]-1,3-cyclohexanedione), isoxachlortole, isoxaflutole, mesotrione, pyrasulfotole, pyrazolynate, pyrazoxyfen, sulcotrione, tefuryltrione, tembotrione, tolpyralate (1-[[1-ethyl-4-[3-(2-methoxyethoxy)-2-methyl-4-(methylsulfonyl)benzoyl]-1H-pyrazol-5-yl]oxy]ethyl methyl carbonate), topramezone, 5-chloro-3-[(2-hydroxy-6-oxo-1-cyclohexen-1-yl)carbonyl]-1-(4-methoxyphenyl)-2(1H)-quinoxalinone, 4-(2,6-diethyl-4-methylphenyl)-5-hydroxy-2,6-dimethyl-3(2H)-pyridazinone, 4-(4-fluorophenyl)-6-[(2-hydroxy-6-oxo-1-cyclohexen-1-yl)carbonyl]-2-methyl-1,2,4-triazine-3,5(2H,4H)-dione, 5-[(2-hydroxy-6-oxo-1-cyclohexen-1-yl)carbonyl]-2-(3-methoxyphenyl)-3-(3-methoxypropyl)-4(3H)-pyrimidinone, 2-methyl-N-(4-methyl-1,2,5-oxadiazol-3-yl)-3-(methylsulfinyl)-4-(trifluoromethyl)benzamide and 2-methyl-3-(methylsulfonyl)-N-(1-methyl-1H-tetrazol-5-yl)-4-(trifluoromethyl)benzamide.

"HST (homogentisate solanesyltransferase) inhibitors" (b13) disrupt a plant's ability to convert homogentisate to 2-methyl-6-solanyl-1,4-benzoquinone, thereby disrupting carotenoid biosynthesis. Examples of HST inhibitors include cyclopyrimorate (6-chloro-3-(2-cyclopropyl-6-methylphenoxy)-4-pyridazinyl 4-morpholinecarboxylate), haloxydine, pyriclor, 3-(2-chloro-3,6-difluorophenyl)-4-hydroxy-1-methyl-1,5-naphthyridin-2(1H)-one, 7-(3,5-dichloro-4-pyridinyl)-5-(2,2-difluoroethyl)-8-hydroxypyrido[2,3-b]pyrazin-6(5H)-one and 4-(2,6-diethyl-4-methylphenyl)-5-hydroxy-2,6-dimethyl-3(2H)-pyridazinone.

HST inhibitors also include compounds of Formulae A and B.

A

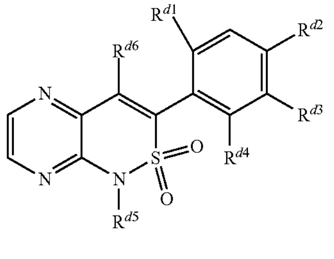

-continued

B

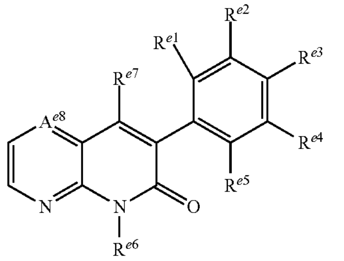

wherein $R^{d1}$ is H, Cl or $CF_3$; $R^{d2}$ is H, Cl or Br; $R^{d3}$ is H or Cl; $R^{d4}$ is H, Cl or $CF_3$; $R^{d5}$ is $CH_3$, $CH_2CH_3$ or $CH_2CHF_2$; and $R^{d6}$ is OH, or —OC(═O)-i-Pr; and $R^{e1}$ is H, F, Cl, $CH_3$ or $CH_2CH_3$; $R^{e2}$ is H or $CF_3$; $R^{e3}$ is H, $CH_3$ or $CH_2CH_3$; $R^{e4}$ is H, F or Br; $R^{e5}$ is Cl, $CH_3$, $CF_3$, $OCF_3$ or $CH_2CH_3$; $R^{e6}$ is H, $CH_3$, $CH_2CHF_2$ or C≡CH; $R^{e7}$ is OH, —OC(═O)Et, —OC(═O)-i-Pr or —OC(═O)-t-Bu; and $A^{e8}$ is N or CH.

"Cellulose biosynthesis inhibitors" (b14) inhibit the biosynthesis of cellulose in certain plants. They are most effective when applied preemergence or early postemergence on young or rapidly growing plants. Examples of cellulose biosynthesis inhibitors include chlorthiamid, dichlobenil, flupoxam, indaziflam ($N^2$-[(1R,2S)-2,3-dihydro-2,6-dimethyl-1H-inden-1-yl]-6-(1-fluoroethyl)-1,3,5-triazine-2,4-diamine), isoxaben and triaziflam.

"Other herbicides" (b15) include herbicides that act through a variety of different modes of action such as mitotic disruptors (e.g., flamprop-M-methyl and flamprop-M-isopropyl), organic arsenicals (e.g., DSMA, and MSMA), 7,8-dihydropteroate synthase inhibitors, chloroplast isoprenoid synthesis inhibitors and cell-wall biosynthesis inhibitors. Other herbicides include those herbicides having unknown modes of action or do not fall into a specific category listed in (b1) through (b14) or act through a combination of modes of action listed above. Examples of other herbicides include aclonifen, asulam, amitrole, bromobutide, cinmethylin, clomazone, cumyluron, daimuron, difenzoquat, etobenzanid, fluometuron, flurenol, fosamine, fosamine-ammonium, dazomet, dymron, ipfencarbazone (1-(2,4-dichlorophenyl)-N-(2,4-difluorophenyl)-1,5-dihydro-N-(1-methylethyl)-5-oxo-4H-1,2,4-triazole-4-carboxamide), metam, methyldymron, oleic acid, oxaziclomefone, pelargonic acid, pyributicarb and 5-[[(2,6-difluorophenyl)methoxy]methyl]-4,5-dihydro-5-methyl-3-(3-methyl-2-thienyl)isoxazole.

"Other herbicides" (b15) also include a compound of Formula (b15A)

(b15A)

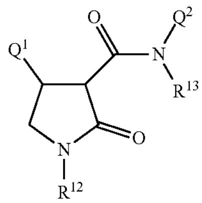

wherein $R^{12}$ is H, $C_1$-$C_6$ alkyl, $C_1$-$C_6$ haloalkyl or $C_4$-$C_8$ cycloalkyl;

$R^{13}$ is H, $C_1$-$C_6$ alkyl or $C_1$-$C_6$ alkoxy;

$Q^1$ is an optionally substituted ring system selected from the group consisting of phenyl, thienyl, pyridinyl, benzodioxolyl, naphthyl, naphthalenyl, benzofuranyl, furanyl, benzothiophenyl and pyrazolyl, wherein when substituted said ring system is substituted by 1 to 3 $R^{14}$;

$Q^2$ is an optionally substituted ring system selected from the group consisting of phenyl, pyridinyl, benzodioxolyl, pyridinonyl, thiadiazolyl, thiazolyl, and oxazolyl, wherein when substituted said ring system is substituted by 1 to 3 $R^{15}$;

each $R^{14}$ is independently halogen, $C_1$-$C_6$ alkyl, $C_1$-$C_6$ haloalkyl, $C_1$-$C_6$ alkoxy, $C_1$-$C_6$ haloalkoxy, $C_3$-$C_8$ cyaloalkyl, cyano, $C_1$-$C_6$ alkylthio, $C_1$-$C_6$ alkylsulfinyl, $C_1$-$C_6$ alkylsulfonyl, $SF_5$, $NHR^{17}$; or phenyl optionally substituted by 1 to 3 $R^{16}$; or pyrazolyl optionally substituted by 1 to 3 $R^{16}$;

each $R^{15}$ is independently halogen, $C_1$-$C_6$ alkyl, $C_1$-$C_6$ haloalkyl, $C_1$-$C_6$ alkoxy, $C_1$-$C_6$ haloalkoxy, cyano, nitro, $C_1$-$C_6$ alkylthio, $C_1$-$C_6$ alkylsulfinyl, $C_1$-$C_6$ alkylsulfonyl;

each $R^{16}$ is independently halogen, $C_1$-$C_6$ alkyl or $C_1$-$C_6$ haloalkyl;

$R^{17}$ is $C_1$-$C_4$ alkoxycarbonyl.

In one Embodiment wherein "other herbicides" (b15) also include a compound of Formula (b15A), it is preferred that $R^{12}$ is H or $C_1$-$C_6$ alkyl; more preferably $R^{12}$ is H or methyl. Preferrably $R^{13}$ is H. Preferably $Q^1$ is either a phenyl ring or a pyridinyl ring, each ring substituted by 1 to 3 $R^{14}$; more preferably $Q^1$ is a phenyl ring substituted by 1 to 2 $R^{14}$. Preferably $Q^2$ is a phenyl ring substituted by 1 to 3 $R^{15}$; more preferably $Q^2$ is a phenyl ring substituted by 1 to 2 $R^{15}$. Preferably each $R^{14}$ is independently halogen, $C_1$-$C_4$ alkyl, $C_1$-$C_3$ haloalkyl, $C_1$-$C_3$ alkoxy or $C_1$-$C_3$ haloalkoxy; more preferably each $R^{14}$ is independently chloro, fluoro, bromo, $C_1$-$C_2$ haloalkyl, $C_1$-$C_2$ haloalkoxy or $C_1$-$C_2$ alkoxy. Preferably each $R^{15}$ is independently halogen, $C_1$-$C_4$ alkyl, $C_1$-$C_3$ haloalkoxy; more preferably each $R^{15}$ is independently chloro, fluoro, bromo, $C_1$-$C_2$ haloalkyl, $C_1$-$C_2$ haloalkoxy or $C_1$-$C_2$ alkoxy. Specifically preferred as "other herbicides" (b15) include any one of the following (b15A-1) through (b15A-15):

(b15A-1)

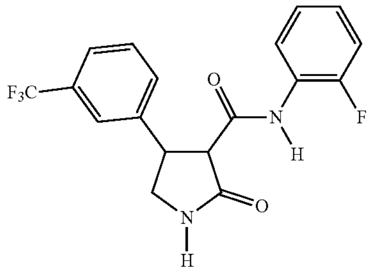

(b15A-2)

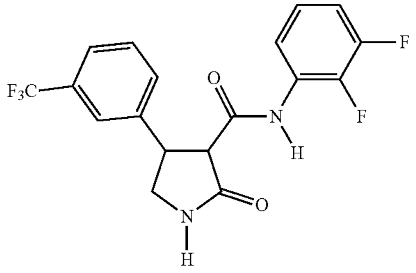

-continued
(b15A-3)
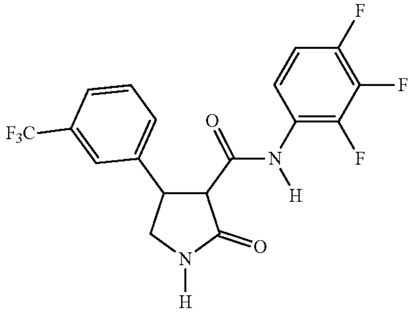
(b15A-4)
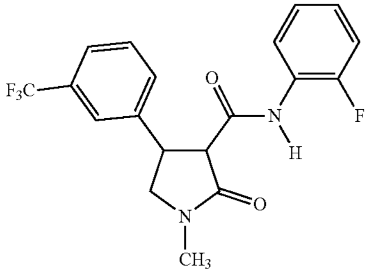
(b15A-5)
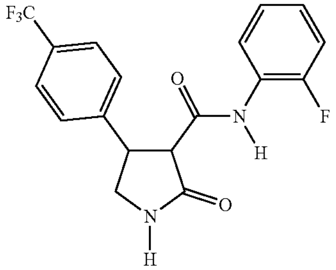
(b15A-6)
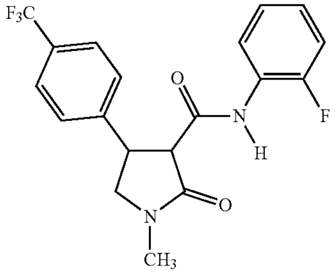
(b15A-7)
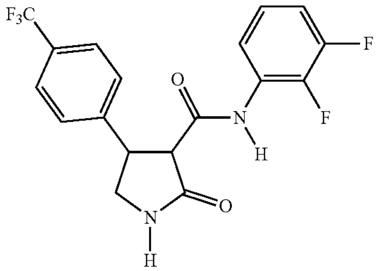
-continued
(b15A-8)
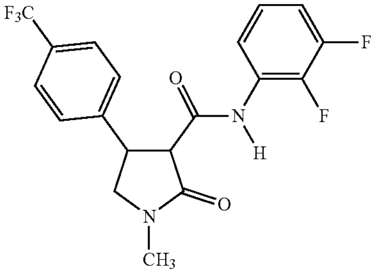
(b15A-9)
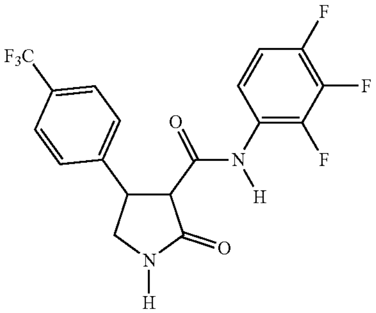
(b15A-10)
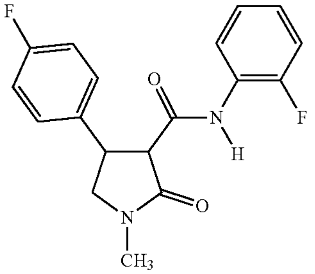
(b15A-11)
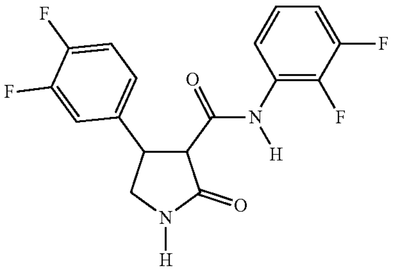
(b15A-12)
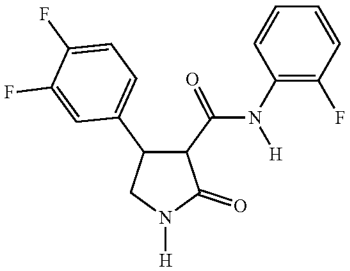

-continued (b15A-13)

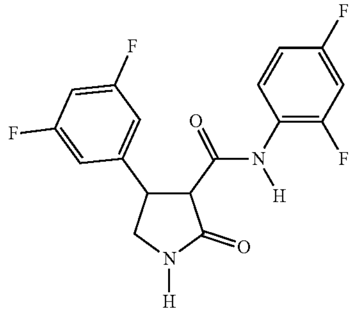

(b15A-14)

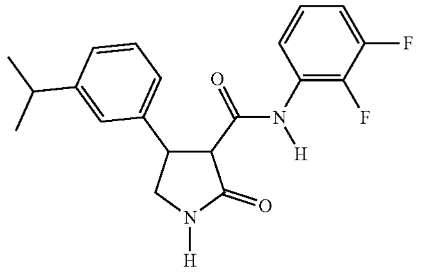

(b15A-15)

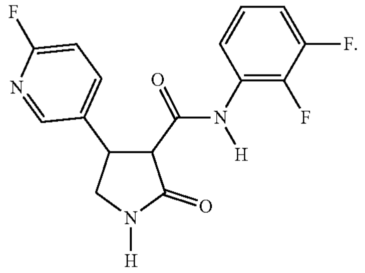

"Other herbicides" (b15) also include a compound of Formula (b15B)

(b15B)

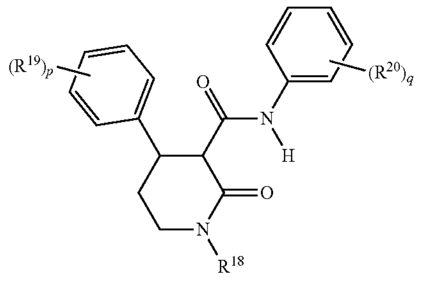

wherein $R^{18}$ is H, $C_1$-$C_6$ alkyl, $C_1$-$C_6$ haloalkyl or $C_4$-$C_8$ cycloalkyl;

each $R^{19}$ is independently halogen, $C_1$-$C_6$ haloalkyl or $C_1$-$C_6$ haloalkoxy;

p is an integer of 0, 1, 2 or 3;

each $R^{20}$ is independently halogen, $C_1$-$C_6$ haloalkyl or $C_1$-$C_6$ haloalkoxy; and q is an integer of 0, 1, 2 or 3.

In one Embodiment wherein "other herbicides" (b15) also include a compound of Formula (b15B), it is preferred that $R^{18}$ is H, methyl, ethyl or propyl; more preferably $R^{18}$ is H or methyl; most preferably $R^{18}$ is H. Preferrably each $R^{19}$ is independently chloro, fluoro, $C_1$-$C_3$ haloalkyl or $C_1$-$C_3$ haloalkoxy; more preferably each $R^{19}$ is independently chloro, fluoro, $C_1$ fluoroalkyl (i.e. fluoromethyl, difluoromethyl or trifluoromethyl) or $C_1$ fluoroalkoxy (i.e. trifluoromethoxy, difluoromethoxy or fluoromethoxy). Preferably each $R^{20}$ is independently chloro, fluoro, $C_1$ haloalkyl or $C_1$ haloalkoxy; more preferably each $R^{20}$ is independently chloro, fluoro, $C_1$ fluoroalkyl (i.e. fluoromethyl, difluorormethyl or trifluromethyl) or $C_1$ fluoroalkoxy (i.e. trifluoromethoxy, difluoromethoxy or fluoromethoxy). Specifically preferred as "other herbicides" (b15) include any one of the following (b15B-1) through (b15B-19):

(b15B-1)

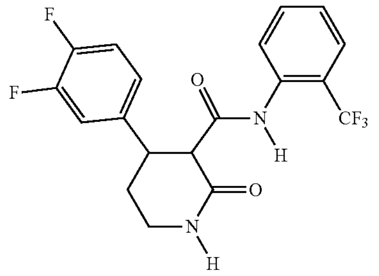

(b15B-2)

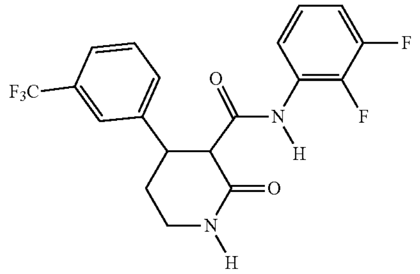

(b15B-3)

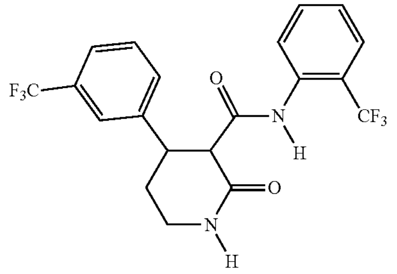

(b15B-4)

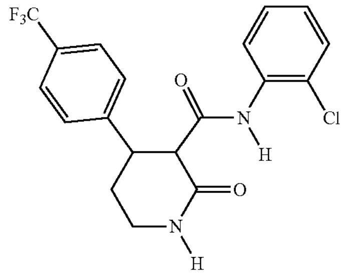

-continued
(b15B-5)
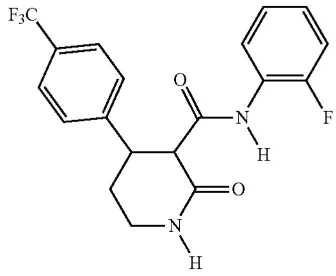
(b15B-6)
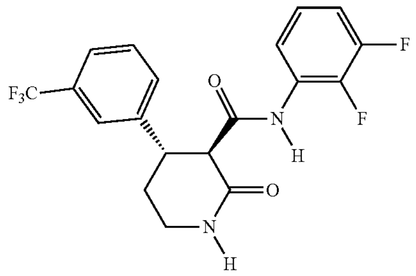
(b15B-7)
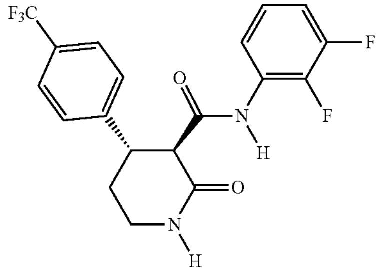
(b15B-8)
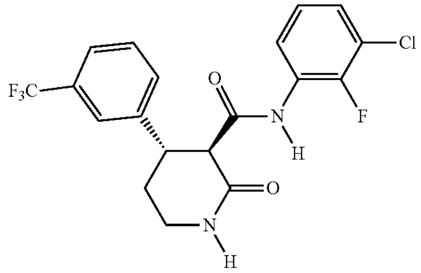
(b15B-9)
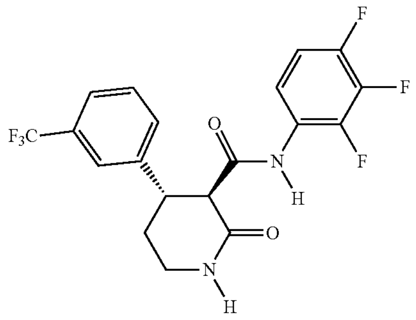
-continued
(b15B-10)
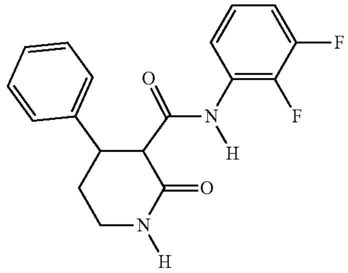
(b15B-11)
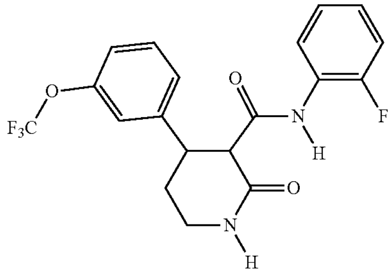
(b15B-12)
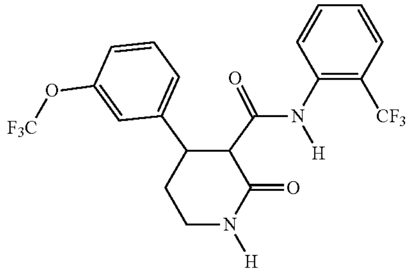
(b15B-13)
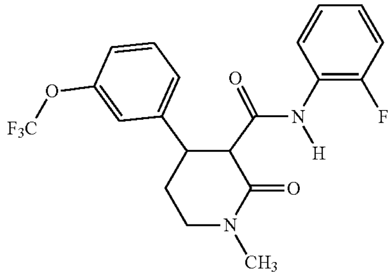
(b15B-14)
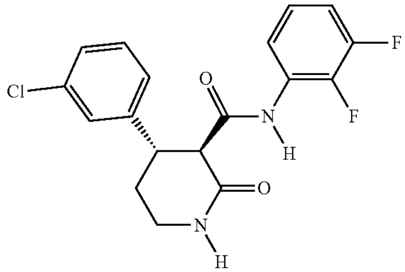

-continued (b15B-15)

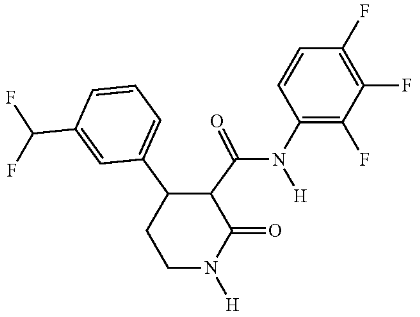

(b15B-16)

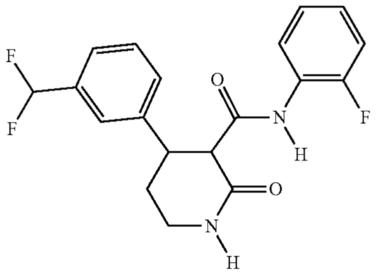

(b15B-17)

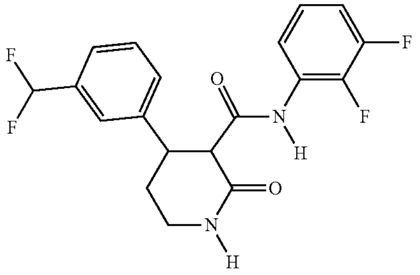

(b15B-18)

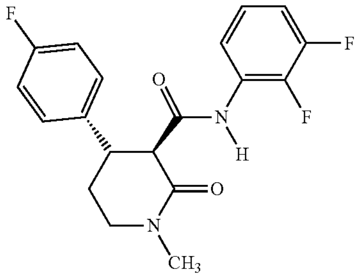

(b15B-19)

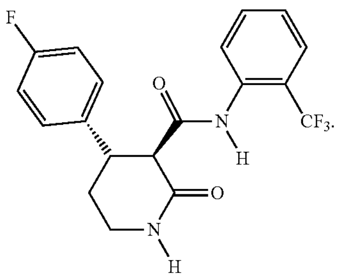

Another Embodiment wherein "other herbicides" (b15) also include a compound of Formula (b15C), (b15C)

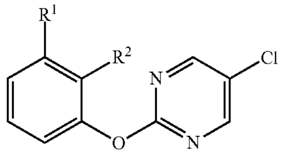

wherein $R^1$ is Cl, Br or CN; and $R^2$ is C(=O)$CH_2CH_2CF_3$, $CH_2CH_2CH_2CH_2CF_3$ or 3-$CHF_2$-isoxazol-5-yl.

"Herbicide safeners" (b16) are substances added to a herbicide formulation to eliminate or reduce phytotoxic effects of the herbicide to certain crops. These compounds protect crops from injury by herbicides but typically do not prevent the herbicide from controlling undesired vegetation. Examples of herbicide safeners include but are not limited to benoxacor, cloquintocet-mexyl, cumyluron, cyometrinil, cyprosulfamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone, naphthalic anhydride, oxabetrinil, N-(aminocarbonyl)-2-methylbenzenesulfonamide and N-(aminocarbonyl)-2-fluorobenzenesulfonamide, 1-bromo-4-[(chloromethyl)sulfonyl]benzene, 2-(dichloromethyl)-2-methyl-1,3-dioxolane (MG 191), 4-(dichloroacetyl)-1-oxa-4-azospiro[4.5]decane (MON 4660), 2,2-dichloro-1-(2,2,5-trimethyl-3-oxazolidinyl)-ethanone and 2-methoxy-N-[[4-[[(methylamino)carbonyl]amino]phenyl]sulfonyl]-benzamide.

Preferred for better control of undesired vegetation (e.g., lower use rate such as from greater-than-additive effects, broader spectrum of weeds controlled, or enhanced crop safety) or for preventing the development of resistant weeds are mixtures of a compound of this invention with a herbicide selected from the group consisting of atrazine, azimsulfuron, beflubutamid, beflubutamid-M, benzisothiazolinone, carfentrazone-ethyl, chlorimuron-ethyl, chlorsulfuron-methyl, clomazone, clopyralid potassium, cloransulam-methyl, 2-[(2,4-dichlorophenyl)methyl]-4,4-dimethyl-isoxazolidinone, 2-[(2,5-dichlorophenyl)methyl]-4,4-dimethyl-isoxazolidinone, ethametsulfuron-methyl, flumetsulam, 4-(4-fluorophenyl)-6-[(2-hydroxy-6-oxo-1-cyclohexen-1-yl)carbonyl]-2-methyl-1,2,4-triazine-3,5-(2H,4H)-dione, flupyrsulfuron-methyl, fluthiacet-methyl, fomesafen, imazethapyr, lenacil, mesotrione, metribuzin, metsulfuron-methyl, pethoxamid, picloram, pyroxasulfone, quinclorac, rimsulfuron, S-metolachlor, sulfentrazone, thifensulfuron-methyl, triflusulfuron-methyl and tribenuron-methyl.

One or more of the following methods and variations as described in Schemes 1-9 can be used to prepare the compounds of Formula 1. The definitions of $R^1$, $R^2$, $R^3$, $R^4$, X, and A in the compounds of Formulae 1-12 below are as defined above in the Summary of the Invention unless otherwise noted. Compounds of Formulae 1a, 3a, 3b, 3c, 3d, 3e, 3f, 3g, 3h, 3i, 6b, and 6c are various subsets of the compounds of Formulae 1, 3 and 6; and all substituents for Formulae 1a, 3a, 3b, 3c, 3d, 3e, 3f, 3g, 3h, 3i, 6b, and 6c are as defined above for Formula 1 unless otherwise noted in the disclosure including the schemes.

As shown in Scheme 1, compounds of Formula 1a (i.e. a compound of Formula 1 wherein $R^{14}$ is H) can be made by reacting substituted 5-hydroxy-3(2H)-pyridazinones of Formula 2 with a suitable electrophilic reagent of Formula 3

(where Z is a leaving group, alternatively known as a nucleofuge, such as a halogen) in the presence of a base in an appropriate solvent.

Scheme 1

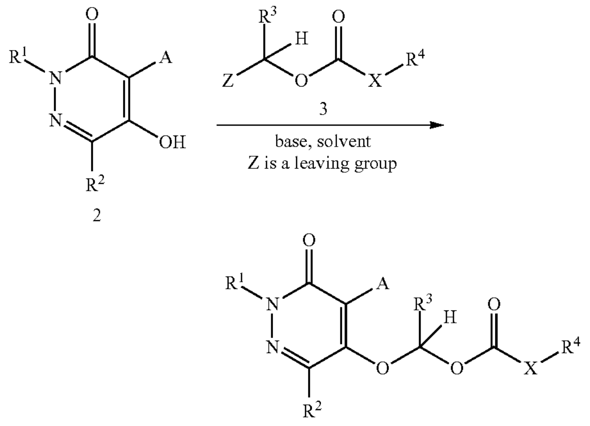

2 3 1a

Examples of suitable bases for Scheme 1 reactions include, but are not limited to, potassium carbonate, cesium carbonate, sodium hydride, triethylamine or potassium tert-butoxide; depending on the specific base used, appropriate solvents can be protic or aprotic, and can be used anhydrous or as aqueous mixtures. Preferred solvents for this reaction include acetonitrile, tetrahydrofuran, 1,2-dimethoxyethane, dioxane, acetone, N,N-dimethylacetamide or N,N-dimethylformamide. The reaction can be performed at temperatures, typically ranging from 0° C. to the reflux temperature of the solvent. The use of a catalyst such as potassium iodide or sodium iodide can sometimes be advantageous in cases where Z is Cl. The amounts of such catalysts used in Scheme 1 reactions typically range from 0.1 to 1 molar equivalent. The use of iodide catalysis in Scheme 1 reactions results in the in-situ generation of compounds of Formula 3 where Z is I. Representative examples of reactions analogous to Scheme 1 reactions can be found in *J. Med. Chem.* 2004, vol. 47, pp. 5690-5699; *J. Med. Chem.* 2015, vol. 58, pp. 8154-8165; *Tetrahedron Lett.*, 2015, vol. 56, pp. 5441-5444, and *Tetrahedron Lett.* 2016, vol. 57, pp. 1619-1621.

The preparations of compounds of Formula 2 have been described in U.S. Pat. Nos. 10,118,917, 10,750,743 and US2020/0109123.

Many compounds of Formula 3 are available from commercial sources. Scheme 2 shows a general method for the preparation of a compound of Formula 3a (i.e. a compound of Formula 3, wherein $R^3$ is H, X is a direct bond and Z is Cl). As shown in Scheme 2, a carboxylic acid of Formula 4 reacts with a chlorosulfuric acid chloromethyl ester of Formula 5 in the presence of a base including, but not limited to sodium bicarbonate or sodium carbonate in solvents that include, but are not limited to dichloromethane, tetrahydrofuran, ethyl acetate, acetonitrile and toluene. In some examples, the use of a phase transfer catalyst is described, along with water as a co-solvent. Typical phase transfer catalysts include, but are not limited to tetra(n-butyl) ammonium hydrogen sulfate, tetra(n-butyl)ammonium iodide and N-benzyl-N,N,N-triethylammonium chloride. The reactions can be carried out at a temperature ranging from 0° C. to the reflux temperature of the solvent. Examples of the reactions in Scheme 2 can be found in *Syn. Comm.* 1984, vol. 14, pp. 857-864; *Syn. Comm.* 1994, vol. 24, pp. 767-772 and *Bioorganic and Med. Chem.* 2006, vol. 14, pp. 2569-2580.

Scheme 2

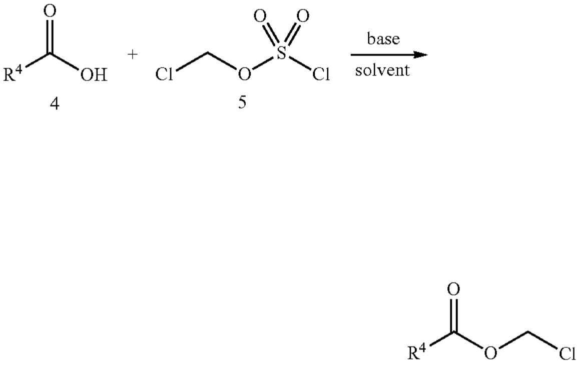

4 5 3a

Alternatively, a compound of Formula 3b (i.e. a compound of Formula 3, wherein X is a direct bond and Z is Cl) or a compound of Formula 3c (i.e. a compound of Formula 3, wherein X is a direct bond and Z is Br) can be prepared by the reactions of acid chlorides of Formula 6b or acid bromides of Formula 6c with aldehydes of Formula 7 as illustrated in Scheme 3. As shown in Scheme 3, compounds of Formulae 6b or 6c and 7 are typically used in equimolar amounts and zinc chloride or zine bromide is employed in amounts typically ranging from 0.1 to 2.0 molar equivalents. Typical solvents include dichloromethane, chloroform and acetonitrile. Reaction temperatures can range from −20° C. up to the reflux temperature of the solvent. Representative examples of the reactions can be found in *J. Med. Chem.* 2009, vol. 52, pp. 771-778; *Bioorganic and Med. Chem. Lett.* 2014, vol. 24, pp. 5587-5592; and *J. Org. Chem.* 1993, vol. 58, pp. 588-599.

Scheme 3

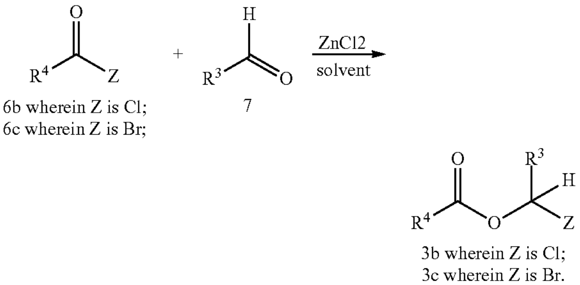

6b wherein Z is Cl;
6c wherein Z is Br;

7

3b wherein Z is Cl;
3c wherein Z is Br.

Compounds of Formula 3d (i.e. a compound of Formula 3, wherein X is a direct bond and Z is I) can be prepared as shown in Scheme 4 by the reaction of compounds of Formula 3b with iodides such as potassium iodide, sodium iodide or the like in a solvent including, but not limited to acetone, acetonitrile or dichloromethane at temperatures ranging from ambient up to the reflux temperature of the solvent. Representative examples of Scheme 5 reactions can be found in *J. Am. Chem. Soc.* 2001, vol. 133, pp. 8139-8140.

Scheme 4

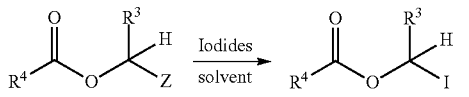

3b 3d

As shown in Scheme 5, compounds of Formula 3e (i.e. a compound of Formula 3, wherein X is O; and Z is Cl) can be prepared by the reactions of chloroformates of Formula 9 with alcohols of Formula 10 as depicted in Scheme 5. Alcohols of Formula 10 are typically used in a range of 0.5 to 10 molar equivalents with a proton acceptor such as, but not limited to pyridine, triethylamine or potassium carbonate in a solvent such as, but not limited to dichloromethane, tetrahydrofuran, water, or diethylether at temperatures typically ranging from 0° C. up to the reflux temperature of the solvent. Representative examples may be found in *J. Med. Chem.* 2009, vol. 52, pp. 771-778 and *Bioorg. And Med. Chem. Lett.* 1997, vol. 7, pp. 1811-1816.

Scheme 5

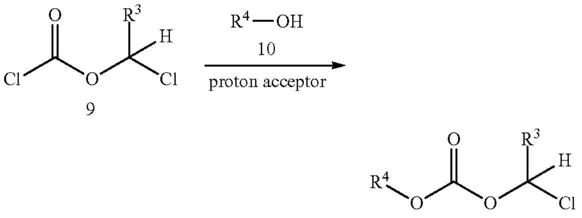

9

3e

Compounds of Formula 3f (i.e. a compound of Formula 3, wherein X is S; and Z is Cl) can be prepared by the reactions of chloroformates of Formula 9 with thiols of Formula 11 as depicted in Scheme 6. Conditions for the reactions in Scheme 6 are analogous to those used in Scheme 5 reactions. Representative procedures can be found in *Synthesis* 1990, pp. 1159-1166 and *J. Med. Chem.* 2017, vol. 60, pp. 7136.

Scheme 6

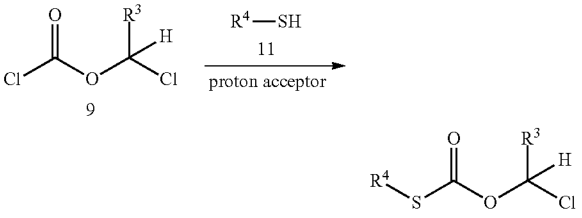

9

3f

Compounds of Formula 3g (i.e. a compound of Formula 3, wherein X is $NR^6$ and Z is Cl) can be prepared as depicted in Scheme 7 using methods analogous to those described for Scheme 5 and Scheme 6 reactions. Representative procedures can be found in *Tetrahedron Lett.* 1999, vol. 40, pp. 607-610, *Bioorg. Med. Chem. Lett.* 2015, vol. 25, pp. 4987-4991 and *Eur. J Pharm. Sci.* 2015, vol. 72, pp. 69-80.

Scheme 7

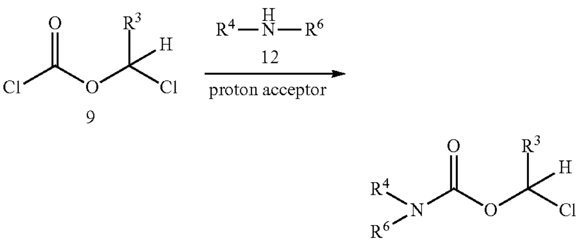

9

3g

Compounds of Formula 9 can be prepared as depicted in Scheme 8 by the reaction of aldehydes of Formula 7 with phosgene or a phosgene equivalent such as trichloromethyl chloroformate (also called diphosgene) or bis(trichloromethyl) carbonate (also called triphosgene) in the presence of 0 to 10 molar equivalents of a base such as pyridine in a solvent such as carbon tetrachloride, diethyl ether, or tetrahydrofuran at temperatures typically ranging from −40° C. up to ambient. Representative examples can be found in *Tetrahedron Lett.* 1989, vol. 30, pp. 2033-2036 and *Synthesis* 2002, pp. 365-370.

Scheme 8

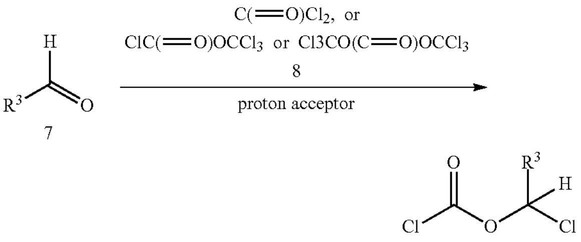

7

9

The preparation of compounds of Formula 3i (i.e. a compound of Formula 3, wherein Z is I) can be achieved by the reaction of a compound of Formula 3h (i.e. a compound of Formula 3, wherein Z is Cl) with 1 to 20 molar equivalents of an iodide source such as, but not limited to sodium iodide or potassium iodide in solvents such as, but not limited to acetone, acetonitrile and dichloromethane as shown in Scheme 9. The reactions are typically carried-out at temperatures ranging from ambient to the reflux temperature of the solvent.

Scheme 9

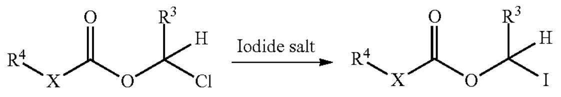

3h 3i

It is recognized by one skilled in the art that various functional groups can be converted into others to provide different compounds of Formula 1. For a valuable resource that illustrates the interconversion of functional groups in a simple and straightforward fashion, see Larock, R. C., *Comprehensive Organic Transformations: A Guide to Functional Group Preparations,* 2*nd Ed.*, Wiley-VCH, New York, 1999. For example, intermediates for the preparation of compounds of Formula 1 may contain aromatic nitro groups, which can be reduced to amino groups, and then be converted via reactions well known in the art such as the Sandmeyer reaction, to various halides, providing compounds of Formula 1. The above reactions can also in many cases be performed in alternate order.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following non-limiting Examples are illustrative of the invention. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. All NMR spectra are reported in $CDCl_3$ downfield from tetramethylsilane at 500 MHz unless otherwise indicated where s means singlet, brs means broad singlet, d means doublet, t means triplet and m means multiplet.

Synthesis Example 1

Preparation of 5-[(acetyloxy)methoxy]-6-chloro-4-(4-chloro-2-methylbenzo[b]thien-3-yl)-2-methyl-3(2H)-pyridazinone (i.e. Compound 1)

Step A: Preparation of 6-chloro-5-[(4-chlorobenzo[b]thien-2-yl)methoxy]-2-methyl-3(2H)-pyridazinone To a stirred solution of 5,6-dichloro-2-methyl-pyridazin-3-one (900 mg, 5.0 mmol), (4-chlorobenzothiophen-2-yl) methanol (1.0 g, 5.0 mmol) in anhydrous N,N-dimethylformamide (20 mL) was added sodium hydride (260 mg, 60% in oil, 6.5 mmol) at 0° C. The resulting mixture was stirred at 25° C. for 18 h and was then poured into saturated aqueous ammonium chloride solution. The resulting mixture was extracted with ethyl acetate (4×) and the combined organic layers were washed with water and brine. A white solid precipitate formed in the organic layer. The organic layer was filtered, and the white solid product was dried under vacuum to give the title compound (1.3 g, 76%).

$^1H$ NMR ($CDCl_3$) δ 7.72 (d, 1H), 7.55 (s, 1H), 7.38 (d, 1H), 7.30 (m, 2H), 6.33 (s, 1H), 5.36 (s, 2H), 3.70 (s, 3H).

Step B: Preparation of 6-chloro-4-(4-chloro-2-methylbenzo[b]thien-3-yl)-5-hydroxy-2-methyl-3(2H)-pyridazinone A solution of 6-chloro-5-[(4-chlorobenzo[b]thien-2-yl)methoxy]-2-methyl-3(2H)-pyridazinone (i.e. the product of Step A) (1.3 g, 3.8 mmol) in xylenes (5 mL) was heated at reflux for 48 h. The resulting mixture was cooled to 25° C. and diluted with hexanes. The resulting mixture was filtered, the solid product was washed with several portions of hexanes and dried to give the title compound as a tan solid (0.60 g, 46%). $^1H$ NMR of the crude product indicated acceptable purity and the crude product was used in the next step without further purification.

Step C: Preparation of 5-[(acetyloxy)methoxy]-6-chloro-4-(4-chloro-2-methylbenzo[b]thien-3-yl)-2-methyl-3(2H)-pyridazinone To a stirred solution of 6-chloro-4-(4-chloro-2-methylbenzo[b]thien-3-yl)-5-hydroxy-2-methyl-3(2H)-pyridazinone (i.e. the product from Step B) (110 mg, 0.32 mmol), chloromethyl acetate (0.11 mL, 1.25 mmol) in anhydrous N,N-dimethylformamide (10 mL) was added sodium hydride (13 mg, 60% in oil, 0.32 mmol) at 25° C. The resulting mixture was stirred at 60° C. for 18 h, cooled to 25° C. and poured into aqueous saturated ammonium chloride solution. The mixture was extracted with ethyl acetate (4×) and the combined organic layers were dried over anhydrous magnesium sulfate, filtered and concentrated. Chromatography of the crude product on silica gel eluting with a gradient of 0% to 100% ethyl acetate in hexanes gave the title product as a yellow solid (21 mg, 16%).

$^1H$ NMR ($CDCl_3$) δ 7.69 (m, 1H), 7.31 (m, 1H), 7.19-7.24 (m, 1H), 5.27-5.30 (m, 2H), 3.80 (s, 3H), 2.37 (s, 3H), 1.74 (s, 3H).

Synthesis Example 2

Preparation of 5-[(Acetyloxy)methoxy]-6-chloro-4-(2,7-dimethyl-1-naphthalenyl)-2-methyl-3(2H)-pyridazinone (i.e. Compound 3)

To a stirred solution of 6-chloro-4-(2,7-dimethyl-1-naphthalenyl)-5-hydroxy-2-methyl-3(2H)-pyridazinone (120 mg, 0.38 mmol, prepared as described in WO 2020069057) and chloromethyl acetate (170 mg, 1.6 mmol) in anhydrous N,N-dimethylformamide (10 mL) was added sodium hydride (63 mg, 60% in oil, 1.6 mmol) at 25° C. The resulting mixture was stirred at 60° C. for 18 h and then was cooled to 25° C. and poured into saturated aqueous ammonium chloride solution. The resulting mixture was extracted with ethyl acetate (3×) and the combined organic extracts were dried over anhydrous magnesium sulfate, filtered and concentrated. Chromatography of the crude product on silica gel elution with a gradient of 30% to 100% ethyl acetate in hexanes gave the title compound as a yellow oil (60 mg, 41%).

$^1$H NMR ($CDCl_3$) δ 7.79 (m, 1H), 7.73 (m, 1H), 7.34 (m, 1H), 7.25-7.30 (m, 1H), 7.16 (s, 1H), 5.03 (m, 1H), 4.93 (m, 1H), 3.84 (s, 3H), 2.45 (s, 3H), 2.32 (s, 3H), 1.82 (s, 3H).

Synthesis Example 3

Preparation of [[3-chloro-5-(2,7-dimethyl-9-anthracenyl)-1,6-dihydro-1-methyl-6-oxo-4-pyridazinyl]oxy]methyl methyl carbonate (i.e. Compound 8)

Step A: Preparation of methyl 5-methyl-2-(p-tolylmethyl)benzoate

Zinc dust (16.0 g, 245 mmol) was suspended in anhydrous tetrahydrofuran (200 mL) and the resulting mixture was heated at 60° C. 1,2-Dibromoethane (0.8 mL) was added to the heated mixture and the resulting mixture was stirred at 60° C. for 3 min, and then cooled to 25° C. Chlorotrimethylsilane (0.8 mL) was added and the resulting mixture was stirred at 25° C. for 3 min and then cooled to 5° C. A solution of 4-methyl benzyl bromide (22.7 g, 128 mmol) in anhydrous tetrahydrofuran (100 mL) was then added dropwise to the above suspension of activated zinc at a rate that maintained reaction temperature below 16° C. The resulting mixture was stirred at 5° C. for 1 h and then treated with a solution of methyl 2-bromo-5-methyl-benzoate (14.9 g, 64 mmol) in anhydrous tetrahydrofuran (100 mL) at a temperature below 10° C., followed by the addition of bis(triphenylphosphine) palladium (II) dichloride (860 mg, 1.23 mmol). The resulting mixture was stirred at ambient temperature for 18 h and was then poured into ice-cold saturated aqueous ammonium chloride solution. The resulting mixture was extracted with ethyl acetate and the organic layer was washed with brine, dried over anhydrous magnesium sulfate, filtered and concentrated. The resulting light brown oil was purified by chromatography on silica gel eluting with a gradient of 0% to 30% ethyl acetate in hexanes to provide the title compound as a colorless oil (15.9 g, 96%).

$^1$H NMR ($CDCl_3$) δ 7.69 (s, 1H), 7.22 (d, 1H), 7.10-7.00 (m, 5H), 4.28 (s, 2H), 3.82 (s, 3H), 2.35 (s, 3H), 2.29 (s, 3H).

Step B: Preparation of 5-methyl-2-(p-tolylmethyl)benzoic acid

Aqueous sodium hydroxide solution (50%, 10 mL) was added to a solution of methyl 5-methyl-2-(p-tolylmethyl)benzoate (i.e. the product of Step A) (15.9 g, 62.5 mmol) in ethanol (250 mL) at ambient temperature. After stirring for 2 days, the resulting mixture was concentrated to remove most of the ethanol. Water (300 mL) was added and the resulting aqueous mixture was washed with diethyl ether (100 mL). The resulting aqueous mixture was cooled in an ice-water bath and was acidified with the addition of concentrated hydrochloric acid dropwise with stirring until pH was 1-2. The resulting beige precipitate was filtered, and the solid product was washed with water and dried under vacuum. The title compound was obtained as a beige solid (14.4 g, 96%).

$^1$H NMR δ 7.86 (s, 1H), 7.28 (d, 1H), 7.11 (d, 1H), 7.06 (m, 4H), 4.77 (broadened s, 1H), 4.36 (s, 2H), 2.36 (s, 3H), 2.30 (s, 3H).

Step C: Preparation of 2,7-dimethyl-10H-anthracen-9-one

5-Methyl-2-(p-tolylmethyl)benzoic acid (i.e. the product of Step B) (14.4 g, 60 mmol) was added in portions to neat concentrated sulfuric acid (120 mL) with ice-water bath cooling. The resulting mixture was stirred at 25° C. for 2 h and then was poured into 500 mL of ice with stirring. The resulting suspension was filtered and the resulting beige solid was washed with water. The resulting solid was dissolved in dichloromethane (300 mL) and the organic solution was washed with 1 N aqueous sodium hydroxide solution (2×), water and brine, dried over anhydrous magnesium sulfate, filtered and concentrated to give the title compound as a beige solid (8.0 g, 60%).

$^1$H NMR ($CDCl_3$) δ 8.17 (s, 2H), 7.42 (dd, 2H), 7.36 (d, 2H), 4.28 (s, 2H), 2.46 (s, 6H).

Step D: Preparation of (2,7-dimethyl-9-anthryl) trifluoromethanesulfonate

A solution of 2,7-dimethyl-10H-anthracen-9-one (i.e. the product from Step C (3.4 g, 15 mmol) in dichloromethane (60 mL) was de-gassed by bubbling nitrogen gas through the solution for 10 min with cooling at 5° C. DBU (3.4 mL, 23 mmol) was added to the resulting solution at a rate that maintained the temperature below 10° C. A solution of trifluoromethanesulfonic anhydride (3.2 mL, 19 mmol) and dichloromethane (15 mL) was added to the resulting solution at a rate that maintained the temperature below 10° C. The resulting light-yellow solution was stirred at 25° C. for 2 h and was then poured into ice-water. The aqueous layer was separated and extracted with dichloromethane and the combined organic layers was washed with water, brine, dried over anhydrous magnesium sulfate, filtered and concentrated to give a crude product that was purified by chromatography on silica gel eluting with a gradient of 0% to 30% ethyl acetate in hexanes to give the title compound as a beige solid (4.1 g, 76%).

$^1$H NMR ($CDCl_3$) δ 8.39 (s, 1H), 7.95 (s, 2H), 7.92 (d, 2H), 7.35 (d, 2H), 2.60 (s, 6H).

Step E: Preparation of 6-chloro-4-(2,7-dimethyl-9-anthracenyl)-5-methoxy-2-methyl-3(2H)-pyridazinone A solution of zinc chloride in 2-methytetrahydrofuran (6.7 mL of a 1.9 M solution, 13 mmol) was added to a solution of 2,2,6,6,-tetramethylpiperidinylmagnesium chloride lithium chloride complex in tetrahydrofuran (25 mL of a 1.0 M solution, 25 mmol) at 5° C. The resulting solution was stirred at 25° C. for 1 h and then cooled to −40° C. and treated with anhydrous tetrahydrofuran (25 mL) followed by 6-chloro-5-methoxy-2-methyl-pyridazin-3(2H)-one (2.0 g, 12 mmol, see J Med. Chem. 2017, vol. 60, pp. 3828-3850 for preparation). The resulting mixture was stirred at 0-5° C. for 1 h, and then was treated with a solution of (2,7-dimethyl-9-anthryl) trifluoromethanesulfonate (i.e. the product from Step D) (4.1 g, 12 mmol) in tetrahydrofuran (35 mL) added at 5° C. The resulting solution was treated with S-Phos-Pd-pre-catalyst-G2 (0.84 g, 1.2 mmol). The resulting mixture was stirred at 25° C. for 18 h and then treated with saturated aqueous ammonium chloride solution (100 mL). The resulting mixture was extracted with ethyl acetate and the organic layer was washed with brine, dried over anhydrous magnesium sulfate, filtered and concentrated to give a crude product that was purified by chromatography on silica gel eluting with 0%-70% ethyl acetate in hexanes. An early eluting fraction contained recovered triflate starting material (i.e. the product from Step D, 2.8 g) followed by a fraction containing the title compound as a light yellow solid (1.2 g, 27%; or 86% based on recovered triflate starting material).

$^1H$ NMR ($CDCl_3$) δ 8.45 (s, 1H), 7.92 (d, 2H), 7.29 (s, 2H), 7.27 (d, 2H), 3.83 (s, 3H), 3.07 (s, 3H), 2.49 (m, 6H).

Step F: Preparation of 6-Chloro-4-(2,7-dimethyl-9-anthracenyl)-5-hydroxy-2-methyl-3(2H)-pyridazinone A mixture of 6-chloro-4-(2,7-dimethyl-9-anthracenyl)-5-methoxy-2-methyl-3(2H)-pyridazinone (i.e. the product from Step E) (2.4 g, 6.3 mmol) and morpholine (12 mL) was heated at 110° C. for 1 h. The resulting mixture was cooled to 0° C. and allowed to stand at this temperature overnight. The resulting mixture was diluted with diethyl ether and filtered. The resulting light orange solid was washed with ether, dried on the frit under nitrogen to give the desired product as the morpholine salt (2.1 g). The salt was suspended in a mixture of 1 N aqueous hydrochloric acid (60 mL) and acetonitrile (10 mL), stirred for 1 h and filtered. The resulting solid was suspended in a solution of acetone (20 mL) and acetonitrile (10 mL) and heated at reflux to obtain a clear solution that was then added dropwise to 1N aqueous hydrochloric acid (60 mL) with stirring. The resulting solid was filtered, washed with water and dried under vacuum to give the title compound as a light yellow solid (1.75 g, 76%).

$^1H$ NMR (DMSO-$d_6$) δ 11.0 (br s, 1H), 8.57 (s, 1H), 8.02 (d, 2H), 7.38 (s, 2H), 7.33 (d, 2H), 3.68 (s, 3H), 2.43 (m, 6H).

Step G: Preparation of [[3-chloro-5-(2,7-dimethyl-9-anthracenyl)-1,6-dihydro-1-methyl-6-oxo-4-pyridazinyl]oxy]methyl methyl carbonate A mixture of 6-chloro-4-(2,7-dimethyl-9-anthracenyl)-5-hydroxy-2-methyl-3(2H)-pyridazinone (i.e. the product from Step F) (100 mg, 0.27 mmol), chloromethyl methyl carbonate (68 mg, 0.55 mmol), potassium iodide (91 mg, 0.55 mmol), potassium carbonate (76 mg, 0.55 mmol), and acetonitrile (4.6 mL) was stirred at 55° C. under $N_2$. After heating for 16 h, the reaction was cooled to 25° C., diluted with dichloromethane, treated with 1.5 g celite and concentrated. The resulting solid was purified by chromatography on silica gel eluting with a gradient of 30% to 100% ethyl acetate in hexanes to give the title compound as a yellow semi-solid (62 mg, 50%).

$^1H$ NMR ($CDCl_3$) δ 8.47 (s, 1H), 7.92 (d, 2H), 7.31 (s, 2H), 7.29 (d, 2H), 4.78 (s, 2H), 3.88 (s, 3H), 3.67 (s, 3H), 2.49 (m, 6H).

Synthesis Example 4

Preparation of [[3-chloro-5-(2,7-dimethyl-9-anthracenyl)-1,6-dihydro-1-methyl-6-oxo-4-pyridazinyl]oxy]methyl 2,2-dimethylpropanoate (i.e. Compound 9)

A mixture of 6-chloro-4-(2,7-dimethyl-9-anthracenyl)-5-hydroxy-2-methyl-3(2H)-pyridazinone (i.e. the product from Step F of Synthesis Example 3) (100 mg, 0.27 mmol), chloromethyl pivalate (83 mg, 0.55 mmol), potassium iodide (91 mg, 0.55 mmol), potassium carbonate (76 mg, 0.55 mmol) and acetonitrile (4.6 mL) was stirred at reflux for 18 h. The resulting mixture was cooled to 25° C., diluted with ethyl acetate, treated with celite (1.5g) and concentrated. Chromatography on silica gel eluting with 20%-100% ethyl acetate in hexanes gave the title compound as a yellow semi-solid (125 mg, 95%).

$^1H$ NMR ($CDCl_3$) δ 8.47 (s, 1H), 7.93 (d, 2H), 7.35 (s, 2H), 7.29 (d, 2H), 4.69 (s, 2H), 3.86 (s, 3H), 2.49 (m, 6H), 1.07 (s, 9H).

Synthesis Example 5

Preparation of 5-[(acetyloxy)methoxy]-4-(9-anthracenyl)-6-chloro-2-methyl-3(2H)-pyridazinone (i.e. Compound 10)

A mixture of 4-(9-anthracenyl)-6-chloro-5-hydroxy-2-methyl-3(2H)-pyridazinone (119 mg, 0.35 mmol, prepared as described in US2020/0109123), chloromethyl acetate (154 mg, 1.40 mmol), cesium carbonate (230 mg, 0.70 m mol), sodium iodide (20 mg, 0.13 mmol) in acetone (5.4 mL) was heated at reflux. After heating for 16 h, the mixture was cooled to ambient temperature and concentrated onto celite (1.5 g). The resulting mixture was purified by MPLC on a 12 g silica gel column eluting with a gradient of 0% to 100% ethyl acetate in hexanes to provide 105 mg of the title compound as a yellow glassy solid.

$^1H$ NMR δ 8.59 (s, 1H), 8.07-8.04 (m, 2H), 7.67-7.63 (m, 2H), 7.51-7.47 (m, 4H), 4.82 (s, 2H), 3.87 (s, 3H), 1.66 (s, 3H).

Synthesis Example 6

Preparation of 5-[(acetyloxy)methoxy]-6-chloro-4-(10-chloro-9-anthracenyl)-2-methyl-3(2H)-pyridazinone (i.e. Compound 11)

A mixture of 6-chloro-4-(10-chloro-9-anthracenyl)-5-hydroxy-2-methyl-3(2H)-pyridazinone (159 mg, 0.43 mmol, prepared as described in US2020/0109123), chloromethyl acetate (140 mg, 1.29 mmol), cesium carbonate (279 mg, 0.83 mmol), sodium iodide (13 mg, 0.08 mmol) in acetone (6.4 mL) was heated at reflux for 16 h. The resulting mixture was cooled to ambient temperature and concentrated onto Celite® diatomaceous earth filter aid (1.5 g). The resulting mixture was purified by MPLC on a 12 g silica gel column eluting with a gradient of 0% to 100% ethyl acetate in hexanes to provide 140 mg of the title compound as a yellow glassy solid.

$^1H$ NMR δ 8.60 (d, 2H), 7.68 (dt, 2H), 7.62 (td, 2H), 7.53 (td, 2H), 4.85 (s, 2H), 3.87 (s, 3H), 1.67 (s, 3H).

By the procedures described herein together with methods known in the art, the following compounds of Tables 1 to 1009 can be prepared. The following abbreviations are used in the Tables which follow: t means tertiary, s means secondary, n means normal, i means iso, c means cyclo, Me means methyl, Et means ethyl, Pr means propyl, Bu means butyl, i-Pr means isopropyl, c-Pr means cyclopropyl, t-Bu means tertiary butyl, Ph means phenyl, OMe means methoxy, OEt means ethoxy, SMe means methylthio, —CN means cyano, —$NO_2$ means nitro, TMS means trimethylsilyl, SOMe means methylsulfinyl, $C_2F_5$ means $CF_2CF_3$ and $SO_2Me$ means methylsulfonyl.

TABLE 1

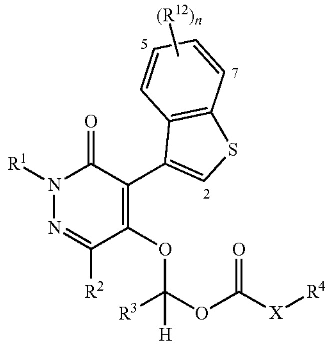

X is a direct bond, $R^1$ is Me, $R^2$ is Me, ($R^{12}$), is 2,5-di-Me (Header Row Phrase)

| $R^3$ | $R^4$ | $R^3$ | $R^4$ | $R^3$ | $R^4$ |
|---|---|---|---|---|---|
| H | Me | H | 2-Et-pentyl | H | 3-heptyn-1-yl |
| H | Et | H | 3-Et-pentyl | H | 4-heptyn-1-yl |
| H | n-Pr | H | 2-butyl | H | 5-heptyn-1-yl |
| H | i-Pr | H | 3-pentyl | H | 6-heptyn-1-yl |
| H | n-Bu | H | 2-hexyl | H | c-Pr |
| H | i-Bu | H | 3-hexyl | H | c-Bu |
| H | s-Bu | H | 2-heptyl | H | c-pentyl |
| H | t-Bu | H | 3-heptyl | H | c-hexyl |
| H | n-pentyl | H | Allyl | H | c-heptyl |
| H | 1-Me-butyl | H | Methyallyl | H | $CH_2$-c-Pr |
| H | 2-Me-butyl | H | 2-buten-1-yl | H | $CH_2$-c-Bu |
| H | 3-Me-butyl | H | 3-buten-1-yl | H | $CH_2$-c-pentyl |
| H | 1,1-di-Me-propyl | H | 2-penten-1-yl | H | $CH_2$-c-hexyl |
| H | 2,2-di-Me-propyl | H | 3-penten-1-yl | H | 1-Me-1-c-pentyl |
| H | 1-Et-propyl | H | 4-penten-1-yl | H | 2-Me-1-c-pentyl |
| H | 1,2-di-Me-propyl | H | 3-Me-2-buten-1-yl | H | 3-Me-1-c-pentyl |
| H | n-hexyl | H | 2-Me-2-buten-1-yl | H | 2,2-di-Me-c-pentyl |
| H | 1-Me-pentyl | H | 2-Me-2-penten-1-yl | H | 1-Et-1-c-pentyl |
| H | 2-Me-pentyl | H | 3-Me-2-penten-1-yl | H | 2-Et-1-c-pentyl |
| H | 3-Me-pentyl | H | 2-hexen-1-yl | H | 1-Me-1-c-hexyl |
| H | 4-Me-pentyl | H | 3-hexen-1-yl | H | 2-Me-1-c-hexyl |
| H | 1,1-di-Me-butyl | H | 4-hexen-1-yl | H | 3-Me-1-c-hexyl |
| H | 1,2-di-Me-butyl | H | 5-hexen-1-yl | H | 4-Me-1-c-hexyl |
| H | 1,3-di-Me-butyl | H | 3-buten-2-yl | H | $CH_2C(O)Me$ |
| H | 1-Et-butyl | H | 3-penten-2-yl | H | $CH_2C(O)Et$ |
| H | 2-Et-butyl | H | 3-hexen-2-yl | H | $CH_2CH_2C(O)Me$ |
| H | 2,2-di-Me-butyl | H | 2-hepten-1-yl | H | $CH_2CH_2C(O)Et$ |
| H | 3,3-di-Me-butyl | H | 3-hepten-1-yl | H | $CH_2CO_2Me$ |
| H | n-heptyl | H | 4-hepten-1-yl | H | $CH_2CO_2Et$ |
| H | 1-Me-hexyl | H | 5-hepten-1-yl | H | $CH_2CO_2$-n-Pr |
| H | 2-Me-hexyl | H | 6-hepten-1-yl | H | $CH_2CO_2$-i-Pr |
| H | 3-Me-hexyl | H | 3-hepten-2-yl | H | $CH_2CO_2$-n-Bu |
| H | 4-Me-hexyl | H | Propargyl | H | $CH_2CH_2CO_2Me$ |
| H | 5-Me-hexyl | H | 2-butyn-1-yl | H | $CH_2CH_2CO_2Et$ |
| H | 1,1-di-Me-pentyl | H | 3-butyn-1-yl | H | $CH_2CH_2CO_2$-n-Pr |
| H | 2,2-di-Me-pentyl | H | 2-pentyl-1-yl- | H | $CH_2CH_2CO_2$-i-Pr |
| H | 3,3,-di-Me-pentyl | H | 3-pentyn-1-yl | H | $CH_2CN$ |
| H | 4,4-di-Me-pentyl | H | 4-pentyn-1-yl | H | $CH_2CH_2CN$ |
| H | 1,2-di-Me-pentyl | H | 2-hexyn-1-yl | H | CH(Me)CN |
| H | 1,3-di-Me-pentyl | H | 3-hexyn-1-yl | H | $CH_2NO_2$ |
| H | 1,4-di-Me-pentyl | H | 4-hexyn-1-yl | H | $CH_2CH_2NO_2$ |
| H | 2,3-di-Me-pentyl | H | 5-hexyn-1-yl | H | $CH(Me)NO_2$ |
| H | 3,4-di-Me-pentyl | H | 2-heptyn-1-yl | H | $CH_2CH_2CH_2NO_2$ |
| H | $CH_2CH_2OMe$ | H | 5-Me-2-thienyl | Me | 3,4-di-Me-pentyl |
| H | $CH_2CH_2OEt$ | H | 5-Me-3-thienyl | Me | 2-Et-pentyl |
| H | $CH_2CH_2O$-n-Pr | Me | Me | Me | 3-Et-pentyl |
| H | $CH_2CH_2O$-i-Pr | Me | Et | Me | 2-butyl |
| H | $CH_2CF_3$ | Me | n-Pr | Me | 3-pentyl |
| H | $CH_2CH_2CF_3$ | Me | i-Pr | Me | 2-hexyl |
| H | $CH_2CH_2OCF_3$ | Me | n-Bu | Me | 3-hexyl |
| H | $CH_2CH_2Cl$ | Me | i-Bu | Me | 2-heptyl |
| H | $CH_2CH_2Br$ | Me | s-Bu | Me | 3-heptyl |
| H | $CH_2CH_2CH_2Cl$ | Me | t-Bu | Me | Allyl |
| H | $CH_2CH_2CH_2Br$ | Me | n-pentyl | Me | Methyallyl |
| H | $CH_2CH_2SMe$ | Me | 1-Me-butyl | Me | 2-buten-1-yl |
| H | $CH_2CH_2Set$ | Me | 2-Me-butyl | Me | 3-buten-1-yl |
| H | Ph | Me | 3-Me-butyl | Me | 2-penten-1-yl |
| H | benzyl | Me | 1,1-di-Me-propyl | Me | 3-penten-1-yl |

TABLE 1-continued

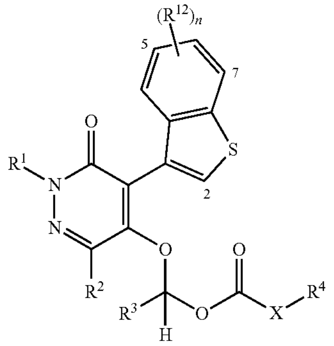

X is a direct bond, $R^1$ is Me, $R^2$ is Me, $(R^{12})$, is 2,5-di-Me (Header Row Phrase)

| $R^3$ | $R^4$ | $R^3$ | $R^4$ | $R^3$ | $R^4$ |
|---|---|---|---|---|---|
| H | 2-Me-Ph | Me | 2,2-di-Me-propyl | Me | 4-penten-1-yl |
| H | 3-Me-Ph | Me | 1-Et-propyl | Me | 3-Me-2-buten-1-yl |
| H | 4-Me-Ph | Me | 1,2-di-Me-propyl | Me | 2-Me-2-buten-1-yl |
| H | 2-Cll-Ph | Me | n-hexyl | Me | 2-Me-2-penten-1-yl |
| H | 3-Cl-Ph | Me | 1-Me-pentyl | Me | 3-Me-2-penten-1-yl |
| H | 4-Cl-Ph | Me | 2-Me-pentyl | Me | 2-hexen-1-yl |
| H | 2,3-di-Cl-Ph | Me | 3-Me-pentyl | Me | 3-hexen-1-yl |
| H | 2,4-di-Cl-Ph | Me | 4-Me-pentyl | Me | 4-hexen-1-yl |
| H | 2,5-di-Cl-Ph | Me | 1,1-di-Me-butyl | Me | 5-hexen-1-yl |
| H | 2,6-di-Cl-Ph | Me | 1,2-di-Me-butyl | Me | 3-buten-2-yl |
| H | 2-Me-benzyl | Me | 1,3-di-Me-butyl | Me | 3-penten-2-yl |
| H | 3-Me-benzyl | Me | 1-Et-butyl | Me | 3-hexen-2-yl |
| H | 4-Me-benzyl | Me | 2-Et-butyl | Me | 2-hepten-1-yl |
| H | 2-Cl-benzyl | Me | 2,2-di-Me-butyl | Me | 3-hepten-1-yl |
| H | 3-Cl-benzyl | Me | 3,3-di-Me-butyl | Me | 4-hepten-1-yl |
| H | 4-Cl-benzyl | Me | n-heptyl | Me | 5-hepten-1-yl |
| H | 2,3-di-Cl-benzyl | Me | 1-Me-hexyl | Me | 6-hepten-1-yl |
| H | 2,4-di-Cl-benzyl | Me | 2-Me-hexyl | Me | 3-hepten-2-yl |
| H | 2-5-di-Cl-benzyl | Me | 3-Me-hexyl | Me | Propargyl |
| H | 2,6-di-Cl-benzyl | Me | 4-Me-hexyl | Me | 2-butyn-1-yl |
| H | 2-pyridyl | Me | 5-Me-hexyl | Me | 3-butyn-1-yl |
| H | 3-pyridyl | Me | 1,1-di-Me-pentyl | Me | 2-pentyl-1-yl- |
| H | 4-pyridyl | Me | 2,2-di-Me-pentyl | Me | 3-pentyn-1-yl |
| H | 2-furyl | Me | 3,3,-di-Me-pentyl | Me | 4-pentyn-1-yl |
| H | 3-furyl | Me | 4,4-di-Me-pentyl | Me | 2-hexyn-1-yl |
| H | 5-Me-2-furyl | Me | 1,2-di-Me-pentyl | Me | 3-hexyn-1-yl |
| H | 5-Me-3-furyl | Me | 1,3-di-Me-pentyl | Me | 4-hexyn-1-yl |
| H | 2-thienyl | Me | 1,4-di-Me-pentyl | Me | 5-hexyn-1-yl |
| H | 3-thienyl | Me | 2,3-di-Me-pentyl | Me | 2-heptyn-1-yl |
| Me | 3-heptyn-1-yl | Me | $CH_2CH_2OEt$ | Me | 5-Me-3-thienyl |
| Me | 4-heptyn-1-yl | Me | $CH_2CH_2O$-n-Pr | Et | Me |
| Me | 5-heptyn-1-yl | Me | $CH_2CH_2O$-i-Pr | Et | Et |
| Me | 6-heptyn-1-yl | Me | $CH_2CF_3$ | Et | n-Pr |
| Me | c-Pr | Me | $CH_2CH_2CF_3$ | Et | i-Pr |
| Me | c-Bu | Me | $CH_2CH_2OCF_3$ | Et | n-Bu |
| Me | c-pentyl | Me | $CH_2CH_2Cl$ | Et | i-Bu |
| Me | c-hexyl | Me | $CH_2CH_2Br$ | Et | s-Bu |
| Me | c-heptyl | Me | $CH_2CH_2CH_2Cl$ | Et | t-Bu |
| Me | $CH_2$-c-Pr | Me | $CH_2CH_2CH_2Br$ | Et | n-pentyl |
| Me | $CH_2$-c-Bu | Me | $CH_2CH_2SMe$ | Et | 1-Me-butyl |
| Me | $CH_2$-c-pentyl | Me | $CH_2CH_2Set$ | Et | 2-Me-butyl |
| Me | $CH_2$-c-hexyl | Me | Ph | Et | 3-Me-butyl |
| Me | 1-Me-1-c-pentyl | Me | benzyl | Et | 1,1-di-Me-propyl |
| Me | 2-Me-1-c-pentyl | Me | 2-Me-Ph | Et | 2,2-di-Me-propyl |
| Me | 3-Me-1-c-pentyl | Me | 3-Me-Ph | Et | 1-Et-propyl |
| Me | 2,2-di-Me-c-pentyl | Me | 4-Me-Ph | Et | 1,2-di-Me-propyl |
| Me | 1-Et-1-c-pentyl | Me | 2-Cl-Ph | Et | n-hexyl |
| Me | 2-Et-1-c-pentyl | Me | 3-Cl-Ph | Et | 1-Me-pentyl |
| Me | 1-Me-1-c-hexyl | Me | 4-Cl-Ph | Et | 2-Me-pentyl |
| Me | 2-Me-1-c-hexyl | Me | 2,3-di-Cl-Ph | Et | 3-Me-pentyl |
| Me | 3-Me-1-c-hexyl | Me | 2,4-di-Cl-Ph | Et | 4-Me-pentyl |
| Me | 4-Me-1-c-hexyl | Me | 2,5-di-Cl-Ph | Et | 1,1-di-Me-butyl |
| Me | $CH_2C(O)Me$ | Me | 2,6-di-Cl-Ph | Et | 1,2-di-Me-butyl |
| Me | $CH_2C(O)Et$ | Me | 2-Me-benzyl | Et | 1,3-di-Me-butyl |
| Me | $CH_2CH_2C(O)Me$ | Me | 3-Me-benzyl | Et | 1-Et-butyl |
| Me | $CH_2CH_2C(O)Et$ | Me | 4-Me-benzyl | Et | 2-Et-butyl |
| Me | $CH_2CO_2Me$ | Me | 2-Cl-benzyl | Et | 2,2-di-Me-butyl |
| Me | $CH_2CO_2Et$ | Me | 3-Cl-benzyl | Et | 3,3-di-Me-butyl |

TABLE 1-continued

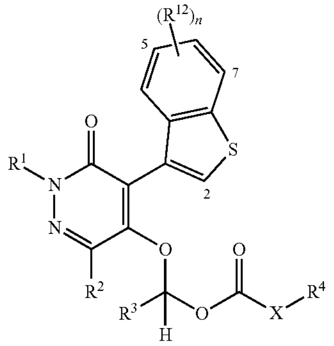

X is a direct bond, $R^1$ is Me, $R^2$ is Me, ($R^{12}$), is 2,5-di-Me (Header Row Phrase)

| $R^3$ | $R^4$ | $R^3$ | $R^4$ | $R^3$ | $R^4$ |
|---|---|---|---|---|---|
| Me | $CH_2CO_2$-n-Pr | Me | 4-Cl-benzyl | Et | n-heptyl |
| Me | $CH_2CO_2$-i-Pr | Me | 2,3-di-Cl-benzyl | Et | 1-Me-hexyl |
| Me | $CH_2CO_2$-n-Bu | Me | 2,4-di-Cl-benzyl | Et | 2-Me-hexyl |
| Me | $CH_2CH_2CO_2Me$ | Me | 2-5-di-Cl-benzyl | Et | 3-Me-hexyl |
| Me | $CH_2CH_2CO_2Et$ | Me | 2,6-di-Cl-benzyl | Et | 4-Me-hexyl |
| Me | $CH_2CH_2CO_2$-n-Pr | Me | 2-pyridyl | Et | 5-Me-hexyl |
| Me | $CH_2CH_2CO_2$-i-Pr | Me | 3-pyridyl | Et | 1,1-di-Me-pentyl |
| Me | $CH_2CN$ | Me | 4-pyridyl | Et | 2,2-di-Me-pentyl |
| Me | $CH_2CH_2CN$ | Me | 2-furyl | Et | 3,3,-di-Me-pentyl |
| Me | CH(Me)CN | Me | 3-furyl | Et | 4,4-di-Me-pentyl |
| Me | $CH_2NO_2$ | Me | 5-Me-2-furyl | Et | 1,2-di-Me-pentyl |
| Me | $CH_2CH_2NO_2$ | Me | 5-Me-3-furyl | Et | 1,3-di-Me-pentyl |
| Me | $CH(Me)NO_2$ | Me | 2-thienyl | Et | 1,4-di-Me-pentyl |
| Me | $CH_2CH_2CH_2NO_2$ | Me | 3-thienyl | Et | 2,3-di-Me-pentyl |
| Me | $CH_2CH_2OMe$ | Me | 5-Me-2-thienyl | Et | 3,4-di-Me pentyl |
| Et | 2-Et-pentyl | Et | 4-heptyn-1-yl | Et | $CH_2CH_2O$-n-Pr |
| Et | 3-Et-pentyl | Et | 5-heptyn-1-yl | Et | $CH_2CH_2O$-i-Pr |
| Et | 2-butyl | Et | 6-heptyn-1-yl | Et | $CH_2CF_3$ |
| Et | 3-pentyl | Et | c-Pr | Et | $CH_2CH_2CF_3$ |
| Et | 2-hexyl | Et | c-Bu | Et | $CH_2CH_2OCF_3$ |
| Et | 3-hexyl | Et | c-pentyl | Et | $CH_2CH_2Cl$ |
| Et | 2-heptyl | Et | c-hexyl | Et | $CH_2CH_2Br$ |
| Et | 3-heptyl | Et | c-heptyl | Et | $CH_2CH_2CH_2Cl$ |
| Et | Allyl | Et | $CH_2$-c-Pr | Et | $CH_2CH_2CH_2Br$ |
| Et | Methyallyl | Et | $CH_2$-c-Bu | Et | $CH_2CH_2SMe$ |
| Et | 2-buten-1-yl | Et | $CH_2$-c-pentyl | Et | $CH_2CH_2Set$ |
| Et | 3-buten-1-yl | Et | $CH_2$-c-hexyl | Et | Ph |
| Et | 2-penten-1-yl | Et | 1-Me-1-c-pentyl | Et | benzyl |
| Et | 3-penten-1-yl | Et | 2-Me-1-c-pentyl | Et | 2-Me-Ph |
| Et | 4-penten-1-yl | Et | 3-Me-1-c-pentyl | Et | 3-Me-Ph |
| Et | 3-Me-2-buten-1-yl | Et | 2,2-di-Me-c-pentyl | Et | 4-Me-Ph |
| Et | 2-Me-2-buten-1-yl | Et | 1-Et-1-c-pentyl | Et | 2-Cl-Ph |
| Et | 2-Me-2-penten-1-yl | Et | 2-Et-1-c-pentyl | Et | 3-Cl-Ph |
| Et | 3-Me-2-penten-1-yl | Et | 1-Me-1-c-hexyl | Et | 4-Cl-Ph |
| Et | 2-hexen-1-yl | Et | 2-Me-1-c-hexyl | Et | 2,3-di-Cl-Ph |
| Et | 3-hexen-1-yl | Et | 3-Me-1-c-hexyl | Et | 2,4-di-Cl-Ph |
| Et | 4-hexen-1-yl | Et | 4-Me-1-c-hexyl | Et | 2,5-di-Cl-Ph |
| Et | 5-hexen-1-yl | Et | $CH_2C(O)Me$ | Et | 2,6-di-Cl-Ph |
| Et | 3-buten-2-yl | Et | $CH_2C(O)Et$ | Et | 2-Me-benzyl |
| Et | 3-penten-2-yl | Et | $CH_2CH_2C(O)Me$ | Et | 3-Me-benzyl |
| Et | 3-hexen-2-yl | Et | $CH_2CH_2C(O)Et$ | Et | 4-Me-benzyl |
| Et | 2-hepten-1-yl | Et | $CH_2CO_2Me$ | Et | 2-Cl-benzyl |
| Et | 3-hepten-1-yl | Et | $CH_2CO_2Et$ | Et | 3-Cl-benzyl |
| Et | 4-hepten-1-yl | Et | $CH_2CO_2$-n-Pr | Et | 4-Cl-benzyl |
| Et | 5-hepten-1-yl | Et | $CH_2CO_2$-i-Pr | Et | 2,3-di-Cl-benzyl |
| Et | 6-hepten-1-yl | Et | $CH_2CO_2$-n-Bu | Et | 2,4-di-Cl-benzyl |
| Et | 3-hepten-2-yl | Et | $CH_2CH_2CO_2Me$ | Et | 2-5-di-Cl-benzyl |
| Et | Propargyl | Et | $CH_2CH_2CO_2Et$ | Et | 2,6-di-Cl-benzyl |
| Et | 2-butyn-1-yl | Et | $CH_2CH_2CO_2$-n-Pr | Et | 2-pyridyl |
| Et | 3-butyn-1-yl | Et | $CH_2CH_2CO_2$-i-Pr | Et | 3-pyridyl |
| Et | 2-pentyl-1-yl- | Et | $CH_2CN$ | Et | 4-pyridyl |
| Et | 3-pentyn-1-yl | Et | $CH_2CH_2CN$ | Et | 2-furyl |
| Et | 4-pentyn-1-yl | Et | CH(Me)CN | Et | 3-furyl |
| Et | 2-hexyn-1-yl | Et | $CH_2NO_2$ | Et | 5-Me-2-furyl |
| Et | 3-hexyn-1-yl | Et | $CH_2CH_2NO_2$ | Et | 5-Me-3-furyl |
| Et | 4-hexyn-1-yl | Et | $CH(Me)NO_2$ | Et | 2-thienyl |
| Et | 5-hexyn-1-yl | Et | $CH_2CH_2CH_2NO_2$ | Et | 3-thienyl |
| Et | 2-heptyn-1-yl | Et | $CH_2CH_2OMe$ | Et | 5-Me-2-thienyl |

TABLE 1-continued

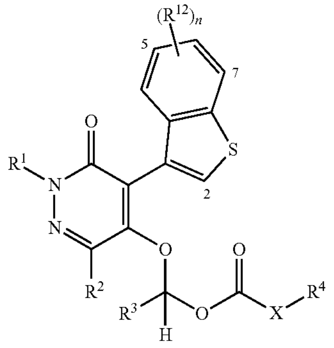

X is a direct bond, $R^1$ is Me, $R^2$ is Me, $(R^{12})$, is 2,5-di-Me (Header Row Phrase)

| $R^3$ | $R^4$ | $R^3$ | $R^4$ | $R^3$ | $R^4$ |
|---|---|---|---|---|---|
| Et | 3-heptyn-1-yl | Et | $CH_2CH_2OEt$ | Et | 5-Me-3-thienyl |
| n-Pr | Me | n-Pr | 3-Et-pentyl | n-Pr | 5-heptyn-1-yl |
| n-Pr | Et | n-Pr | 2-butyl | n-Pr | 6-heptyn-1-yl |
| n-Pr | n-Pr | n-Pr | 3-pentyl | n-Pr | c-Pr |
| n-Pr | i-Pr | n-Pr | 2-hexyl | n-Pr | c-Bu |
| n-Pr | n-Bu | n-Pr | 3-hexyl | n-Pr | c-pentyl |
| n-Pr | i-Bu | n-Pr | 2-heptyl | n-Pr | c-hexyl |
| n-Pr | s-Bu | n-Pr | 3-heptyl | n-Pr | c-heptyl |
| n-Pr | t-Bu | n-Pr | Allyl | n-Pr | $CH_2$-c-Pr |
| n-Pr | n-pentyl | n-Pr | Methyallyl | n-Pr | $CH_2$-c-Bu |
| n-Pr | 1-Me-butyl | n-Pr | 2-buten-1-yl | n-Pr | $CH_2$-c-pentyl |
| n-Pr | 2-Me-butyl | n-Pr | 3-buten-1-yl | n-Pr | $CH_2$-c-hexyl |
| n-Pr | 3-Me-butyl | n-Pr | 2-penten-1-yl | n-Pr | 1-Me-1-c-pentyl |
| n-Pr | 1,1-di-Me-propyl | n-Pr | 3-penten-1-yl | n-Pr | 2-Me-1-c-pentyl |
| n-Pr | 2,2-di-Me-propyl | n-Pr | 4-penten-1-yl | n-Pr | 3-Me-1-c-pentyl |
| n-Pr | 1-Et-propyl | n-Pr | 3-Me-2-buten-1-yl | n-Pr | 2,2-di-Me-c-pentyl |
| n-Pr | 1,2-di-Me-propyl | n-Pr | 2-Me-2-buten-1-yl | n-Pr | 1-Et-1-c-pentyl |
| n-Pr | n-hexyl | n-Pr | 2-Me-2-penten-1-yl | n-Pr | 2-Et-1-c-pentyl |
| n-Pr | 1-Me-pentyl | n-Pr | 3-Me-2-penten-1-yl | n-Pr | 1-Me-1-c-hexyl |
| n-Pr | 2-Me-pentyl | n-Pr | 2-hexen-1-yl | n-Pr | 2-Me-1-c-hexyl |
| n-Pr | 3-Me-pentyl | n-Pr | 3-hexen-1-yl | n-Pr | 3-Me-1-c-hexyl |
| n-Pr | 4-Me-pentyl | n-Pr | 4-hexen-1-yl | n-Pr | 4-Me-1-c-hexyl |
| n-Pr | 1,1-di-Me-butyl | n-Pr | 5-hexen-1-yl | n-Pr | $CH_2C(O)Me$ |
| n-Pr | 1,2-di-Me-butyl | n-Pr | 3-buten-2-yl | n-Pr | $CH_2C(O)Et$ |
| n-Pr | 1,3-di-Me-butyl | n-Pr | 3-penten-2-yl | n-Pr | $CH_2CH_2C(O)Me$ |
| n-Pr | 1-Et-butyl | n-Pr | 3-hexen-2-yl | n-Pr | $CH_2CH_2C(O)Et$ |
| n-Pr | 2-Et-butyl | n-Pr | 2-hepten-1-yl | n-Pr | $CH_2CO_2Me$ |
| n-Pr | 2,2-di-Me-butyl | n-Pr | 3-hepten-1-yl | n-Pr | $CH_2CO_2Et$ |
| n-Pr | 3,3-di-Me-butyl | n-Pr | 4-hepten-1-yl | n-Pr | $CH_2CO_2$-n-Pr |
| n-Pr | n-heptyl | n-Pr | 5-hepten-1-yl | n-Pr | $CH_2CO_2$-i-Pr |
| n-Pr | 1-Me-hexyl | n-Pr | 6-hepten-1-yl | n-Pr | $CH_2CO_2$-n-Bu |
| n-Pr | 2-Me-hexyl | n-Pr | 3-hepten-2-yl | n-Pr | $CH_2CH_2CO_2Me$ |
| n-Pr | 3-Me-hexyl | n-Pr | Propargyl | n-Pr | $CH_2CH_2CO_2Et$ |
| n-Pr | 4-Me-hexyl | n-Pr | 2-butyn-1-yl | n-Pr | $CH_2CH_2CO_2$-n-Pr |
| n-Pr | 5-Me-hexyl | n-Pr | 3-butyn-1-yl | n-Pr | $CH_2CH_2CO_2$-i-Pr |
| n-Pr | 1,1-di-Me-pentyl | n-Pr | 2-pentyl-1-yl- | n-Pr | $CH_2CN$ |
| n-Pr | 2,2-di-Me-pentyl | n-Pr | 3-pentyn-1-yl | n-Pr | $CH_2CH_2CN$ |
| n-Pr | 3,3,-di-Me-pentyl | n-Pr | 4-pentyn-1-yl | n-Pr | CH(Me)CN |
| n-Pr | 4,4-di-Me-pentyl | n-Pr | 2-hexyn-1-yl | n-Pr | $CH_2NO_2$ |
| n-Pr | 1,2-di-Me-pentyl | n-Pr | 3-hexyn-1-yl | n-Pr | $CH_2CH_2NO_2$ |
| n-Pr | 1,3-di-Me-pentyl | n-Pr | 4-hexyn-1-yl | n-Pr | $CH(Me)NO_2$ |
| n-Pr | 1,4-di-Me-pentyl | n-Pr | 5-hexyn-1-yl | n-Pr | $CH_2CH_2CH_2NO_2$ |
| n-Pr | 2,3-di-Me-pentyl | n-Pr | 2-heptyn-1-yl | n-Pr | $CH_2CH_2OMe$ |
| n-Pr | 3,4-di-Me-pentyl | n-Pr | 3-heptyn-1-yl | n-Pr | $CH_2CH_2OEt$ |
| n-Pr | 2-Et-pentyl | n-Pr | 4-heptyn-1-yl | n-Pr | $CH_2CH_2O$-n-Pr |
| n-Pr | $CH_2CH_2O$-i-Pr | c-Pr | Et | c-Pr | 2-butyl |
| n-Pr | $CH_2CF_3$ | c-Pr | n-Pr | c-Pr | 3-pentyl |
| n-Pr | $CH_2CH_2CF_3$ | c-Pr | i-Pr | c-Pr | 2-hexyl |
| n-Pr | $CH_2CH_2OCF_3$ | c-Pr | n-Bu | c-Pr | 3-hexyl |
| n-Pr | $CH_2CH_2Cl$ | c-Pr | i-Bu | c-Pr | 2-heptyl |
| n-Pr | $CH_2CH_2Br$ | c-Pr | s-Bu | c-Pr | 3-heptyl |
| n-Pr | $CH_2CH_2CH_2Cl$ | c-Pr | t-Bu | c-Pr | Allyl |
| n-Pr | $CH_2CH_2CH_2Br$ | c-Pr | n-pentyl | c-Pr | Methyallyl |
| n-Pr | $CH_2CH_2SMe$ | c-Pr | 1-Me-butyl | c-Pr | 2-buten-1-yl |
| n-Pr | $CH_2CH_2Set$ | c-Pr | 2-Me-butyl | c-Pr | 3-buten-1-yl |
| n-Pr | Ph | c-Pr | 3-Me-butyl | c-Pr | 2-penten-1-yl |
| n-Pr | benzyl | c-Pr | 1,1-di-Me-propyl | c-Pr | 3-penten-1-yl |
| n-Pr | 2-Me-Ph | c-Pr | 2,2-di-Me-propyl | c-Pr | 4-penten-1-yl |

TABLE 1-continued

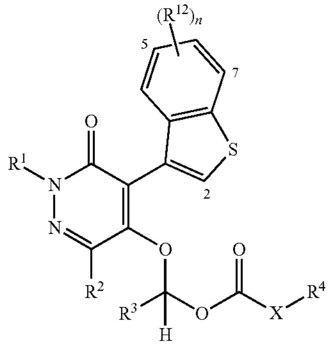

X is a direct bond, $R^1$ is Me, $R^2$ is Me, $(R^{12})_n$ is 2,5-di-Me (Header Row Phrase)

| $R^3$ | $R^4$ | $R^3$ | $R^4$ | $R^3$ | $R^4$ |
|---|---|---|---|---|---|
| n-Pr | 3-Me-Ph | c-Pr | 1-Et-propyl | c-Pr | 3-Me-2-buten-1-yl |
| n-Pr | 4-Me-Ph | c-Pr | 1,2-di-Me-propyl | c-Pr | 2-Me-2-buten-1-yl |
| n-Pr | 2-Cl-Ph | c-Pr | n-hexyl | c-Pr | 2-Me-2-penten-1-yl |
| n-Pr | 3-Cl-Ph | c-Pr | 1-Me-pentyl | c-Pr | 3-Me-2-penten-1-yl |
| n-Pr | 4-Cl-Ph | c-Pr | 2-Me-pentyl | c-Pr | 2-hexen-1-yl |
| n-Pr | 2,3-di-Cl-Ph | c-Pr | 3-Me-pentyl | c-Pr | 3-hexen-1-yl |
| n-Pr | 2,4-di-Cl-Ph | c-Pr | 4-Me-pentyl | c-Pr | 4-hexen-1-yl |
| n-Pr | 2,5-di-Cl-Ph | c-Pr | 1,1-di-Me-butyl | c-Pr | 5-hexen-1-yl |
| n-Pr | 2,6-di-Cl-Ph | c-Pr | 1,2-di-Me-butyl | c-Pr | 3-buten-2-yl |
| n-Pr | 2-Me-benzyl | c-Pr | 1,3-di-Me-butyl | c-Pr | 3-penten-2-yl |
| n-Pr | 3-Me-benzyl | c-Pr | 1-Et-butyl | c-Pr | 3-hexen-2-yl |
| n-Pr | 4-Me-benzyl | c-Pr | 2-Et-butyl | c-Pr | 2-hepten-1-yl |
| n-Pr | 2-Cl-benzyl | c-Pr | 2,2-di-Me-butyl | c-Pr | 3-hepten-1-yl |
| n-Pr | 3-Cl-benzyl | c-Pr | 3,3-di-Me-butyl | c-Pr | 4-hepten-1-yl |
| n-Pr | 4-Cl-benzyl | c-Pr | n-heptyl | c-Pr | 5-hepten-1-yl |
| n-Pr | 2,3-di-Cl-benzyl | c-Pr | 1-Me-hexyl | c-Pr | 6-hepten-1-yl |
| n-Pr | 2,4-di-Cl-benzyl | c-Pr | 2-Me-hexyl | c-Pr | 3-hepten-2-yl |
| n-Pr | 2-5-di-Cl-benzyl | c-Pr | 3-Me-hexyl | c-Pr | Propargyl |
| n-Pr | 2,6-di-Cl-benzyl | c-Pr | 4-Me-hexyl | c-Pr | 2-butyn-1-yl |
| n-Pr | 2-pyridyl | c-Pr | 5-Me-hexyl | c-Pr | 3-butyn-1-yl |
| n-Pr | 3-pyridyl | c-Pr | 1,1-di-Me-pentyl | c-Pr | 2-pentyl-1-yl- |
| n-Pr | 4-pyridyl | c-Pr | 2,2-di-Me-pentyl | c-Pr | 3-pentyn-1-yl |
| n-Pr | 2-furyl | c-Pr | 3,3,-di-Me-pentyl | c-Pr | 4-pentyn-1-yl |
| n-Pr | 3-furyl | c-Pr | 4,4-di-Me-pentyl | c-Pr | 2-hexyn-1-yl |
| n-Pr | 5-Me-2-furyl | c-Pr | 1,2-di-Me-pentyl | c-Pr | 3-hexyn-1-yl |
| n-Pr | 5-Me-3-furyl | c-Pr | 1,3-di-Me-pentyl | c-Pr | 4-hexyn-1-yl |
| n-Pr | 2-thienyl | c-Pr | 1,4-di-Me-pentyl | c-Pr | 5-hexyn-1-yl |
| n-Pr | 3-thienyl | c-Pr | 2,3-di-Me-pentyl | c-Pr | 2-heptyn-1-yl |
| n-Pr | 5-Me-2-thienyl | c-Pr | 3,4-di-Me pentyl | c-Pr | 3-heptyn-1-yl |
| n-Pr | 5-Me-3-thienyl | c-Pr | 2-Et-pentyl | c-Pr | 4-heptyn-1-yl |
| c-Pr | Me | c-Pr | 3-Et-pentyl | c-Pr | 5-heptyn-1-yl |
| c-Pr | 6-heptyn-1-yl | c-Pr | $CH_2CF_3$ | $CO_2Et$ | n-Pr |
| c-Pr | c-Pr | c-Pr | $CH_2CH_2CF_3$ | $CO_2Et$ | i-Pr |
| c-Pr | c-Bu | c-Pr | $CH_2CH_2OCF_3$ | $CO_2Et$ | n-Bu |
| c-Pr | c-pentyl | c-Pr | $CH_2CH_2Cl$ | $CO_2Et$ | i-Bu |
| c-Pr | c-hexyl | c-Pr | $CH_2CH_2Br$ | $CO_2Et$ | s-Bu |
| c-Pr | c-heptyl | c-Pr | $CH_2CH_2CH_2Cl$ | $CO_2Et$ | t-Bu |
| c-Pr | $CH_2$-c-Pr | c-Pr | $CH_2CH_2CH_2Br$ | $CO_2Et$ | n-pentyl |
| c-Pr | $CH_2$-c-Bu | c-Pr | $CH_2CH_2SMe$ | $CO_2Et$ | 1-Me-butyl |
| c-Pr | $CH_2$-c-pentyl | c-Pr | $CH_2CH_2Set$ | $CO_2Et$ | 2-Me-butyl |
| c-Pr | $CH_2$-c-hexyl | c-Pr | Ph | $CO_2Et$ | 3-Me-butyl |
| c-Pr | 1-Me-1-c-pentyl | c-Pr | benzyl | $CO_2Et$ | 1,1-di-Me-propyl |
| c-Pr | 2-Me-1-c-pentyl | c-Pr | 2-Me-Ph | $CO_2Et$ | 2,2-di-Me-propyl |
| c-Pr | 3-Me-1-c-pentyl | c-P | 3-Me-Ph | $CO_2Et$ | 1-Et-propyl |
| c-Pr | 2,2-di-Me-c-pentyl | c-Pr | 4-Me-Ph | $CO_2Et$ | 1,2-di-Me-propyl |
| c-Pr | 1-Et-1-c-pentyl | c-Pr | 2-Cl-Ph | $CO_2Et$ | n-hexyl |
| c-Pr | 2-Et-1-c-pentyl | c-Pr | 3-Cl-Ph | $CO_2Et$ | 1-Me-pentyl |
| c-Pr | 1-Me-1-c-hexyl | c-Pr | 4-Cl-Ph | $CO_2Et$ | 2-Me-pentyl |
| c-Pr | 2-Me-1-c-hexyl | c-Pr | 2,3-di-Cl-Ph | $CO_2Et$ | 3-Me-pentyl |
| c-Pr | 3-Me-1-c-hexyl | c-Pr | 2,4-di-Cl-Ph | $CO_2Et$ | 4-Me-pentyl |
| c-Pr | 4-Me-1-c-hexyl | c-Pr | 2,5-di-Cl-Ph | $CO_2Et$ | 1,1-di-Me-butyl |
| c-Pr | $CH_2C(O)Me$ | c-Pr | 2,6-di-Cl-Ph | $CO_2Et$ | 1,2-di-Me-butyl |
| c-Pr | $CH_2C(O)Et$ | c-Pr | 2-Me-benzyl | $CO_2Et$ | 1,3-di-Me-butyl |
| c-Pr | $CH_2CH_2C(O)Me$ | c-Pr | 3-Me-benzyl | $CO_2Et$ | 1-Et-butyl |
| c-Pr | $CH_2CH_2C(O)Et$ | c-Pr | 4-Me-benzyl | $CO_2Et$ | 2-Et-butyl |
| c-Pr | $CH_2CO_2Me$ | c-Pr | 2-Cl-benzyl | $CO_2Et$ | 2,2-di-Me-butyl |
| c-Pr | $CH_2CO_2Et$ | c-Pr | 3-Cl-benzyl | $CO_2Et$ | 3,3-di-Me-butyl |
| c-Pr | $CH_2CO_2$-n-Pr | c-Pr | 4-Cl-benzyl | $CO_2Et$ | n-heptyl |

TABLE 1-continued

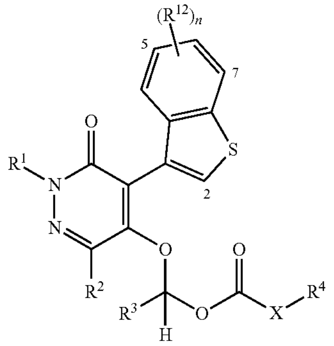

X is a direct bond, $R^1$ is Me, $R^2$ is Me, $(R^{12})$, is 2,5-di-Me (Header Row Phrase)

| $R^3$ | $R^4$ | $R^3$ | $R^4$ | $R^3$ | $R^4$ |
|---|---|---|---|---|---|
| c-Pr | $CH_2CO_2$-i-Pr | c-Pr | 2,3-di-Cl-benzyl | $CO_2Et$ | 1-Me-hexyl |
| c-Pr | $CH_2CO_2$-n-Bu | c-Pr | 2,4-di-Cl-benzyl | $CO_2Et$ | 2-Me-hexyl |
| c-Pr | $CH_2CH_2CO_2Me$ | c-Pr | 2-5-di-Cl-benzyl | $CO_2Et$ | 3-Me-hexyl |
| c-Pr | $CH_2CH_2CO_2Et$ | c-Pr | 2,6-di-Cl-benzyl | $CO_2Et$ | 4-Me-hexyl |
| c-Pr | $CH_2CH_2CO_2$-n-Pr | c-Pr | 2-pyridyl | $CO_2Et$ | 5-Me-hexyl |
| c-Pr | $CH_2CH_2CO_2$-i-Pr | c-Pr | 3-pyridyl | $CO_2Et$ | 1,1-di-Me-pentyl |
| c-Pr | $CH_2CN$ | c-Pr | 4-pyridyl | $CO_2Et$ | 2,2-di-Me-pentyl |
| c-Pr | $CH_2CH_2CN$ | c-Pr | 2-furyl | $CO_2Et$ | 3,3,-di-Me-pentyl |
| c-Pr | CH(Me)CN | c-Pr | 3-furyl | $CO_2Et$ | 4,4-di-Me-pentyl |
| c-Pr | $CH_2NO_2$ | c-Pr | 5-Me-2-furyl | $CO_2Et$ | 1,2-di-Me-pentyl |
| c-Pr | $CH_2CH_2NO_2$ | c-Pr | 5-Me-3-furyl | $CO_2Et$ | 1,3-di-Me-pentyl |
| c-Pr | $CH(Me)NO_2$ | c-Pr | 2-thienyl | $CO_2Et$ | 1,4-di-Me-pentyl |
| c-Pr | $CH_2CH_2CH_2NO_2$ | c-Pr | 3-thienyl | $CO_2Et$ | 2,3-di-Me-pentyl |
| c-Pr | $CH_2CH_2OMe$ | c-Pr | 5-Me-2-thienyl | $CO_2Et$ | 3,4-di-Me pentyl |
| c-Pr | $CH_2CH_2OEt$ | c-Pr | 5-Me-3-thienyl | $CO_2Et$ | 2-Et-pentyl |
| c-Pr | $CH_2CH_2O$-n-Pr | $CO_2Et$ | Me | $CO_2Et$ | 3-Et-pentyl |
| c-Pr | $CH_2CH_2O$-i-Pr | $CO_2Et$ | Et | $CO_2Et$ | 2-butyl |
| $CO_2Et$ | 3-pentyl | $CO_2Et$ | c-Pr | $CO_2Et$ | $CH_2CH_2CF_3$ |
| $CO_2Et$ | 2-hexyl | $CO_2Et$ | c-Bu | $CO_2Et$ | $CH_2CH_2OCF_3$ |
| $CO_2Et$ | 3-hexyl | $CO_2Et$ | c-pentyl | $CO_2Et$ | $CH_2CH_2Cl$ |
| $CO_2Et$ | 2-heptyl | $CO_2Et$ | c-hexyl | $CO_2Et$ | $CH_2CH_2Br$ |
| $CO_2Et$ | 3-heptyl | $CO_2Et$ | c-heptyl | $CO_2Et$ | $CH_2CH_2CH_2Cl$ |
| $CO_2Et$ | Allyl | $CO_2Et$ | $CH_2$-c-Pr | $CO_2Et$ | $CH_2CH_2CH_2Br$ |
| $CO_2Et$ | Methyallyl | $CO_2Et$ | $CH_2$-c-Bu | $CO_2Et$ | $CH_2CH_2SMe$ |
| $CO_2Et$ | 2-buten-1-yl | $CO_2Et$ | $CH_2$-c-pentyl | $CO_2Et$ | $CH_2CH_2Set$ |
| $CO_2Et$ | 3-buten-1-yl | $CO_2Et$ | $CH_2$-c-hexyl | $CO_2Et$ | Ph |
| $CO_2Et$ | 2-penten-1-yl | $CO_2Et$ | 1-Me-1-c-pentyl | $CO_2Et$ | benzyl |
| $CO_2Et$ | 3-penten-1-yl | $CO_2Et$ | 2-Me-1-c-pentyl | $CO_2Et$ | 2-Me-Ph |
| $CO_2Et$ | 4-penten-1-yl | $CO_2Et$ | 3-Me-1-c-pentyl | $CO_2Et$ | 3-Me-Ph |
| $CO_2Et$ | 3-Me-2-buten-1-yl | $CO_2Et$ | 2,2-di-Me-c-pentyl | $CO_2Et$ | 4-Me-Ph |
| $CO_2Et$ | 2-Me-2-buten-1-yl | $CO_2Et$ | 1-Et-1-c-pentyl | $CO_2Et$ | 2-Cl-Ph |
| $CO_2Et$ | 2-Me-2-penten-1-yl | $CO_2Et$ | 2-Et-1-c-pentyl | $CO_2Et$ | 3-Cl-Ph |
| $CO_2Et$ | 3-Me-2-penten-1-yl | $CO_2Et$ | 1-Me-1-c-hexyl | $CO_2Et$ | 4-Cl-Ph |
| $CO_2Et$ | 2-hexen-1-yl | $CO_2Et$ | 2-Me-1-c-hexyl | $CO_2Et$ | 2,3-di-Cl-Ph |
| $CO_2Et$ | 3-hexen-1-yl | $CO_2Et$ | 3-Me-1-c-hexyl | $CO_2Et$ | 2,4-di-Cl-Ph |
| $CO_2Et$ | 4-hexen-1-yl | $CO_2Et$ | 4-Me-1-c-hexyl | $CO_2Et$ | 2,5-di-Cl-Ph |
| $CO_2Et$ | 5-hexen-1-yl | $CO_2Et$ | $CH_2C(O)Me$ | $CO_2Et$ | 2,6-di-Cl-Ph |
| $CO_2Et$ | 3-buten-2-yl | $CO_2Et$ | $CH_2C(O)Et$ | $CO_2Et$ | 2-Me-benzyl |
| $CO_2Et$ | 3-penten-2-yl | $CO_2Et$ | $CH_2CH_2C(O)Me$ | $CO_2Et$ | 3-Me-benzyl |
| $CO_2Et$ | 3-hexen-2-yl | $CO_2Et$ | $CH_2CH_2C(O)Et$ | $CO_2Et$ | 4-Me-benzyl |
| $CO_2Et$ | 2-hepten-1-yl | $CO_2Et$ | $CH_2CO_2Me$ | $CO_2Et$ | 2-Cl-benzyl |
| $CO_2Et$ | 3-hepten-1-yl | $CO_2Et$ | $CH_2CO_2Et$ | $CO_2Et$ | 3-Cl-benzyl |
| $CO_2Et$ | 4-hepten-1-yl | $CO_2Et$ | $CH_2CO_2$-n-Pr | $CO_2Et$ | 4-Cl-benzyl |
| $CO_2Et$ | 5-hepten-1-yl | $CO_2Et$ | $CH_2CO_2$-i-Pr | $CO_2Et$ | 2,3-di-Cl-benzyl |
| $CO_2Et$ | 6-hepten-1-yl | $CO_2Et$ | $CH_2CO_2$-n-Bu | $CO_2Et$ | 2,4-di-Cl-benzyl |
| $CO_2Et$ | 3-hepten-2-yl | $CO_2Et$ | $CH_2CH_2CO_2Me$ | $CO_2Et$ | 2-5-di-Cl-benzyl |
| $CO_2Et$ | Propargyl | $CO_2Et$ | $CH_2CH_2CO_2Et$ | $CO_2Et$ | 2,6-di-Cl-benzyl |
| $CO_2Et$ | 2-butyn-1-yl | $CO_2Et$ | $CH_2CH_2CO_2$-n-Pr | $CO_2Et$ | 2-pyridyl |
| $CO_2Et$ | 3-butyn-1-yl | $CO_2Et$ | $CH_2CH_2CO_2$-i-Pr | $CO_2Et$ | 3-pyridyl |
| $CO_2Et$ | 2-pentyl-1-yl- | $CO_2Et$ | $CH_2CN$ | $CO_2Et$ | 4-pyridyl |
| $CO_2Et$ | 3-pentyn-1-yl | $CO_2Et$ | $CH_2CH_2CN$ | $CO_2Et$ | 2-furyl |
| $CO_2Et$ | 4-pentyn-1-yl | $CO_2Et$ | CH(Me)CN | $CO_2Et$ | 3-furyl |
| $CO_2Et$ | 2-hexyn-1-yl | $CO_2Et$ | $CH_2NO_2$ | $CO_2Et$ | 5-Me-2-furyl |
| $CO_2Et$ | 3-hexyn-1-yl | $CO_2Et$ | $CH_2CH_2NO_2$ | $CO_2Et$ | 5-Me-3-furyl |
| $CO_2Et$ | 4-hexyn-1-yl | $CO_2Et$ | $CH(Me)NO_2$ | $CO_2Et$ | 2-thienyl |
| $CO_2Et$ | 5-hexyn-1-yl | $CO_2Et$ | $CH_2CH_2CH_2NO_2$ | $CO_2Et$ | 3-thienyl |
| $CO_2Et$ | 2-heptyn-1-yl | $CO_2Et$ | $CH_2CH_2OMe$ | $CO_2Et$ | 5-Me-2-thienyl |
| $CO_2Et$ | 3-heptyn-1-yl | $CO_2Et$ | $CH_2CH_2OEt$ | $CO_2Et$ | 5-Me-3-thienyl |

TABLE 1-continued

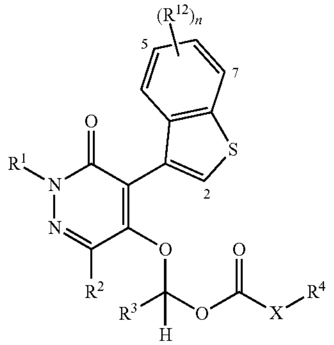

X is a direct bond, $R^1$ is Me, $R^2$ is Me, $(R^{12})$, is 2,5-di-Me (Header Row Phrase)

| $R^3$ | $R^4$ | $R^3$ | $R^4$ | $R^3$ | $R^4$ |
|---|---|---|---|---|---|
| $CO_2Et$ | 4-heptyn-1-yl | $CO_2Et$ | $CH_2CH_2O$-n-Pr | Ph | Me |
| $CO_2Et$ | 5-heptyn-1-yl | $CO_2Et$ | $CH_2CH_2O$-i-Pr | Ph | Et |
| $CO_2Et$ | 6-heptyn-1-yl | $CO_2Et$ | $CH_2CF_3$ | Ph | n-Pr |
| Ph | i-Pr | Ph | 2-hexyl | Ph | c-Bu |
| Ph | n-Bu | Ph | 3-hexyl | Ph | c-pentyl |
| Ph | i-Bu | Ph | 2-heptyl | Ph | c-hexyl |
| Ph | s-Bu | Ph | 3-heptyl | Ph | c-heptyl |
| Ph | t-Bu | Ph | Allyl | Ph | $CH_2$-c-Pr |
| Ph | n-pentyl | Ph | Methyallyl | Ph | $CH_2$-c-Bu |
| Ph | 1-Me-butyl | Ph | 2-buten-1-yl | Ph | $CH_2$-c-pentyl |
| Ph | 2-Me-butyl | Ph | 3-buten-1-yl | Ph | $CH_2$-c-hexyl |
| Ph | 3-Me-butyl | Ph | 2-penten-1-yl | Ph | 1-Me-1-c-pentyl |
| Ph | 1,1-di-Me-propyl | Ph | 3-penten-1-yl | Ph | 2-Me-1-c-pentyl |
| Ph | 2,2-di-Me-propyl | Ph | 4-penten-1-yl | Ph | 3-Me-1-c-pentyl |
| Ph | 1-Et-propyl | Ph | 3-Me-2-buten-1-yl | Ph | 2,2-di-Me-c-pentyl |
| Ph | 1,2-di-Me-propyl | Ph | 2-Me-2-buten-1-yl | Ph | 1-Et-1-c-pentyl |
| Ph | n-hexyl | Ph | 2-Me-2-penten-1-yl | Ph | 2-Et-1-c-pentyl |
| Ph | 1-Me-pentyl | Ph | 3-Me-2-penten-1-yl | Ph | 1-Me-1-c-hexyl |
| Ph | 2-Me-pentyl | Ph | 2-hexen-1-yl | Ph | 2-Me-1-c-hexyl |
| Ph | 3-Me-pentyl | Ph | 3-hexen-1-yl | Ph | 3-Me-1-c-hexyl |
| Ph | 4-Me-pentyl | Ph | 4-hexen-1-yl | Ph | 4-Me-1-c-hexyl |
| Ph | 1,1-di-Me-butyl | Ph | 5-hexen-1-yl | Ph | $CH_2C(O)Me$ |
| Ph | 1,2-di-Me-butyl | Ph | 3-buten-2-yl | Ph | $CH_2C(O)Et$ |
| Ph | 1,3-di-Me-butyl | Ph | 3-penten-2-yl | Ph | $CH_2CH_2C(O)Me$ |
| Ph | 1-Et-butyl | Ph | 3-hexen-2-yl | Ph | $CH_2CH_2C(O)Et$ |
| Ph | 2-Et-butyl | Ph | 2-hepten-1-yl | Ph | $CH_2CO_2Me$ |
| Ph | 2,2-di-Me-butyl | Ph | 3-hepten-1-yl | Ph | $CH_2CO_2Et$ |
| Ph | 3,3-di-Me-butyl | Ph | 4-hepten-1-yl | Ph | $CH_2CO_2$-n-Pr |
| Ph | n-heptyl | Ph | 5-hepten-1-yl | Ph | $CH_2CO_2$-i-Pr |
| Ph | 1-Me-hexyl | Ph | 6-hepten-1-yl | Ph | $CH_2CO_2$-n-Bu |
| Ph | 2-Me-hexyl | Ph | 3-hepten-2-yl | Ph | $CH_2CH_2CO_2Me$ |
| Ph | 3-Me-hexyl | Ph | Propargyl | Ph | $CH_2CH_2CO_2Et$ |
| Ph | 4-Me-hexyl | Ph | 2-butyn-1-yl | Ph | $CH_2CH_2CO_2$-n-Pr |
| Ph | 5-Me-hexyl | Ph | 3-butyn-1-yl | Ph | $CH_2CH_2CO_2$-i-Pr |
| Ph | 1,1-di-Me-pentyl | Ph | 2-pentyl-1-yl- | Ph | $CH_2CN$ |
| Ph | 2,2-di-Me-pentyl | Ph | 3-pentyn-1-yl | Ph | $CH_2CH_2CN$ |
| Ph | 3,3,-di-Me-pentyl | Ph | 4-pentyn-1-yl | Ph | CH(Me)CN |
| Ph | 4,4-di-Me-pentyl | Ph | 2-hexyn-1-yl | Ph | $CH_2NO_2$ |
| Ph | 1,2-di-Me-pentyl | Ph | 3-hexyn-1-yl | Ph | $CH_2CH_2NO_2$ |
| Ph | 1,3-di-Me-pentyl | Ph | 4-hexyn-1-yl | Ph | $CH(Me)NO_2$ |
| Ph | 1,4-di-Me-pentyl | Ph | 5-hexyn-1-yl | Ph | $CH_2CH_2CH_2NO_2$ |
| Ph | 2,3-di-Me-pentyl | Ph | 2-heptyn-1-yl | Ph | $CH_2CH_2OMe$ |
| Ph | 3,4-di-Me-pentyl | Ph | 3-heptyn-1-yl | Ph | $CH_2CH_2OEt$ |
| Ph | 2-Et-pentyl | Ph | 4-heptyn-1-yl | Ph | $CH_2CH_2O$-n-Pr |
| Ph | 3-Et-pentyl | Ph | 5-heptyn-1-yl | Ph | $CH_2CH_2O$-i-Pr |
| Ph | 2-butyl | Ph | 6-heptyn-1-yl | Ph | $CH_2CF_3$ |
| Ph | 3-pentyl | Ph | c-Pr | Ph | $CH_2CH_2CF_3$ |
| Ph | $CH_2CH_2OCF_3$ | 4-Cl-Ph | n-Bu | 4-Cl-Ph | 3-hexyl |
| Ph | $CH_2CH_2Cl$ | 4-Cl-Ph | i-Bu | 4-Cl-Ph | 2-heptyl |
| Ph | $CH_2CH_2Br$ | 4-Cl-Ph | s-Bu | 4-Cl-Ph | 3-heptyl |
| Ph | $CH_2CH_2CH_2Cl$ | 4-Cl-Ph | t-Bu | 4-Cl-Ph | Allyl |
| Ph | $CH_2CH_2CH_2Br$ | 4-Cl-Ph | n-pentyl | 4-Cl-Ph | Methyallyl |
| Ph | $CH_2CH_2SMe$ | 4-Cl-Ph | 1-Me-butyl | 4-Cl-Ph | 2-buten-1-yl |
| Ph | $CH_2CH_2Set$ | 4-Cl-Ph | 2-Me-butyl | 4-Cl-Ph | 3-buten-1-yl |
| Ph | Ph | 4-Cl-Ph | 3-Me-butyl | 4-Cl-Ph | 2-penten-1-yl |
| Ph | benzyl | 4-Cl-Ph | 1,1-di-Me-propyl | 4-Cl-Ph | 3-penten-1-yl |
| Ph | 2-Me-Ph | 4-Cl-Ph | 2,2-di-Me-propyl | 4-Cl-Ph | 4-penten-1-yl |
| Ph | 3-Me-Ph | 4-Cl-Ph | 1-Et-propyl | 4-Cl-Ph | 3-Me-2-buten-1-yl |

TABLE 1-continued

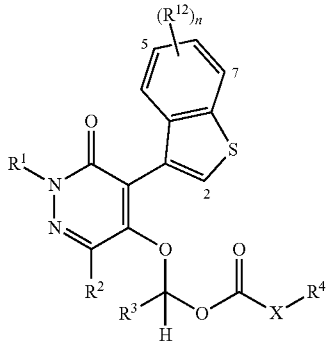

X is a direct bond, $R^1$ is Me, $R^2$ is Me, $(R^{12})_n$ is 2,5-di-Me (Header Row Phrase)

| $R^3$ | $R^4$ | $R^3$ | $R^4$ | $R^3$ | $R^4$ |
|---|---|---|---|---|---|
| Ph | 4-Me-Ph | 4-Cl-Ph | 1,2-di-Me-propyl | 4-Cl-Ph | 2-Me-2-buten-1-yl |
| Ph | 2-Cl-Ph | 4-Cl-Ph | n-hexyl | 4-Cl-Ph | 2-Me-2-penten-1-yl |
| Ph | 3-Cl-Ph | 4-Cl-Ph | 1-Me-pentyl | 4-Cl-Ph | 3-Me-2-penten-1-yl |
| Ph | 4-Cl-Ph | 4-Cl-Ph | 2-Me-pentyl | 4-Cl-Ph | 2-hexen-1-yl |
| Ph | 2,3-di-Cl-Ph | 4-Cl-Ph | 3-Me-pentyl | 4-Cl-Ph | 3-hexen-1-yl |
| Ph | 2,4-di-Cl-Ph | 4-Cl-Ph | 4-Me-pentyl | 4-Cl-Ph | 4-hexen-1-yl |
| Ph | 2,5-di-Cl-Ph | 4-Cl-Ph | 1,1-di-Me-butyl | 4-Cl-Ph | 5-hexen-1-yl |
| Ph | 2,6-di-Cl-Ph | 4-Cl-Ph | 1,2-di-Me-butyl | 4-Cl-Ph | 3-buten-2-yl |
| Ph | 2-Me-benzyl | 4-Cl-Ph | 1,3-di-Me-butyl | 4-Cl-Ph | 3-penten-2-yl |
| Ph | 3-Me-benzyl | 4-Cl-Ph | 1-Et-butyl | 4-Cl-Ph | 3-hexen-2-yl |
| Ph | 4-Me-benzyl | 4-Cl-Ph | 2-Et-butyl | 4-Cl-Ph | 2-hepten-1-yl |
| Ph | 2-Cl-benzyl | 4-Cl-Ph | 2,2-di-Me-butyl | 4-Cl-Ph | 3-hepten-1-yl |
| Ph | 3-Cl-benzyl | 4-Cl-Ph | 3,3-di-Me-butyl | 4-Cl-Ph | 4-hepten-1-yl |
| Ph | 4-Cl-benzyl | 4-Cl-Ph | n-heptyl | 4-Cl-Ph | 5-hepten-1-yl |
| Ph | 2,3-di-Cl-benzyl | 4-Cl-Ph | 1-Me-hexyl | 4-Cl-Ph | 6-hepten-1-yl |
| Ph | 2,4-di-Cl-benzyl | 4-Cl-Ph | 2-Me-hexyl | 4-Cl-Ph | 3-hepten-2-yl |
| Ph | 2-5-di-Cl-benzyl | 4-Cl-Ph | 3-Me-hexyl | 4-Cl-Ph | Propargyl |
| Ph | 2,6-di-Cl-benzyl | 4-Cl-Ph | 4-Me-hexyl | 4-Cl-Ph | 2-butyn-1-yl |
| Ph | 2-pyridyl | 4-Cl-Ph | 5-Me-hexyl | 4-Cl-Ph | 3-butyn-1-yl |
| Ph | 3-pyridyl | 4-Cl-Ph | 1,1-di-Me-pentyl | 4-Cl-Ph | 2-pentyl-1-yl- |
| Ph | 4-pyridyl | 4-Cl-Ph | 2,2-di-Me-pentyl | 4-Cl-Ph | 3-pentyn-1-yl |
| Ph | 2-furyl | 4-Cl-Ph | 3,3,-di-Me-pentyl | 4-Cl-Ph | 4-pentyn-1-yl |
| Ph | 3-furyl | 4-Cl-Ph | 4,4-di-Me-pentyl | 4-Cl-Ph | 2-hexyn-1-yl |
| Ph | 5-Me-2-furyl | 4-Cl-Ph | 1,2-di-Me-pentyl | 4-Cl-Ph | 3-hexyn-1-yl |
| Ph | 5-Me-3-furyl | 4-Cl-Ph | 1,3-di-Me-pentyl | 4-Cl-Ph | 4-hexyn-1-yl |
| Ph | 2-thienyl | 4-Cl-Ph | 1,4-di-Me-pentyl | 4-Cl-Ph | 5-hexyn-1-yl |
| Ph | 3-thienyl | 4-Cl-Ph | 2,3-di-Me-pentyl | 4-Cl-Ph | 2-heptyn-1-yl |
| Ph | 5-Me-2-thienyl | 4-Cl-Ph | 3,4-di-Me pentyl | 4-Cl-Ph | 3-heptyn-1-yl |
| Ph | 5-Me-3-thienyl | 4-Cl-Ph | 2-Et-pentyl | 4-Cl-Ph | 4-heptyn-1-yl |
| 4-Cl-Ph | Me | 4-Cl-Ph | 3-Et-pentyl | 4-Cl-Ph | 5-heptyn-1-yl |
| 4-Cl-Ph | Et | 4-Cl-Ph | 2-butyl | 4-Cl-Ph | 6-heptyn-1-yl |
| 4-Cl-Ph | n-Pr | 4-Cl-Ph | 3-pentyl | 4-Cl-Ph | c-Pr |
| 4-Cl-Ph | i-Pr | 4-Cl-Ph | 2-hexyl | 4-Cl-Ph | c-Bu |
| 4-Cl-Ph | c-pentyl | 4-Cl-Ph | $CH_2CH_2CO_2$-n-Pr | 4-Cl-Ph | 3-Cl-Ph |
| 4-Cl-Ph | c-hexyl | 4-Cl-Ph | $CH_2CH_2CO_2$-i-Pr | 4-Cl-Ph | 4-Cl-Ph |
| 4-Cl-Ph | c-heptyl | 4-Cl-Ph | $CH_2CN$ | 4-Cl-Ph | 2,3-di-Cl-Ph |
| 4-Cl-Ph | $CH_2$-c-Pr | 4-Cl-Ph | $CH_2CH_2CN$ | 4-Cl-Ph | 2,4-di-Cl-Ph |
| 4-Cl-Ph | $CH_2$-c-Bu | 4-Cl-Ph | CH(Me)CN | 4-Cl-Ph | 2,5-di-Cl-Ph |
| 4-Cl-Ph | $CH_2$-c-pentyl | 4-Cl-Ph | $CH_2NO_2$ | 4-Cl-Ph | 2,6-di-Cl-Ph |
| 4-Cl-Ph | $CH_2$-c-hexyl | 4-Cl-Ph | $CH_2CH_2NO_2$ | 4-Cl-Ph | 2-Me-benzyl |
| 4-Cl-Ph | 1-Me-1-c-pentyl | 4-Cl-Ph | CH(Me)NO2 | 4-Cl-Ph | 3-Me-benzyl |
| 4-Cl-Ph | 2-Me-1-c-pentyl | 4-Cl-Ph | $CH_2CH_2CH_2NO_2$ | 4-Cl-Ph | 4-Me-benzyl |
| 4-Cl-Ph | 3-Me-1-c-pentyl | 4-Cl-Ph | $CH_2CH_2OMe$ | 4-Cl-Ph | 2-Cl-benzyl |
| 4-Cl-Ph | 2,2-di-Me-c-pentyl | 4-Cl-Ph | $CH_2CH_2OEt$ | 4-Cl-Ph | 3-Cl-benzyl |
| 4-Cl-Ph | 1-Et-1-c-pentyl | 4-Cl-Ph | $CH_2CH_2O$-n-Pr | 4-Cl-Ph | 4-Cl-benzyl |
| 4-Cl-Ph | 2-Et-1-c-pentyl | 4-Cl-Ph | $CH_2CH_2O$-i-Pr | 4-Cl-Ph | 2,3-di-Cl-benzyl |
| 4-Cl-Ph | 1-Me-1-c-hexyl | 4-Cl-Ph | $CH_2CF_3$ | 4-Cl-Ph | 2,4-di-Cl-benzyl |
| 4-Cl-Ph | 2-Me-1-c-hexyl | 4-Cl-Ph | $CH_2CH_2CF_3$ | 4-Cl-Ph | 2-5-di-Cl-benzyl |
| 4-Cl-Ph | 3-Me-1-c-hexyl | 4-Cl-Ph | $CH_2CH_2OCF_3$ | 4-Cl-Ph | 2,6-di-Cl-benzyl |
| 4-Cl-Ph | 4-Me-1-c-hexyl | 4-Cl-Ph | $CH_2CH_2Cl$ | 4-Cl-Ph | 2-pyridyl |
| 4-Cl-Ph | $CH_2C(O)Me$ | 4-Cl-Ph | $CH_2CH_2Br$ | 4-Cl-Ph | 3-pyridyl |
| 4-Cl-Ph | $CH_2C(O)Et$ | 4-Cl-Ph | $CH_2CH_2CH_2Cl$ | 4-Cl-Ph | 4-pyridyl |
| 4-Cl-Ph | $CH_2CH_2C(O)Me$ | 4-Cl-Ph | $CH_2CH_2CH_2Br$ | 4-Cl-Ph | 2-furyl |
| 4-Cl-Ph | $CH_2CH_2C(O)Et$ | 4-Cl-Ph | $CH_2CH_2SMe$ | 4-Cl-Ph | 3-furyl |
| 4-Cl-Ph | $CH_2CO_2Me$ | 4-Cl-Ph | $CH_2CH_2Set$ | 4-Cl-Ph | 5-Me-2-furyl |
| 4-Cl-Ph | $CH_2CO_2Et$ | 4-Cl-Ph | Ph | 4-Cl-Ph | 5-Me-3-furyl |
| 4-Cl-Ph | $CH_2CO_2$-n-Pr | 4-Cl-Ph | benzyl | 4-Cl-Ph | 2-thienyl |
| 4-Cl-Ph | $CH_2CO_2$-i-Pr | 4-Cl-Ph | 2-Me-Ph | 4-Cl-Ph | 3-thienyl |

TABLE 1-continued

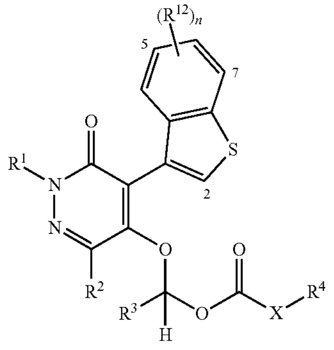

X is a direct bond, $R^1$ is Me, $R^2$ is Me, $(R^{12})_n$ is 2,5-di-Me (Header Row Phrase)

| $R^3$ | $R^4$ | $R^3$ | $R^4$ | $R^3$ | $R^4$ |
|---|---|---|---|---|---|
| 4-Cl-Ph | $CH_2CO_2$-n-Bu | 4-Cl-Ph | 3-Me-Ph | 4-Cl-Ph | 5-Me-2-thienyl |
| 4-Cl-Ph | $CH_2CH_2CO_2Me$ | 4-Cl-Ph | 4-Me-Ph | 4-Cl-Ph | 5-Me-3-thienyl |
| 4-Cl-Ph | $CH_2CH_2CO_2Et$ | 4-Cl-Ph | 2-Cl-Ph | | |

This disclosure also includes TABLES 2 through 160 wherein the Header Row Phrase in TABLE 1 (i.e. "X is a direct bond, $R^1$ is Me, $R^2$ is Me, $(R^{12})_n$ is 2,5-di-Me") is replaced with the Header Row Phrase listed in the respective TABLE, and the remaining variables $R^3$ and $R^4$ in each table are as defined in TABLE 1.

| TABLE | Header Row Phrase |
|---|---|
| 2 | X is a direct bond, $R^1$ is Me, $R^2$ is Me, $(R^{12})_n$ is 2,5,7-tri-Me |
| 3 | X is a direct bond, $R^1$ is Me, $R^2$ is Me, $(R^{12})_n$ is 5-Cl-2-Me |
| 4 | X is a direct bond, $R^1$ is Me, $R^2$ is Me, $(R^{12})_n$ is 2-Br-5-Me |
| 5 | X is a direct bond, $R^1$ is Me, $R^2$ is Me, $(R^{12})_n$ is 5-Cl-2,7-di-Me |
| 6 | X is a direct bond, $R^1$ is Me, $R^2$ is Me, $(R^{12})_n$ is 2-Et-5-Me |
| 7 | X is a direct bond, $R^1$ is Me, $R^2$ is Me, $(R^{12})_n$ is 2-Me |
| 8 | X is a direct bond, $R^1$ is Me, $R^2$ is Me, $(R^{12})_n$ is 7-F-2-Me |
| 9 | X is a direct bond, $R^1$ is Me, $R^2$ is Me, $(R^{12})_n$ is 2,4,6-tri-Me |
| 10 | X is a direct bond, $R^1$ is Me, $R^2$ is Me, $(R^{12})_n$ is 2-Br-5-F |
| 11 | X is O, $R^1$ is Me, $R^2$ is Me, $(R^{12})_n$ is 2,5-di-Me |
| 12 | X is O, $R^1$ is Me, $R^2$ is Me, $(R^{12})_n$ is 2,5,7-tri-Me |
| 13 | X is O, $R^1$ is Me, $R^2$ is Me, $(R^{12})_n$ is 5-Cl-2-Me |
| 14 | X is O, $R^1$ is Me, $R^2$ is Me, $(R^{12})_n$ is 2-Br-5-Me |
| 15 | X is O, $R^1$ is Me, $R^2$ is Me, $(R^{12})_n$ is 5-Cl-2,7-di-Me |
| 16 | X is O, $R^1$ is Me, $R^2$ is Me, $(R^{12})_n$ is 2-Et-5-Me |
| 17 | X is O, $R^1$ is Me, $R^2$ is Me, $(R^{12})_n$ is 2-Me |
| 18 | X is O, $R^1$ is Me, $R^2$ is Me, $(R^{12})_n$ is 7-F-2-Me |
| 19 | X is O, $R^1$ is Me, $R^2$ is Me, $(R^{12})_n$ is 2,4,6-tri-Me |
| 20 | X is O, $R^1$ is Me, $R^2$ is Me, $(R^{12})_n$ is 2-Br-5-F |
| 21 | X is S, $R^1$ is Me, $R^2$ is Me, $(R^{12})_n$ is 2,5-di-Me |
| 22 | X is S, $R^1$ is Me, $R^2$ is Me, $(R^{12})_n$ is 2,5,7-tri-Me |
| 23 | X is S, $R^1$ is Me, $R^2$ is Me, $(R^{12})_n$ is 5-Cl-2-Me |
| 24 | X is S, $R^1$ is Me, $R^2$ is Me, $(R^{12})_n$ is 2-Br-5-Me |
| 25 | X is S, $R^1$ is Me, $R^2$ is Me, $(R^{12})_n$ is 5-Cl-2,7-di-Me |
| 26 | X is S, $R^1$ is Me, $R^2$ is Me, $(R^{12})_n$ is 2-Et-5-Me |
| 27 | X is S, $R^1$ is Me, $R^2$ is Me, $(R^{12})_n$ is 2-Me |
| 28 | X is S, $R^1$ is Me, $R^2$ is Me, $(R^{12})_n$ is 7-F-2-Me |
| 29 | X is S, $R^1$ is Me, $R^2$ is Me, $(R^{12})_n$ is 2,4,6-tri-Me |
| 30 | X is S, $R^1$ is Me, $R^2$ is Me, $(R^{12})_n$ is 2-Br-5-F |
| 31 | X is N—Me, $R^1$ is Me, $R^2$ is Me, $(R^{12})_n$ is 2,5-di-Me |
| 32 | X is N—Me, $R^1$ is Me, $R^2$ is Me, $(R^{12})_n$ is 2,5,7-tri-Me |
| 33 | X is N—Me, $R^1$ is Me, $R^2$ is Me, $(R^{12})_n$ is 5-Cl-2-Me |
| 34 | X is N—Me, $R^1$ is Me, $R^2$ is Me, $(R^{12})_n$ is 2-Br-5-Me |
| 35 | X is N—Me, $R^1$ is Me, $R^2$ is Me, $(R^{12})_n$ is 5-Cl-2,7-di-Me |
| 36 | X is N—Me, $R^1$ is Me, $R^2$ is Me, $(R^{12})_n$ is 2-Et-5-Me |
| 37 | X is N—Me, $R^1$ is Me, $R^2$ is Me, $(R^{12})_n$ is 2-Me |
| 38 | X is N—Me, $R^1$ is Me, $R^2$ is Me, $(R^{12})_n$ is 7-F-2-Me |
| 39 | X is N—Me, $R^1$ is Me, $R^2$ is Me, $(R^{12})_n$ is 2,4,6-tri-Me |
| 40 | X is N—Me, $R^1$ is Me, $R^2$ is Me, $(R^{12})_n$ is 2-Br-5-F |
| 41 | X is a direct bond, $R^1$ is Et, $R^2$ is Me, $(R^{12})_n$ is 2,5-di-Me |

-continued

| TABLE | Header Row Phrase |
|---|---|
| 42 | X is a direct bond, $R^1$ is Et, $R^2$ is Me, $(R^{12})_n$ is 2,5,7-tri-Me |
| 43 | X is a direct bond, $R^1$ is Et, $R^2$ is Me, $(R^{12})_n$ is 5-Cl-2-Me |
| 44 | X is a direct bond, $R^1$ is Et, $R^2$ is Me, $(R^{12})_n$ is 2-Br-5-Me |
| 45 | X is a direct bond, $R^1$ is Et, $R^2$ is Me, $(R^{12})_n$ is 5-Cl-2,7-di-Me |
| 46 | X is a direct bond, $R^1$ is Et, $R^2$ is Me, $(R^{12})_n$ is 2-Et-5-Me |
| 47 | X is a direct bond, $R^1$ is Et, $R^2$ is Me, $(R^{12})_n$ is 2-Me |
| 48 | X is a direct bond, $R^1$ is Et, $R^2$ is Me, $(R^{12})_n$ is 7-F-2-Me |
| 49 | X is a direct bond, $R^1$ is Et, $R^2$ is Me, $(R^{12})_n$ is 2,4,6-tri-Me |
| 50 | X is a direct bond, $R^1$ is Et, $R^2$ is Me, $(R^{12})_n$ is 2-Br-5-F |
| 51 | X is O, $R^1$ is Et, $R^2$ is Me, $(R^{12})_n$ is 2,5-di-Me |
| 52 | X is O, $R^1$ is Et, $R^2$ is Me, $(R^{12})_n$ is 2,5,7-tri-Me |
| 53 | X is O, $R^1$ is Et, $R^2$ is Me, $(R^{12})_n$ is 5-Cl-2-Me |
| 54 | X is O, $R^1$ is Et, $R^2$ is Me, $(R^{12})_n$ is 2-Br-5-Me |
| 55 | X is O, $R^1$ is Et, $R^2$ is Me, $(R^{12})_n$ is 5-Cl-2,7-di-Me |
| 56 | X is O, $R^1$ is Et, $R^2$ is Me, $(R^{12})_n$ is 2-Et-5-Me |
| 57 | X is O, $R^1$ is Et, $R^2$ is Me, $(R^{12})_n$ is 2-Me |
| 58 | X is O, $R^1$ is Et, $R^2$ is Me, $(R^{12})_n$ is 7-F-2-Me |
| 59 | X is O, $R^1$ is Et, $R^2$ is Me, $(R^{12})_n$ is 2,4,6-tri-Me |
| 60 | X is O, $R^1$ is Et, $R^2$ is Me, $(R^{12})_n$ is 2-Br-5-F |
| 61 | X is S, $R^1$ is Et, $R^2$ is Me, $(R^{12})_n$ is 2,5-di-Me |
| 62 | X is S, $R^1$ is Et, $R^2$ is Me, $(R^{12})_n$ is 2,5,7-tri-Me |
| 63 | X is S, $R^1$ is Et, $R^2$ is Me, $(R^{12})_n$ is 5-Cl-2-Me |
| 64 | X is S, $R^1$ is Et, $R^2$ is Me, $(R^{12})_n$ is 2-Br-5-Me |
| 65 | X is S, $R^1$ is Et, $R^2$ is Me, $(R^{12})_n$ is 5-Cl-2,7-di-Me |
| 66 | X is S, $R^1$ is Et, $R^2$ is Me, $(R^{12})_n$ is 2-Et-5-Me |
| 67 | X is S, $R^1$ is Et, $R^2$ is Me, $(R^{12})_n$ is 2-Me |
| 68 | X is S, $R^1$ is Et, $R^2$ is Me, $(R^{12})_n$ is 7-F-2-Me |
| 69 | X is S, $R^1$ is Et, $R^2$ is Me, $(R^{12})_n$ is 2,4,6-tri-Me |
| 70 | X is S, $R^1$ is Et, $R^2$ is Me, $(R^{12})_n$ is 2-Br-5-F |
| 71 | X is N—Me, $R^1$ is Et, $R^2$ is Me, $(R^{12})_n$ is 2,5-di-Me |
| 72 | X is N—Me, $R^1$ is Et, $R^2$ is Me, $(R^{12})_n$ is 2,5,7-tri-Me |
| 73 | X is N—Me, $R^1$ is Et, $R^2$ is Me, $(R^{12})_n$ is 5-Cl-2-Me |
| 74 | X is N—Me, $R^1$ is Et, $R^2$ is Me, $(R^{12})_n$ is 2-Br-5-Me |
| 75 | X is N—Me, $R^1$ is Et, $R^2$ is Me, $(R^{12})_n$ is 5-Cl-2,7-di-Me |
| 76 | X is N—Me, $R^1$ is Et, $R^2$ is Me, $(R^{12})_n$ is 2-Et-5-Me |
| 77 | X is N—Me, $R^1$ is Et, $R^2$ is Me, $(R^{12})_n$ is 2-Me |
| 78 | X is N—Me, $R^1$ is Et, $R^2$ is Me, $(R^{12})_n$ is 7-F-2-Me |
| 79 | X is N—Me, $R^1$ is Et, $R^2$ is Me, $(R^{12})_n$ is 2,4,6-tri-Me |
| 80 | X is N—Me, $R^1$ is Et, $R^2$ is Me, $(R^{12})_n$ is 2-Br-5-F |
| 81 | X is a direct bond, $R^1$ is Me, $R^2$ is Cl, $(R^{12})_n$ is 2,5-di-Me |
| 82 | X is a direct bond, $R^1$ is Me, $R^2$ is Cl, $(R^{12})_n$ is 2,5,7-tri-Me |
| 83 | X is a direct bond, $R^1$ is Me, $R^2$ is Cl, $(R^{12})_n$ is 5-Cl-2-Me |
| 84 | X is a direct bond, $R^1$ is Me, $R^2$ is Cl, $(R^{12})_n$ is 2-Br-5-Me |
| 85 | X is a direct bond, $R^1$ is Me, $R^2$ is Cl, $(R^{12})_n$ is 5-Cl-2,7-di-Me |
| 86 | X is a direct bond, $R^1$ is Me, $R^2$ is Cl, $(R^{12})_n$ is 2-Et-5-Me |
| 87 | X is a direct bond, $R^1$ is Me, $R^2$ is Cl, $(R^{12})_n$ is 2-Me |
| 88 | X is a direct bond, $R^1$ is Me, $R^2$ is Cl, $(R^{12})_n$ is 7-F-2-Me |

-continued

| TABLE | Header Row Phrase |
|---|---|
| 89 | X is a direct bond, $R^1$ is Me, $R^2$ is Cl, $(R^{12})_n$ is 2,4,6-tri-Me |
| 90 | X is a direct bond, $R^1$ is Me, $R^2$ is Cl, $(R^{12})_n$ is 2-Br-5-F |
| 91 | X is O, $R^1$ is Me, $R^2$ is Cl, $(R^{12})_n$ is 2,5-di-Me |
| 92 | X is O, $R^1$ is Me, $R^2$ is Cl, $(R^{12})_n$ is 2,5,7-tri-Me |
| 93 | X is O, $R^1$ is Me, $R^2$ is Cl, $(R^{12})_n$ is 5-Cl-2-Me |
| 94 | X is O, $R^1$ is Me, $R^2$ is Cl, $(R^{12})_n$ is 2-Br-5-Me |
| 95 | X is O, $R^1$ is Me, $R^2$ is Cl, $(R^{12})_n$ is 5-Cl-2,7-di-Me |
| 96 | X is O, $R^1$ is Me, $R^2$ is Cl, $(R^{12})_n$ is 2-Et-5-Me |
| 97 | X is O, $R^1$ is Me, $R^2$ is Cl, $(R^{12})_n$ is 2-Me |
| 98 | X is O, $R^1$ is Me, $R^2$ is Cl, $(R^{12})_n$ is 7-F-2-Me |
| 99 | X is O, $R^1$ is Me, $R^2$ is Cl, $(R^{12})_n$ is 2,4,6-tri-Me |
| 100 | X is O, $R^1$ is Me, $R^2$ is Cl, $(R^{12})_n$ is 2-Br-5-F |
| 101 | X is S, $R^1$ is Me, $R^2$ is Cl, $(R^{12})_n$ is 2,5-di-Me |
| 102 | X is S, $R^1$ is Me, $R^2$ is Cl, $(R^{12})_n$ is 2,5,7-tri-Me |
| 103 | X is S, $R^1$ is Me, $R^2$ is Cl, $(R^{12})_n$ is 5-Cl-2-Me |
| 104 | X is S, $R^1$ is Me, $R^2$ is Cl, $(R^{12})_n$ is 2-Br-5-Me |
| 105 | X is S, $R^1$ is Me, $R^2$ is Cl, $(R^{12})_n$ is 5-Cl-2,7-di-Me |
| 106 | X is S, $R^1$ is Me, $R^2$ is Cl, $(R^{12})_n$ is 2-Et-5-Me |
| 107 | X is S, $R^1$ is Me, $R^2$ is Cl, $(R^{12})_n$ is 2-Me |
| 108 | X is S, $R^1$ is Me, $R^2$ is Cl, $(R^{12})_n$ is 7-F-2-Me |
| 109 | X is S, $R^1$ is Me, $R^2$ is Cl, $(R^{12})_n$ is 2,4,6-tri-Me |
| 110 | X is S, $R^1$ is Me, $R^2$ is Cl, $(R^{12})_n$ is 2-Br-5-F |
| 111 | X is N—Me, $R^1$ is Me, $R^2$ is Cl, $(R^{12})_n$ is 2,5-di-Me |
| 112 | X is N—Me, $R^1$ is Me, $R^2$ is Cl, $(R^{12})_n$ is 2,5,7-tri-Me |
| 113 | X is N—Me, $R^1$ is Me, $R^2$ is Cl, $(R^{12})_n$ is 5-Cl-2-Me |
| 114 | X is N—Me, $R^1$ is Me, $R^2$ is Cl, $(R^{12})_n$ is 2-Br-5-Me |
| 115 | X is N—Me, $R^1$ is Me, $R^2$ is Cl, $(R^{12})_n$ is 5-Cl-2,7-di-Me |
| 116 | X is N—Me, $R^1$ is Me, $R^2$ is Cl, $(R^{12})_n$ is 2-Et-5-Me |
| 117 | X is N—Me, $R^1$ is Me, $R^2$ is Cl, $(R^{12})_n$ is 2-Me |
| 118 | X is N—Me, $R^1$ is Me, $R^2$ is Cl, $(R^{12})_n$ is 7-F-2-Me |
| 119 | X is N—Me, $R^1$ is Me, $R^2$ is Cl, $(R^{12})_n$ is 2,4,6-tri-Me |
| 120 | X is N—Me, $R^1$ is Me, $R^2$ is Cl, $(R^{12})_n$ is 2-Br-5-F |
| 121 | X is a direct bond, $R^1$ is Et, $R^2$ is Cl, $(R^{12})_n$ is 2,5-di-Me |
| 122 | X is a direct bond, $R^1$ is Et, $R^2$ is Cl, $(R^{12})_n$ is 2,5,7-tri-Me |
| 123 | X is a direct bond, $R^1$ is Et, $R^2$ is Cl, $(R^{12})_n$ is 5-Cl-2-Me |
| 124 | X is a direct bond, $R^1$ is Et, $R^2$ is Cl, $(R^{12})_n$ is 2-Br-5-Me |
| 125 | X is a direct bond, $R^1$ is Et, $R^2$ is Cl, $(R^{12})_n$ is 5-Cl-2,7-di-Me |
| 126 | X is a direct bond, $R^1$ is Et, $R^2$ is Cl, $(R^{12})_n$ is 2-Et-5-Me |
| 127 | X is a direct bond, $R^1$ is Et, $R^2$ is Cl, $(R^{12})_n$ is 2-Me |
| 128 | X is a direct bond, $R^1$ is Et, $R^2$ is Cl, $(R^{12})_n$ is 7-F-2-Me |
| 129 | X is a direct bond, $R^1$ is Et, $R^2$ is Cl, $(R^{12})_n$ is 2,4,6-tri-Me |
| 130 | X is a direct bond, $R^1$ is Et, $R^2$ is Cl, $(R^{12})_n$ is 2-Br-5-F |
| 131 | X is O, $R^1$ is Et, $R^2$ is Cl, $(R^{12})_n$ is 2,5-di-Me |
| 132 | X is O, $R^1$ is Et, $R^2$ is Cl, $(R^{12})_n$ is 2,5,7-tri-Me |
| 133 | X is O, $R^1$ is Et, $R^2$ is Cl, $(R^{12})_n$ is 5-Cl-2-Me |
| 134 | X is O, $R^1$ is Et, $R^2$ is Cl, $(R^{12})_n$ is 2-Br-5-Me |
| 135 | X is O, $R^1$ is Et, $R^2$ is Cl, $(R^{12})_n$ is 5-Cl-2,7-di-Me |
| 136 | X is O, $R^1$ is Et, $R^2$ is Cl, $(R^{12})_n$ is 2-Et-5-Me |
| 137 | X is O, $R^1$ is Et, $R^2$ is Cl, $(R^{12})_n$ is 2-Me |
| 138 | X is O, $R^1$ is Et, $R^2$ is Cl, $(R^{12})_n$ is 7-F-2-Me |
| 139 | X is O, $R^1$ is Et, $R^2$ is Cl, $(R^{12})_n$ is 2,4,6-tri-Me |
| 140 | X is O, $R^1$ is Et, $R^2$ is Cl, $(R^{12})_n$ is 2-Br-5-F |
| 141 | X is S, $R^1$ is Et, $R^2$ is Cl, $(R^{12})_n$ is 2,5-di-Me |
| 142 | X is S, $R^1$ is Et, $R^2$ is Cl, $(R^{12})_n$ is 2,5,7-tri-Me |
| 143 | X is S, $R^1$ is Et, $R^2$ is Cl, $(R^{12})_n$ is 5-Cl-2-Me |
| 144 | X is S, $R^1$ is Et, $R^2$ is Cl, $(R^{12})_n$ is 2-Br-5-Me |
| 145 | X is S, $R^1$ is Et, $R^2$ is Cl, $(R^{12})_n$ is 5-Cl-2,7-di-Me |
| 146 | X is S, $R^1$ is Et, $R^2$ is Cl, $(R^{12})_n$ is 2-Et-5-Me |
| 147 | X is S, $R^1$ is Et, $R^2$ is Cl, $(R^{12})_n$is 2-Me |
| 148 | X is S, $R^1$ is Et, $R^2$ is Cl, $(R^{12})_n$ is 7-F-2-Me |
| 149 | X is S, $R^1$ is Et, $R^2$ is Cl, $(R^{12})_n$ is 2,4,6-tri-Me |
| 150 | X is S, $R^1$ is Et, $R^2$ is Cl, $(R^{12})_n$ is 2-Br-5-F |
| 151 | X is N—Me, $R^1$ is Et, $R^2$ is Cl, $(R^{12})_n$ is 2,5-di-Me |
| 152 | X is N—Me, $R^1$ is Et, $R^2$ is Cl, $(R^{12})_n$ is 2,5,7-tri-Me |
| 153 | X is N—Me, $R^1$ is Et, $R^2$ is Cl, $(R^{12})_n$ is 5-Cl-2-Me |
| 154 | X is N—Me, $R^1$ is Et, $R^2$ is Cl, $(R^{12})_n$ is 2-Br-5-Me |
| 155 | X is N—Me, $R^1$ is Et, $R^2$ is Cl, $(R^{12})_n$ is 5-Cl-2,7-di-Me |
| 156 | X is N—Me, $R^1$ is Et, $R^2$ is Cl, $(R^{12})_n$ is 2-Et-5-Me |
| 157 | X is N—Me, $R^1$ is Et, $R^2$ is Cl, $(R^{12})_n$ is 2-Me |
| 158 | X is N—Me, $R^1$ is Et, $R^2$ is Cl, $(R^{12})_n$ is 7-F-2-Me |
| 159 | X is N—Me, $R^1$ is Et, $R^2$ is Cl, $(R^{12})_n$ is 2,4,6-tri-Me |
| 160 | X is N—Me, $R^1$ is Et, $R^2$ is Cl, $(R^{12})_n$ is 2-Br-5-F |

TABLE 161

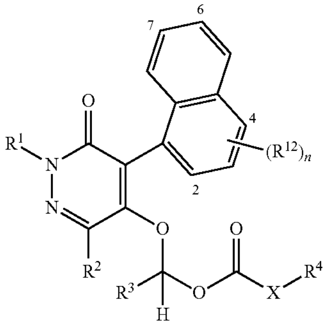

Header Row Phase: X is a direct bond, $R^1$ is Me, $R^2$ is Me, $(R^{12})_n$ is H; The remaining variables (i.e. $R^3$ and $R^4$) are defined in TABLE 1.

| TABLE | Header Row Phrase |
|---|---|
| 162 | X is a direct bond, $R^1$ is Me, $R^2$ is Me, $(R^{12})_n$ is 2-Me |
| 163 | X is a direct bond, $R^1$ is Me, $R^2$ is Me, $(R^{12})_n$ is 2-Cl |
| 164 | X is a direct bond, $R^1$ is Me, $R^2$ is Me, $(R^{12})_n$ is $OCF_2H$ |
| 165 | X is a direct bond, $R^1$ is Me, $R^2$ is Me, $(R^{12})_n$ is 2,7-di-Cl |
| 166 | X is a direct bond, $R^1$ is Me, $R^2$ is Me, $(R^{12})_n$ is 2-Cl-7-F |
| 167 | X is a direct bond, $R^1$ is Me, $R^2$ is Me, $(R^{12})_n$ is 7-Cl-2-Me |
| 168 | X is a direct bond, $R^1$ is Me, $R^2$ is Me, $(R^{12})_n$ is 4-Cl-2-Me |
| 169 | X is a direct bond, $R^1$ is Me, $R^2$ is Me, $(R^{12})_n$ is 2,7-di-Me |
| 170 | X is a direct bond, $R^1$ is Me, $R^2$ is Me, $(R^{12})_n$ is 7-F-2-Me |
| 171 | X is a direct bond, $R^1$ is Me, $R^2$ is Me, $(R^{12})_n$ is 4-Cl-7-F-2-Me |
| 172 | X is a direct bond, $R^1$ is Me, $R^2$ is Me, $(R^{12})_n$ is 2,4-di-Me |
| 173 | X is a direct bond, $R^1$ is Me, $R^2$ is Me, $(R^{12})_n$ is 4-F |
| 174 | X is a direct bond, $R^1$ is Me, $R^2$ is Me, $(R^{12})_n$ is 2-Et-7-Me |
| 175 | X is O, $R^1$ is Me, $R^2$ is Me, $(R^{12})_n$ is H |
| 176 | X is O, $R^1$ is Me, $R^2$ is Me, $(R^{12})_n$ is 2-Me |
| 177 | X is O, $R^1$ is Me, $R^2$ is Me, $(R^{12})_n$ is 2-Cl |
| 178 | X is O, $R^1$ is Me, $R^2$ is Me, $(R^{12})_n$ is $OCF_2H$ |
| 179 | X is O, $R^1$ is Me, $R^2$ is Me, $(R^{12})_n$ is 2,7-di-Cl |
| 180 | X is O, $R^1R^1$ is Me, $R^2$ is Me, $(R^{12})_n$ is 2-Cl-7-F |
| 181 | X is O, $R^1$ is Me, $R^2$ is Me, $(R^{12})_n$ is 7-Cl-2-Me |
| 182 | X is O, $R^1$ is Me, $R^2$ is Me, $(R^{12})_n$ is 4-Cl-2-Me |
| 183 | X is O, $R^1$ is Me, $R^2R^2$ is Me, $(R^{12})_n$ is 2,7-di-Me |
| 184 | X is O, $R^1$ is Me, $R^2$ is Me, $(R^{12})_n$ is 7-F-2-Me |
| 185 | X is O, $R^1$ is Me, $R^2$ is Me, $(R^{12})_n$ is 4-Cl-7-F-2-Me |
| 186 | X is O, $R^1$ is Me, $R^2$ is Me, $(R^{12})_n$ is 2,4-di-Me |
| 187 | X is O, $R^1$ is Me, $R^2$ is Me, $(R^{12})_n$ is 4-F |
| 188 | X is O, $R^1$ is Me, $R^2$ is Me, $(R^{12})_n$ is 2-Et-7-Me |
| 189 | X is S, $R^1$ is Me, $R^2$ is Me, $(R^{12})_n$ is H |
| 190 | X is S, $R^1$ is Me, $R^2$ is Me, $(R^{12})_n$ is 2-Me |
| 191 | X is S, $R^1$ is Me, $R^2$ is Me, $(R^{12})_n$ is 2-Cl |
| 192 | X is S, $R^1$ is Me, $R^2$ is Me, $(R^{12})_n$ is $OCF_2H$ |
| 193 | X is S, $R^1$ is Me, $R^2$ is Me, $(R^{12})_n$ is 2,7-di-Cl |
| 194 | X is S, $R^1$ is Me, $R^2$ is Me, $(R^{12})_n$ is 2-Cl-7-F |
| 195 | X is S, $R^1$ is Me, $R^2$ is Me, $(R^{12})_n$ is 7-Cl-2-Me |
| 196 | X is S, $R^1$ is Me, $R^2$ is Me, $(R^{12})_n$ is 4-Cl-2-Me |
| 197 | X is S, $R^1$ is Me, $R^2$ is Me, $(R^{12})_n$ is 2,7-di-Me |
| 198 | X is S, $R^1$ is Me, $R^2$ is Me, $(R^{12})_n$ is 7-F-2-Me |
| 199 | Xi s S, $R^1$ is Me, $R^2$ is Me, $(R^{12})_n$ is 4-Cl-7-F-2-Me |
| 200 | X is S, $R^1$ is Me, $R^2$ is Me, $(R^{12})_n$ is 2,4-di-Me |
| 201 | X is S, $R^1$ is Me, $R^2$ is Me, $(R^{12})_n$ is 4-F |
| 202 | X is S, $R^1$ is Me, $R^2$ is Me, $(R^{12})_n$ is 2-Et-7-Me |
| 203 | X is N-Me, $R^1$ is Me, $R^2$ is Me, $(R^{12})_n$ is H |
| 204 | X is N-Me, $R^1$ is Me, $R^2$ is Me, $(R^{12})_n$ is 2-Me |
| 205 | X is N-Me, $R^1$ is Me, $R^2$ is Me, $(R^{12})_n$ is 2-Cl |
| 206 | X is N-Me, $R^1$ is Me, $R^2$ is Me, $(R^{12})_n$ is $OCF_2H$ |
| 207 | X is N-Me, $R^1$ is Me, $R^2$ is Me, $(R^{12})_n$ is 2,7-di-Cl |
| 208 | X is N-Me, $R^1$ is Me, $R^2$ is Me, $(R^{12})_n$ is 2-Cl-7-F |
| 209 | X is N-Me, $R^1$ is Me, $R^2$ is Me, $(R^{12})_n$ is 7-Cl-2-Me |
| 210 | X is N-Me, $R^1$ is Me, $R^2$ is Me, $(R^{12})_n$ is 4-Cl-2-Me |
| 211 | X is N-Me, $R^1$ is Me, $R^2$ is Me, $(R^{12})_n$ is 2,7-di-Me |
| 212 | X is N-Me, $R^1$ is Me, $R^2$ is Me, $(R^{12})_n$ is 7-F-2-Me |
| 213 | X is N-Me, $R^1$ is Me, $R^2$ is Me, $(R^{12})_n$ is 4-Cl-7-F-2-Me |
| 214 | X is N-Me, $R^1$ is Me, $R^2$ is Me, $(R^{12})_n$ is 2,4-di-Me |
| 215 | X is N-Me, $R^1$ is Me, $R^2$ is Me, $(R^{12})_n$ is 4-F |

TABLE 161-continued

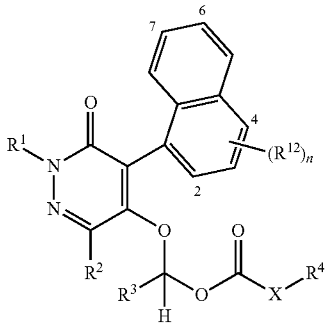

Header Row Phase: X is a direct bond,
$R^1$ is Me, $R^2$ is Me, $(R^{12})_n$ is H;
The remaining variables (i.e. $R^3$ and $R^4$)
are defined in TABLE 1.

| TABLE | Header Row Phrase |
|---|---|
| 216 | X is N-Me, $R^1$ is Me, $R^2$ is Me, $(R^{12})_n$ is 2-Et-7-Me |
| 217 | X is a direct bond, $R^1$ is Et, $R^2$ is Me, $(R^{12})_n$ is H |
| 218 | X is a direct bond, $R^1$ is Et, $R^2$ is Me, $(R^{12})_n$ is 2-Me |
| 219 | X is a direct bond, $R^1$ is Et, $R^2$ is Me, $(R^{12})_n$, is 2-Cl |
| 220 | X is a direct bond, $R^1$ is Et, $R^2$ is Me, $(R^{12})_n$, is $OCF_2H$ |
| 221 | X is a direct bond, $R^1$ is Et, $R^2$ is Me, $(R^{12})_n$ is 2,7-di-Cl |
| 222 | X is a direct bond, $R^1$ is Et, $R^2$ is Me, $(R^{12})_n$ is 2-Cl-7-F |
| 223 | X is a direct bond, $R^1$ is Et, $R^2$ is Me, $(R^{12})_n$ is 7-Cl-2-Me |
| 224 | X is a direct bond, $R^1$ is Et, $R^2$ is Me, $(R^{12})_n$ is 4-Cl-2-Me |
| 225 | X is a direct bond, $R^1$ is Et, $R^2$ is Me, $(R^{12})_n$ is 2,7-di-Me |
| 226 | X is a direct bond, $R^1$ is Et, $R^2$ is Me, $(R^{12})_n$ is 7-F-2-Me |
| 227 | X is a direct bond, $R^1$ is Et, $R^2$ is Me, $(R^{12})_n$ is 4-Cl-7-F-2-Me |
| 228 | X is a direct bond, $R^1$ is Et, $R^2$ is Me, $(R^{12})_n$ is 2,4-di-Me |
| 229 | X is a direct bond, $R^1$ is Et, $R^2$ is Me, $(R^{12})_n$ is 4-F |
| 230 | X is a direct bond, $R^1$ is Et, $R^2$ is Me, $(R^{12})_n$ is 2-Et-7-Me |
| 231 | X is O, $R^1$ is Et, $R^2$ is Me, $(R^{12})_n$ is H |
| 232 | X is O, $R^1$ is Et, $R^2$ is Me, $(R^{12})_n$ is 2-Me |
| 233 | X is O, $R^1$ is Et, $R^2$ is Me, $(R^{12})_n$ is 2-Cl |
| 234 | X is O, $R^1$ is Et, $R^2$ is Me, $(R^{12})_n$ is $OCF_2H$ |
| 235 | X is O, $R^1$ is Et, $R^2$ is Me, $(R^{12})_n$ is 2,7-di-Cl |
| 236 | X is O, $R^1$ is Et, $R^2$ is Me, $(R^{12})_n$ is 2-Cl-7-F |
| 237 | X is O, $R^1$ is Et, $R^2$ is Me, $(R^{12})_n$ is 7-Cl-2-Me |
| 238 | X is O, $R^1$ is Et, $R^2$ is Me, $(R^{12})_n$ is 4-Cl-2-Me |
| 239 | X is O, $R^1$ is Et, $R^2$ is Me, $(R^{12})_n$ is 2,7-di-Me |
| 240 | X is O, $R^1$ is Et, $R^2$ is Me, $(R^{12})_n$ is 7-F-2-Me |
| 241 | X is O, $R^1$ is Et, $R^2$ is Me, $(R^{12})_n$ is 4-Cl-7-F-2-Me |
| 242 | X is O, $R^1$ is Et, $R^2$ is Me, $(R^{12})_n$ is 2,4-di-Me |
| 243 | X is O, $R^1$ is Et, $R^2$ is Me, $(R^{12})_n$ is 4-F |
| 244 | X is O, $R^1$ is Et, $R^2$ is Me, $(R^{12})_n$ is 2-Et-7-Me |
| 245 | X is S, $R^1$ is Et, $R^2$ is Me, $(R^{12})_n$ is H |
| 246 | X is S, $R^1$ is Et, $R^2$ is Me, $(R^{12})_n$ is 2-Me |
| 247 | X is S, $R^1$ is Et, $R^2$ is Me, $(R^{12})_n$ is 2-Cl |
| 248 | X is S, $R^1$ is Et, $R^2$ is Me, $(R^{12})_n$ is $OCF_2H$ |
| 249 | X is S, $R^1$ is Et, $R^2$ is Me, $(R^{12})_n$ is 2,7-di-Cl |
| 250 | X is S, $R^1$ is Et, $R^2$ is Me, $(R^{12})_n$ is 2-Cl-7-F |
| 251 | X is S, $R^1$ is Et, $R^2$ is Me, $(R^{12})_n$ is 7-Cl-2-Me |
| 252 | X is S, $R^1$ is Et, $R^2$ is Me, $(R^{12})_n$ is 4-Cl-2-Me |
| 253 | X is S, $R^1$ is Et, $R^2$ is Me, $(R^{12})_n$ is 2,7-di-Me |
| 254 | Xi s S, $R^1$ is Et, $R^2$ is Me, $(R^{12})_n$ is 7-F-2-Me |
| 255 | X is S, $R^1$ is Et, $R^2$ is Me, $(R^{12})_n$ is 4-Cl-7-F-2-Me |
| 256 | X is S, $R^1$ is Et, $R^2$ is Me, $(R^{12})_n$ is 2,4-di-Me |
| 257 | X is S, $R^1$ is Et, $R^2$ is Me, $(R^{12})_n$ is 4-F |
| 258 | X is S, $R^1$ is Et, $R^2$ is Me, $(R^{12})_n$ is 2-Et-7-Me |
| 259 | X is N-Me, $R^1$ is Et, $R^2$ is Me, $(R^{12})_n$ is H |
| 260 | X is N-Me, $R^1$ is Et, $R^2$ is Me, $(R^{12})_n$ is 2-Me |
| 261 | X is N-Me, $R^1$ is Et, $R^2$ is Me, $(R^{12})_n$ is 2-Cl |
| 262 | X is N-Me, $R^1$ is Et, $R^2$ is Me, $(R^{12})_n$ is OCF2H |
| 263 | X is N-Me, $R^1$ is Et, $R^2$ is Me, $(R^{12})_n$ is 2,7-di-Cl |
| 264 | X is N-Me, $R^1$ is Et, $R^2$ is Me, $(R^{12})_n$ is 2-Cl-7-F |
| 265 | X is N-Me, $R^1$ is Et, $R^2$ is Me, $(R^{12})_n$ is 7-Cl-2-Me |

TABLE 161-continued

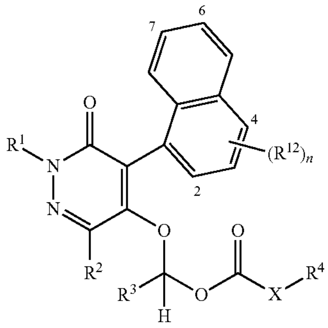

Header Row Phase: X is a direct bond,
$R^1$ is Me, $R^2$ is Me, $(R^{12})_n$ is H;
The remaining variables (i.e. $R^3$ and $R^4$)
are defined in TABLE 1.

| TABLE | Header Row Phrase |
|---|---|
| 266 | X is N-Me, $R^1$ is Et, $R^2$ is Me, $(R^{12})_n$ is 4-Cl-2-Me |
| 267 | X is N-Me, $R^1$ is Et, $R^2$ is Me, $(R^{12})_n$ is 2,7-di-Me |
| 268 | X is N-Me, $R^1$ is Et, $R^2$ is Me, $(R^{12})_n$ is 7-F-2-Me |
| 269 | X is N-Me, $R^1$ is Et, $R^2$ is Me, $(R^{12})_n$ is 4-Cl-7-F-2-Me |
| 270 | X is N-Me, $R^1$ is Et, $R^2$ is Me, $(R^{12})_n$ is 2,4-di-Me |
| 271 | X is N-Me, $R^1$ is Et, $R^2$ is Me, $(R^{12})_n$ is 4-F |
| 272 | X is N-Me, $R^1$ is Et, $R^2$ is Me, $(R^{12})_n$ is 2-Et-7-Me |
| 273 | X is a direct bond, $R^1$ is Me, $R^2$ is Cl, $(R^{12})_n$ is H |
| 274 | X is a direct bond, $R^1$ is Me, $R^2$ is Cl, $(R^{12})_n$ is 2-Me |
| 275 | X is a direct bond, $R^1$ is Me, $R^2$ is Cl, $(R^{12})_n$ is 2-Cl |
| 276 | X is a direct bond, $R^1$ is Me, $R^2$ is Cl, $(R^{12})_n$ is $OCF_2H$ |
| 277 | X is a direct bond, $R^1$ is Me, $R^2$ is Cl, $(R^{12})_n$ is 2,7-di-Cl |
| 278 | X is a direct bond, $R^1$ is Me, $R^2$ is Cl,$(R^{12})_n$ is 2-Cl-7-F |
| 279 | X is a direct bond, $R^1$ is Me, $R^2$ is Cl, $(R^{12})_n$ is 7-Cl-2-Me |
| 280 | X is a direct bond, $R^1$ is Me, $R^2$ is Cl, $(R^{12})_n$ is 4-Cl-2-Me |
| 281 | X is a direct bond, $R^1$ is Me, $R^2$ is Cl, $(R^{12})_n$ is 2,7-di-Me |
| 282 | X is a direct bond, $R^1$ is Me, $R^2$ is Cl, $(R^{12})_n$ is 7-F-2-Me |
| 283 | X is a direct bond, $R^1$ is Me, $R^2$ is Cl, $(R^{12})_n$ is 4-Cl-7-F-2-Me |
| 284 | X is a direct bond, $R^1$ is Me, $R^2$ is Cl, $(R^{12})_n$ is 2,4-di-Me |
| 285 | X is a direct bond, $R^1$ is Me, $R^2$ is Cl, $(R^{12})_n$ is 4-F |
| 286 | X is a direct bond, $R^1$ is Me, $R^2$ is Cl, $(R^{12})_n$ is 2-Et-7-Me |
| 287 | X is O, $R^1$ is Me, $R^2$ is Cl, $(R^{12})_n$ is H |
| 288 | X is O, $R^1$ is Me, $R^2$ is Cl, $(R^{12})_n$ is 2-Me |
| 289 | X is O, $R^1$ is Me, $R^2$ is Cl, $(R^{12})_n$ is 2-Cl |
| 290 | X is O, $R^1$ is Me, $R^2$ is Cl, $(R^{12})_n$ is $OCF_2H$ |
| 291 | X is O, $R^1$ is Me, $R^2$ is Cl, $(R^{12})_n$ is 2,7-di-Cl |
| 292 | X is O, $R^1$ is Me, $R^2$ is Cl, $(R^{12})_n$ is 2-Cl-7-F |
| 293 | X is O, $R^1$ is Me, $R^2$ is Cl, $(R^{12})_n$ is 7-Cl-2-Me |
| 294 | X is O, $R^1$ is Me, $R^2$ is Cl, $(R^{12})_n$ is 4-Cl-2-Me |
| 295 | X is O, $R^1$ is Me, $R^2$ is Cl, $(R^{12})_n$ is 2,7-di-Me |
| 296 | X is O, $R^1$ is Me, $R^2$ is Cl, $(R^{12})_n$ is 7-F-2-Me |
| 297 | X is O, $R^1$ is Me, $R^2$ is Cl, $(R^{12})_n$ is 4-Cl-7-F-2-Me |
| 298 | X is O, $R^1$ is Me, $R^2$ is Cl, $(R^{12})_n$ is 2,4-di-Me |
| 299 | X is O, $R^1$ is Me, $R^2$ is Cl, $(R^{12})_n$ is 4-F |
| 300 | X is O, $R^1$ is Me, $R^2$ is Cl, $(R^{12})_n$ is 2-Et-7-Me |
| 301 | X is S, $R^1$ is Me, $R^2$ is Cl, $(R^{12})_n$ is H |
| 302 | X is S, $R^1$ is Me, $R^2$ is Cl, $(R^{12})_n$, is 2-Me |
| 303 | X is S, $R^1$ is Me, $R^2$ is Cl, $(R^{12})_n$ is 2-Cl |
| 304 | X is S, $R^1$ is Me, $R^2$ is Cl, $(R^{12})_n$ is $OCF_2H$ |
| 305 | X is S, $R^1$ is Me, $R^2$ is Cl, $(R^{12})_n$is 2,7-di-Cl |
| 306 | X is S, $R^1$ is Me, $R^2$ is Cl, $(R^{12})_n$ is 2-Cl-7-F |
| 307 | X is S, $R^1$ is Me, $R^2$ is Cl, $(R^{12})_n$ is 7-Cl-2-Me |
| 308 | X is S, $R^1$ is Me, $R^2$ is Cl, $(R^{12})_n$ is 4-Cl-2-Me |
| 309 | X is S, $R^1$ is Me, $R^2$ is Cl, $(R^{12})_n$ is 2,7-di-Me |
| 310 | X is S, $R^1$ is Me, $R^2$ is Cl, $(R^{12})_n$ is 7-F-2-Me |
| 311 | X is S, $R^1$ is Me, $R^2$ is Cl, $(R^{12})_n$ is 4-Cl-7-F-2-Me |
| 312 | X is S, $R^1$ is Me, $R^2$ is Cl, $(R^{12})_n$ is 2,4-di-Me |
| 313 | X is S, $R^1$ is Me, $R^2$ is Cl, $(R^{12})_n$ is 4-F |
| 314 | X is S, $R^1$ is Me, $R^2$ is Cl, $(R^{12})_n$ is 2-Et-7-Me |
| 315 | X is N-Me, $R^1$ is Me,$R^2$ is Cl, $(R^{12})_n$ is H |

TABLE 161-continued

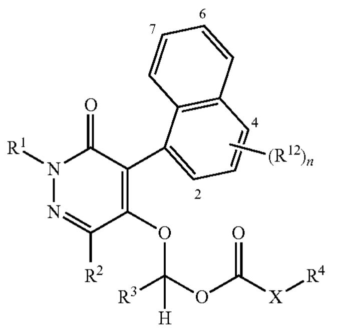

Header Row Phase: X is a direct bond, $R^1$ is Me, $R^2$ is Me, $(R^{12})_n$ is H; The remaining variables (i.e. $R^3$ and $R^4$) are defined in TABLE 1.

| TABLE | Header Row Phrase |
|---|---|
| 316 | X is N-Me, $R^1$ is Me, $R^2$ is Cl, $(R^{12})_n$ is 2-Me |
| 317 | X is N-Me, $R^1$ is Me, $R^2$ is Cl, $(R^{12})_n$ is 2-Cl |
| 318 | X is N-Me, $R^1$ is Me, $R^2$ is Cl, $(R^{12})_n$ is $OCF_2H$ |
| 319 | X is N-Me, $R^1$ is Me, $R^2$ is Cl, $(R^{12})_n$, is 2,7-di-Cl |
| 320 | X is N-Me, $R^1$ is Me, $R^2$ is Cl, $(R^{12})_n$, is 2-Cl-7-F |
| 321 | X is N-Me, $R^1$ is Me, $R^2$ is Cl, $(R^{12})_n$ is 7-Cl-2-Me |
| 322 | X is N-Me, $R^1$ is Me, $R^2$ is Cl, $(R^{12})_n$ is 4-Cl-2-Me |
| 323 | X is N-Me, $R^1$ is Me, $R^2$ is Cl, $(R^{12})_n$ is 2,7-di-Me |
| 324 | X is N-Me, $R^1$ is Me, $R^2$ is Cl, $(R^{12})_n$ is 7-F-2-Me |
| 325 | X is N-Me, $R^1$ is Me, $R^2$ is Cl, $(R^{12})_n$ is 4-Cl-7-F-2-Me |
| 326 | X is N-Me, $R^1$ is Me, $R^2$ is Cl, $(R^{12})_n$ is 2,4-di-Me |
| 327 | X is N-Me, $R^1$ is Me, $R^2$ is Cl, $(R^{12})_n$ is 4-F |
| 328 | X is N-Me, $R^1$ is Me, $R^2$ is Cl, $(R^{12})_n$ is 2-Et-7-Me |
| 329 | X is a direct bond, $R^1$ is Et, $R^2$ is Cl, $(R^{12})_n$ is H |
| 330 | X is a direct bond, $R^1$ is Et, $R^2$ is Cl, $(R^{12})_n$ is 2-Me |
| 331 | X is a direct bond, $R^1$ is Et, $R^2$ is Cl, $(R^{12})_n$ is 2-Cl |
| 332 | X is a direct bond, $R^1$ is Et, $R^2$ is Cl, $(R^{12})_n$ is $OCF_2H$ |
| 333 | X is a direct bond, $R^1$ is Et, $R^2$ is Cl, $(R^{12})_n$ is 2,7-di-Cl |
| 334 | X is a direct bond, $R^1$ is Et, $R^2$ is Cl, $(R^{12})_n$ is 2-Cl-7-F |
| 335 | X is a direct bond, $R^1$ is Et, $R^2$ is Cl, $(R^{12})_n$ is 7-Cl-2-Me |
| 336 | X is a direct bond, $R^1$ is Et, $R^2$ is Cl, $(R^{12})_n$ is 4-Cl-2-Me |
| 337 | X is a direct bond, $R^1$ is Et, $R^2$ is Cl, $(R^{12})_n$ is 2,7-di-Me |
| 338 | X is a direct bond, $R^1$ is Et, $R^2$ is Cl, $(R^{12})_n$ is 7-F-2-Me |
| 339 | X is a direct bond, $R^1$ is Et, $R^2$ is Cl, $(R^{12})_n$ is 4-Cl-7-F-2-Me |
| 340 | X is a direct bond, $R^1$ is Et, $R^2$ is Cl, $(R^{12})_n$ is 2,4-di-Me |
| 341 | X is a direct bond, $R^1$ is Et, $R^2$ is Cl, $(R^{12})_n$ is 4-F |
| 342 | X is a direct bond, $R^1$ is Et, $R^2$ is Cl, $(R^{12})_n$ is 2-Et-7-Me |
| 343 | Xi s O, $R^1$ is Et, $R^2$ is Cl, $(R^{12})_n$ is H |
| 344 | X is O, $R^1$ is Et, $R^2$ is Cl, $(R^{12})_n$ is 2-Me |
| 345 | X is O, $R^1$ is Et, $R^2$ is Cl, $(R^{12})_n$ is 2-Cl |
| 346 | X is O, $R^1$ is Et, $R^2$ is Cl, $(R^{12})_n$ is $OCF_2H$ |
| 347 | X is O, $R^1$ is Et, $R^2$ is Cl, $(R^{12})_n$ is 2,7-di-Cl |
| 348 | X is O, $R^1$ is Et, $R^2$ is Cl, $(R^{12})_n$ is 2-Cl-7-F |
| 349 | X is O, $R^1$ is Et, $R^2$ is Cl, $(R^{12})_n$ is 7-Cl-2-Me |
| 350 | X is O, $R^1$ is Et, $R^2$ is Cl, $(R^{12})_n$ is 4-Cl-2-Me |
| 351 | X is O, $R^1$ is Et, $R^2$ is Cl, $(R^{12})_n$ is 2,7-di-Me |
| 352 | X is O, $R^1$ is Et, $R^2$ is Cl, $(R^{12})_n$ is 7-F-2-Me |
| 353 | X is O, $R^1$ is Et, $R^2$ is Cl, $(R^{12})_n$ is 4-Cl-7-F-2-Me |
| 354 | X is O, $R^1$ is Et, $R^2$ is Cl, $(R^{12})_n$ is 2,4-di-Me |
| 355 | X is O, $R^1$ is Et, $R^2$ is Cl, $(R^{12})_n$ is 4-F |
| 356 | X is O, $R^1$ is Et, $R^2$ is Cl, $(R^{12})_n$ is 2-Et-7-Me |
| 357 | X is S, $R^1$ is Et, $R^2$ is Cl, $(R^{12})_n$ is H |

TABLE 161-continued

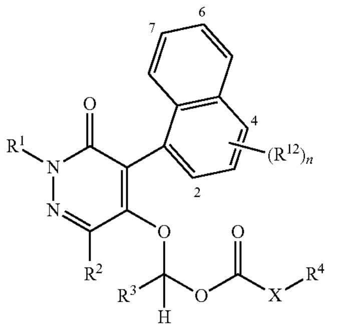

Header Row Phase: X is a direct bond, $R^1$ is Me, $R^2$ is Me, $(R^{12})_n$ is H; The remaining variables (i.e. $R^3$ and $R^4$) are defined in TABLE 1.

| TABLE | Header Row Phrase |
|---|---|
| 358 | X is S, $R^1$ is Et, $R^2$ is Cl, $(R^{12})_n$ is 2-Me |
| 359 | X is S, $R^1$ is Et, $R^2$ is Cl, $(R^{12})_n$ is 2-Cl |
| 360 | X is S, $R^1$ is Et, $R^2$ is Cl, $(R^{12})_n$ is $OCF_2H$ |
| 361 | X is S, $R^1$ is Et, $R^2$ is Cl, $(R^{12})_n$ is 2,7-di-Cl |
| 362 | X is S, $R^1$ is Et, $R^2$ is Cl, $(R^{12})_n$ is 2-Cl-7-F |
| 363 | X is S, $R^1$ is Et, $R^2$ is Cl, $(R^{12})_n$ is 7-Cl-2-Me |
| 364 | X is S, $R^1$ is Et, $R^2$ is Cl, $(R^{12})_n$ is 4-Cl-2-Me |
| 365 | X is S, $R^1$ is Et, $R^2$ is Cl, $(R^{12})_n$, is 2,7-di-Me |
| 366 | X is S, $R^1$ is Et, $R^2$ is Cl, $(R^{12})_n$ is 7-F-2-Me |
| 367 | X is S, $R^1$ is Et, $R^2$ is Cl, $(R^{12})_n$ is 4-Cl-7-F-2-Me |
| 368 | X is S, $R^1$ is Et, $R^2$ is Cl, $(R^{12})_n$ is 2,4-di-Me |
| 369 | X is S, $R^1$ is Et, $R^2$ is Cl, $(R^{12})_n$ is 4-F |
| 370 | X is S, $R^1$ is Et, $R^2$ is Cl, $(R^{12})_n$ is 2-Et-7-Me |
| 371 | X is N-Me, $R^1$ is Et, $R^2$ is Cl, $(R^{12})_n$ is H |
| 372 | X is N-Me, $R^1$ is Et, $R^2$ is Cl, $(R^{12})_n$ is 2-Me |
| 373 | X is N-Me, $R^1$ is Et, $R^2$ is Cl, $(R^{12})_n$ is 2-Cl |
| 374 | X is N-Me, $R^1$ is Et, $R^2$ is Cl, $(R^{12})_n$ is $OCF_2H$ |
| 375 | X is N-Me, $R^1$ is Et, $R^2$ is Cl, $(R^{12})_n$ is 2,7-di-Cl |
| 376 | X is N-Me, $R^1$ is Et, $R^2$ is Cl, $(R^{12})_n$ is 2-Cl-7-F |
| 377 | X is N-Me, $R^1$ is Et, $R^2$ is Cl, $(R^{12})_n$ is 7-Cl-2-Me |
| 378 | X is N-Me, $R^1$ is Et, $R^2$ is Cl, $(R^{12})_n$ is 4-Cl-2-Me |
| 379 | X is N-Me, $R^1$ is Et, $R^2$ is Cl, $(R^{12})_n$ is 2,7-di-Me |
| 380 | X is N-Me, $R^1$ is Et, $R^2$ is Cl, $(R^{12})_n$ is 7-F-2-Me |
| 381 | X is N-Me, $R^1$ is Et, $R^2$ is Cl, $(R^{12})_n$ is 4-Cl-7-F-2-Me |
| 382 | X is N-Me, $R^1$ is Et, $R^2$ is Cl, $(R^{12})_n$ is 2,4-di-Me |
| 383 | X is N-Me, $R^1$ is Et, $R^2$ is Cl, $(R^{12})_n$ is 4-F |
| 384 | X is N-Me, $R^1$ is Et, $R^2$ is Cl, $(R^{12})_n$ is 2-Et-7-Me |

This disclosure also includes TABLES 162 through 384 wherein the Header Row Phrase in TABLE 161 (i.e. "X is a direct bond, $R^1$ is Me, $R^2$ is Me, $(R^{12})_n$ is H") is replaced with the Header Row Phrase listed in the respective TABLE, and the remaining variables are as defined in TABLE 1.

TABLE 385

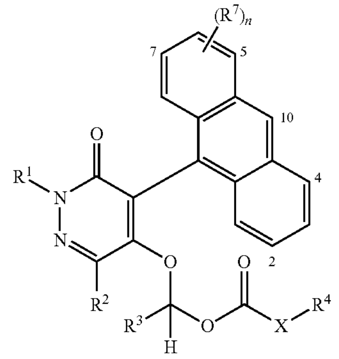

Header Row Phrase: X is a direct bond, $R^1$ is Me, $R^2$ is Me, $(R^{12})n$ is H; The remaining variables (i.e. $R^3$ and $R^4$) are as defined in TABLE 1.

| TABLE | Header Row Phrase |
|---|---|
| 386 | X is a direct bond, $R^1$ is Me, $R^2$ is Me, $(R^7)_n$, is 10-Br |
| 387 | X is a direct bond, $R^1$ is Me, $R^2$ is Me, $(R^7)_n$, is 10-Cl |
| 388 | X is a direct bond, $R^1$ is Me, $R^2$ is Me, $(R^7)_n$, is 10-Me |
| 389 | X is a direct bond, $R^1$ is Me, $R^2$ is Me, $(R^7)_n$, is 2-F |
| 390 | X is a direct bond, $R^1$ is Me, $R^2$ is Me, $(R^7)_n$, is 2-Cl |
| 391 | X is a direct bond, $R^1$ is Me, $R^2$ is Me, $(R^7)_n$, is 2-OMe |
| 392 | X is a direct bond, $R^1$ is Me, $R^2$ is Me, $(R^7)_n$, is 2-Me |
| 393 | X is a direct bond, $R^1$ is Me, $R^2$ is Me, $(R^7)_n$, is 2,4-di-Me |
| 394 | X is a direct bond, $R^1$ is Me, $R^2$ is Me, $(R^7)_n$, is 2-Cl-7-F |
| 395 | X is a direct bond, $R^1$ is Me, $R^2$ is Me, $(R^7)_n$, is 2-F-7-Me |
| 396 | X is a direct bond, $R^1$ is Me, $R^2$ is Me, $(R^7)_n$, is 2,7-di-Me |
| 397 | X is a direct bond, $R^1$ is Me, $R^2$ is Me, $(R^7)_n$, is 2,5-di-Cl |
| 398 | X is a direct bond, $R^1$ is Me, $R^2$ is Me, $(R^7)_n$, is 2-Cl-5-F |
| 399 | X is a direct bond, $R^1$ is Me, $R^2$ is Me, $(R^7)_n$, is 2,6-di-Cl-7-F |
| 400 | X is a direct bond, $R^1$ is Me, $R^2$ is Me, $(R^7)_n$, is 2-Cl-6,7-di-F |
| 401 | X is a direct bond, $R^1$ is Me, $R^2$ is Me, $(R^7)_n$, is 2,7-di-Cl-6-F |
| 402 | X is a direct bond, $R^1$ is Me, $R^2$ is Me, $(R^7)_n$, is 2-F-7-OMe |
| 403 | X is a direct bond, $R^1$ is Me, $R^2$ is Me, $(R^7)_n$, is 2-Cl-5,7-di-F |
| 404 | X is a direct bond, $R^1$ is Me, $R^2$ is Me, $(R^7)_n$, is 2,5-di-Cl-7-F |
| 405 | X is a direct bond, $R^1$ is Me, $R^2$ is Me, $(R^7)_n$, is 2,7-di-Cl-5-F |
| 406 | X is a direct bond, $R^1$ is Me, $R^2$ is Me, $(R^7)_n$, is 2-F-5,7-di-Me |
| 407 | X is a direct bond, $R^1$ is Me, $R^2$ is Me, $(R^7)_n$, is 2-F-5-Me |
| 408 | X is a direct bond, $R^1$ is Me, $R^2$ is Me, $(R^7)_n$, is 2-$OCF_2H$ |
| 409 | X is a direct bond, $R^1$ is Me, $R^2$ is Me, $(R^7)_n$, is 2-$OCF_2H$-7-Me |
| 410 | X is a direct bond, $R^1$ is Me, $R^2$ is Me, $(R^7)_n$, is 2-$OCF_2H$-7-F |
| 411 | X is a direct bond, $R^1$ is Me, $R^2$ is Me, $(R^7)_n$, is 2-$OCF_2H$-7-Cl |
| 412 | X is O, $R^1$ is Me, $R^2$ is Me, $(R^7)_n$, is H |
| 413 | X is O, $R^1$ is Me, $R^2$ is Me, $(R^7)_n$, is 10-Br |
| 414 | X is O, $R^1$ is Me, $R^2$ is Me, $(R^7)_n$, is 10-Cl |
| 415 | X is O, $R^1$ is Me, $R^2$ is Me, $(R^7)_n$, is 10-Me |
| 416 | X is O, $R^1$ is Me, $R^2$ is Me, $(R^7)_n$, is 2-F |
| 417 | X is O, $R^1$ is Me, $R^2$ is Me, $(R^7)_n$, is 2-Cl |
| 418 | X is O, $R^1$ is Me, $R^2$ is Me, $(R^7)_n$, is 2-OMe |
| 419 | X is O, $R^1$ is Me, $R^2$ is Me, $(R^7)_n$, is 2-Me |
| 420 | X is O, $R^1$ is Me, $R^2$ is Me, $(R^7)_n$, is 2,4-di-Me |
| 421 | X is O, $R^1$ is Me, $R^2$ is Me, $(R^7)_n$, is 2-Cl-7-F |
| 422 | X is O, $R^1$ is Me, $R^2$ is Me, $(R^7)_n$, is 2-F-7-Me |
| 423 | X is O, $R^1$ is Me, $R^2$ is Me, $(R^7)_n$, is 2,7-di-Me |
| 424 | X is O, $R^1$ is Me, $R^2$ is Me, $(R^7)_n$, is 2,5-di-Cl |
| 425 | X is O, $R^1$ is Me, $R^2$ is Me, $(R^7)_n$, is 2-Cl-5-F |
| 426 | X is O, $R^1$ is Me, $R^2$ is Me, $(R^7)_n$, is 2,6-di-Cl-7-F |
| 427 | X is O, $R^1$ is Me, $R^2$ is Me, $(R^7)_n$, is 2-Cl-6,7-di-F |
| 428 | X is O, $R^1$ is Me, $R^2$ is Me, $(R^7)_n$, is 2,7-di-Cl-6-F |
| 429 | X is O, $R^1$ is Me, $R^2$ is Me, $(R^7)_n$, is 2-F-7-OMe |
| 430 | X is O, $R^1$ is Me, $R^2$ is Me, $(R^7)_n$, is 2-Cl-5,7-di-F |
| 431 | X is O, $R^1$ is Me, $R^2$ is Me, $(R^7)_n$, is 2,5-di-Cl-7-F |
| 432 | X is O, $R^1$ is Me, $R^2$ is Me, $(R^7)_n$, is 2,7-di-Cl-5-F |
| 433 | X is O, $R^1$ is Me, $R^2$ is Me, $(R^7)_n$, is 2-F-5,7-di-Me |
| 434 | X is O, $R^1$ is Me, $R^2$ is Me, $(R^7)_n$, is 2-F-5-Me |
| 435 | X is O, $R^1$ is Me, $R^2$ is Me, $(R^7)_n$, is 2-$OCF_2H$ |
| 436 | X is O, $R^1$ is Me, $R^2$ is Me, $(R^7)_n$, is 2-$OCF_2H$-7-Me |
| 437 | X is O, $R^1$ is Me, $R^2$ is Me, $(R^7)_n$, is 2-$OCF_2H$-7-F |
| 438 | X is O, $R^1$ is Me, $R^2$ is Me, $(R^7)_n$, is 2-$OCF_2H$-7-Cl |
| 439 | X is S, $R^1$ is Me, $R^2$ is Me, $(R^7)_n$, is H |
| 440 | X is S, $R^1$ is Me, $R^2$ is Me, $(R^7)_n$, is 10-Br |
| 441 | X is S, $R^1$ is Me, $R^2$ is Me, $(R^7)_n$, is 10-Cl |
| 442 | X is S, $R^1$ is Me, $R^2$ is Me, $(R^7)_n$, is 10-Me |

TABLE 385-continued

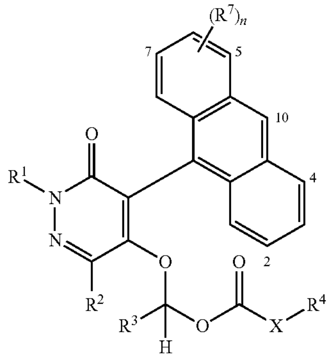

Header Row Phrase: X is a direct bond, $R^1$ is Me, $R^2$ is Me, $(R^{12})n$ is H; The remaining variables (i.e. $R^3$ and $R^4$) are as defined in TABLE 1.

| TABLE | Header Row Phrase |
|---|---|
| 443 | X is S, $R^1$ is Me, $R^2$ is Me, $(R^7)_n$, is 2-F |
| 444 | X is S, $R^1$ is Me, $R^2$ is Me, $(R^7)_n$, is 2-Cl |
| 445 | X is S, $R^1$ is Me, $R^2$ is Me, $(R^7)_n$, is 2-OMe |
| 446 | X is S, $R^1$ is Me, $R^2$ is Me, $(R^7)_n$, is 2-Me |
| 447 | X is S, $R^1$ is Me, $R^2$ is Me, $(R^7)_n$, is 2,4-di-Me |
| 448 | X is S, $R^1$ is Me, $R^2$ is Me, $(R^7)_n$, is 2-Cl-7-F |
| 449 | X is S, $R^1$ is Me, $R^2$ is Me, $(R^7)_n$, is 2-F-7-Me |
| 450 | X is S, $R^1$ is Me, $R^2$ is Me, $(R^7)_n$, is 2,7-di-Me |
| 451 | X is S, $R^1$ is Me, $R^2$ is Me, $(R^7)_n$, is 2,5-di-Cl |
| 452 | X is S, $R^1$ is Me, $R^2$ is Me, $(R^7)_n$, is 2-Cl-5-F |
| 453 | X is S, $R^1$ is Me, $R^2$ is Me, $(R^7)_n$, is 2,6-di-Cl-7-F |
| 454 | X is S, $R^1$ is Me, $R^2$ is Me, $(R^7)_n$, is 2-Cl-6,7-di-F |
| 455 | X is S, $R^1$ is Me, $R^2$ is Me, $(R^7)_n$, is 2,7-di-Cl-6-F |
| 456 | X is S, $R^1$ is Me, $R^2$ is Me, $(R^7)_n$, is 2-F-7-OMe |
| 457 | X is S, $R^1$ is Me, $R^2$ is Me, $(R^7)_n$, is 2-Cl-5,7-di-F |
| 458 | X is S, $R^1$ is Me, $R^2$ is Me, $(R^7)_n$, is 2,5-di-Cl-7-F |
| 459 | X is S, $R^1$ is Me, $R^2$ is Me, $(R^7)_n$, is 2,7-di-Cl-5-F |
| 460 | X is S, $R^1$ is Me, $R^2$ is Me, $(R^7)_n$, is 2-F-5,7-di-Me |
| 461 | X is S, $R^1$ is Me, $R^2$ is Me, $(R^7)_n$, is 2-F-5-Me |
| 462 | X is S, $R^1$ is Me, $R^2$ is Me, $(R^7)_n$, is 2-$OCF_2H$ |
| 463 | X is S, $R^1$ is Me, $R^2$ is Me, $(R^7)_n$, is 2-$OCF_2H$-7-Me |
| 464 | X is S, $R^1$ is Me, $R^2$ is Me, $(R^7)_n$, is 2-$OCF_2H$-7-F |
| 465 | X is S, $R^1$ is Me, $R^2$ is Me, $(R^7)_n$, is 2-$OCF_2H$-7-Cl |
| 466 | X is N-Me, $R^1$ is Me, $R^2$ is Me, $(R^7)_n$, is H |
| 467 | X is N-Me, $R^1$ is Me, $R^2$ is Me, $(R^7)_n$, is 10-Br |
| 468 | X is N-Me, $R^1$ is Me, $R^2$ is Me, $(R^7)_n$, is 10-Cl |
| 469 | X is N-Me, $R^1$ is Me, $R^2$ is Me, $(R^7)_n$, is 10-Me |
| 470 | X is N-Me, $R^1$ is Me, $R^2$ is Me, $(R^7)_n$, is 2-F |
| 471 | X is N-Me, $R^1$ is Me, $R^2$ is Me, $(R^7)_n$, is 2-Cl |
| 472 | X is N-Me, $R^1$ is Me, $R^2$ is Me, $(R^7)_n$, is 2-OMe |
| 473 | X is N-Me, $R^1$ is Me, $R^2$ is Me, $(R^7)_n$, is 2-Me |
| 474 | X is N-Me, $R^1$ is Me, $R^2$ is Me, $(R^7)_n$, is 2,4-di-Me |
| 475 | X is N-Me, $R^1$ is Me, $R^2$ is Me, $(R^7)_n$, is 2-Cl-7-F |
| 476 | X is N-Me, $R^1$ is Me, $R^2$ is Me, $(R^7)_n$, is 2-F-7-Me |
| 477 | X is N-Me, $R^1$ is Me, $R^2$ is Me, $(R^7)_n$, is 2,7-di-Me |
| 478 | X is N-Me, $R^1$ is Me, $R^2$ is Me, $(R^7)_n$, is 2,5-di-Cl |
| 479 | X is N-Me, $R^1$ is Me, $R^2$ is Me, $(R^7)_n$, is 2-Cl-5-F |
| 480 | X is N-Me, $R^1$ is Me, $R^2$ is Me, $(R^7)_n$, is 2,6-di-Cl-7-F |
| 481 | X is N-Me, $R^1$ is Me, $R^2$ is Me, $(R^7)_n$, is 2-Cl-6,7-di-F |
| 482 | X is N-Me, $R^1$ is Me, $R^2$ is Me, $(R^7)_n$, is 2,7-di-Cl-6-F |
| 483 | X is N-Me, $R^1$ is Me, $R^2$ is Me, $(R^7)_n$, is 2-F-7-OMe |
| 484 | X is N-Me, $R^1$ is Me, $R^2$ is Me, $(R^7)_n$, is 2-Cl-5,7-di-F |
| 485 | X is N-Me, $R^1$ is Me, $R^2$ is Me, $(R^7)_n$, is 2,5-di-Cl-7-F |
| 486 | X is N-Me, $R^1$ is Me, $R^2$ is Me, $(R^7)_n$, is 2,7-di-Cl-5-F |
| 487 | X is N-Me, $R^1$ is Me, $R^2$ is Me, $(R^7)_n$, is 2-F-5,7-di-Me |
| 488 | X is N-Me, $R^1$ is Me, $R^2$ is Me, $(R^7)_n$, is 2-F-5-Me |
| 489 | X is N-Me, $R^1$ is Me, $R^2$ is Me, $(R^7)_n$, is 2-$OCF_2H$ |
| 490 | X is N-Me, $R^1$ is Me, $R^2$ is Me, $(R^7)_n$, is 2-$OCF_2H$-7-Me |
| 491 | X is N-Me, $R^1$ is Me, $R^2$ is Me, $(R^7)_n$, is 2-$OCF_2H$-7-F |
| 492 | X is N-Me, $R^1$ is Me, $R^2$ is Me, $(R^7)_n$, is 2-$OCF_2H$-7-Cl |
| 493 | X is a direct bond, $R^1$ is Et, $R^2$ is Me, $(R^7)_n$, is H |
| 494 | X is a direct bond, $R^1$ is Et, $R^2$ is Me, $(R^7)_n$, is 10-Br |
| 495 | X is a direct bond, $R^1$ is Et, $R^2$ is Me, $(R^7)_n$, is 10-Cl |
| 496 | X is a direct bond, $R^1$ is Et, $R^2$ is Me, $(R^7)_n$, is 10-Me |
| 497 | X is a direct bond, $R^1$ is Et, $R^2$ is Me, $(R^7)_n$, is 2-F |
| 498 | X is a direct bond, $R^1$ is Et, $R^2$ is Me, $(R^7)_n$, is 2-Cl |
| 499 | X is a direct bond, $R^1$ is Et, $R^2$ is Me, $(R^7)_n$, is 2-OMe |

TABLE 385-continued

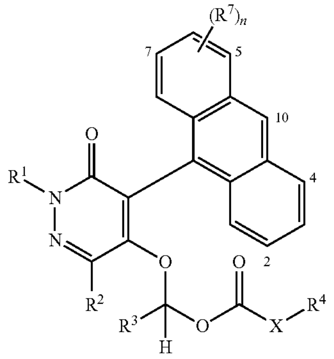

Header Row Phrase: X is a direct bond, $R^1$ is Me, $R^2$ is Me, $(R^{12})n$ is H; The remaining variables (i.e. $R^3$ and $R^4$) are as defined in TABLE 1.

| TABLE | Header Row Phrase |
|---|---|
| 500 | X is a direct bond, $R^1$ is Et, $R^2$ is Me, $(R^7)_n$, is 2-Me |
| 501 | X is a direct bond, $R^1$ is Et, $R^2$ is Me, $(R^7)_n$, is 2,4-di-Me |
| 502 | X is a direct bond, $R^1$ is Et, $R^2$ is Me, $(R^7)_n$, is 2-Cl-7-F |
| 503 | X is a direct bond, $R^1$ is Et, $R^2$ is Me, $(R^7)_n$, is 2-F-7-Me |
| 504 | X is a direct bond, $R^1$ is Et, $R^2$ is Me, $(R^7)_n$, is 2,7-di-Me |
| 505 | X is a direct bond, $R^1$ is Et, $R^2$ is Me, $(R^7)_n$, is 2,5-di-Cl |
| 506 | X is a direct bond, $R^1$ is Et, $R^2$ is Me, $(R^7)_n$, is 2-Cl-5-F |
| 507 | X is a direct bond, $R^1$ is Et, $R^2$ is Me, $(R^7)_n$, is 2,6-di-Cl-7-F |
| 508 | X is a direct bond, $R^1$ is Et, $R^2$ is Me, $(R^7)_n$, is 2-Cl-6,7-di-F |
| 509 | X is a direct bond, $R^1$ is Et, $R^2$ is Me, $(R^7)_n$, is 2,7-di-Cl-6-F |
| 510 | X is a direct bond, $R^1$ is Et, $R^2$ is Me, $(R^7)_n$, is 2-F-7-OMe |
| 511 | X is a direct bond, $R^1$ is Et, $R^2$ is Me, $(R^7)_n$, is 2-Cl-5,7-di-F |
| 512 | X is a direct bond, $R^1$ is Et, $R^2$ is Me, $(R^7)_n$, is 2,5-di-Cl-7-F |
| 513 | X is a direct bond, $R^1$ is Et, $R^2$ is Me, $(R^7)_n$, is 2,7-di-Cl-5-F |
| 514 | X is a direct bond, $R^1$ is Et, $R^2$ is Me, $(R^7)_n$, is 2-F-5,7-di-Me |
| 515 | X is a direct bond, $R^1$ is Et, $R^2$ is Me, $(R^7)_n$, is 2-F-5-Me |
| 516 | X is a direct bond, $R^1$ is Et, $R^2$ is Me, $(R^7)_n$, is 2-$OCF_2H$ |
| 517 | X is a direct bond, $R^1$ is Et, $R^2$ is Me, $(R^7)_n$, is 2-$OCF_2H$-7-Me |
| 518 | X is a direct bond, $R^1$ is Et, $R^2$ is Me, $(R^7)_n$, is 2-$OCF_2H$-7-F |
| 519 | X is a direct bond, $R^1$ is Et, $R^2$ is Me, $(R^7)_n$, is 2-$OCF_2H$-7-Cl |
| 520 | X is O, $R^1$ is Et, $R^2$ is Me, $(R^7)_n$, is H |
| 521 | X is O, $R^1$ is Et, $R^2$ is Me, $(R^7)_n$, is 10-Br |
| 522 | X is O, $R^1$ is Et, $R^2$ is Me, $(R^7)_n$, is 10-Cl |
| 523 | X is O, $R^1$ is Et, $R^2$ is Me, $(R^7)_n$, is 10-Me |
| 524 | X is O, $R^1$ is Et, $R^2$ is Me, $(R^7)_n$, is 2-F |
| 525 | X is O, $R^1$ is Et, $R^2$ is Me, $(R^7)_n$, is 2-Cl |
| 526 | X is O, $R^1$ is Et, $R^2$ is Me, $(R^7)_n$, is 2-OMe |
| 527 | X is O, $R^1$ is Et, $R^2$ is Me, $(R^7)_n$, is 2-Me |
| 528 | X is O, $R^1$ is Et, $R^2$ is Me, $(R^7)_n$, is 2,4-di-Me |
| 529 | X is O, $R^1$ is Et, $R^2$ is Me, $(R^7)_n$, is 2-Cl-7-F |
| 530 | X is O, $R^1$ is Et, $R^2$ is Me, $(R^7)_n$, is 2-F-7-Me |
| 531 | X is O, $R^1$ is Et, $R^2$ is Me, $(R^7)_n$, is 2,7-di-Me |
| 532 | X is O, $R^1$ is Et, $R^2$ is Me, $(R^7)_n$, is 2,5-di-Cl |
| 533 | X is O, $R^1$ is Et, $R^2$ is Me, $(R^7)_n$, is 2-Cl-5-F |
| 534 | X is O, $R^1$ is Et, $R^2$ is Me, $(R^7)_n$, is 2,6-di-Cl-7-F |
| 535 | X is O, $R^1$ is Et, $R^2$ is Me, $(R^7)_n$, is 2-Cl-6,7-di-F |
| 536 | X is O, $R^1$ is Et, $R^2$ is Me, $(R^7)_n$, is 2,7-di-Cl-6-F |
| 537 | X is O, $R^1$ is Et, $R^2$ is Me, $(R^7)_n$, is 2-F-7-OMe |
| 538 | X is O, $R^1$ is Et, $R^2$ is Me, $(R^7)_n$, is 2-Cl-5,7-di-F |
| 539 | X is O, $R^1$ is Et, $R^2$ is Me, $(R^7)_n$, is 2,5-di-Cl-7-F |
| 540 | X is O, $R^1$ is Et, $R^2$ is Me, $(R^7)_n$, is 2,7-di-Cl-5-F |
| 541 | X is O, $R^1$ is Et, $R^2$ is Me, $(R^7)_n$, is 2-F-5,7-di-Me |
| 542 | X is O, $R^1$ is Et, $R^2$ is Me, $(R^7)_n$, is 2-F-5-Me |
| 543 | X is O, $R^1$ is Et, $R^2$ is Me, $(R^7)_n$, is 2-$OCF_2H$ |
| 544 | X is O, $R^1$ is Et, $R^2$ is Me, $(R^7)_n$, is 2-$OCF_2H$-7-Me |
| 545 | X is O, $R^1$ is Et, $R^2$ is Me, $(R^7)_n$, is 2-$OCF_2H$-7-F |
| 546 | X is O, $R^1$ is Et, $R^2$ is Me, $(R^7)_n$, is 2-$OCF_2H$-7-Cl |
| 547 | X is S, $R^1$ is Et, $R^2$ is Me, $(R^7)_n$, is H |
| 548 | X is S, $R^1$ is Et, $R^2$ is Me, $(R^7)_n$, is 10-Br |
| 549 | X is S, $R^1$ is Et, $R^2$ is Me, $(R^7)_n$, is 10-Cl |
| 550 | X is S, $R^1$ is Et, $R^2$ is Me, $(R^7)_n$, is 10-Me |
| 551 | X is S, $R^1$ is Et, $R^2$ is Me, $(R^7)_n$, is 2-F |
| 552 | X is S, $R^1$ is Et, $R^2$ is Me, $(R^7)_n$, is 2-Cl |
| 553 | X is S, $R^1$ is Et, $R^2$ is Me, $(R^7)_n$, is 2-OMe |
| 554 | X is S, $R^1$ is Et, $R^2$ is Me, $(R^7)_n$, is 2-Me |
| 555 | X is S, $R^1$ is Et, $R^2$ is Me, $(R^7)_n$, is 2,4-di-Me |
| 556 | X is S, $R^1$ is Et, $R^2$ is Me, $(R^7)_n$, is 2-Cl-7-F |

TABLE 385-continued

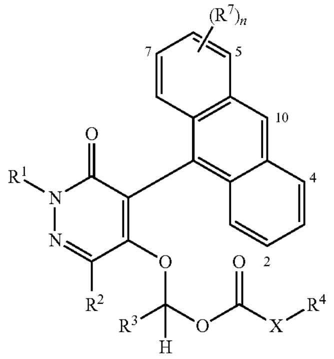

Header Row Phrase: X is a direct bond, $R^1$ is Me, $R^2$ is Me, $(R^{12})n$ is H; The remaining variables (i.e. $R^3$ and $R^4$) are as defined in TABLE 1.

| TABLE | Header Row Phrase |
|---|---|
| 557 | X is S, $R^1$ is Et, $R^2$ is Me, $(R^7)_n$, is 2-F-7-Me |
| 558 | X is S, $R^1$ is Et, $R^2$ is Me, $(R^7)_n$, is 2,7-di-Me |
| 559 | X is S, $R^1$ is Et, $R^2$ is Me, $(R^7)_n$, is 2,5-di-Cl |
| 560 | X is S, $R^1$ is Et, $R^2$ is Me, $(R^7)_n$, is 2-Cl-5-F |
| 561 | X is S, $R^1$ is Et, $R^2$ is Me, $(R^7)_n$, is 2,6-di-Cl-7-F |
| 562 | X is S, $R^1$ is Et, $R^2$ is Me, $(R^7)_n$, is 2-Cl-6,7-di-F |
| 563 | X is S, $R^1$ is Et, $R^2$ is Me, $(R^7)_n$, is 2,7-di-Cl-6-F |
| 564 | X is S, $R^1$ is Et, $R^2$ is Me, $(R^7)_n$, is 2-F-7-OMe |
| 565 | X is S, $R^1$ is Et, $R^2$ is Me, $(R^7)_n$, is 2-Cl-5,7-di-F |
| 566 | X is S, $R^1$ is Et, $R^2$ is Me, $(R^7)_n$, is 2,5-di-Cl-7-F |
| 567 | X is S, $R^1$ is Et, $R^2$ is Me, $(R^7)_n$, is 2,7-di-Cl-5-F |
| 568 | X is S, $R^1$ is Et, $R^2$ is Me, $(R^7)_n$, is 2-F-5,7-di-Me |
| 569 | X is S, $R^1$ is Et, $R^2$ is Me, $(R^7)_n$, is 2-F-5-Me |
| 570 | X is S, $R^1$ is Et, $R^2$ is Me, $(R^7)_n$, is 2-$OCF_2H$ |
| 571 | X is S, $R^1$ is Et, $R^2$ is Me, $(R^7)_n$, is 2-$OCF_2H$-7-Me |
| 572 | X is S, $R^1$ is Et, $R^2$ is Me, $(R^7)_n$, is 2-$OCF_2H$-7-F |
| 573 | X is S, $R^1$ is Et, $R^2$ is Me, $(R^7)_n$, is 2-$OCF_2H$-7-Cl |
| 574 | X is N-Me, $R^1$ is Et, $R^2$ is Me, $(R^7)_n$, is H |
| 575 | X is N-Me, $R^1$ is Et, $R^2$ is Me, $(R^7)_n$, is 10-Br |
| 576 | X is N-Me, $R^1$ is Et, $R^2$ is Me, $(R^7)_n$, is 10-Cl |
| 577 | X is N-Me, $R^1$ is Et, $R^2$ is Me, $(R^7)_n$, is 10-Me |
| 578 | X is N-Me, $R^1$ is Et, $R^2$ is Me, $(R^7)_n$, is 2-F |
| 579 | X is N-Me, $R^1$ is Et, $R^2$ is Me, $(R^7)_n$, is 2-Cl |
| 580 | X is N-Me, $R^1$ is Et, $R^2$ is Me, $(R^7)_n$, is 2-OMe |
| 581 | X is N-Me, $R^1$ is Et, $R^2$ is Me, $(R^7)_n$, is 2-Me |
| 582 | X is N-Me, $R^1$ is Et, $R^2$ is Me, $(R^7)_n$, is 2,4-di-Me |
| 583 | X is N-Me, $R^1$ is Et, $R^2$ is Me, $(R^7)_n$, is 2-Cl-7-F |
| 584 | X is N-Me, $R^1$ is Et, $R^2$ is Me, $(R^7)_n$, is 2-F-7-Me |
| 585 | X is N-Me, $R^1$ is Et, $R^2$ is Me, $(R^7)_n$, is 2,7-di-Me |
| 586 | X is N-Me, $R^1$ is Et, $R^2$ is Me, $(R^7)_n$, is 2,5-di-Cl |
| 587 | X is N-Me, $R^1$ is Et, $R^2$ is Me, $(R^7)_n$, is 2-Cl-5-F |
| 588 | X is N-Me, $R^1$ is Et, $R^2$ is Me, $(R^7)_n$, is 2,6-di-Cl-7-F |
| 589 | X is N-Me, $R^1$ is Et, $R^2$ is Me, $(R^7)_n$, is 2-Cl-6,7-di-F |
| 590 | X is N-Me, $R^1$ is Et, $R^2$ is Me, $(R^7)_n$, is 2,7-di-Cl-6-F |
| 591 | X is N-Me, $R^1$ is Et, $R^2$ is Me, $(R^7)_n$, is 2-F-7-OMe |
| 592 | X is N-Me, $R^1$ is Et, $R^2$ is Me, $(R^7)_n$, is 2-Cl-5,7-di-F |
| 593 | X is N-Me, $R^1$ is Et, $R^2$ is Me, $(R^7)_n$, is 2,5-di-Cl-7-F |
| 594 | X is N-Me, $R^1$ is Et, $R^2$ is Me, $(R^7)_n$, is 2,7-di-Cl-5-F |
| 595 | X is N-Me, $R^1$ is Et, $R^2$ is Me, $(R^7)_n$, is 2-F-5,7-di-Me |
| 596 | X is N-Me, $R^1$ is Et, $R^2$ is Me, $(R^7)_n$, is 2-F-5-Me |
| 597 | X is N-Me, $R^1$ is Et, $R^2$ is Me, $(R^7)_n$, is 2-$OCF_2H$ |
| 598 | X is N-Me, $R^1$ is Et, $R^2$ is Me, $(R^7)_n$, is 2-$OCF_2H$-7-Me |
| 599 | X is N-Me, $R^1$ is Et, $R^2$ is Me, $(R^7)_n$, is 2-$OCF_2H$-7-F |
| 600 | X is N-Me, $R^1$ is Et, $R^2$ is Me, $(R^7)_n$, is 2-$OCF_2H$-7-Cl |
| 601 | X is a direct bond, $R^1$ is Me, $R^2$ is Cl, $(R^7)_n$, is H |
| 602 | X is a direct bond, $R^1$ is Me, $R^2$ is Cl, $(R^7)_n$, is 10-Br |
| 603 | X is a direct bond, $R^1$ is Me, $R^2$ is Cl, $(R^7)_n$, is 10-Cl |
| 604 | X is a direct bond, $R^1$ is Me, $R^2$ is Cl, $(R^7)_n$, is 10-Me |
| 605 | X is a direct bond, $R^1$ is Me, $R^2$ is Cl, $(R^7)_n$, is 2-F |
| 606 | X is a direct bond, $R^1$ is Me, $R^2$ is Cl, $(R^7)_n$, is 2-Cl |
| 607 | X is a direct bond, $R^1$ is Me, $R^2$ is Cl, $(R^7)_n$, is 2-OMe |
| 608 | X is a direct bond, $R^1$ is Me, $R^2$ is Cl, $(R^7)_n$, is 2-Me |
| 609 | X is a direct bond, $R^1$ is Me, $R^2$ is Cl, $(R^7)_n$, is 2,4-di-Me |
| 610 | X is a direct bond, $R^1$ is Me, $R^2$ is Cl, $(R^7)_n$, is 2-Cl-7-F |
| 611 | X is a direct bond, $R^1$ is Me, $R^2$ is Cl, $(R^7)_n$, is 2-F-7-Me |
| 612 | X is a direct bond, $R^1$ is Me, $R^2$ is Cl, $(R^7)_n$, is 2,7-di-Me |
| 613 | X is a direct bond, $R^1$ is Me, $R^2$ is Cl, $(R^7)_n$, is 2,5-di-Cl |

TABLE 385-continued

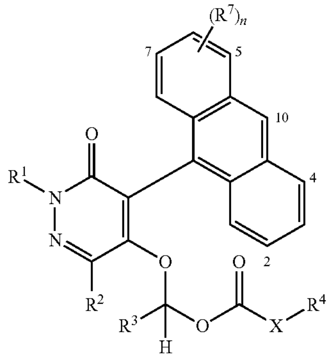

Header Row Phrase: X is a direct bond, $R^1$ is Me, $R^2$ is Me, $(R^{12})n$ is H;
The remaining variables (i.e. $R^3$ and $R^4$) are as defined in TABLE 1.

| TABLE | Header Row Phrase |
|---|---|
| 614 | X is a direct bond, $R^1$ is Me, $R^2$ is Cl, $(R^7)_n$, is 2-Cl-5-F |
| 615 | X is a direct bond, $R^1$ is Me, $R^2$ is Cl, $(R^7)_n$, is 2,6-di-Cl-7-F |
| 616 | X is a direct bond, $R^1$ is Me, $R^2$ is Cl, $(R^7)_n$, is 2-Cl-6,7-di-F |
| 617 | X is a direct bond, $R^1$ is Me, $R^2$ is Cl, $(R^7)_n$, is 2,7-di-Cl-6-F |
| 618 | X is a direct bond, $R^1$ is Me, $R^2$ is Cl, $(R^7)_n$, is 2-F-7-OMe |
| 619 | X is a direct bond, $R^1$ is Me, $R^2$ is Cl, $(R^7)_n$, is 2-Cl-5,7-di-F |
| 620 | X is a direct bond, $R^1$ is Me, $R^2$ is Cl, $(R^7)_n$, is 2,5-di-Cl-7-F |
| 621 | X is a direct bond, $R^1$ is Me, $R^2$ is Cl, $(R^7)_n$, is 2,7-di-Cl-5-F |
| 622 | X is a direct bond, $R^1$ is Me, $R^2$ is Cl, $(R^7)_n$, is 2-F-5,7-di-Me |
| 623 | X is a direct bond, $R^1$ is Me, $R^2$ is Cl, $(R^7)_n$, is 2-F-5-Me |
| 624 | X is a direct bond, $R^1$ is Me, $R^2$ is Cl, $(R^7)_n$, is 2-$OCF_2H$ |
| 625 | X is a direct bond, $R^1$ is Me, $R^2$ is Cl, $(R^7)_n$, is 2-$OCF_2H$-7-Me |
| 626 | X is a direct bond, $R^1$ is Me, $R^2$ is Cl, $(R^7)_n$, is 2-$OCF_2H$-7-F |
| 627 | X is a direct bond, $R^1$ is Me, $R^2$ is Cl, $(R^7)_n$, is 2-$OCF_2H$-7-Cl |
| 628 | X is O, $R^1$ is Me, $R^2$ is Cl, $(R^7)_n$, is H |
| 629 | X is O, $R^1$ is Me, $R^2$ is Cl, $(R^7)_n$, is 10-Br |
| 630 | X is O, $R^1$ is Me, $R^2$ is Cl, $(R^7)_n$, is 10-Cl |
| 631 | X is O, $R^1$ is Me, $R^2$ is Cl, $(R^7)_n$, is 10-Me |
| 632 | X is O, $R^1$ is Me, $R^2$ is Cl, $(R^7)_n$, is 2-F |
| 633 | X is O, $R^1$ is Me, $R^2$ is Cl, $(R^7)_n$, is 2-Cl |
| 634 | X is O, $R^1$ is Me, $R^2$ is Cl, $(R^7)_n$, is 2-OMe |
| 635 | X is O, $R^1$ is Me, $R^2$ is Cl, $(R^7)_n$, is 2-Me |
| 636 | X is O, $R^1$ is Me, $R^2$ is Cl, $(R^7)_n$, is 2,4-di-Me |
| 637 | X is O, $R^1$ is Me, $R^2$ is Cl, $(R^7)_n$, is 2-Cl-7-F |
| 638 | X is O, $R^1$ is Me, $R^2$ is Cl, $(R^7)_n$, is 2-F-7-Me |
| 639 | X is O, $R^1$ is Me, $R^2$ is Cl, $(R^7)_n$, is 2,7-di-Me |
| 640 | X is O, $R^1$ is Me, $R^2$ is Cl, $(R^7)_n$, is 2,5-di-Cl |
| 641 | X is O, $R^1$ is Me, $R^2$ is Cl, $(R^7)_n$, is 2-Cl-5-F |
| 642 | X is O, $R^1$ is Me, $R^2$ is Cl, $(R^7)_n$, is 2,6-di-Cl-7-F |
| 643 | X is O, $R^1$ is Me, $R^2$ is Cl, $(R^7)_n$, is 2-Cl-6,7-di-F |
| 644 | X is O, $R^1$ is Me, $R^2$ is Cl, $(R^7)_n$, is 2,7-di-Cl-6-F |
| 645 | X is O, $R^1$ is Me, $R^2$ is Cl, $(R^7)_n$, is 2-F-7-OMe |
| 646 | X is O, $R^1$ is Me, $R^2$ is Cl, $(R^7)_n$, is 2-Cl-5,7-di-F |
| 647 | X is O, $R^1$ is Me, $R^2$ is Cl, $(R^7)_n$, is 2,5-di-Cl-7-F |
| 648 | X is O, $R^1$ is Me, $R^2$ is Cl, $(R^7)_n$, is 2,7-di-Cl-5-F |
| 649 | X is O, $R^1$ is Me, $R^2$ is Cl, $(R^7)_n$, is 2-F-5,7-di-Me |
| 650 | X is O, $R^1$ is Me, $R^2$ is Cl, $(R^7)_n$, is 2-F-5-Me |
| 651 | X is O, $R^1$ is Me, $R^2$ is Cl, $(R^7)_n$, is 2-$OCF_2H$ |
| 652 | X is O, $R^1$ is Me, $R^2$ is Cl, $(R^7)_n$, is 2-$OCF_2H$-7-Me |
| 653 | X is O, $R^1$ is Me, $R^2$ is Cl, $(R^7)_n$, is 2-$OCF_2H$-7-F |
| 654 | X is O, $R^1$ is Me, $R^2$ is Cl, $(R^7)_n$, is 2-$OCF_2H$-7-Cl |
| 655 | X is S, $R^1$ is Me, $R^2$ is Cl, $(R^7)_n$, is H |
| 656 | X is S, $R^1$ is Me, $R^2$ is Cl, $(R^7)_n$, is 10-Br |
| 657 | X is S, $R^1$ is Me, $R^2$ is Cl, $(R^7)_n$, is 10-Cl |
| 658 | X is S, $R^1$ is Me, $R^2$ is Cl, $(R^7)_n$, is 10-Me |
| 659 | X is S, $R^1$ is Me, $R^2$ is Cl, $(R^7)_n$, is 2-F |
| 660 | X is S, $R^1$ is Me, $R^2$ is Cl, $(R^7)_n$, is 2-Cl |
| 661 | X is S, $R^1$ is Me, $R^2$ is Cl, $(R^7)_n$, is 2-OMe |
| 662 | X is S, $R^1$ is Me, $R^2$ is Cl, $(R^7)_n$, is 2-Me |
| 663 | X is S, $R^1$ is Me, $R^2$ is Cl, $(R^7)_n$, is 2,4-di-Me |
| 664 | X is S, $R^1$ is Me, $R^2$ is Cl, $(R^7)_n$, is 2-Cl-7-F |
| 665 | X is S, $R^1$ is Me, $R^2$ is Cl, $(R^7)_n$, is 2-F-7-Me |
| 666 | X is S, $R^1$ is Me, $R^2$ is Cl, $(R^7)_n$, is 2,7-di-Me |
| 667 | X is S, $R^1$ is Me, $R^2$ is Cl, $(R^7)_n$, is 2,5-di-Cl |
| 668 | X is S, $R^1$ is Me, $R^2$ is Cl, $(R^7)_n$, is 2-Cl-5-F |
| 669 | X is S, $R^1$ is Me, $R^2$ is Cl, $(R^7)_n$, is 2,6-di-Cl-7-F |
| 670 | X is S, $R^1$ is Me, $R^2$ is Cl, $(R^7)_n$, is 2-Cl-6,7-di-F |

TABLE 385-continued

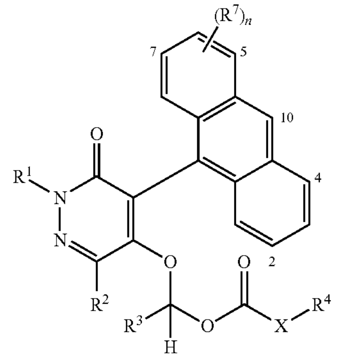

Header Row Phrase: X is a direct bond, $R^1$ is Me, $R^2$ is Me, $(R^{12})n$ is H;
The remaining variables (i.e. $R^3$ and $R^4$) are as defined in TABLE 1.

| TABLE | Header Row Phrase |
|---|---|
| 671 | X is S, $R^1$ is Me, $R^2$ is Cl, $(R^7)_n$, is 2,7-di-Cl-6-F |
| 672 | X is S, $R^1$ is Me, $R^2$ is Cl, $(R^7)_n$, is 2-F-7-OMe |
| 673 | X is S, $R^1$ is Me, $R^2$ is Cl, $(R^7)_n$, is 2-Cl-5,7-di-F |
| 674 | X is S, $R^1$ is Me, $R^2$ is Cl, $(R^7)_n$, is 2,5-di-Cl-7-F |
| 675 | X is S, $R^1$ is Me, $R^2$ is Cl, $(R^7)_n$, is 2,7-di-C1-5-F |
| 676 | X is S, $R^1$ is Me, $R^2$ is Cl, $(R^7)_n$, is 2-F-5,7-di-Me |
| 677 | X is S, $R^1$ is Me, $R^2$ is Cl, $(R^7)_n$, is 2-F-5-Me |
| 678 | X is S, $R^1$ is Me, $R^2$ is Cl, $(R^7)_n$, is 2-$OCF_2H$ |
| 679 | X is S, $R^1$ is Me, $R^2$ is Cl, $(R^7)_n$, is 2-$OCF_2H$-7-Me |
| 680 | X is S, $R^1$ is Me, $R^2$ is Cl, $(R^7)_n$, is 2-$OCF_2H$-7-F |
| 681 | X is S, $R^1$ is Me, $R^2$ is Cl, $(R^7)_n$, is 2-$OCF_2H$-7-Cl |
| 682 | X is N-Me, $R^1$ is Me, $R^2$ is Cl, $(R^7)_n$, is H |
| 683 | X is N-Me, $R^1$ is Me, $R^2$ is Cl, $(R^7)_n$, is 10-Br |
| 684 | X is N-Me, $R^1$ is Me, $R^2$ is Cl, $(R^7)_n$, is 10-Cl |
| 685 | X is N-Me, $R^1$ is Me, $R^2$ is Cl, $(R^7)_n$, is 10-Me |
| 686 | X is N-Me, $R^1$ is Me, $R^2$ is Cl, $(R^7)_n$, is 2-F |
| 687 | X is N-Me, $R^1$ is Me, $R^2$ is Cl, $(R^7)_n$, is 2-Cl |
| 688 | X is N-Me, $R^1$ is Me, $R^2$ is Cl, $(R^7)_n$, is 2-OMe |
| 689 | X is N-Me, $R^1$ is Me, $R^2$ is Cl, $(R^7)_n$, is 2-Me |
| 690 | X is N-Me, $R^1$ is Me, $R^2$ is Cl, $(R^7)_n$, is 2,4-di-Me |
| 691 | X is N-Me, $R^1$ is Me, $R^2$ is Cl, $(R^7)_n$, is 2-Cl-7-F |
| 692 | X is N-Me, $R^1$ is Me, $R^2$ is Cl, $(R^7)_n$, is 2-F-7-Me |
| 693 | X is N-Me, $R^1$ is Me, $R^2$ is Cl, $(R^7)_n$, is 2,7-di-Me |
| 694 | X is N-Me, $R^1$ is Me, $R^2$ is Cl, $(R^7)_n$, is 2,5-di-Cl |
| 695 | X is N-Me, $R^1$ is Me, $R^2$ is Cl, $(R^7)_n$, is 2-Cl-5-F |
| 696 | X is N-Me, $R^1$ is Me, $R^2$ is Cl, $(R^7)_n$, is 2,6-di-Cl-7-F |
| 697 | X is N-Me, $R^1$ is Me, $R^2$ is Cl, $(R^7)_n$, is 2-Cl-6,7-di-F |
| 698 | X is N-Me, $R^1$ is Me, $R^2$ is Cl, $(R^7)_n$, is 2,7-di-Cl-6-F |
| 699 | X is N-Me, $R^1$ is Me, $R^2$ is Cl, $(R^7)_n$, is 2-F-7-OMe |
| 700 | X is N-Me, $R^1$ is Me, $R^2$ is Cl, $(R^7)_n$, is 2-Cl-5,7-di-F |
| 701 | X is N-Me, $R^1$ is Me, $R^2$ is Cl, $(R^7)_n$, is 2,5-di-Cl-7-F |
| 702 | X is N-Me, $R^1$ is Me, $R^2$ is Cl, $(R^7)_n$, is 2,7-di-Cl-5-F |
| 703 | X is N-Me, $R^1$ is Me, $R^2$ is Cl, $(R^7)_n$, is 2-F-5,7-di-Me |
| 704 | X is N-Me, $R^1$ is Me, $R^2$ is Cl, $(R^7)_n$, is 2-F-5-Me |
| 705 | X is N-Me, $R^1$ is Me, $R^2$ is Cl, $(R^7)_n$, is 2-$OCF_2H$ |
| 706 | X is N-Me, $R^1$ is Me, $R^2$ is Cl, $(R^7)_n$, is 2-$OCF_2H$-7-Me |
| 707 | X is N-Me, $R^1$ is Me, $R^2$ is Cl, $(R^7)_n$, is 2-$OCF_2H$-7-F |
| 708 | X is N-Me, $R^1$ is Me, $R^2$ is Cl, $(R^7)_n$, is 2-$OCF_2H$-7-Cl |
| 709 | X is a direct bond, $R^1$ is Et, $R^2$ is Cl, $(R^7)_n$, is H |
| 710 | X is a direct bond, $R^1$ is Et, $R^2$ is Cl, $(R^7)_n$, is 10-Br |
| 711 | X is a direct bond, $R^1$ is Et, $R^2$ is Cl, $(R^7)_n$, is 10-Cl |
| 712 | X is a direct bond, $R^1$ is Et, $R^2$ is Cl, $(R^7)_n$, is 10-Me |
| 713 | X is a direct bond, $R^1$ is Et, $R^2$ is Cl, $(R^7)_n$, is 2-F |
| 714 | X is a direct bond, $R^1$ is Et, $R^2$ is Cl, $(R^7)_n$, is 2-Cl |
| 715 | X is a direct bond, $R^1$ is Et, $R^2$ is Cl, $(R^7)_n$, is 2-OMe |
| 716 | X is a direct bond, $R^1$ is Et, $R^2$ is Cl, $(R^7)_n$, is 2-Me |
| 717 | X is a direct bond, $R^1$ is Et, $R^2$ is Cl, $(R^7)_n$, is 2,4-di-Me |
| 718 | X is a direct bond, $R^1$ is Et, $R^2$ is Cl, $(R^7)_n$, is 2-Cl-7-F |
| 719 | X is a direct bond, $R^1$ is Et, $R^2$ is Cl, $(R^7)_n$, is 2-F-7-Me |
| 720 | X is a direct bond, $R^1$ is Et, $R^2$ is Cl, $(R^7)_n$, is 2,7-di-Me |
| 721 | X is a direct bond, $R^1$ is Et, $R^2$ is Cl, $(R^7)_n$, is 2,5-di-Cl |
| 722 | X is a direct bond, $R^1$ is Et, $R^2$ is Cl, $(R^7)_n$, is 2-Cl-5-F |
| 723 | X is a direct bond, $R^1$ is Et, $R^2$ is Cl, $(R^7)_n$, is 2,6-di-Cl-7-F |
| 724 | X is a direct bond, $R^1$ is Et, $R^2$ is Cl, $(R^7)_n$, is 2-Cl-6,7-di-F |
| 725 | X is a direct bond, $R^1$ is Et, $R^2$ is Cl, $(R^7)_n$, is 2,7-di-Cl-6-F |
| 726 | X is a direct bond, $R^1$ is Et, $R^2$ is Cl, $(R^7)_n$, is 2-F-7-OMe |
| 727 | X is a direct bond, $R^1$ is Et, $R^2$ is Cl, $(R^7)_n$, is 2-Cl-5,7-di-F |

TABLE 385-continued

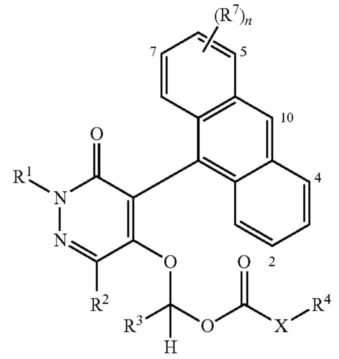

Header Row Phrase: X is a direct bond, $R^1$ is Me, $R^2$ is Me, $(R^{12})n$ is H; The remaining variables (i.e. $R^3$ and $R^4$) are as defined in TABLE 1.

| TABLE | Header Row Phrase |
|---|---|
| 728 | X is a direct bond, $R^1$ is Et, $R^2$ is Cl, $(R^7)_n$, is 2,5-di-Cl-7-F |
| 729 | X is a direct bond, $R^1$ is Et, $R^2$ is Cl, $(R^7)_n$, is 2,7-di-Cl-5-F |
| 730 | X is a direct bond, $R^1$ is Et, $R^2$ is Cl, $(R^7)_n$, is 2-F-5,7-di-Me |
| 731 | X is a direct bond, $R^1$ is Et, $R^2$ is Cl, $(R^7)_n$, is 2-F-5-Me |
| 732 | X is a direct bond, $R^1$ is Et, $R^2$ is Cl, $(R^7)_n$, is 2-$OCF_2H$ |
| 733 | X is a direct bond, $R^1$ is Et, $R^2$ is Cl, $(R^7)_n$, is 2-$OCF_2H$-7-Me |
| 734 | X is a direct bond, $R^1$ is Et, $R^2$ is Cl, $(R^7)_n$, is 2-$OCF_2H$-7-F |
| 735 | X is a direct bond, $R^1$ is Et, $R^2$ is Cl, $(R^7)_n$, is 2-$OCF_2H$-7-Cl |
| 736 | X is O, $R^1$ is Et, $R^2$ is Cl, $(R^7)_n$, is H |
| 737 | X is O, $R^1$ is Et, $R^2$ is Cl, $(R^7)_n$, is 10-Br |
| 738 | X is O, $R^1$ is Et, $R^2$ is Cl, $(R^7)_n$, is 10-Cl |
| 739 | X is O, $R^1$ is Et, $R^2$ is Cl, $(R^7)_n$, is 10-Me |
| 740 | X is O, $R^1$ is Et, $R^2$ is Cl, $(R^7)_n$, is 2-F |
| 741 | X is O, $R^1$ is Et, $R^2$ is Cl, $(R^7)_n$, is 2-Cl |
| 742 | X is O, $R^1$ is Et, $R^2$ is Cl, $(R^7)_n$, is 2-OMe |
| 743 | X is O, $R^1$ is Et, $R^2$ is Cl, $(R^7)_n$, is 2-Me |
| 744 | X is O, $R^1$ is Et, $R^2$ is Cl, $(R^7)_n$, is 2,4-di-Me |
| 745 | X is O, $R^1$ is Et, $R^2$ is Cl, $(R^7)_n$, is 2-Cl-7-F |
| 746 | X is O, $R^1$ is Et, $R^2$ is Cl, $(R^7)_n$, is 2-F-7-Me |
| 747 | X is O, $R^1$ is Et, $R^2$ is Cl, $(R^7)_n$, is 2,7-di-Me |
| 748 | X is O, $R^1$ is Et, $R^2$ is Cl, $(R^7)_n$, is 2,5-di-Cl |
| 749 | X is O, $R^1$ is Et, $R^2$ is Cl, $(R^7)_n$, is 2-Cl-5-F |
| 750 | X is O, $R^1$ is Et, $R^2$ is Cl, $(R^7)_n$, is 2,6-di-Cl-7-F |
| 751 | X is O, $R^1$ is Et, $R^2$ is Cl, $(R^7)_n$, is 2-Cl-6,7-di-F |
| 752 | X is O, $R^1$ is Et, $R^2$ is Cl, $(R^7)_n$, is 2,7-di-Cl-6-F |
| 753 | X is O, $R^1$ is Et, $R^2$ is Cl, $(R^7)_n$, is 2-F-7-OMe |
| 754 | X is O, $R^1$ is Et, $R^2$ is Cl, $(R^7)_n$, is 2-Cl-5,7-di-F |
| 755 | X is O, $R^1$ is Et, $R^2$ is Cl, $(R^7)_n$, is 2,5-di-Cl-7-F |
| 756 | X is O, $R^1$ is Et, $R^2$ is Cl, $(R^7)_n$, is 2,7-di-Cl-5-F |
| 757 | X is O, $R^1$ is Et, $R^2$ is Cl, $(R^7)_n$, is 2-F-5,7-di-Me |
| 758 | X is O, $R^1$ is Et, $R^2$ is Cl, $(R^7)_n$, is 2-F-5-Me |
| 759 | X is O, $R^1$ is Et, $R^2$ is Cl, $(R^7)_n$, is 2-$OCF_2H$ |
| 760 | X is O, $R^1$ is Et, $R^2$ is Cl, $(R^7)_n$, is 2-$OCF_2H$-7-Me |
| 761 | X is O, $R^1$ is Et, $R^2$ is Cl, $(R^7)_n$, is 2-$OCF_2H$-7-F |
| 762 | X is O, $R^1$ is Et, $R^2$ is Cl, $(R^7)_n$, is 2-$OCF_2H$-7-Cl |
| 763 | X is S, $R^1$ is Et, $R^2$ is Cl, $(R^7)_n$, is H |
| 764 | X is S, $R^1$ is Et, $R^2$ is Cl, $(R^7)_n$, is 10-Br |
| 765 | X is S, $R^1$ is Et, $R^2$ is Cl, $(R^7)_n$, is 10-Cl |
| 766 | X is S, $R^1$ is Et, $R^2$ is Cl, $(R^7)_n$, is 10-Me |
| 767 | X is S, $R^1$ is Et, $R^2$ is Cl, $(R^7)_n$, is 2-F |
| 768 | X is S, $R^1$ is Et, $R^2$ is Cl, $(R^7)_n$, is 2-Cl |
| 769 | X is S, $R^1$ is Et, $R^2$ is Cl, $(R^7)_n$, is 2-OMe |
| 770 | X is S, $R^1$ is Et, $R^2$ is Cl, $(R^7)_n$, is 2-Me |
| 771 | X is S, $R^1$ is Et, $R^2$ is Cl, $(R^7)_n$, is 2,4-di-Me |
| 772 | X is S, $R^1$ is Et, $R^2$ is Cl, $(R^7)_n$, is 2-Cl-7-F |
| 773 | X is S, $R^1$ is Et, $R^2$ is Cl, $(R^7)_n$, is 2-F-7-Me |
| 774 | X is S, $R^1$ is Et, $R^2$ is Cl, $(R^7)_n$, is 2,7-di-Me |
| 775 | X is S, $R^1$ is Et, $R^2$ is Cl, $(R^7)_n$, is 2,5-di-Cl |
| 776 | X is S, $R^1$ is Et, $R^2$ is Cl, $(R^7)_n$, is 2-Cl-5-F |
| 777 | X is S, $R^1$ is Et, $R^2$ is Cl, $(R^7)_n$, is 2,6-di-Cl-7-F |
| 778 | X is S, $R^1$ is Et, $R^2$ is Cl, $(R^7)_n$, is 2-Cl-6,7-di-F |
| 779 | X is S, $R^1$ is Et, $R^2$ is Cl, $(R^7)_n$, is 2,7-di-Cl-6-F |
| 780 | X is S, $R^1$ is Et, $R^2$ is Cl, $(R^7)_n$, is 2-F-7-OMe |
| 781 | X is S, $R^1$ is Et, $R^2$ is Cl, $(R^7)_n$, is 2-Cl-5,7-di-F |
| 782 | X is S, $R^1$ is Et, $R^2$ is Cl, $(R^7)_n$, is 2,5-di-Cl-7-F |
| 783 | X is S, $R^1$ is Et, $R^2$ is Cl, $(R^7)_n$, is 2,7-di-Cl-5-F |
| 784 | X is S, $R^1$ is Et, $R^2$ is Cl, $(R^7)_n$, is 2-F-5,7-di-Me |

TABLE 385-continued

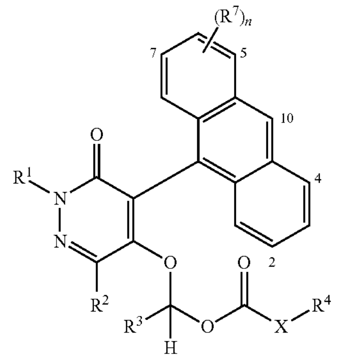

Header Row Phrase: X is a direct bond, $R^1$ is Me, $R^2$ is Me, $(R^{12})n$ is H; The remaining variables (i.e. $R^3$ and $R^4$) are as defined in TABLE 1.

| TABLE | Header Row Phrase |
|---|---|
| 785 | X is S, $R^1$ is Et, $R^2$ is Cl, $(R^7)_n$, is 2-F-5-Me |
| 786 | X is S, $R^1$ is Et, $R^2$ is Cl, $(R^7)_n$, is 2-$OCF_2H$ |
| 787 | X is S, $R^1$ is Et, $R^2$ is Cl, $(R^7)_n$, is 2-$OCF_2H$-7-Me |
| 788 | X is S, $R^1$ is Et, $R^2$ is Cl, $(R^7)_n$, is 2-$OCF_2H$-7-F |
| 789 | X is S, $R^1$ is Et, $R^2$ is Cl, $(R^7)_n$, is 2-$OCF_2H$-7-Cl |
| 790 | X is N-Me, $R^1$ is Et, $R^2$ is Cl, $(R^7)_n$, is H |
| 791 | X is N-Me, $R^1$ is Et, $R^2$ is Cl, $(R^7)_n$, is 10-Br |
| 792 | X is N-Me, $R^1$ is Et, $R^2$ is Cl, $(R^7)_n$, is 10-Cl |
| 793 | X is N-Me, $R^1$ is Et, $R^2$ is Cl, $(R^7)_n$, is 10-Me |
| 794 | X is N-Me, $R^1$ is Et, $R^2$ is Cl, $(R^7)_n$, is 2-F |
| 795 | X is N-Me, $R^1$ is Et, $R^2$ is Cl, $(R^7)_n$, is 2-Cl |
| 796 | X is N-Me, $R^1$ is Et, $R^2$ is Cl, $(R^7)_n$, is 2-OMe |
| 797 | X is N-Me, $R^1$ is Et, $R^2$ is Cl, $(R^7)_n$, is 2-Me |
| 798 | X is N-Me, $R^1$ is Et, $R^2$ is Cl, $(R^7)_n$, is 2,4-di-Me |
| 799 | X is N-Me, $R^1$ is Et, $R^2$ is Cl, $(R^7)_n$, is 2-Cl-7-F |
| 800 | X is N-Me, $R^1$ is Et, $R^2$ is Cl, $(R^7)_n$, is 2-F-7-Me |
| 801 | X is N-Me, $R^1$ is Et, $R^2$ is Cl, $(R^7)_n$, is 2,7-di-Me |
| 802 | X is N-Me, $R^1$ is Et, $R^2$ is Cl, $(R^7)_n$, is 2,5-di-Cl |
| 803 | X is N-Me, $R^1$ is Et, $R^2$ is Cl, $(R^7)_n$, is 2-Cl-5-F |
| 804 | X is N-Me, $R^1$ is Et, $R^2$ is Cl, $(R^7)_n$, is 2,6-di-Cl-7-F |
| 805 | X is N-Me, $R^1$ is Et, $R^2$ is Cl, $(R^7)_n$, is 2-Cl-6,7-di-F |
| 806 | X is N-Me, $R^1$ is Et, $R^2$ is Cl, $(R^7)_n$, is 2,7-di-Cl-6-F |
| 807 | X is N-Me, $R^1$ is Et, $R^2$ is Cl, $(R^7)_n$, is 2-F-7-OMe |
| 808 | X is N-Me, $R^1$ is Et, $R^2$ is Cl, $(R^7)_n$, is 2-Cl-5,7-di-F |
| 809 | X is N-Me, $R^1$ is Et, $R^2$ is Cl, $(R^7)_n$, is 2,5-di-Cl-7-F |
| 810 | X is N-Me, $R^1$ is Et, $R^2$ is Cl, $(R^7)_n$, is 2,7-di-Cl-5-F |
| 811 | X is N-Me, $R^1$ is Et, $R^2$ is Cl, $(R^7)_n$, is 2-F-5,7-di-Me |
| 812 | X is N-Me, $R^1$ is Et, $R^2$ is Cl, $(R^7)_n$, is 2-F-5-Me |
| 813 | X is N-Me, $R^1$ is Et, $R^2$ is Cl, $(R^7)_n$, is 2-$OCF_2H$ |
| 814 | X is N-Me, $R^1$ is Et, $R^2$ is Cl, $(R^7)_n$, is 2-$OCF_2H$-7-Me |
| 815 | X is N-Me, $R^1$ is Et, $R^2$ is Cl, $(R^7)_n$, is 2-$OCF_2H$-7-F |
| 816 | X is N-Me, $R^1$ is Et, $R^2$ is Cl, $(R^7)_n$, is 2-$OCF_2H$-7-Cl |

This disclosure also includes TABLES 386 through 816 wherein the Header Row Phrase in TABLE 385 (i.e. "X is a direct bond, $R^1$ is Me, $R^2$ is Me, $(R^{12})_n$ is H") is replaced with the Header Row Phrase listed in the respective TABLE, and the remaining variables are as defined in TABLE 1.

TABLE 817

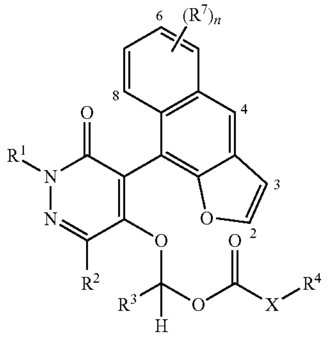

| TABLE | Header Row Phrase |
|---|---|
| 818 | X is a direct bond, $R^1$ is Me, $R^2$ is Me, $(R^7)$n is 2-Me |
| 819 | X is a direct bond, $R^1$ is Me, $R^2$ is Me, $(R^7)$n is 3-Me |
| 820 | X is a direct bond, $R^1$ is Me, $R^2$ is Me, $(R^7)$n is 2,3-di-Me |
| 821 | X is a direct bond, $R^1$ is Me, $R^2$ is Me, $(R^7)$n is 4-Me |
| 822 | X is a direct bond, $R^1$ is Me, $R^2$ is Me, $(R^7)$n is 4-Cl |
| 823 | X is O, $R^1$ is Me, $R^2$ is Me, $(R^7)$n is H |
| 824 | X is O, $R^1$ is Me, $R^2$ is Me, $(R^7)$n is 2-Me |
| 825 | X is O, $R^1$ is Me, $R^2$ is Me, $(R^7)$n is 3-Me |
| 826 | X is O, $R^1$ is Me, $R^2$ is Me, $(R^7)$n is 2,3-di-Me |
| 827 | X is O, $R^1$ is Me, $R^2$ is Me, $(R^7)$n is 4-Me |
| 828 | X is O, $R^1$ is Me, $R^2$ is Me, $(R^7)$n is 4-Cl |
| 829 | X is S, $R^1$ is Me, $R^2$ is Me, $(R^7)$n is H |
| 830 | X is S, $R^1$ is Me, $R^2$ is Me, $(R^7)$n is 2-Me |
| 831 | X is S, $R^1$ is Me, $R^2$ is Me, $(R^7)$n is 3-Me |
| 832 | X is S, $R^1$ is Me, $R^2$ is Me, $(R^7)$n is 2,3-di-Me |
| 833 | X is S, $R^1$ is Me, $R^2$ is Me, $(R^7)$n is 4-Me |
| 834 | X is S, $R^1$ is Me, $R^2$ is Me, $(R^7)$n is 4-Cl |
| 835 | X is N-Me, $R^1$ is Me, $R^2$ is Me, $(R^7)$n is H |
| 836 | X is N-Me, $R^1$ is Me, $R^2$ is Me, $(R^7)$n is 2-Me |
| 837 | X is N-Me, $R^1$ is Me, $R^2$ is Me, $(R^7)$n is 3-Me |
| 838 | X is N-Me, $R^1$ is Me, $R^2$ is Me, $(R^7)$n is 2,3-di-Me |
| 839 | X is N-Me, $R^1$ is Me, $R^2$ is Me, $(R^7)$n is 4-Me |
| 840 | X is N-Me, $R^1$ is Me, $R^2$ is Me, $(R^7)$n is 4-Cl |
| 841 | X is a direct bond, $R^1$ is Et, $R^2$ is Me, $(R^7)$n is H |
| 842 | X is a direct bond, $R^1$ is Et, $R^2$ is Me, $(R^7)$n is 2-Me |
| 843 | X is a direct bond, $R^1$ is Et, $R^2$ is Me, $(R^7)$n is 3-Me |
| 844 | X is a direct bond, $R^1$ is Et, $R^2$ is Me, $(R^7)$n is 2,3-di-Me |
| 845 | X is a direct bond, $R^1$ is Et, $R^2$ is Me, $(R^7)$n is 4-Me |
| 846 | X is a direct bond, $R^1$ is Et, $R^2$ is Me, $(R^7)$n is 4-Cl |
| 847 | X is O, $R^1$ is Et, $R^2$ is Me, $(R^7)$n is H |
| 848 | X is O, $R^1$ is Et, $R^2$ is Me, $(R^7)$n is 2-Me |
| 849 | X is O, $R^1$ is Et, $R^2$ is Me, $(R^7)$n is 3-Me |
| 850 | X is O, $R^1$ is Et, $R^2$ is Me, $(R^7)$n is 2,3-di-Me |
| 851 | X is O, $R^1$ is Et, $R^2$ is Me, $(R^7)$n is 4-Me |
| 852 | X is O, $R^1$ is Et, $R^2$ is Me, $(R^7)$n is 4-Cl |
| 853 | X is S, $R^1$ is Et, $R^2$ is Me, $(R^7)$n is H |
| 854 | X is S, $R^1$ is Et, $R^2$ is Me, $(R^7)$n is 2-Me |
| 855 | X is S, $R^1$ is Et, $R^2$ is Me, $(R^7)$n is 3-Me |
| 856 | X is S, $R^1$ is Et, $R^2$ is Me, $(R^7)$n is 2,3-di-Me |
| 857 | X is S, $R^1$ is Et, $R^2$ is Me, $(R^7)$n is 4-Me |
| 858 | X is S, $R^1$ is Et, $R^2$ is Me, $(R^7)$n is 4-Cl |
| 859 | X is N-Me, $R^1$ is Et, $R^2$ is Me, $(R^7)$n is H |
| 860 | X is N-Me, $R^1$ is Et, $R^2$ is Me, $(R^7)$n is 2-Me |
| 861 | X is N-Me, $R^1$ is Et, $R^2$ is Me, $(R^7)$n is 3-Me |
| 862 | X is N-Me, $R^1$ is Et, $R^2$ is Me, $(R^7)$n is 2,3-di-Me |
| 863 | X is N-Me, $R^1$ is Et, $R^2$ is Me, $(R^7)$n is 4-Me |
| 864 | X is N-Me, $R^1$ is Et, $R^2$ is Me, $(R^7)$n is 4-Cl |
| 865 | X is a direct bond, $R^1$ is Me, $R^2$ is Cl, $(R^7)$n is H |
| 866 | X is a direct bond, $R^1$ is Me, $R^2$ is Cl, $(R^7)$n is 2-Me |
| 867 | X is a direct bond, $R^1$ is Me, $R^2$ is Cl, $(R^7)$n is 3-Me |
| 868 | X is a direct bond, $R^1$ is Me, $R^2$ is Cl, $(R^7)$n is 2,3-di-Me |
| 869 | X is a direct bond, $R^1$ is Me, $R^2$ is Cl, $(R^7)$n is 4-Me |
| 870 | X is a direct bond, $R^1$ is Me, $R^2$ is Cl, $(R^7)$n is 4-Cl |
| 871 | X is O, $R^1$ is Me, $R^2$ is Cl, $(R^7)$n is H |

TABLE 817-continued

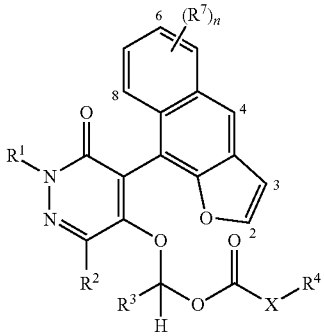

| TABLE | Header Row Phrase |
|---|---|
| 872 | X is O, $R^1$ is Me, $R^2$ is Cl, $(R^7)$n is 2-Me |
| 873 | X is O, $R^1$ is Me, $R^2$ is Cl, $(R^7)$n is 3-Me |
| 874 | X is O, $R^1$ is Me, $R^2$ is Cl, $(R^7)$n is 2,3-di-Me |
| 875 | X is O, $R^1$ is Me, $R^2$ is Cl, $(R^7)$n is 4-Me |
| 876 | X is O, $R^1$ is Me, $R^2$ is Cl, $(R^7)$n is 4-Cl |
| 877 | X is S, $R^1$ is Me, $R^2$ is Cl, $(R^7)$n is H |
| 878 | X is S, $R^1$ is Me, $R^2$ is Cl, $(R^7)$n is 2-Me |
| 879 | X is S, $R^1$ is Me, $R^2$ is Cl, $(R^7)$n is 3-Me |
| 880 | X is S, $R^1$ is Me, $R^2$ is Cl, $(R^7)$n is 2,3-di-Me |
| 881 | X is S, $R^1$ is Me, $R^2$ is Cl, $(R^7)$n is 4-Me |
| 882 | X is S, $R^1$ is Me, $R^2$ is Cl, $(R^7)$n is 4-Cl |
| 883 | X is N-Me, $R^1$ is Me, $R^2$ is Cl, $(R^7)$n is H |
| 884 | X is N-Me, $R^1$ is Me, $R^2$ is Cl, $(R^7)$n is 2-Me |
| 885 | X is N-Me, $R^1$ is Me, $R^2$ is Cl, $(R^7)$n is 3-Me |
| 886 | X is N-Me, $R^1$ is Me, $R^2$ is Cl, $(R^7)$n is 2,3-di-Me |
| 887 | X is N-Me, $R^1$ is Me, $R^2$ is Cl, $(R^7)$n is 4-Me |
| 888 | X is N-Me, $R^1$ is Me, $R^2$ is Cl, $(R^7)$n is 4-Cl |
| 889 | X is a direct bond, $R^1$ is Et, $R^2$ is Cl, $(R^7)$n is H |
| 890 | X is a direct bond, $R^1$ is Et, $R^2$ is Cl, $(R^7)$n is 2-Me |
| 891 | X is a direct bond, $R^1$ is Et, $R^2$ is Cl, $(R^7)$n is 3-Me |
| 892 | X is a direct bond, $R^1$ is Et, $R^2$ is Cl, $(R^7)$n is 2,3-di-Me |
| 893 | X is a direct bond, $R^1$ is Et, $R^2$ is Cl, $(R^7)$n is 4-Me |
| 894 | X is a direct bond, $R^1$ is Et, $R^2$ is Cl, $(R^7)$n is 4-Cl |
| 895 | X is O, $R^1$ is Et, $R^2$ is Cl, $(R^7)$n is H |
| 896 | X is O, $R^1$ is Et, $R^2$ is Cl, $(R^7)$n is 2-Me |
| 897 | X is O, $R^1$ is Et, $R^2$ is Cl, $(R^7)$n is 3-Me |
| 898 | X is O, $R^1$ is Et, $R^2$ is Cl, $(R^7)$n is 2,3-di-Me |
| 899 | X is O, $R^1$ is Et, $R^2$ is Cl, $(R^7)$n is 4-Me |
| 900 | X is O, $R^1$ is Et, $R^2$ is Cl, $(R^7)$n is 4-Cl |
| 901 | X is S, $R^1$ is Et, $R^2$ is Cl, $(R^7)$n is H |
| 902 | X is S, $R^1$ is Et, $R^2$ is Cl, $(R^7)$n is 2-Me |
| 903 | X is S, $R^1$ is Et, $R^2$ is Cl, $(R^7)$n is 3-Me |
| 904 | X is S, $R^1$ is Et, $R^2$ is Cl, $(R^7)$n is 2,3-di-Me |
| 905 | X is S, $R^1$ is Et, $R^2$ is Cl, $(R^7)$n is 4-Me |
| 906 | X is S, $R^1$ is Et, $R^2$ is Cl, $(R^7)$n is 4-Cl |
| 907 | X is N-Me, $R^1$ is Et, $R^2$ is Cl, $(R^7)$n is H |
| 908 | X is N-Me, $R^1$ is Et, $R^2$ is Cl, $(R^7)$n is 2-Me |
| 909 | X is N-Me, $R^1$ is Et, $R^2$ is Cl, $(R^7)$n is 3-Me |
| 910 | X is N-Me, $R^1$ is Et, $R^2$ is Cl, $(R^7)$n is 2,3-di-Me |
| 911 | X is N-Me, $R^1$ is Et, $R^2$ is Cl, $(R^7)$n is 4-Me |
| 912 | X is N-Me, $R^1$ is Et, $R^2$ is Cl, $(R^7)$n is 4-Cl |

This disclosure also includes TABLES 818 through 912 wherein the Header Row Phrase in TABLE 817 (i.e. "X is a direct bond, $R^1$ is Me, $R^2$ is Me, $(R^{12})_n$ is H") is replaced with the Header Row Phrase listed in the respective TABLE, and the remaining variables (i.e. $R^3$ and $R^4$) are as defined in TABLE 1.

TABLE 913

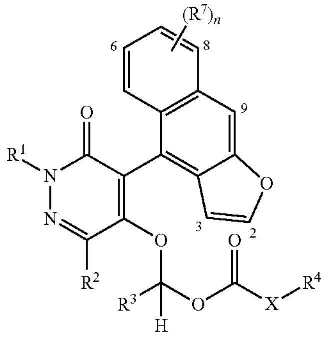

Header Row Phrase: X is a direct bond, $R^1$ is Me, $R^2$ is Me, $(R^7)_n$ is H; The remaining variables (i.e. $R^3$ and $R^4$) are as defined in TABLE 1.

| TABLE | Header Row |
|---|---|
| 914 | X is a direct bond, $R^1$ is Me, $R^2$ is Me, $(R^7)_n$ is 2-Me |
| 915 | X is a direct bond, $R^1$ is Me, $R^2$ is Me, $(R^7)_n$ is 3-Me |
| 916 | X is a direct bond, $R^1$ is Me, $R^2$ is Me, $(R^7)_n$ is 2,3-di-Me |
| 917 | X is a direct bond, $R^1$ is Me, $R^2$ is Me, $(R^7)_n$ is 9-Me |
| 918 | X is a direct bond, $R^1$ is Me, $R^2$ is Me, $(R^7)_n$ is 9-Cl |
| 919 | X is O, $R^1$ is Me, $R^2$ is Me, $(R^7)_n$ is H |
| 920 | X is O, $R^1$ is Me, $R^2$ is Me, $(R^7)_n$ is 2-Me |
| 921 | X is O, $R^1$ is Me, $R^2$ is Me, $(R^7)_n$ is 3-Me |
| 922 | X is O, $R^1$ is Me, $R^2$ is Me, $(R^7)_n$ is 2,3-di-Me |
| 923 | X is O, $R^1$ is Me, $R^2$ is Me, $(R^7)_n$ is 9-Me |
| 924 | X is O, $R^1$ is Me, $R^2$ is Me, $(R^7)_n$ is 9-Cl |
| 925 | X is S, $R^1$ is Me, $R^2$ is Me, $(R^7)_n$ is H |
| 926 | X is S, $R^1$ is Me, $R^2$ is Me, $(R^7)_n$ is 2-Me |
| 927 | X is S, $R^1$ is Me, $R^2$ is Me, $(R^7)_n$ is 3-Me |
| 928 | X is S, $R^1$ is Me, $R^2$ is Me, $(R^7)_n$ is 2,3-di-Me |
| 929 | X is S, $R^1$ is Me, $R^2$ is Me, $(R^7)_n$ is 9-Me |
| 930 | X is S, $R^1$ is Me, $R^2$ is Me, $(R^7)_n$ is 9-Cl |
| 931 | X is N-Me, $R^1$ is Me, $R^2$ is Me, $(R^7)_n$ is H |
| 932 | X is N-Me, $R^1$ is Me, $R^2$ is Me, $(R^7)_n$ is 2-Me |
| 933 | X is N-Me, $R^1$ is Me, $R^2$ is Me, $(R^7)_n$ is 3-Me |
| 934 | X is N-Me, $R^1$ is Me, $R^2$ is Me, $(R^7)_n$ is 2,3-di-Me |
| 935 | X is N-Me, $R^1$ is Me, $R^2$ is Me, $(R^7)_n$ is 9-Me |
| 936 | X is N-Me, $R^1$ is Me, $R^2$ is Me, $(R^7)_n$ is 9-Cl |
| 937 | X is a direct bond, $R^1$ is Et, $R^2$ is Me, $(R^7)_n$ is H |
| 938 | X is a direct bond, $R^1$ is Et, $R^2$ is Me, $(R^7)_n$ is 2-Me |
| 939 | X is a direct bond, $R^1$ is Et, $R^2$ is Me, $(R^7)_n$ is 3-Me |
| 940 | X is a direct bond, $R^1$ is Et, $R^2$ is Me, $(R^7)_n$ is 2,3-di-Me |
| 941 | X is a direct bond, $R^1$ is Et, $R^2$ is Me, $(R^7)_n$ is 9-Me |
| 942 | X is a direct bond, $R^1$ is Et, $R^2$ is Me, $(R^7)_n$ is 9-Cl |
| 943 | X is O, $R^1$ is Et, $R^2$ is Me, $(R^7)_n$ is H |
| 944 | X is O, $R^1$ is Et, $R^2$ is Me, $(R^7)_n$ is 2-Me |
| 945 | X is O, $R^1$ is Et, $R^2$ is Me, $(R^7)_n$ is 3-Me |
| 946 | X is O, $R^1$ is Et, $R^2$ is Me, $(R^7)_n$ is 2,3-di-Me |
| 947 | X is O, $R^1$ is Et, $R^2$ is Me, $(R^7)_n$ is 9-Me |
| 948 | X is O, $R^1$ is Et, $R^2$ is Me, $(R^7)_n$ is 9-Cl |
| 949 | X is S, $R^1$ is Et, $R^2$ is Me, $(R^7)_n$ is H |
| 950 | X is S, $R^1$ is Et, $R^2$ is Me, $(R^7)_n$ is 2-Me |
| 951 | X is S, $R^1$ is Et, $R^2$ is Me, $(R^7)_n$ is 3-Me |
| 952 | X is S, $R^1$ is Et, $R^2$ is Me, $(R^7)_n$ is 2,3-di-Me |
| 953 | X is S, $R^1$ is Et, $R^2$ is Me, $(R^7)_n$ is 9-Me |
| 954 | X is S, $R^1$ is Et, $R^2$ is Me, $(R^7)_n$ is 9-Cl |
| 955 | X is N-Me, $R^1$ is Et, $R^2$ is Me, $(R^7)_n$ is H |
| 956 | X is N-Me, $R^1$ is Et, $R^2$ is Me, (R7 R7 is 2-Me |
| 957 | X is N-Me, $R^1$ is Et, $R^2$ is Me, $(R^7)_n$ is 3-Me |
| 958 | X is N-Me, $R^1$ is Et, $R^2$ is Me, $(R^7)_n$ is 2,3-di-Me |
| 959 | X is N-Me, $R^1$ is Et, $R^2$ is Me, $(R^7)_n$ is 9-Me |
| 960 | X is N-Me, $R^1$ is Et, $R^2$ is Me, $(R^7)_n$ is 9-Cl |
| 961 | X is a direct bond, $R^1$ is Me, $R^2$ is Cl, $(R^7)_n$ is H |
| 962 | X is a direct bond, $R^1$ is Me, $R^2$ is Cl, $(R^7)_n$ is 2-Me |
| 963 | X is a direct bond, $R^1$ is Me, $R^2$ is Cl, $(R^7)_n$ is 3-Me |
| 964 | X is a direct bond, $R^1$ is Me, $R^2$ is Cl, $(R^7)_n$ is 2,3-di-Me |
| 965 | X is a direct bond, $R^1$ is Me, $R^2$ is Cl, $(R^7)_n$ is 9-Me |
| 966 | X is a direct bond, $R^1$ is Me, $R^2$ is Cl, $(R^7)_n$ is 9-Cl |
| 967 | X is O, $R^1$ is Me, $R^2$ is Cl, $(R^7)_n$ is H |
| 968 | X is O, $R^1$ is Me, $R^2$ is Cl, $(R^7)_n$ is 2-Me |
| 969 | X is O, $R^1$ is Me, $R^2$ is Cl, $(R^7)_n$ is 3-Me |
| 970 | X is O, $R^1$ is Me, $R^2$ is Cl, $(R^7)_n$ is 2,3-di-Me |
| 971 | X is O, $R^1$ is Me, $R^2$ is Cl, $(R^7)_n$ is 9-Me |

TABLE 913-continued

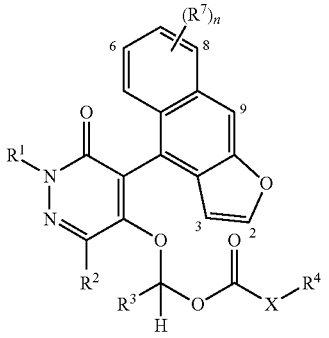

Header Row Phrase: X is a direct bond, $R^1$ is Me, $R^2$ is Me, $(R^7)_n$ is H; The remaining variables (i.e. $R^3$ and $R^4$) are as defined in TABLE 1.

| TABLE | Header Row |
|---|---|
| 972 | X is O, $R^1$ is Me, $R^2$ is Cl, $(R^7)_n$ is 9-Cl |
| 973 | X is S, $R^1$ is Me, $R^2$ is Cl, $(R^7)_n$ is H |
| 974 | X is S, $R^1$ is Me, $R^2$ is Cl, $(R^7)_n$ is 2-Me |
| 975 | X is S, $R^1$ is Me, $R^2$ is Cl, $(R^7)_n$ is 3-Me |
| 976 | X is S, $R^1$ is Me, $R^2$ is Cl, $(R^7)_n$ is 2,3-di-Me |
| 977 | X is S, $R^1$ is Me, $R^2$ is Cl, $(R^7)_n$ is 9-Me |
| 978 | X is S, $R^1$ is Me, $R^2$ is Cl, $(R^7)_n$ is 9-Cl |
| 979 | X is N-Me, $R^1$ is Me, $R^2$ is Cl, $(R^7)_n$ is H |
| 980 | X is N-Me, $R^1$ is Me, $R^2$ is Cl, $(R^7)_n$ is 2-Me |
| 981 | X is N-Me, $R^1$ is Me, $R^2$ is Cl, $(R^7)_n$ is 3-Me |
| 982 | X is N-Me, $R^1$ is Me, $R^2$ is Cl, $(R^7)_n$ is 2,3-di-Me |
| 983 | X is N-Me, $R^1$ is Me, $R^2$ is Cl, $(R^7)_n$ is 9-Me |
| 984 | X is N-Me, $R^1$ is Me, $R^2$ is Cl, $(R^7)_n$ is 9-Cl |
| 985 | X is a direct bond, $R^1$ is Et, $R^2$ is Cl, $(R^7)_n$ is H |
| 986 | X is a direct bond, $R^1$ is Et, $R^2$ is Cl, $(R^7)_n$ is 2-Me |
| 987 | X is a direct bond, $R^1$ is Et, $R^2$ is Cl, $(R^7)_n$ is 3-Me |
| 988 | X is a direct bond, $R^1$ is Et, $R^2$ is Cl, $(R^7)_n$ is 2,3-di-Me |
| 989 | X is a direct bond, $R^1$ is Et, $R^2$ is Cl, $(R^7)_n$ is 9-Me |
| 990 | X is a direct bond, $R^1$ is Et, $R^2$ is Cl, $(R^7)_n$ is 9-Cl |
| 991 | X is O, $R^1$ is Et, $R^2$ is Cl, $(R^7)_n$ is H |
| 992 | X is O, $R^1$ is Et, $R^2$ is Cl, $(R^7)_n$ is 2-Me |
| 993 | X is O, $R^1$ is Et, $R^2$ is Cl, $(R^7)_n$ is 3-Me |
| 994 | X is O, $R^1$ is Et, $R^2$ is Cl, $(R^7)_n$ is 2,3-di-Me |
| 995 | X is O, $R^1$ is Et, $R^2$ is Cl, $(R^7)_n$ is 9-Me |
| 996 | X is O, $R^1$ is Et, $R^2$ is Cl, $(R^7)_n$ is 9-Cl |
| 997 | X is S, $R^1$ is Et, $R^2$ is Cl, $(R^7)_n$ is H |
| 998 | X is S, $R^1$ is Et, $R^2$ is Cl, $(R^7)_n$ is 2-Me |
| 999 | X is S, $R^1$ is Et, $R^2$ is Cl, $(R^7)_n$ is 3-Me |
| 1000 | X is S, $R^1$ is Et, $R^2$ is Cl, $(R^7)_n$ is 2,3-di-Me |
| 1001 | X is S, $R^1$ is Et, $R^2$ is Cl, $(R^7)_n$ is 9-Me |
| 1002 | X is S, $R^1$ is Et, $R^2$ is Cl, $(R^7)_n$ is 9-Cl |
| 1003 | X is N-Me, $R^1$ is Et, $R^2$ is Cl, $(R^7)_n$ is H |
| 1004 | X is N-Me, $R^1$ is Et, $R^2$ is Cl, $(R^7)_n$ is 2-Me |
| 1005 | X is N-Me, $R^1$ is Et, $R^2$ is Cl, $(R^7)_n$ is 3-Me |
| 1006 | X is N-Me, $R^1$ is Et, $R^2$ is Cl, $(R^7)_n$ is 2,3-di-Me |
| 1007 | X is N-Me, $R^1$ is Et, $R^2$ is Cl, $(R^7)_n$ is 9-Me |
| 1008 | X is N-Me, $R^1$ is Et, $R^2$ is Cl, $(R^7)_n$ is 9-Cl |

This disclosure also includes TABLES 914 through 1008 wherein the Header Row Phrase in TABLE 913 (i.e. "X is a direct bond, $R^1$ is Me, $R^2$ is Me, $(R^{12})_n$ is H") is replaced with the Header Row Phrase listed in the respective TABLE, and the remaining variables (i.e. $R^3$ and $R^4$) are as defined in TABLE 1.

This disclosure also includes TABLE 1009 as below.

TABLE 1009

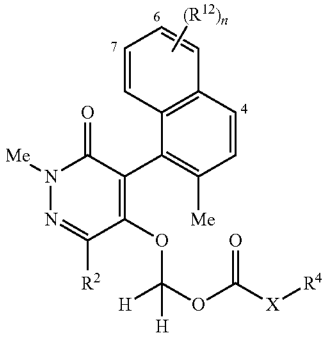

| Cmpd # | |
|---|---|
| 1009-1 | $R^2$ is Cl, $(R^{12})_n$ is 7-Me, X is DB, $R^4$ is Me |
| 1009-2 | $R^2$ is Cl, $(R^{12})_n$ is 7-Me, X is DB, $R^4$ is Et |
| 1009-3 | $R^2$ is Cl, $(R^{12})_n$ is 7-Me, X is DB, $R^4$ is $NMe_2$ |
| 1009-4 | $R^2$ is Cl, $(R^{12})_n$ is 7-Me, X is DB, $R^4$ is i-pro |
| 1009-5 | $R^2$ is Cl, $(R^{12})_n$ is 7-Me, X is DB, $R^4$ is t-Bu |
| 1009-6 | $R^2$ is Cl, $(R^{12})_n$ is 7-Me, X is O, $R^4$ is Me |
| 1009-7 | $R^2$ is Cl, $(R^{12})_n$ is 7-Me, X is O, $R^4$ is Et |
| 1009-8 | $R^2$ is Cl, $(R^{12})_n$ is 7-Me, X is O, $R^4$ is $NMe_2$ |
| 1009-9 | $R^2$ is Cl, $(R^{12})_n$ is 7-Me, X is O, $R^4$ is i-pro |
| 1009-10 | $R^2$ is Cl, $(R^{12})_n$ is 7-Me, X is O, $R^4$ is t-Bu |
| 1009-11 | $R^2$ is Cl, $(R^{12})_n$ is 7-Me, X is NMe, $R^4$ is Me |
| 1009-12 | $R^2$ is Cl, $(R^{12})_n$ is 7-Me, X is NMe, $R^4$ is Et |
| 1009-13 | $R^2$ is Cl, $(R^{12})_n$ is 7-Me, X is NMe, $R^4$ is $NMe_2$ |
| 1009-14 | $R^2$ is Cl, $(R^{12})_n$ is 7-Me, X is NMe, $R^4$ is i-pro |
| 1009-15 | $R^2$ is Cl, $(R^{12})_n$ is 7-Me, X is NMe, $R^4$ is t-Bu |
| 1009-16 | $R^2$ is Cl, $(R^{12})_n$ is 4-Cl, 7-F, X is DB, $R^4$ is Me |
| 1009-17 | $R^2$ is Cl, $(R^{12})_n$ is 4-Cl, 7-F, X is DB, $R^4$ is Et |
| 1009-18 | $R^2$ is Cl, $(R^{12})_n$ is 4-Cl, 7-F, X is DB, $R^4$ is $NMe_2$ |
| 1009-19 | $R^2$ is Cl, $(R^{12})_n$ is 4-Cl, 7-F, X is DB, $R^4$ is i-pro |
| 1009-20 | $R^2$ is Cl, $(R^{12})_n$ is 4-Cl, 7-F, X is DB, $R^4$ is t-Bu |
| 1009-21 | $R^2$ is Cl, $(R^{12})_n$ is 4-Cl, 7-F, X is O, $R^4$ is Me |
| 1009-22 | $R^2$ is Cl, $(R^{12})_n$ is 4-Cl, 7-F, X is O, $R^4$ is Et |
| 1009-23 | $R^2$ is Cl, $(R^{12})_n$ is 4-Cl, 7-F, X is O, $R^4$ is $NMe_2$ |
| 1009-24 | $R^2$ is Cl, $(R^{12})_n$ is 4-Cl, 7-F, X is O, $R^4$ is i-pro |
| 1009-25 | $R^2$ is Cl, $(R^{12})_n$ is 4-Cl, 7-F, X is O, $R^4$ is t-Bu |
| 1009-26 | $R^2$ is Cl, $(R^{12})_n$ is 4-Cl, 7-F, X is NMe, $R^4$ is Me |
| 1009-27 | $R^2$ is Cl, $(R^{12})_n$ is 4-Cl, 7-F, X is NMe, $R^4$ is Et |
| 1009-28 | $R^2$ is Cl, $(R^{12})_n$ is 4-Cl, 7-F, X is NMe, $R^4$ is $NMe_2$ |
| 1009-29 | $R^2$ is Cl, $(R^{12})_n$ is 4-Cl, 7-F, X is NMe, $R^4$ is i-pro |
| 1009-30 | $R^2$ is Cl, $(R^{12})_n$ is 4-Cl, 7-F, X is NMe, $R^4$ is t-Bu |
| 1009-31 | $R^2$ is Me, $(R^{12})_n$ is 7-Me, X is DB, $R^4$ is Me |
| 1009-32 | $R^2$ is Me, $(R^{12})_n$ is 7-Me, X is DB, $R^4$ is Et |
| 1009-33 | $R^2$ is Me, $(R^{12})_n$ is 7-Me, X is DB, $R^4$ is $NMe_2$ |
| 1009-34 | $R^2$ is Me, $(R^{12})_n$ is 7-Me, X is DB, $R^4$ is i-pro |
| 1009-35 | $R^2$ is Me, $(R^{12})_n$ is 7-Me, X is DB, $R^4$ is t-Bu |
| 1009-36 | $R^2$ is Me, $(R^{12})_n$ is 7-Me, X is O, $R^4$ is Me |
| 1009-37 | $R^2$ is Me, $(R^{12})_n$ is 7-Me, X is O, $R^4$ is Et |
| 1009-38 | $R^2$ is Me, $(R^{12})_n$ is 7-Me, X is O, $R^4$ is $NMe_2$ |
| 1009-39 | $R^2$ is Me, $(R^{12})_n$ is 7-Me, X is O, $R^4$ is i-pro |
| 1009-40 | $R^2$ is Me, $(R^{12})_n$ is 7-Me, X is O, $R^4$ is t-Bu |
| 1009-41 | $R^2$ is Me, $(R^{12})_n$ is 7-Me, X is NMe, $R^4$ is Me |
| 1009-42 | $R^2$ is Me, $(R^{12})_n$ is 7-Me, X is NMe, $R^4$ is Et |
| 1009-43 | $R^2$ is Me, $(R^{12})_n$ is 7-Me, X is NMe, $R^4$ is $NMe_2$ |
| 1009-44 | $R^2$ is Me, $(R^{12})_n$ is 7-Me, X is NMe, $R^4$ is i-pro |
| 1009-45 | $R^2$ is Me, $(R^{12})_n$ is 7-Me, X is NMe, $R^4$ is t-Bu |
| 1009-46 | $R^2$ is Me, $(R^{12})_n$ is 4-Cl, 7-F, X is DB, $R^4$ is Me |
| 1009-47 | $R^2$ is Me, $(R^{12})_n$ is 4-Cl, 7-F, X is DB, $R^4$ is Et |
| 1009-48 | $R^2$ is Me, $(R^{12})_n$ is 4-Cl, 7-F, X is DB, $R^4$ is $NMe_2$ |
| 1009-49 | $R^2$ is Me, $(R^{12})_n$ is 4-Cl, 7-F, X is DB, $R^4$ is i-pro |
| 1009-50 | $R^2$ is Me, $(R^{12})_n$ is 4-Cl, 7-F, X is DB, $R^4$ is t-Bu |
| 1009-51 | $R^2$ is Me, $(R^{12})_n$ is 4-Cl, 7-F, X is O, $R^4$ is Me |
| 1009-52 | $R^2$ is Me, $(R^{12})_n$ is 4-Cl, 7-F, X is O, $R^4$ is Et |
| 1009-53 | $R^2$ is Me, $(R^{12})_n$ is 4-Cl, 7-F, X is O, $R^4$ is $NMe_2$ |
| 1009-54 | $R^2$ is Me, $(R^{12})_n$ is 4-Cl, 7-F, X is O, $R^4$ is i-pro |
| 1009-55 | $R^2$ is Me, $(R^{12})_n$ is 4-Cl, 7-F, X is O, $R^4$ is t-Bu |
| 1009-56 | $R^2$ is Me, $(R^{12})_n$ is 4-Cl, 7-F, X is NMe, $R^4$ is Me |
| 1009-57 | $R^2$ is Me, $(R^{12})_n$ is 4-Cl, 7-F, X is NMe, $R^4$ is Et |
| 1009-58 | $R^2$ is Me, $(R^{12})_n$ is 4-Cl, 7-F, X is NMe, $R^4$ is $NMe_2$ |
| 1009-59 | $R^2$ is Me, $(R^{12})_n$ is 4-Cl, 7-F, X is NMe, $R^4$ is i-pro |
| 1009-60 | $R^2$ is Me, $(R^{12})_n$ is 4-Cl, 7-F, X is NMe, $R^4$ is t-Bu |

Formulation/Utility

A compound of this invention will generally be used as a herbicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil-in-water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil-in-water emulsion, flowable concentrate and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |

-continued

| | Weight Percent | | |
|---|---|---|---|
| | Active Ingredient | Diluent | Surfactant |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, New Jersey.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook,* 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modem Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook,* 8th Ed., Blackwell Scientific Publications, Oxford, 1989; and *Developments in formulation technology*, PJB Publications, Richmond, U K, 2000.

In the following Examples, all percentages are by weight and all formulations are prepared in conventional ways. Compound numbers refer to compounds in Index Table A. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

High Strength Concentrate

| | |
|---|---|
| Compound 2 | 98.5% |
| silica aerogel | 0.5% |
| synthetic amorphous fine silica | 1.0% |

Example B

Wettable Powder

| | |
|---|---|
| Compound 2 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

Granule

| | |
|---|---|
| Compound 2 | 10.0% |
| attapulgite granules (low volatile matter, 0.71/0.30 mm; U.S.S. No. 25-50 sieves) | 90.0% |

Example D

Extruded Pellet

| | |
|---|---|
| Compound 2 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

Emulsifiable Concentrate

| | |
|---|---|
| Compound 2 | 10.0% |
| polyoxyethylene sorbitol hexoleate | 20.0% |
| $C_6$-$C_{10}$ fatty acid methyl ester | 70.0% |

Example F

Microemulsion

| | |
|---|---|
| Compound 2 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

Suspension Concentrate

| | |
|---|---|
| Compound 2 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example H

Emulsion in Water

| | |
|---|---|
| Compound 2 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example I

Oil Dispersion

| | |
|---|---|
| Compound 2 | 25% |
| polyoxyethylene sorbitol hexaoleate | 15% |
| organically modified bentonite clay | 2.5% |
| fatty acid methyl ester | 57.5% |

The present disclosure also includes Examples A through I above except that "Compound 2" is replaced with "Compound 1", "Compound 3", "Compound 4", "Compound 5", "Compound 6", "Compound 7", "Compound 8", "Compound 9", "Compound 10", "Compound 11", "Compound 12", "Compound 13", "Compound 14", "Compound 15", "Compound 16", "Compound 17", "Compound 18", "Compound 19", "Compound 20", "Compound 21", "Compound 22", "Compound 23", "Compound 24", "Compound 25", "Compound 26", "Compound 27", "Compound 28", "Compound 29" or "Compound 30".

Test results indicate that the compounds of the present invention are highly active preemergent and/or postemergent herbicides and/or plant growth regulants. The compounds of the mention generally show highest activity for postemergence weed control (i.e. applied after weed seedlings emerge from the soil) and preemergence weed control (i.e. applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this invention, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays. Compounds of this invention may show tolerance to important agronomic crops including, but is not limited to, alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as eucalyptus and conifers (e.g., loblolly pine), and turf species (e.g., Kentucky bluegrass, St. Augustine grass, Kentucky fescue and Bermuda grass). Compounds of this invention can be used in crops genetically transformed or bred to incorporate resistance to herbicides, express proteins toxic to invertebrate pests (such as *Bacillus thuringiensis* toxin), and/or express other useful traits. Those skilled in the art will appreciate that not all compounds are equally effective against all weeds. Alternatively, the subject compounds are useful to modify plant growth.

As the compounds of the invention have both preemergent and postemergent herbicidal activity, to control undesired vegetation by killing or injuring the vegetation or reducing its growth, the compounds can be usefully applied by a variety of methods involving contacting a herbicidally effective amount of a compound of the invention, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation. Undesired vegetation includes at least one selected from the group consisting of grass weeds and broadleaf weeds. Undesired vegetation is selected from the group consisting of annual bluegrass, Benghal dayflower, blackgrass, black nightshade, broadleaf signalgrass, Canada thistle, cheat, common cocklebur (*Xanthium pensylvanicum*), common ragweed, corn poppies, field violet, giant foxtail, goosegrass, green foxtail, guinea grass, hairy beggarticks, herbicide-resistant black grass, horseweed, Italian rye grass, jimsonweed, Johnson grass (*Sorghum halepense*), large crabgrass, little seed canary grass, morning glory, Pennsylvania smartweed, pitted morning glory, prickly sida, quackgrass, redroot pigweed, shattercane, shepherd's purse, silky windgrass, sunflower (as weed in potato), wild buckwheat (*Polygonum convolvulus*), wild mustard (*Brassica kaber*), wild oat (*Avena fatua*), wild pointsettia, yellow foxtail, and yellow nutsedge (*Cyperus esculentus*).

A herbicidally effective amount of the compounds of this invention is determined by a number of factors. These factors include: formulation selected, method of application, amount and type of vegetation present, growing conditions, etc. In general, a herbicidally effective amount of compounds of this invention is about 0.001 to 20 kg/ha with a preferred range of about 0.004 to 1 kg/ha. One skilled in the art can easily determine the herbicidally effective amount necessary for the desired level of weed control.

In one common embodiment, a compound of the invention is applied, typically in a formulated composition, to a locus comprising desired vegetation (e.g., crops) and undesired vegetation (i.e. weeds), both of which may be seeds, seedlings and/or larger plants, in contact with a growth medium (e.g., soil). In this locus, a composition comprising a compound of the invention can be directly applied to a plant or a part thereof, particularly of the undesired vegetation, and/or to the growth medium in contact with the plant.

Although most typically, compounds of the invention are used to control undesired vegetation, contact of desired vegetation in the treated locus with compounds of the invention may result in super-additive or enhanced effects with genetic traits in the desired vegetation, including traits incorporated through genetic modification. For example, resistance to phytophagous insect pests or plant diseases, tolerance to biotic/abiotic stresses or storage stability may be greater than expected from the genetic traits in the desired vegetation.

Compounds of this invention can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of the compounds of the invention with other herbicides can broaden the spectrum of activity against additional weed species, and suppress the proliferation of any resistant biotypes. Thus the present invention also pertains to a composition comprising a compound of Formula 1 (in a herbicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

A mixture of one or more of the following herbicides with a compound of this invention may be particularly useful for weed control: acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, bixlozone, beflubutamid, beflubutamid-M, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clacyfos, clefoxydim, clethodim, clodinafop-propargyl, clomazone, clomeprop, clopyralid, clopyralid-olamine, cloransulam-methyl, cumyluron, cyanazine, cycloate, cyclopyrimorate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimesulfazet, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, epyrifenacil, esprocarb, ethalfluralin, ethametsulfuron-methyl, ethiozin, ethofumesate, ethoxyfen, ethoxysulfuron, etobenzanid, fenoxaprop-ethyl, fenoxaprop-P-ethyl, fenoxasulfone, fenquinotrione, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glufosinate-P, glyphosate and its salts such as ammonium, isopropylammonium, potassium, sodium (including sesquisodium) and trimesium (alternatively named sulfosate), halauxifen, halauxifen-methyl, halosulfuron-methyl, haloxyfop-etotyl, haloxyfop-methyl, hexazinone, hydantocidin, imazamethabenz-methyl, imazamox, imazapic, imazapyr, imazaquin, imazaquin-ammonium, imazethapyr, imazethapyr-ammonium, imazosulfuron, indanofan, indaziflam, iofensulfuron, iodosulfuron-methyl, ioxynil, ioxynil octanoate, ioxynil-sodium, ipfencarbazone, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, metazosulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, napropamide-M, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyrisulfuron, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, tetflupyrolimet, thenylchlor, thiazopyr, thiencarbazone, thifensulfuron-methyl, thiobencarb, tiafenacil, tiocarbazil, tolpyralate, topramezone, tralkoxydim, tri-allate, triafamone, triasulfuron, triaziflam, tribenuron-methyl, triclopyr, triclopyr-butotyl, triclopyr-triethylammonium, tridiphane, trietazine, trifloxysulfuron, trifludimoxazin, trifluralin, triflusulfuron-methyl, tritosulfuron, vernolate, 3-(2-chloro-3,6-difluorophenyl)-4-hydroxy-1-methyl-1,5-naphthyridin-2(1H)-one, 5-chloro-3-[(2-hydroxy-6-oxo-1-cyclohexen-1-yl)carbonyl]-1-(4-methoxyphenyl)-2(1H)-quinoxalinone, 2-chloro-N-(1-methyl-1H-tetrazol-5-yl)-6-(trifluoromethyl)-3-pyridinecarboxamide, 7-(3,5-dichloro-4-pyridinyl)-5-(2,2-difluoroethyl)-8-hydroxypyrido[2,3-b]pyrazin-6(5H)-one), 4-(2,6-diethyl-4-methylphenyl)-5-hydroxy-2,6-dimethyl-3(2H)-pyridazinone), 5-[[(2,6-difluorophenyl)methoxy]methyl]-4,5-dihydro-5-methyl-3-(3-methyl-2-thienyl)isoxazole (previously methioxolin), 4-(4-fluorophenyl)-6-[(2-hydroxy-6-oxo-1-cyclohexen-1-yl)carbonyl]-2-methyl-1,2,4-triazine-3,5(2H,4H)-dione, methyl 4-amino-3-chloro-6-(4-chloro-2-fluoro-3-methoxyphenyl)-5-fluoro-2-pyridinecarboxylate, 2-methyl-3-(methylsulfonyl)-N-(1-methyl-1H-tetrazol-5-yl)-4-(trifluoromethyl)benzamide and 2-methyl-N-(4-methyl-1,2,5-oxadiazol-3-yl)-3-(methylsulfinyl)-4-(trifluoromethyl)benzamide. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub.

Preferred for better control of undesired vegetation (e.g., lower use rate such as from enhanced effects, broader spectrum of weeds controlled, or enhanced crop safety) or for preventing the development of resistant weeds are mixtures of a compound of this invention with a herbicide selected from the group consisting of atrazine, azimsulfuron, S-beflubutamid, benzisothiazolinone, carfentrazone-ethyl, chlorimuron-ethyl, chlorsulfuron-methyl, clomazone, clopyralid potassium, cloransulam-methyl, 2-[(2,4-dichlorophenyl)methyl]-4,4-dimethyl-3-isoxazolidinone, 2-[(2,5-dichlorophenyl)methyl]-4,4-dimethyl-3-isoxazolidinone, ethametsulfuron-methyl, flumetsulam, 4-(4-fluorophenyl)-6-[(2-hydroxy-6-oxo-1-cyclohexen-1-yl)carbonyl]-2-methyl-1,2,4-triazine-3,5-(2H,4H)-dione, flupyrsulfuron-methyl, fluthiacet-methyl, fomesafen, imazethapyr, lenacil, mesotrione, metribuzin, metsulfuron-methyl, pethoxamid, picloram, pyroxasulfone, quinclorac, rimsulfuron, S-metolachlor, sulfentrazone, thifensulfuron-methyl, triflusulfuron-methyl and tribenuron-methyl.

Compounds of this invention can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual, 13th Edition*, C. D. S. Tomlin, Ed., British Crop Protection Council, Farnham, Surrey, U. K., 2003 and *The BioPesticide Manual, 2nd Edition*, L. G. Copping, Ed., British Crop Protection Council, Famham, Surrey, U. K., 2001.

For embodiments where one or more of these various mixing partners are used, the mixing partners are typically used in the amounts similar to amounts customary when the mixture partners are used alone. More particularly in mixtures, active ingredients are often applied at an application rate between one-half and the full application rate specified on product labels for use of active ingredient alone. These amounts are listed in references such as *The Pesticide Manual* and *The BioPesticide Manual*. The weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by the compound of Formula 1 alone.

In certain instances, combinations of a compound of this invention with other biologically active (particularly herbicidal) compounds or agents (i.e. active ingredients) can result in a greater-than-additive (i.e. enhanced) effect on weeds and/or a less-than-additive effect (i.e. safening) on crops or other desirable plants. Reducing the quantity of active ingredients released in the environment while ensuring effective pest control is always desirable. Ability to use greater amounts of active ingredients to provide more effective weed control without excessive crop injury is also desirable. When the enhanced effects of herbicidal mixtures of active ingredients occurs on weeds at application rates giving agronomically satisfactory levels of weed control, such combinations can be advantageous for reducing crop production cost and decreasing environmental load. When safening of herbicidal active ingredients occurs on crops, such combinations can be advantageous for increasing crop protection by reducing weed competition.

Of note is a combination of a compound of the invention with at least one other herbicidal active ingredient. Of particular note is such a combination where the other herbicidal active ingredient has different site of action from the compound of the invention. In certain instances, a combination with at least one other herbicidal active ingredient having a similar spectrum of control but a different site of action will be particularly advantageous for resistance management. Thus, a composition of the present invention can further comprise (in a herbicidally effective amount) at least one additional herbicidal active ingredient having a similar spectrum of control but a different site of action.

Compounds of this invention can also be used in combination with herbicide safeners such as allidochlor, benoxacor, cloquintocet-mexyl, cumyluron, cyometrinil, cyprosulfonamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone naphthalic anhydride (1,8-naphthalic anhydride), oxabetrinil, N-(aminocarbonyl)-2-methylbenzenesulfonamide, N-(aminocarbonyl)-2-fluorobenzenesulfonamide, 1-bromo-4-[(chloromethyl)sulfonyl]benzene (BCS), 4-(dichloroacetyl)-1-oxa-4-azospiro[4.5]decane (MON 4660), 2-(dichloromethyl)-2-methyl-1,3-dioxolane (MG 191), ethyl 1,6-dihydro-1-(2-methoxyphenyl)-6-oxo-2-phenyl-5-pyrimidinecarboxylate, 2-hydroxy-N,N-dimethyl-6-(trifluoromethyl)pyridine-3-carboxamide, and 3-oxo-1-cyclohexen-1-yl 1-(3,4-dimethylphenyl)-1,6-dihydro-6-oxo-2-phenyl-5-pyrimidinecarboxylate, 2,2-dichloro-1-(2,2,5-trimethyl-3-oxazolidinyl)-ethanone and 2-methoxy-N-[[4-[[(methylamino)carbonyl]amino]phenyl]sulfonyl]-benzamide to increase safety to certain crops. Antidotally effective amounts of the herbicide safeners can be applied at the same time as the compounds of this invention, or applied as seed treatments. Therefore an aspect of the present invention relates to a herbicidal mixture comprising a compound of this invention and an antidotally effective amount of a herbicide safener. Seed treatment is particularly useful for selective weed control, because it physically restricts antidoting to the crop plants. Therefore a particularly useful embodiment of the present invention is a method for selectively controlling the growth of undesired vegetation in a crop comprising contacting the locus of the crop with a herbicidally effective amount of a compound of this invention wherein seed from which the crop is grown is treated with an antidotally effective amount of safener. Antidotally effective amounts of safeners can be easily determined by one skilled in the art through simple experimentation.

Compounds of the invention can also be mixed with: (1) polynucleotides including but not limited to DNA, RNA, and/or chemically modified nucleotides influencing the amount of a particular target through down regulation, interference, suppression or silencing of the genetically derived transcript that render a herbicidal effect; or (2) polynucleotides including but not limited to DNA, RNA, and/or chemically modified nucleotides influencing the amount of a particular target through down regulation, interference, suppression or silencing of the genetically derived transcript that render a safening effect.

Of note is a composition comprising a compound of the invention (in a herbicidally effective amount), at least one additional active ingredient selected from the group consisting of other herbicides and herbicide safeners (in an effective amount), and at least one component selected from the group consisting of surfactants, solid diluents and liquid diluents.

Table A1 lists specific combinations of a Component (a) with Component (b) illustrative of the mixtures, compositions and methods of the present invention. Compound No. (Compound Number) (i.e. Compound 1) in the Component (a) column is identified in Index Table A. The second column of Table A1 lists the specific Component (b) compound (e.g., "2,4-D" in the first line). The third, fourth and fifth columns of Table A1 lists ranges of weight ratios for rates at which the Component (a) compound is typically applied to a field-grown crop relative to Component (b) (i.e. (a):(b)). Thus, for example, the first line of Table A1 specifically discloses the combination of Component (a) (i.e. Compound 1 in Index Table A) with 2,4-D is typically applied in a weight ratio between 1:384-6:1. The remaining lines of Table A1 are to be construed similarly.

TABLE A1

| Component (a) (Compound No.) | Component (b) | Typical Weight Ratio | More Typical Weight Ratio | Most Typical Weight Ratio |
|---|---|---|---|---|
| 1 | 2,4-D | 1:384-6:1 | 1:128-2:1 | 1:12-1:2 |
| 1 | Acetochlor | 1:1536-2:1 | 1:512-1:2 | 1:48-1:6 |
| 1 | Acifluorfen | 1:192-12:1 | 1:64-4:1 | 1:6-2:1 |
| 1 | Aclonifen | 1:1714-2:1 | 1:571-1:3 | 1:53-1:6 |
| 1 | Alachlor | 1:1536-2:1 | 1:512-1:2 | 1:48-1:6 |
| 1 | Ametryn | 1:768-3:1 | 1:256-1:1 | 1:24-1:3 |
| 1 | Amicarbazone | 1:384-6:1 | 1:128-2:1 | 1:12-1:2 |
| 1 | Amidosulfuron | 1:13-168:1 | 1:4-56:1 | 2:1-21:1 |
| 1 | Aminocyclopyrachlor | 1:96-24:1 | 1:32-8:1 | 1:3-3:1 |
| 1 | Aminopyralid | 1:41-56:1 | 1:13-19:1 | 1:1-7:1 |
| 1 | Amitrole | 1:1536-2:1 | 1:512-1:2 | 1:48-1:6 |
| 1 | Anilofos | 1:192-12:1 | 1:64-4:1 | 1:6-2:1 |
| 1 | Asulam | 1:1920-2:1 | 1:640-1:3 | 1:60-1:7 |
| 1 | Atrazine | 1:384-6:1 | 1:128-2:1 | 1:12-1:2 |
| 1 | Azimsulfuron | 1:13-168:1 | 1:4-56:1 | 2:1-21:1 |
| 1 | Beflubutamid | 1:685-4:1 | 1:228-2:1 | 1:21-1:3 |
| 1 | Benfuresate | 1:1234-2:1 | 1:411-1:2 | 1:38-1:5 |
| 1 | Bensulfuron-methyl | 1:51-45:1 | 1:17-15:1 | 1:1-6:1 |
| 1 | Bentazone | 1:384-6:1 | 1:128-2:1 | 1:12-1:2 |
| 1 | Benzobicyclon | 1:171-14:1 | 1:57-5:1 | 1:5-2:1 |
| 1 | Benzofenap | 1:514-5:1 | 1:171-2:1 | 1:16-1:2 |
| 1 | Bicyclopyrone | 1:85-27:1 | 1:28-9:1 | 1:2-4:1 |
| 1 | Bifenox | 1:514-5:1 | 1:171-2:1 | 1:16-1:2 |
| 1 | Bispyribac-sodium | 1:20-112:1 | 1:6-38:1 | 1:1-14:1 |
| 1 | Bromacil | 1:768-3:1 | 1:256-1:1 | 1:24-1:3 |
| 1 | Bromobutide | 1:768-3:1 | 1:256-1:1 | 1:24-1:3 |
| 1 | Bromoxynil | 1:192-12:1 | 1:64-4:1 | 1:6-2:1 |
| 1 | Butachlor | 1:1536-2:1 | 1:512-1:2 | 1:48-1:6 |
| 1 | Butafenacil | 1:85-27:1 | 1:28-9:1 | 1:2-4:1 |
| 1 | Butylate | 1:3085-1:2 | 1:1028-1:5 | 1:96-1:11 |

TABLE A1-continued

| Component (a) (Compound No.) | Component (b) | Typical Weight Ratio | More Typical Weight Ratio | Most Typical Weight Ratio |
|---|---|---|---|---|
| 1 | Carfenstrole | 1:384-6:1 | 1:128-2:1 | 1:12-1:2 |
| 1 | Carfentrazone-ethyl | 1:257-9:1 | 1:85-3:1 | 1:8-2:1 |
| 1 | Chlorimuron-ethyl | 1:17-135:1 | 1:5-45:1 | 1:1-17:1 |
| 1 | Chlorotoluron | 1:1536-2:1 | 1:512-1:2 | 1:48-1:6 |
| 1 | Chlorsulfuron | 1:13-168:1 | 1:4-56:1 | 2:1-21:1 |
| 1 | Cincosulfuron | 1:34-68:1 | 1:11-23:1 | 1:1-9:1 |
| 1 | Cinidon-ethyl | 1:768-3:1 | 1:256-1:1 | 1:24-1:3 |
| 1 | Cinmethylin | 1:68-34:1 | 1:22-12:1 | 1:2-5:1 |
| 1 | Clacyfos | 1:384-6:1 | 1:128-2:1 | 1:12-1:2 |
| 1 | Clethodim | 1:96-24:1 | 1:32-8:1 | 1:3-3:1 |
| 1 | Clodinafop-propargyl | 1:41-56:1 | 1:13-19:1 | 1:1-7:1 |
| 1 | Clomazone | 1:768-3:1 | 1:256-1:1 | 1:24-1:3 |
| 1 | Clomeprop | 1:342-7:1 | 1:114-3:1 | 1:10-1:2 |
| 1 | Clopyralid | 1:384-6:1 | 1:128-2:1 | 1:12-1:2 |
| 1 | Cloransulam-methyl | 1:24-96:1 | 1:8-32:1 | 1:1-12:1 |
| 1 | Cumyluron | 1:768-3:1 | 1:256-1:1 | 1:24-1:3 |
| 1 | Cyanazine | 1:768-3:1 | 1:256-1:1 | 1:24-1:3 |
| 1 | Cyclopyrimorate | 1:34-68:1 | 1:11-23:1 | 1:1-9:1 |
| 1 | Cyclosulfamuron | 1:34-68:1 | 1:11-23:1 | 1:1-9:1 |
| 1 | Cycloxydim | 1:192-12:1 | 1:64-4:1 | 1:6-2:1 |
| 1 | Cyhalofop | 1:51-45:1 | 1:17-15:1 | 1:1-6:1 |
| 1 | Daimuron | 1:384-6:1 | 1:128-2:1 | 1:12-1:2 |
| 1 | Desmedipham | 1:644-4:1 | 1:214-2:1 | 1:20-1:3 |
| 1 | Dicamba | 1:384-6:1 | 1:128-2:1 | 1:12-1:2 |
| 1 | Dichlobenil | 1:2742-1:2 | 1:914-1:4 | 1:85-1:10 |
| 1 | Dichlorprop | 1:1851-2:1 | 1:617-1:3 | 1:57-1:7 |
| 1 | Diclofop-methyl | 1:768-3:1 | 1:256-1:1 | 1:24-1:3 |
| 1 | Diclosulam | 1:20-112:1 | 1:6-38:1 | 1:1-14:1 |
| 1 | Difenzoquat | 1:576-4:1 | 1:192-2:1 | 1:18-1:2 |
| 1 | Diflufenican | 1:1714-2:1 | 1:571-1:3 | 1:53-1:6 |
| 1 | Diflufenzopyr | 1:24-96:1 | 1:8-32:1 | 1:1-12:1 |
| 1 | Dimethachlor | 1:1536-2:1 | 1:512-1:2 | 1:48-1:6 |
| 1 | Dimethametryn | 1:384-6:1 | 1:128-2:1 | 1:12-1:2 |
| 1 | Dimethenamid-P | 1:768-3:1 | 1:256-1:1 | 1:24-1:3 |
| 1 | Dithiopyr | 1:384-6:1 | 1:128-2:1 | 1:12-1:2 |
| 1 | Diuron | 1:768-3:1 | 1:256-1:1 | 1:24-1:3 |
| 1 | EPTC | 1:1536-2:1 | 1:512-1:2 | 1:48-1:6 |
| 1 | Esprocarb | 1:2742-1:2 | 1:914-1:4 | 1:85-1:10 |
| 1 | Ethalfluralin | 1:768-3:1 | 1:256-1:1 | 1:24-1:3 |
| 1 | Ethametsulfuron-methyl | 1:34-68:1 | 1:11-23:1 | 1:1-9:1 |
| 1 | Ethoxyfen | 1:17-135:1 | 1:5-45:1 | 1:1-17:1 |
| 1 | Ethoxysulfuron | 1:41-56:1 | 1:13-19:1 | 1:1-7:1 |
| 1 | Etobenzanid | 1:514-5:1 | 1:171-2:1 | 1:16-1:2 |
| 1 | Fenoxaprop-ethyl | 1:240-10:1 | 1:80-4:1 | 1:7-2:1 |
| 1 | Fenoxasulfone | 1:171-14:1 | 1:57-5:1 | 1:5-2:1 |
| 1 | Fenquinotrione | 1:85-27:1 | 1:28-9:1 | 1:2-4:1 |
| 1 | Fentrazamide | 1:34-68:1 | 1:11-23:1 | 1:1-9:1 |
| 1 | Flazasulfuron | 1:34-68:1 | 1:11-23:1 | 1:1-9:1 |
| 1 | Florasulam | 1:5-420:1 | 1:1-140:1 | 5:1-53:1 |
| 1 | Fluazifop-butyl | 1:384-6:1 | 1:128-2:1 | 1:12-1:2 |
| 1 | Flucarbazone | 1:17-135:1 | 1:5-45:1 | 1:1-17:1 |
| 1 | Flucetosulfuron | 1:17-135:1 | 1:5-45:1 | 1:1-17:1 |
| 1 | Flufenacet | 1:514-5:1 | 1:171-2:1 | 1:16-1:2 |
| 1 | Flumetsulam | 1:48-48:1 | 1:16-16:1 | 1:1-6:1 |
| 1 | Flumiclorac-pentyl | 1:20-112:1 | 1:6-38:1 | 1:1-14:1 |
| 1 | Flumioxazin | 1:51-45:1 | 1:17-15:1 | 1:1-6:1 |
| 1 | Fluometuron | 1:768-3:1 | 1:256-1:1 | 1:24-1:3 |
| 1 | Flupyrsulfuron-methyl | 1:6-336:1 | 1:2-112:1 | 4:1-42:1 |
| 1 | Fluridone | 1:768-3:1 | 1:256-1:1 | 1:24-1:3 |
| 1 | Fluroxypyr | 1:192-12:1 | 1:64-4:1 | 1:6-2:1 |
| 1 | Flurtamone | 1:1714-2:1 | 1:571-1:3 | 1:53-1:6 |
| 1 | Fluthiacet-methyl | 1:96-42:1 | 1:32-14:1 | 1:1-6:1 |
| 1 | Fomesafen | 1:192-12:1 | 1:64-4:1 | 1:6-2:1 |
| 1 | Foramsulfuron | 1:27-84:1 | 1:9-28:1 | 1:1-11:1 |
| 1 | Glufosinate | 1:576-4:1 | 1:192-2:1 | 1:18-1:2 |
| 1 | Glyphosate | 1:576-4:1 | 1:192-2:1 | 1:18-1:2 |
| 1 | Halosulfuron-methyl | 1:34-68:1 | 1:11-23:1 | 1:1-9:1 |
| 1 | Halauxifen | 1:41-56:1 | 1:13-19:1 | 1:1-7:1 |
| 1 | Halauxifen methyl | 1:41-56:1 | 1:13-19:1 | 1:1-7:1 |
| 1 | Haloxyfop-methyl | 1:68-34:1 | 1:22-12:1 | 1:2-5:1 |
| 1 | Hexazinone | 1:384-6:1 | 1:128-2:1 | 1:12-1:2 |
| 1 | Imazamox | 1:27-84:1 | 1:9-28:1 | 1:1-11:1 |
| 1 | Imazapic | 1:41-56:1 | 1:13-19:1 | 1:1-7:1 |
| 1 | Imazapyr | 1:171-14:1 | 1:57-5:1 | 1:5-2:1 |
| 1 | Imazaquin | 1:68-34:1 | 1:22-12:1 | 1:2-5:1 |
| 1 | Imazethabenz-methyl | 1:342-7:1 | 1:114-3:1 | 1:10-1:2 |
| 1 | Imazethapyr | 1:48-48:1 | 1:16-16:1 | 1:1-6:1 |

TABLE A1-continued

| Component (a) (Compound No.) | Component (b) | Typical Weight Ratio | More Typical Weight Ratio | Most Typical Weight Ratio |
|---|---|---|---|---|
| 1 | Imazosulfuron | 1:54-42:1 | 1:18-14:1 | 1:1-6:1 |
| 1 | Indanofan | 1:685-4:1 | 1:228-2:1 | 1:21-1:3 |
| 1 | Indaziflam | 1:51-45:1 | 1:17-15:1 | 1:1-6:1 |
| 1 | Iodosulfuron-methyl | 1:6-336:1 | 1:2-112:1 | 4:1-42:1 |
| 1 | Ioxynil | 1:384-6:1 | 1:128-2:1 | 1:12-1:2 |
| 1 | Ipfencarbazone | 1:171-14:1 | 1:57-5:1 | 1:5-2:1 |
| 1 | Isoproturon | 1:768-3:1 | 1:256-1:1 | 1:24-1:3 |
| 1 | Isoxaben | 1:576-4:1 | 1:192-2:1 | 1:18-1:2 |
| 1 | Isoxaflutole | 1:120-20:1 | 1:40-7:1 | 1:3-3:1 |
| 1 | Lactofen | 1:85-27:1 | 1:28-9:1 | 1:2-4:1 |
| 1 | Lenacil | 1:768-3:1 | 1:256-1:1 | 1:24-1:3 |
| 1 | Linuron | 1:768-3:1 | 1:256-1:1 | 1:24-1:3 |
| 1 | MCPA | 1:384-6:1 | 1:128-2:1 | 1:12-1:2 |
| 1 | MCPB | 1:576-4:1 | 1:192-2:1 | 1:18-1:2 |
| 1 | Mecoprop | 1:1536-2:1 | 1:512-1:2 | 1:48-1:6 |
| 1 | Mefenacet | 1:768-3:1 | 1:256-1:1 | 1:24-1:3 |
| 1 | Mefluidide | 1:384-6:1 | 1:128-2:1 | 1:12-1:2 |
| 1 | Mesosulfuron-methyl | 1:10-224:1 | 1:3-75:1 | 3:1-28:1 |
| 1 | Mesotrione | 1:85-27:1 | 1:28-9:1 | 1:2-4:1 |
| 1 | Metamifop | 1:85-27:1 | 1:28-9:1 | 1:2-4:1 |
| 1 | Metazachlor | 1:768-3:1 | 1:256-1:1 | 1:24-1:3 |
| 1 | Metazosulfuron | 1:51-45:1 | 1:17-15:1 | 1:1-6:1 |
| 1 | Methabenzthiazuron | 1:1536-2:1 | 1:512-1:2 | 1:48-1:6 |
| 1 | Metolachlor | 1:1536-2:1 | 1:512-1:2 | 1:48-1:6 |
| 1 | Metosulam | 1:17-135:1 | 1:5-45:1 | 1:1-17:1 |
| 1 | Metribuzin | 1:384-6:1 | 1:128-2:1 | 1:12-1:2 |
| 1 | Metsulfuron-methyl | 1:4-560:1 | 1:1-187:1 | 7:1-70:1 |
| 1 | Molinate | 1:2057-2:1 | 1:685-1:3 | 1:64-1:8 |
| 1 | Napropamide | 1:768-3:1 | 1:256-1:1 | 1:24-1:3 |
| 1 | Napropamide-M | 1:384-6:1 | 1:128-2:1 | 1:12-1:2 |
| 1 | Naptalam | 1:384-6:1 | 1:128-2:1 | 1:12-1:2 |
| 1 | Nicosulfuron | 1:24-96:1 | 1:8-32:1 | 1:1-12:1 |
| 1 | Norflurazon | 1:2304-1:1 | 1:768-1:3 | 1:72-1:8 |
| 1 | Orbencarb | 1:2742-1:2 | 1:914-1:4 | 1:85-1:10 |
| 1 | Orthosulfamuron | 1:41-56:1 | 1:13-19:1 | 1:1-7:1 |
| 1 | Oryzalin | 1:1028-3:1 | 1:342-1:2 | 1:32-1:4 |
| 1 | Oxadiargyl | 1:768-3:1 | 1:256-1:1 | 1:24-1:3 |
| 1 | Oxadiazon | 1:1097-3:1 | 1:365-1:2 | 1:34-1:4 |
| 1 | Oxasulfuron | 1:54-42:1 | 1:18-14:1 | 1:1-6:1 |
| 1 | Oxaziclomefone | 1:85-27:1 | 1:28-9:1 | 1:2-4:1 |
| 1 | Oxyfluorfen | 1:768-3:1 | 1:256-1:1 | 1:24-1:3 |
| 1 | Paraquat | 1:384-6:1 | 1:128-2:1 | 1:12-1:2 |
| 1 | Pendimethalin | 1:768-3:1 | 1:256-1:1 | 1:24-1:3 |
| 1 | Penoxsulam | 1:20-112:1 | 1:6-38:1 | 1:1-14:1 |
| 1 | Penthoxamid | 1:768-3:1 | 1:256-1:1 | 1:24-1:3 |
| 1 | Pentoxazone | 1:205-12:1 | 1:68-4:1 | 1:6-2:1 |
| 1 | Phenmedipham | 1:205-12:1 | 1:68-4:1 | 1:6-2:1 |
| 1 | Picloram | 1:192-12:1 | 1:64-4:1 | 1:6-2:1 |
| 1 | Picolinafen | 1:68-34:1 | 1:22-12:1 | 1:2-5:1 |
| 1 | Pinoxaden | 1:51-45:1 | 1:17-15:1 | 1:1-6:1 |
| 1 | Pretilachlor | 1:384-6:1 | 1:128-2:1 | 1:12-1:2 |
| 1 | Primisulfuron-methyl | 1:17-135:1 | 1:5-45:1 | 1:1-17:1 |
| 1 | Prodiamine | 1:768-3:1 | 1:256-1:1 | 1:24-1:3 |
| 1 | Profoxydim | 1:85-27:1 | 1:28-9:1 | 1:2-4:1 |
| 1 | Prometryn | 1:768-3:1 | 1:256-1:1 | 1:24-1:3 |
| 1 | Propachlor | 1:2304-1:1 | 1:768-1:3 | 1:72-1:8 |
| 1 | Propanil | 1:768-3:1 | 1:256-1:1 | 1:24-1:3 |
| 1 | Propaquizafop | 1:96-24:1 | 1:32-8:1 | 1:3-3:1 |
| 1 | Propoxycarbazone | 1:34-68:1 | 1:11-23:1 | 1:1-9:1 |
| 1 | Propyrisulfuron | 1:34-68:1 | 1:11-23:1 | 1:1-9:1 |
| 1 | Propyzamide | 1:768-3:1 | 1:256-1:1 | 1:24-1:3 |
| 1 | Prosulfocarb | 1:2400-1:2 | 1:800-1:4 | 1:75-1:9 |
| 1 | Prosulfuron | 1:13-168:1 | 1:4-56:1 | 2:1-21:1 |
| 1 | Pyraclonil | 1:85-27:1 | 1:28-9:1 | 1:2-4:1 |
| 1 | Pyraflufen-ethyl | 1:10-224:1 | 1:3-75:1 | 3:1-28:1 |
| 1 | Pyrasulfotole | 1:27-84:1 | 1:9-28:1 | 1:1-11:1 |
| 1 | Pyrazolynate | 1:1714-2:1 | 1:571-1:3 | 1:53-1:6 |
| 1 | Pyrazosulfuron-ethyl | 1:20-112:1 | 1:6-38:1 | 1:1-14:1 |
| 1 | Pyrazoxyfen | 1:10-224:1 | 1:3-75:1 | 3:1-28:1 |
| 1 | Pyribenzoxim | 1:20-112:1 | 1:6-38:1 | 1:1-14:1 |
| 1 | Pyributicarb | 1:768-3:1 | 1:256-1:1 | 1:24-1:3 |
| 1 | Pyridate | 1:576-4:1 | 1:192-2:1 | 1:18-1:2 |
| 1 | Pyriftalid | 1:20-112:1 | 1:6-38:1 | 1:1-14:1 |
| 1 | Pyriminobac-methyl | 1:41-56:1 | 1:13-19:1 | 1:1-7:1 |
| 1 | Pyrimisulfan | 1:34-68:1 | 1:11-23:1 | 1:1-9:1 |
| 1 | Pyrithiobac | 1:48-48:1 | 1:16-16:1 | 1:1-6:1 |
| 1 | Pyroxasulfone | 1:171-14:1 | 1:57-5:1 | 1:5-2:1 |

TABLE A1-continued

| Component (a) (Compound No.) | Component (b) | Typical Weight Ratio | More Typical Weight Ratio | Most Typical Weight Ratio |
|---|---|---|---|---|
| 1 | Pyroxsulam | 1:10-224:1 | 1:3-75:1 | 3:1-28:1 |
| 1 | Quinclorac | 1:384-6:1 | 1:128-2:1 | 1:12-1:2 |
| 1 | Quizalofop-ethyl | 1:85-27:1 | 1:28-9:1 | 1:2-4:1 |
| 1 | Rimsulfuron | 1:27-84:1 | 1:9-28:1 | 1:1-11:1 |
| 1 | Saflufenacil | 1:51-45:1 | 1:17-15:1 | 1:1-6:1 |
| 1 | Sethoxydim | 1:192-12:1 | 1:64-4:1 | 1:6-2:1 |
| 1 | Simazine | 1:768-3:1 | 1:256-1:1 | 1:24-1:3 |
| 1 | Sulcotrione | 1:240-10:1 | 1:80-4:1 | 1:7-2:1 |
| 1 | Sulfentrazone | 1:294-8:1 | 1:98-3:1 | 1:9-1:2 |
| 1 | Sulfometuron-methyl | 1:68-34:1 | 1:22-12:1 | 1:2-5:1 |
| 1 | Sulfosulfuron | 1:17-135:1 | 1:5-45:1 | 1:1-17:1 |
| 1 | Tebuthiuron | 1:768-3:1 | 1:256-1:1 | 1:24-1:3 |
| 1 | Tefuryltrione | 1:85-27:1 | 1:28-9:1 | 1:2-4:1 |
| 1 | Tembotrione | 1:63-37:1 | 1:21-13:1 | 1:1-5:1 |
| 1 | Tepraloxydim | 1:51-45:1 | 1:17-15:1 | 1:1-6:1 |
| 1 | Terbacil | 1:576-4:1 | 1:192-2:1 | 1:18-1:2 |
| 1 | Terbuthylazine | 1:1714-2:1 | 1:571-1:3 | 1:53-1:6 |
| 1 | Terbutryn | 1:384-6:1 | 1:128-2:1 | 1:12-1:2 |
| 1 | Thenylchlor | 1:171-14:1 | 1:57-5:1 | 1:5-2:1 |
| 1 | Thiazopyr | 1:768-3:1 | 1:256-1:1 | 1:24-1:3 |
| 1 | Thiencarbazone | 1:6-336:1 | 1:2-112:1 | 4:1-42:1 |
| 1 | Thifensulfuron-methyl | 1:10-224:1 | 1:3-75:1 | 3:1-28:1 |
| 1 | Tiafenacil | 1:85-27:1 | 1:28-9:1 | 1:2-4:1 |
| 1 | Thiobencarb | 1:1536-2:1 | 1:512-1:2 | 1:48-1:6 |
| 1 | Topramezone | 1:13-168:1 | 1:4-56:1 | 2:1-21:1 |
| 1 | Tralkoxydim | 1:137-17:1 | 1:45-6:1 | 1:4-3:1 |
| 1 | Triallate | 1:1536-2:1 | 1:512-1:2 | 1:48-1:6 |
| 1 | Triasulfuron | 1:10-224:1 | 1:3-75:1 | 3:1-28:1 |
| 1 | Triaziflam | 1:342-7:1 | 1:114-3:1 | 1:10-1:2 |
| 1 | Tribenuron-methyl | 1:6-336:1 | 1:2-112:1 | 4:1-42:1 |
| 1 | Triclopyr | 1:384-6:1 | 1:128-2:1 | 1:12-1:2 |
| 1 | Trifloxy sulfuron | 1:5-420:1 | 1:1-140:1 | 5:1-53:1 |
| 1 | Trifluralin | 1:576-4:1 | 1:192-2:1 | 1:18-1:2 |
| 1 | Triflusulfuron-methyl | 1:34-68:1 | 1:11-23:1 | 1:1-9:1 |
| 1 | Tritosulfuron | 1:27-84:1 | 1:9-28:1 | 1:1-11:1 |

Table A2 is constructed the same as Table A1 above except that entries below the "Component (a)" column heading are replaced with the respective Component (a) Column Entry shown below. Compound No. in the Component (a) column is identified in Index Table A. Thus, for example, in Table A2 the entries below the "Component (a)" column heading all recite "Compound 2" (i.e. Compound 2 identified in Index Table A), and the first line below the column headings in Table A2 specifically discloses a mixture of Compound 2 with 2,4-D. Tables A3 through A60 are constructed similarly.

| Table Number | Component (a) Column Entries |
|---|---|
| A2 | Compound 2 |
| A3 | Compound 3 |
| A4 | Compound 4 |
| A5 | Compound 5 |
| A6 | Compound 6 |
| A7 | Compound 7 |
| A8 | Compound 8 |
| A9 | Compound 9 |
| A10 | Compound 10 |
| A11 | Compound 11 |
| A12 | Compound 12 |
| A13 | Compound 13 |
| A14 | Compound 14 |
| A15 | Compound 15 |
| A16 | Compound 16 |
| A17 | Compound 17 |
| A18 | Compound 18 |
| A19 | Compound 19 |
| A20 | Compound 20 |
| A21 | Compound 21 |

-continued

| Table Number | Component (a) Column Entries |
|---|---|
| A22 | Compound 22 |
| A23 | Compound 23 |
| A24 | Compound 24 |
| A25 | Compound 25 |
| A26 | Compound 26 |
| A27 | Compound 27 |
| A28 | Compound 28 |
| A29 | Compound 29 |
| A30 | Compound 30 |

Preferred for belier control of undesired vegetation (e.g., lower use rate such as from enhanced effects, broader spectrum of weeds controlled, or enhanced crop safety) or for preventing the development of resistant weeds are mixtures of a compound of this invention with a herbicide selected from the group consisting of chlorimuron-ethyl, nicosulfuron, mesotrione, thifensulfuron-methyl, flupyrsulfuron-methyl, tribenuron, pyroxasulfone, pinoxaden, tembotrione, pyroxsulam, metolachlor and S-metolachlor.

In one aspect, group —$CR^3R^{14}OCOXR^4$ in the compounds of Formula 1 are surprisingly important. These compounds have been discovered to have improved herbicidal activities on certain weeds for certain crops, more favorable pharmacokinetic properties or better tox profiles, compared to the compounds without this group (i.e. the group is replaced by H or by certain other groups). This surprising improvement indicates that the group —$CR^3R^{14}OCOXR^4$ is not a simple cleavable group. The improved pharmacokinetic properties or better tox profiles can be evaluated by the protocols described as follows.

Rat Acute Toxicity Study

An acute oral toxicity study is conducted in rats. Two groups of rats are arranged for dosing with the test material. Group 1, consisting of 2 rats, is scheduled to receive 300 mg/kg body weight, and group 2, consisting of 1 rat, is scheduled to receive 50 mg/kg body weight. The rat in group 2 is dosed depending on findings from group 1. Each group animals are dosed once and observed for 14 d. The animals are observed for mortality, morbidity and general health twice daily. Clinical Observations (skin and fur characteristics, eye and mucous membranes, respiratory, circulatory, autonomic and central nervous systems, somatomotor and behavior patterns) are monitored prior to dosing, on study day 8 and then study day 15. Any unscheduled observations will also be recorded during the study. Body weights are measured prior to dosing, study day 8 and study day 15. Any unscheduled terminations are recorded and body weights of animals are measured accordingly.

Toxicokinetics and Oral Toxicity Screen in Rats after a Single Dose 3 rats are administered test material at 2 different dose levels, 25 mg/kg body weight and 300 mg/kg body weight. The animals are observed for a duration of 7 d. Body weights are measured a day before dosing, just prior to dosing and daily thereafter. Mortality and morbidity are checked twice daily. Blood is collected from the animals at 0.5, 1, 2, 4, 8, 12, 24, 48, 72, 96, 120, 144, 168 h, and at sacrifice. Following dosing, approximately 0.2 mL of blood is collected at the intervals outlined in the Study Design, into tubes containing EDTA and kept on ice until processing into plasma. Processing occurs within approximately 2 h of collection. To separate plasma from red blood cells, whole blood is centrifuged at 4° C. for 5 minutes at approximately 2500 rpm. Plasma is stored frozen (≤10° C.) until analysis. At sacrifice, blood is collected before processing to plasma as above. 0.5 μm of peri-renal fat is collected form the animals at day of sacrifice and stored at ≤10° C. until analysis. Plasma and fat are analyzed by ultra-high-performance liquid chromatography with tandem mass spectrometry detection (LC-MS/MS) to determine the concentration of test substance. The concentration time course data for plasma from each animal is analyzed to determine pharmacokinetic parameters such as the terminal half-life (T½, h), area-under-the-curve (AUC, h×ng/mL), peak concentration (Cmax, ng/mL), and time to peak concentration (Tmax, h). These pharmacokinetic parameters along with dose normalized values for AUC and Cmax are calculated by non-compartmental analysis using a commercially available software program. In addition, the fat:plasma concentration ratio is determined at the terminal sacrifice.

Plasma Protein Binding

Studies are carried out in rat plasma, and collected on K2EDTA. An Equilibrium Dialysis device is used for all experiments. Stock solutions of the test articles and control compound are first prepared in dimethyl sulfoxide (DMSO). Aliquots of the DMSO solutions are dosed into 1.0 mL of plasma at a dosing concentration of 5 μM for the test article and 10 μM for a co-dosed control compound. Plasma (300 μL), containing test article and control compound, are loaded into two wells of a 96-well dialysis plate. Blank phosphate-buffered saline (500 μL) is added to each corresponding receiver chamber. The device is then placed into an enclosed heated rocker that is pre-warmed to 37° C., and allowed to incubate for 4 h, then both sides are sampled. Aliquots (50 μL for donor, 200 μL for receiver) are removed from the chambers and placed into a 96-well plate. Plasma (50 μL) is added to the wells containing the receiver samples, and 200 μL of PBS is added to the wells containing the donor samples. Two volumes of acetonitrile are added to each well, and the plate is mixed and then centrifuged at 3,000 rpm for 10 min. Aliquots of the supernatant are removed, diluted 1:1 into water, and analyzed by LC-MS/MS. Protein binding values are calculated as follows: % Bound=[(PARR in Donor−PARR in Receiver)/(PARR in Donor)]×100; PARR=peak area response ratio to internal standard, including applicable dilution factors.

Blood to Plasma Partitioning

Studies are carried out in rat whole blood, and collected on K2EDTA. The blood is kept on ice prior to the experiments. Hematocrit (the ratio of the volume of red blood cells to the total blood) is measured (n=3) by centrifugation of the whole blood for 5 minutes using micro-hematocrit capillary tubes. Control plasma is obtained from a portion of the whole blood by centrifugation at 1,000 g for 10 min. The whole blood and control plasma are adjusted to pH 7.4 and then warmed at 37° C. in a water bath for 10 min. Aliquots of the whole blood and control plasma are spiked with the test article and a control compound. The final concentration is 5 μM for test article and 5 μM for the control compounds in the incubation. All samples are then incubated at 37° C. in a shaking water bath. The total organic solvent content in the incubation was less than ≤1.0%. After incubation for 60 min (n=2), the incubated whole blood is removed from the water bath and the plasma is separated by centrifugation at 1,000 g for 10 minutes. Aliquots of the control plasma are also removed. All samples are treated with three volumes of ice-cold acetonitrile containing an internal standard. After the removal of plasma proteins by centrifugation at 1,640g (3,000 rpm) for 10 minutes at 4° C., the supernatants are diluted with water and analyzed by LC-MS/MS.

The RBC to Plasma Partitioning (KRBC/P) and Whole Blood to Plasma Partitioning (KWB/P) are calculated as follows: KRBC/P=(1/H)*(CCP/CP-1)+1 KWB/P=CCP/CP; H=Hematocrit CCP=Response ratio in control plasma CP=Response ratio in blood plasma.

Stability in Hepatocytes

Frozen rat cryopreserved hepatocytes are provided. The hepatocytes are thawed and prepared according to the vendor's instructions, pooled into a buffer (pH 7.4), and kept on ice prior to the experiments. The hepatocyte suspension is equilibrated in a shaking water bath at 37° C. for 3 min, and then the reaction is initiated by spiking the test article into the hepatocyte suspension (1.0×106 cells/mL) at a final test article concentration of 1 μM. The final DMSO content in the incubation mixture is ≤0.1%. The reaction mixture is incubated in a shaking water bath at 37° C. Positive control compounds A (1 μM) and B (100 μM), are performed in parallel to confirm the activity of the hepatocytes. Aliquots of the test article are withdrawn (n=1) at 0, 5, 15, 30, 60, 90, 120, and 240 min. Aliquots of A are withdrawn (n=1) at 0, 5, 15, 30, 60, and 120 min. Aliquots of control compound B are withdrawn (n=1) at 0 and 15 minutes. Experiments are also run concurrently in assay buffer without hepatocytes. Samples from these experiments are taken at 0, 120, and 240 min. The reaction is immediately terminated by adding three volumes of ice-cold acetonitrile containing an internal standard. The samples are then mixed and centrifuged to precipitate proteins. An aliquot of the supernatant is then diluted with water. Calibration standards for the analysis of control compound B metabolites are prepared in matched matrix. Test articles and control compound A samples are analyzed without calibration standards. All samples are analyzed by LC-MS/MS. The peak area response ratio (PARR) vs. internal standard is compared to the PARR at time 0 to determine the percent remaining at each time point. Half-lives and clearance values are calculated using commercially available graphing software, fitting to a single-phase exponential decay equation.

The following Tests demonstrate the control efficacy of the compounds of this invention against specific weeds. The weed control afforded by the compounds is not limited, however, to these species. See Index Table A for compound descriptions. The following abbreviations are used in the Index Table which follows: "Cmpd. No." stands for "Compound Number", "Ex." stands for "Example" and is followed by a number indicating in which example the compound is prepared. $^{1}H$ NMR spectra are reported in ppm downfield from tetramethylsilane in $CDCl_3$ solution unless indicated otherwise; i-Pr means isopropyl, t-Bu means tertiary butyl, "s" means singlet, "d" means doublet, "dd" means doublet of doublets, "ddd" means doublet of doublets of doublets, "t" means triplet, "dt" means doublet of triplets, "td" means triplet of doublets, "q" means quintet, and "m" means multiplet.

INDEX TABLE A

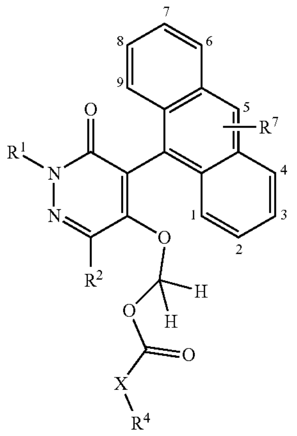

$R^3$ is H;

| Cmpd # | $R^1$ | $R^2$ | X | $R^4$ | $R^7$ | M.S. | M.P. (° C.) |
|---|---|---|---|---|---|---|---|
| 14 | $CH_3$ | $CH_3$ | DB* | $CH_3$ | 5-Br | ** | |
| 11 | $CH_3$ | Cl | DB* | $CH_3$ | 5-Cl | ** | |
| 12 | $CH_3$ | $CH_3$ | DB* | $CH_3$ | 5-Cl | ** | |
| 13 | $CH_3$ | $CH_3$ | DB* | $CH_3$ | H | ** | |
| 10 | $CH_3$ | Cl | DB* | $CH_3$ | H | ** | |
| 16 | $CH_3$ | $CH_3$ | DB* | $N(CH_3)_2$ | 2-F,8-$CH_3$ | 450.5 | |
| 15 | $CH_3$ | $CH_3$ | O | $CH_3$ | 2-F,8-$CH_3$ | 437.5 | |
| 22 | $CH_3$ | Cl | O | *i*-propyl | 2-$CH_3$, 8-$CH_3$ | ** | |
| 17 | $CH_3$ | CH | O | *i*-propyl | 2-F, 8-$CH_3$ | 465.5 | |
| 8 | $CH_3$ | Cl | O | $CH_3$ | 2-$CH_3$, 8-$CH_3$ | 453.4 | |
| 18 | $CH_3$ | Cl | DB* | $N(CH_3)_2$ | 2-$CH_3$, 8-$CH_3$ | 466.5 | |
| 29 | $CH_3$ | $CH_3$ | DB* | $CH_3$ | 2-$CH_3$, 6-F, 8-$CH_3$ | 435.3 | |
| 24 | $CH_3$ | $CH_3$ | DB* | $CH_3$ | 2-F, 8-$CH_3$ | 421.4 | |
| 27 | $CH_3$ | $CH_3$ | DB* | $CH_3$ | 2-$CH_3$, 4-$CH_3$, 8-F | 435.4 | |
| 19 | $CH_3$ | Cl | DB* | *t*-Bu | H | 451.5 | |
| 20 | $CH_3$ | Cl | DB* | *t*-Bu | 6-$CH_3$, 8-$CH_3$ | 479.5 | |
| 21 | $CH_3$ | $CH_3$ | DB* | *t*-Bu | 2-$CH_3$, 8-F | 463.6 | |
| 9 | $CH_3$ | Cl | DB* | *t*-Bu | 2-$CH_3$, 8-$CH_3$ | 479.5 | |
| 25 | $CH_3$ | $CH_3$ | DB* | $CH_3$ | 2,4-di-$OCH_3$, 8-F | 467.4 | |
| 26 | $CH_3$ | $CH_3$ | DB* | $CH_3$ | 2-$OCH_3$, 8-F | 437.4 | |
| 28 | $CH_3$ | $CH_3$ | DB* | $CH_3$ | 4-$CH_3$, 8-F | 421.3 | |
| 23 | $CH_3$ | Cl | DB* | $CH_3$ | 2-$CH_3$, 8-$CH_3$ | 437.4 | |

$R^7$ is attached to at least one carbon labeled 1, 2, 3, 4, 5, 6, 7, 8 or 9 and the position of $R^7$ is indicated by the number before the dash and atom. *DB means direct bond. **See Index Table C for $^{1}H$ NMR

INDEX TABLE B

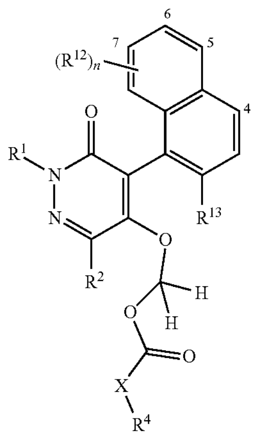

| Cmpd # | $R^1$ | $R^2$ | X | $R^4$ | $(R^{12})_n$ | $R^{13}$ | M.S. | M.P. (° C.) |
|---|---|---|---|---|---|---|---|---|
| 4 | $CH_3$ | Cl | DB* | *t*-Bu | 7-F | $CH_3$ | ** | |
| 6 | $CH_3$ | Cl | DB* | *i*-propyl | H | $CH_3$ | | 133-137 |
| 5 | $CH_3$ | Cl | DB* | CH3 | H | $CH_3$ | 373.3 | |
| 3 | $CH_3$ | Cl | DB* | CH3 | 7-CH3 | $CH_3$ | ** | |
| 7 | $CH_3$ | Cl | DB* | *t*-Bu | H | $CH_3$ | 415.1 | |
| 30 | $CH_3$ | $CH_3$ | DB* | *t*-Bu | 4-Cl, 7-F | $CH_3$ | ** | |

*DB means direct bond. **See Index Table D for $^1$H NMR

INDEX TABLE C

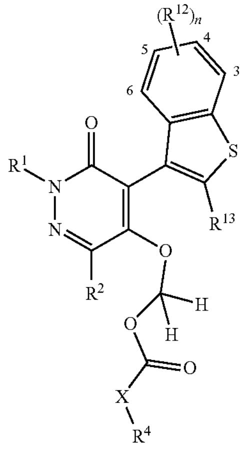

| Cmpd # | $R^1$ | $R^2$ | X | $R^4$ | $(R^{12})_n$ | $R^{13}$ | M.S. | M.P. (° C.) |
|---|---|---|---|---|---|---|---|---|
| 1 | $CH_3$ | Cl | DB* | $CH_3$ | 6-Cl | $CH_3$ | ** | |
| 2 | $CH_3$ | $CH_3$ | DB* | $CH_3$ | 5-F | Br | 443.0 | |

*DB means direct bond. **See Index Table D for $^1$H NMR

INDEX TABLE D

| Cmpd. No. | $^1$H NMR Data[a] ($CDCl_3$ solution unless indicated otherwise) |
|---|---|
| 14 | δ 8.62 (d, 2H), 7.71 (d, 2H), 7.61 (ddd, 2H), 7.51 (ddd, 2H), 4.67 (s, 2H), 3.84 (s, 3H), 2.38 (S, 3H), 1.70 (s, 3H) |
| 11 | δ 8.60 (d, 2H), 7.68 (dt, 2H), 7.62 (td, 2H), 7.53 (td, 2H, 4.85 (s, 2H), 3.87 (s, 3H), 1.67 (s, 3H) |
| 12 | δ 8.59 (d, 2H), 7.71 (d, 2H), 7.61 (td, 2H), 7.52 (td, 2H), 4.67 (s, 2H). 3.84 (s, 3H), 2.38 (s, 3H), 1.72 (s, 3H) |
| 13 | δ 8.56 (s, 1H), 8.06-8.02 (m, 2H), 7.71-7.66 (m, 2H), 7.49-7.45 (m, 4H), 4.63 (s, 2H), 3.84 (s, 3H), 2.38 (s, 3H), 1.73 (s, 3H) |
| 10 | δ 8.59 (s, 1H), 8.07-8.04 (m, 2H), 7.67-7.63 (m, 2H), 7.51-7.47 (m, 4H), 4.82 (s, 2H), 3.87 (s, 3H), 1.66 (s, 3H) |
| 22 | δ 8.47 (s, 1H), 7.93 (d, 2H), 7.29 (s, 2H), 7.27 (d, 2H), 4.80 (q, 1H), 4.72 (s, 2H), 3.87 (s, 3H), 2.48 (s, 6H), 1.25 (d, 6H) |
| 1 | δ 7.69 (m, 1H), 7.31 (m, 1H), 7.19-7.24 (m, 1H), 5.27-5.30 (m, 2H), 3.80 (s, 3H), 2.37 (s, 3H), 1.74 (s, 3H) |
| 4 | δ 7.80-7.88 (m, 2H), 7.38-7.43 (m, 1H), 7.19-7.26 (m, 1H), 7.07 (m, 1H), 5.02 (m, 1H), 4.75 (d, 1H), 3.83 (s, 3H), 2.37 (s, 3H), 1.11 (s, 9H) |
| 3 | δ 7.79 (m, 1H), 7.73 (m, 1H), 7.34 (m, 1H), 7.25-7.30 (m, 1H), 7.16 (s, 1H), 5.03 (m, 1H), 4.93 (m, 1H), 3.84 (s, 3H), 2.45 (s, 3H), 2.32 (s, 3H), 1.82 (s, 3H) |
| 30 | δ 8.29 (dd, 1H), 7.53 (s, 1H), 7.33 (dd, 1H), 7.10 (dd, 1H), 4.98 (d, 1H), 4.68 (d, 1H), 3.80 (s, 3H), 2.35 (s, 3H), 2.28 (s, 3H), 1.12 (s, 9H). |

[a] $^1$H NMR data are in ppm downfield from tetramethylsilane.

BIOLOGICAL EXAMPLES OF THE INVENTION

Test A

Seeds of plant species selected from barnyardgrass (*Echinochloa crus-galli*), blackgrass (*Alopecurus myosuroides*), corn (*Zea mays*), foxtail, giant (giant foxtail, *Setaria faberi*), foxtail, green (green foxtail, *Setaria viridis*), goosegrass (*Eleusine indica*), kochia (*Bassia scoparia*), oat, wild (wild oat, *Avena fatua*), palmer amaranth (pigweed, palmer, *Amaranthus palmeri*), redroot pigweed (*Amaranthus retroflexus*), ragweed (common ragweed, *Ambrosia artemisiifolia*), ryegrass, Italian (Italian ryegrass, *Lolium multiflorum*), and soybean (*Glycine max*) were planted into a blend of loam soil and sand and treated preemergence with a directed soil spray using test chemicals formulated in a non-phytotoxic solvent mixture which included a surfactant.

At the same time, plants selected from these crop and weed species and also wheat (*Triticum aestivum*), galium (catchweed bedstraw, *Galium aparine*) and horseweed (*Erigeron canadensis*) were planted in pots containing the same blend of loam soil and sand and treated with postemergence applications of test chemicals formulated in the same manner. Plants ranged in height from 2 to 10 cm and were in the one- to two-leaf stage for the postemergence treatment. Treated plants and untreated controls were maintained in a greenhouse for 10 days, after which time all treated plants were compared to untreated controls and visually evaluated for injury. Plant response ratings, summarized in Table A, are based on a 0 to 100 scale where 0 is no effect and 100 is complete control. A dash (-) response means no test result.

TABLE A

| 125 g ai/ha | Compounds | | | | | | | | | | | | | |
|---|---|---|---|---|---|---|---|---|---|---|---|---|---|---|
| Preemergence | 1 | 2 | 3 | 4 | 5 | 6 | 7 | 8 | 9 | 10 | 11 | 12 | 13 | 14 |
| Barnyardgrass | 0 | 0 | 100 | 100 | 100 | 0 | 90 | — | — | 0 | 30 | 90 | 30 | 80 |
| Blackgrass | — | — | — | — | — | — | — | 0 | 0 | — | — | — | — | — |
| Corn | — | — | — | — | — | — | — | 60 | 0 | — | — | — | — | — |
| Foxtail, Giant | — | 60 | 100 | — | — | — | — | 70 | 50 | 20 | 60 | 80 | 20 | 100 |
| Foxtail, Green | 10 | — | — | 100 | 90 | 50 | 100 | — | — | — | — | — | — | — |
| Goosegrass | — | — | — | — | — | — | — | 0 | 10 | — | — | — | — | — |
| Kochia | 10 | 50 | 90 | 100 | 70 | 50 | 70 | 100 | 100 | 0 | 10 | 100 | 0 | 30 |
| Oat, Wild | — | — | — | — | — | — | — | 0 | 0 | — | — | — | — | — |
| Pigweed, Palmer | — | — | — | — | — | — | — | 100 | 100 | — | — | — | — | — |
| Pigweed, Redroot | 90 | 100 | 100 | 100 | 100 | 100 | 100 | — | — | 100 | 100 | 100 | 100 | 100 |
| Ragweed | 20 | 90 | 90 | 100 | 100 | 80 | 90 | 100 | 60 | 40 | — | 80 | — | 100 |
| Ryegrass, Italian | 10 | 100 | 100 | 100 | 100 | 70 | 90 | 10 | 0 | 10 | 30 | 90 | 70 | 100 |
| Soybean | — | — | — | — | — | — | — | 0 | 0 | — | — | — | — | — |
| Wheat | — | — | — | — | — | — | — | 0 | 0 | — | — | — | — | — |

| 125 g ai/ha | Compounds | | | | | | | | | | | | | |
|---|---|---|---|---|---|---|---|---|---|---|---|---|---|---|
| Preemergence | 15 | 16 | 17 | 18 | 19 | 20 | 21 | 22 | 23 | 24 | 25 | 26 | 27 | 28 |
| Barnyardgrass | — | — | — | — | — | — | — | — | 80 | 90 | 0 | 70 | 30 | 0 |
| Blackgrass | 10 | 0 | 20 | 0 | 10 | 10 | 40 | 0 | — | — | — | — | — | — |
| Corn | 30 | 0 | 30 | 0 | 0 | 0 | 0 | 0 | — | — | — | — | — | — |
| Foxtail, Giant | 100 | 0 | 100 | 0 | 70 | 20 | 100 | 30 | 20 | 100 | 0 | 90 | 70 | 0 |
| Foxtail, Green | — | — | — | — | — | — | — | — | — | — | — | — | — | — |
| Goosegrass | 90 | 0 | 60 | 0 | 30 | 0 | 60 | 0 | — | — | — | — | — | — |
| Kochia | 100 | 0 | 90 | 0 | 80 | 0 | 100 | 70 | 90 | 90 | 0 | 90 | 80 | 20 |
| Oat, Wild | 20 | 0 | 0 | 0 | 0 | 0 | 40 | 20 | — | — | — | — | — | — |
| Pigweed, Palmer | 100 | 0 | 100 | 40 | 100 | 60 | 100 | 100 | — | — | — | — | — | — |
| Pigweed, Redroot | — | — | — | — | — | — | — | — | 100 | 100 | 30 | 100 | 100 | 100 |
| Ragweed | 100 | 0 | 100 | 0 | 80 | 50 | 90 | 90 | 90 | 90 | 0 | 30 | 100 | 100 |
| Ryegrass, Italian | 100 | 0 | 80 | 0 | 80 | 0 | 90 | 0 | 0 | 80 | 0 | 90 | 90 | 0 |
| Soybean | 10 | 0 | 0 | 0 | 0 | 0 | 0 | 0 | — | — | — | — | — | — |
| Wheat | 0 | 0 | 0 | 0 | 0 | 0 | 0 | 0 | — | — | — | — | — | — |

TABLE A-continued

| 125 g ai/ha Preemergence | Compounds 29 | 30 |
|---|---|---|
| Barnyardgrass | 70 | 80 |
| Blackgrass | — | — |
| Corn | — | — |
| Foxtail, Giant | 20 | — |
| Foxtail, Green | — | 100 |
| Goosegrass | — | — |
| Kochia | 100 | 20 |
| Oat, Wild | — | — |
| Pigweed, Palmer | — | — |
| Pigweed, Redroot | 100 | 100 |
| Ragweed | 90 | 90 |
| Ryegrass, Italian | 60 | 100 |
| Soybean | — | — |
| Wheat | — | — |

| 31 g ai/ha | Compounds | | | | | | | | | | | | | |
|---|---|---|---|---|---|---|---|---|---|---|---|---|---|---|
| Preemergence | 1 | 2 | 3 | 4 | 5 | 6 | 7 | 8 | 9 | 10 | 11 | 12 | 13 | 14 |
| Barnyardgrass | 0 | 0 | 60 | 10 | 80 | 0 | 50 | — | — | 0 | 20 | 20 | 0 | 10 |
| Blackgrass | — | — | — | — | — | — | — | 0 | 0 | — | — | — | — | — |
| Corn | — | — | — | — | — | — | — | 0 | 0 | — | | — | — | |
| Foxtail, Giant | — | 30 | 10 | — | — | — | — | 30 | 0 | 0 | 10 | 10 | 0 | 60 |
| Foxtail, Green | 0 | — | — | 70 | 50 | 0 | 60 | — | — | — | — | — | — | — |
| Goosegrass | — | — | — | — | — | — | — | 0 | 10 | — | — | — | — | — |
| Kochia | 0 | 20 | 10 | 20 | 40 | 10 | 10 | 60 | 50 | 0 | 0 | 0 | 0 | 20 |
| Oat, Wild | — | — | — | — | — | — | — | 0 | 0 | — | — | — | — | — |
| Pigweed, Palmer | — | — | — | — | — | — | — | 100 | 40 | — | — | — | — | — |
| Pigweed, Redroot | 80 | 90 | 100 | 100 | 100 | 90 | 100 | — | — | 100 | 100 | 100 | 100 | 100 |
| Ragweed | 10 | 70 | 90 | 100 | 100 | 10 | 50 | 40 | 0 | 40 | — | 60 | — | 90 |
| Ryegrass, Italian | 0 | 70 | 20 | 90 | 70 | 20 | 50 | 0 | 0 | 0 | 0 | 70 | 30 | 80 |
| Soybean | — | — | — | — | — | — | — | 0 | 0 | — | — | — | — | — |
| Wheat | — | — | — | — | — | — | — | 0 | 0 | — | — | — | — | — |

| 31 g ai/ha | Compounds | | | | | | | | | | | | | |
|---|---|---|---|---|---|---|---|---|---|---|---|---|---|---|
| Preemergence | 15 | 16 | 17 | 18 | 19 | 20 | 21 | 22 | 23 | 24 | 25 | 26 | 27 | 28 |
| Barnyardgrass | — | — | — | — | — | — | — | — | 30 | 60 | 0 | 10 | 0 | 0 |
| Blackgrass | 30 | 0 | 0 | 0 | 0 | 0 | 0 | 0 | — | — | — | — | — | — |
| Corn | 0 | 0 | 0 | 0 | 0 | 0 | 0 | 0 | — | — | — | — | — | — |
| Foxtail, Giant | 100 | 0 | 100 | 0 | 10 | 0 | 80 | 0 | 0 | 90 | 0 | 20 | 0 | 0 |
| Foxtail, Green | — | — | — | — | — | — | — | — | — | — | — | — | — | — |
| Goosegrass | 50 | 0 | 50 | 0 | 0 | 0 | 40 | 0 | — | — | — | — | — | — |
| Kochia | 90 | 0 | 90 | 0 | 0 | 0 | 100 | 40 | 60 | 70 | 0 | 20 | 0 | 0 |
| Oat, Wild | 20 | 0 | 0 | 0 | 0 | 0 | 0 | 0 | — | — | — | — | — | — |
| Pigweed, Palmer | 100 | 10 | 100 | 0 | 90 | 30 | 100 | 80 | — | — | — | — | — | — |
| Pigweed, Redroot | — | — | — | — | — | — | — | — | 100 | 100 | 0 | 100 | 100 | 100 |
| Ragweed | 100 | 0 | 100 | 0 | 80 | 0 | 50 | 20 | 40 | 90 | 0 | 30 | 50 | 90 |
| Ryegrass, Italian | 50 | 0 | 30 | 0 | 0 | 0 | 40 | 0 | 0 | 50 | 0 | 10 | 10 | 0 |
| Soybean | 0 | 0 | 0 | 0 | 0 | 0 | 0 | 0 | — | — | — | — | — | — |
| Wheat | 0 | 0 | 0 | 0 | 0 | 0 | 0 | 0 | — | — | — | — | — | — |

| 31 g ai/ha Preemergence | Compounds 29 | 30 |
|---|---|---|
| Barnyardgrass | 0 | 0 |
| Blackgrass | — | — |
| Corn | — | — |
| Foxtail, Giant | 0 | — |
| Foxtail, Green | — | 20 |
| Goosegrass | — | — |
| Kochia | 20 | 20 |
| Oat, Wild | — | — |
| Pigweed, Palmer | — | — |
| Pigweed, Redroot | 100 | 80 |
| Ragweed | 90 | 80 |
| Ryegrass, Italian | 0 | 100 |
| Soybean | — | — |
| Wheat | — | — |

TABLE A-continued

| 125 g ai/ha | Compounds | | | | | | | | | | | | | |
|---|---|---|---|---|---|---|---|---|---|---|---|---|---|---|
| Postemergence | 1 | 2 | 3 | 4 | 5 | 6 | 7 | 8 | 9 | 10 | 11 | 12 | 13 | 14 |
| Barnyardgrass | 40 | 60 | 90 | 60 | 80 | 50 | 80 | — | — | 10 | 30 | 60 | 40 | 80 |
| Blackgrass | 0 | 30 | 30 | 70 | 50 | 40 | 30 | 0 | 0 | 0 | 10 | 30 | 40 | 30 |
| Corn | 0 | 30 | 20 | 0 | 10 | 0 | 10 | 20 | 20 | 20 | 10 | 10 | 0 | 0 |
| Foxtail, Giant | — | 90 | 90 | — | — | — | — | 70 | 40 | 50 | 80 | 80 | 60 | 90 |
| Foxtail, Green | 10 | — | — | 80 | 80 | 60 | 70 | — | — | — | — | — | — | — |
| Galium | 90 | 100 | 100 | 100 | 100 | 90 | 90 | 100 | 100 | 100 | 100 | 100 | 100 | 100 |
| Goosegrass | — | — | — | — | — | — | — | 0 | 30 | — | — | — | — | — |
| Horseweed | — | — | — | — | — | — | — | 100 | 100 | — | — | — | — | — |
| Kochia | 50 | 80 | 80 | 40 | 60 | 60 | 70 | 100 | 90 | 10 | 50 | 80 | 50 | 60 |
| Oat, Wild | — | — | — | — | — | — | — | 10 | 0 | — | — | — | — | — |
| Pigweed, Palmer | — | — | — | — | — | — | — | 100 | 80 | — | — | — | — | — |
| Pigweed, Redroot | 90 | 90 | 100 | 100 | 100 | 100 | 90 | — | — | 100 | 100 | 100 | 100 | 100 |
| Ragweed | 90 | 100 | 100 | 100 | 90 | 80 | 90 | 100 | 100 | 100 | 100 | 100 | 100 | 100 |
| Ryegrass, Italian | 30 | 100 | 100 | 90 | 80 | 70 | 70 | 10 | 10 | 0 | 70 | 100 | 100 | 100 |
| Soybean | — | — | — | — | — | — | — | 60 | 60 | — | — | — | — | — |
| Wheat | 0 | 40 | 20 | 70 | 30 | 10 | 50 | 0 | 0 | 0 | 0 | 10 | 0 | 40 |

| 125 g ai/ha | Compounds | | | | | | | | | | | | | |
|---|---|---|---|---|---|---|---|---|---|---|---|---|---|---|
| Postemergence | 15 | 16 | 17 | 18 | 19 | 20 | 21 | 22 | 23 | 24 | 25 | 26 | 27 | 28 |
| Barnyardgrass | — | — | — | — | — | — | — | — | 90 | 90 | 10 | 40 | 30 | 0 |
| Blackgrass | 10 | 0 | 10 | 0 | 0 | 0 | 20 | 0 | 20 | 20 | 10 | 10 | 0 | 0 |
| Corn | 50 | 0 | 30 | 0 | 20 | 20 | 40 | 0 | 40 | 20 | 20 | 10 | 10 | 0 |
| Foxtail, Giant | 100 | 20 | 100 | 0 | 50 | 30 | 100 | 20 | 50 | 90 | 20 | 70 | 30 | 0 |
| Foxtail, Green | — | — | — | — | — | — | — | — | — | — | — | — | — | — |
| Galium | 100 | 50 | 100 | 30 | 100 | 50 | 100 | 100 | 100 | 100 | 60 | 100 | 100 | 100 |
| Goosegrass | 60 | 0 | 50 | 0 | 10 | 30 | 30 | 0 | — | — | — | — | — | — |
| Horseweed | 100 | 10 | 100 | 20 | 90 | 80 | 100 | 70 | — | — | — | — | — | — |
| Kochia | 100 | 80 | 100 | 70 | 80 | 60 | 100 | 60 | 80 | 100 | 10 | 80 | 70 | 30 |
| Oat, Wild | 40 | 0 | 30 | 0 | 10 | 0 | 40 | 0 | — | — | — | — | — | — |
| Pigweed, Palmer | 100 | 60 | 100 | 50 | 100 | 50 | 100 | 90 | — | — | — | — | — | — |
| Pigweed, Redroot | — | — | — | — | — | — | — | — | 100 | 100 | 90 | 100 | 100 | 100 |
| Ragweed | 100 | 30 | 100 | 100 | 100 | 70 | 100 | 80 | 100 | 100 | 0 | 100 | 90 | 100 |
| Ryegrass, Italian | 100 | 0 | 100 | 0 | 10 | 0 | 100 | 30 | 40 | 90 | 0 | 90 | 100 | 60 |
| Soybean | 90 | 30 | 80 | 20 | 30 | 0 | 100 | 20 | — | — | — | — | — | — |
| Wheat | 0 | 0 | 0 | 0 | 0 | 0 | 0 | 10 | 0 | 0 | 0 | 60 | 0 | 0 |

| 125 g ai/ha | Compounds | |
|---|---|---|
| Postemergence | 29 | 30 |
| Barnyardgrass | 90 | 50 |
| Blackgrass | 20 | 80 |
| Corn | 0 | 10 |
| Foxtail, Giant | 20 | — |
| Foxtail, Green | — | 80 |
| Galium | 100 | 100 |
| Goosegrass | — | — |
| Horseweed | — | — |
| Kochia | 100 | 30 |
| Oat, Wild | — | — |
| Pigweed, Palmer | — | — |
| Pigweed, Redroot | 100 | 90 |
| Ragweed | 100 | 100 |
| Ryegrass, Italian | 60 | 100 |
| Soybean | — | — |
| Wheat | 0 | 60 |

| 31 g ai/ha | Compounds | | | | | | | | | | | | | |
|---|---|---|---|---|---|---|---|---|---|---|---|---|---|---|
| Postemergence | 1 | 2 | 3 | 4 | 5 | 6 | 7 | 8 | 9 | 10 | 11 | 12 | 13 | 14 |
| Barnyardgrass | 0 | 50 | 60 | 20 | 40 | 20 | 10 | — | — | 20 | 20 | 10 | 10 | 30 |
| Blackgrass | 0 | 30 | 10 | 20 | 20 | 0 | 0 | 0 | 0 | 30 | 40 | 0 | 0 | 20 |
| Corn | 0 | 0 | 0 | 0 | 0 | 0 | 10 | 0 | 0 | 10 | 0 | 0 | 0 | 0 |
| Foxtail, Giant | — | 50 | 80 | — | — | — | — | 10 | 20 | 10 | 30 | 20 | 10 | 30 |
| Foxtail, Green | 0 | — | — | 40 | 40 | 0 | 10 | — | — | — | — | — | — | — |
| Galium | 70 | 90 | 100 | 70 | 100 | 70 | 70 | 100 | 70 | 90 | 100 | 100 | 100 | 100 |
| Goosegrass | — | — | — | — | — | — | — | 0 | 30 | — | — | — | — | — |
| Horseweed | — | — | — | — | — | — | — | 100 | 100 | — | — | — | — | — |
| Kochia | 10 | 70 | 60 | 10 | 30 | 10 | 30 | 90 | 70 | 0 | 0 | 40 | 10 | 30 |
| Oat, Wild | — | — | — | — | — | — | — | 0 | 0 | — | — | — | — | — |
| Pigweed, Palmer | — | — | — | — | — | — | — | 70 | 80 | — | — | — | — | — |
| Pigweed, Redroot | 80 | 80 | 100 | 70 | 90 | 60 | 80 | — | — | 100 | 100 | 100 | 100 | 100 |
| Ragweed | 70 | 70 | 90 | 50 | 80 | 70 | 70 | 100 | 80 | 100 | 100 | 90 | 90 | 90 |

TABLE A-continued

| | | | | | | | | | | | | | | |
|---|---|---|---|---|---|---|---|---|---|---|---|---|---|---|
| Ryegrass, Italian | 10 | 80 | 80 | 50 | 30 | 50 | 50 | 10 | 0 | 0 | 10 | 80 | 70 | 80 |
| Soybean | — | — | — | — | — | — | — | 40 | 40 | — | — | — | — | — |
| Wheat | 0 | 0 | 0 | 40 | 10 | 0 | 0 | 0 | 0 | 0 | 0 | 0 | 0 | 0 |

| 31 g ai/ha | Compounds | | | | | | | | | | | | | |
|---|---|---|---|---|---|---|---|---|---|---|---|---|---|---|
| Postemergence | 15 | 16 | 17 | 18 | 19 | 20 | 21 | 22 | 23 | 24 | 25 | 26 | 27 | 28 |
| Barnyardgrass | — | — | — | — | — | — | — | — | 30 | 80 | 0 | 20 | 20 | 0 |
| Blackgrass | 0 | 0 | 0 | 0 | 0 | 0 | 20 | 0 | 40 | 0 | 0 | 0 | 0 | 0 |
| Corn | 0 | 0 | 0 | 0 | 10 | 10 | 30 | 0 | 0 | 10 | 0 | 0 | 0 | 0 |
| Foxtail, Giant | 100 | 0 | 100 | 0 | 10 | 20 | 90 | 20 | 0 | 90 | 0 | 20 | 0 | 0 |
| Foxtail, Green | — | — | — | — | — | — | — | — | — | — | — | — | — | — |
| Galium | 100 | 0 | 100 | 0 | 100 | 50 | 100 | 100 | 70 | 100 | 50 | 80 | 70 | 100 |
| Goosegrass | 30 | 0 | 30 | 0 | 10 | 30 | 20 | 0 | — | — | — | — | — | — |
| Horseweed | 100 | 10 | 100 | — | 100 | 90 | 100 | 50 | — | — | — | — | — | — |
| Kochia | 100 | 60 | 100 | 40 | 40 | 40 | 90 | 60 | 20 | 90 | 0 | 40 | 10 | 0 |
| Oat, Wild | 20 | 0 | 10 | 0 | 10 | 0 | 10 | 0 | — | — | — | — | — | — |
| Pigweed, Palmer | 100 | 100 | 90 | 30 | 100 | 50 | 100 | 100 | — | — | — | — | — | — |
| Pigweed, Redroot | — | — | — | — | — | — | — | — | 100 | 100 | 80 | 100 | 100 | 100 |
| Ragweed | 100 | 10 | 100 | 30 | 100 | 70 | 100 | 80 | 70 | 80 | 0 | 90 | 90 | 100 |
| Ryegrass, Italian | 100 | 0 | 70 | 0 | 0 | 0 | 80 | 0 | 0 | 90 | 0 | 20 | 100 | 30 |
| Soybean | 80 | 10 | 60 | 0 | 0 | 0 | 100 | 0 | — | — | — | — | — | — |
| Wheat | 0 | 0 | 0 | 0 | 0 | 0 | 0 | 0 | 0 | 0 | 0 | 20 | 0 | 0 |

| 31 g ai/ha | Compounds | |
|---|---|---|
| Postemergence | 29 | 30 |
| Barnyardgrass | 20 | 20 |
| Blackgrass | 0 | 40 |
| Corn | 0 | 0 |
| Foxtail, Giant | 20 | — |
| Foxtail, Green | — | 30 |
| Galium | 90 | 100 |
| Goosegrass | — | — |
| Horseweed | — | — |
| Kochia | 60 | 10 |
| Oat, Wild | — | — |
| Pigweed, Palmer | — | — |
| Pigweed, Redroot | 100 | 80 |
| Ragweed | 100 | 20 |
| Ryegrass, Italian | 40 | 80 |
| Soybean | — | — |
| Wheat | 0 | 20 |

Test B

Plant species in the flooded paddy test selected from barnyardgrass (*Echinochloa crus-galli*), ducksalad (*Heteranthera limosa*), rice (*Oryza sativa*), and sedge, umbrella (small-flower umbrella sedge, *Cyperus difformis*) were grown to the 2-leaf stage for testing. At time of treatment, test pots were flooded to 3 cm above the soil surface, treated by application of test compounds directly to the paddy water, and then maintained at that water depth for the duration of the test. Treated plants and controls were maintained in a greenhouse for 10 to 14 days, after which time all species were compared to controls and visually evaluated. Plant response ratings, summarized in Table B, are based on a scale of 0 to 100 where 0 is no effect and 100 is complete control. A dash (-) response means no test result.

TABLE B

| 250 g ai/ha | Compounds | | | | | | | | | | | | | |
|---|---|---|---|---|---|---|---|---|---|---|---|---|---|---|
| Flood | 1 | 2 | 3 | 4 | 5 | 6 | 7 | 8 | 9 | 10 | 11 | 12 | 13 | 14 |
| Barnyardgrass | 0 | 0 | 98 | 75 | 40 | 10 | 0 | 90 | 98 | 15 | 15 | 0 | 0 | 20 |
| Ducksalad | 0 | 20 | 95 | 95 | 80 | 70 | 0 | 95 | 100 | 95 | 80 | 70 | 0 | 80 |
| Rice | 10 | 0 | 0 | 35 | 35 | 0 | 0 | 0 | 0 | 0 | 0 | 0 | 0 | 0 |
| Sedge, Umbrella | 0 | 45 | 98 | 95 | 85 | 75 | 0 | 95 | 100 | 95 | 95 | 85 | 0 | 90 |

| 250 g ai/ha | Compounds | | | | | | | | | | | | | |
|---|---|---|---|---|---|---|---|---|---|---|---|---|---|---|
| Flood | 15 | 16 | 17 | 18 | 19 | 20 | 21 | 22 | 23 | 24 | 25 | 26 | 27 | 28 |
| Barnyardgrass | 50 | 0 | 70 | 0 | 35 | 25 | 98 | 40 | 60 | 70 | 0 | 60 | 0 | 0 |
| Ducksalad | 95 | 0 | 85 | 0 | 100 | 100 | 100 | 90 | 95 | 75 | 0 | 80 | 65 | 65 |
| Rice | 65 | 0 | 45 | 0 | 0 | 0 | 60 | 0 | 0 | 50 | 0 | 10 | 15 | 0 |
| Sedge, Umbrella | 90 | 0 | 85 | 15 | 85 | 90 | 100 | 55 | 75 | 80 | 0 | 85 | 65 | 70 |

TABLE B-continued

| 250 g ai/ha | Compounds | |
|---|---|---|
| Flood | 29 | 30 |
| Barnyardgrass | 55 | 40 |
| Ducksalad | 95 | 75 |
| Rice | 0 | 35 |
| Sedge, Umbrella | 98 | 100 |

What is claimed is:

1. A compound of Formula 1, all stereoisomers, N-oxides, and salts thereof

1

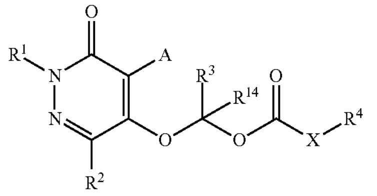

wherein $R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy, benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy; or a 5- or 6-membered saturated or partially saturated heterocyclic ring containing ring members selected from carbon and up to 1 O and 1 S, said ring optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

$R^2$ is H, halogen, cyano, formyl, $C_1$-$C_7$ alkyl, $C_3$-$C_8$ alkylcarbonylalkyl, $C_3$-$C_8$ alkoxycarbonylalkyl, $C_2$-$C_4$ alkylcarbonyl, $C_2$-$C_7$ alkylcarbonyloxy, $C_4$-$C_7$ alkylcycloalkyl, $C_3$-$C_7$ alkenyl, $C_3$-$C_7$ alkynyl, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_1$-$C_7$ alkoxy, $C_1$-$C_5$ alkylthio or $C_2$-$C_3$ alkoxycarbonyl; or phenyl optionally substituted by halogen, $C_1$-$C_4$ alkyl or $C_1$-$C_4$ haloalkyl;

$R^3$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy; or a 5- or 6-membered saturated or partially saturated heterocyclic ring containing ring members selected from carbon and up to 1 O and 1 S, said ring optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

$R^4$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy, $(CH_2CH_2O)_tR^5$; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy; or a 5- or 6-membered saturated or partially saturated heterocyclic ring containing ring members selected from carbon and up to 1 O and 1 S, said ring optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

$R^5$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy; or a 5- or 6-membered saturated or partially saturated heterocyclic ring containing ring members selected from carbon and up to 1 O and 1 S, said ring optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

t is an integer from 1 to 10;

X is a direct bond, O, S or $NR^6$;

$R^6$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy; or a 5- or 6-membered saturated or partially saturated heterocyclic ring containing ring members selected from carbon and up to 1 O and 1 S, said ring optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy; or $R^4$ and $R^6$ can be taken together with the nitrogen atom to which they are attached to form a 3 to 7 membered ring, containing carbon atoms and optionally 1 to 3 oxygen, sulfur or nitrogen atoms as ring members, wherein up to 2 carbon atom ring members are independently selected from C(═O) and C(═S), and the sulfur atom ring member is selected from S, S(O) or $S(O)_2$, said ring being optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

A is selected from

A-1

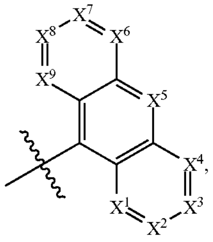

A-2

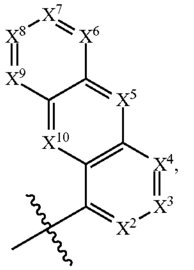

A-3

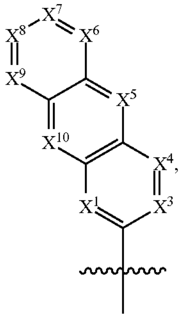

-continued

A-4

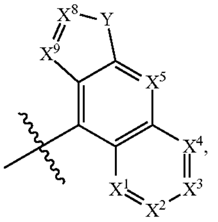

A-5

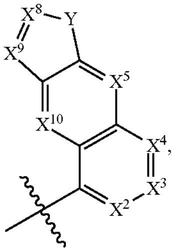

A-6

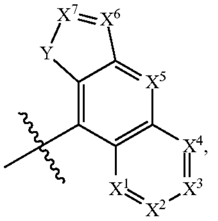

A-7

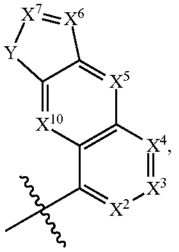

A-8

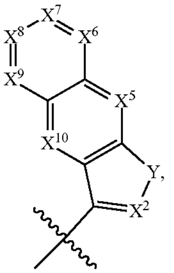

A-9

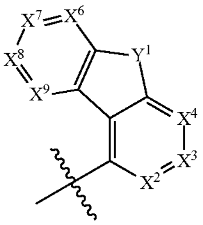

and

-continued

A-10

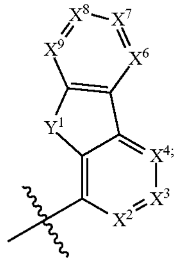

A-11

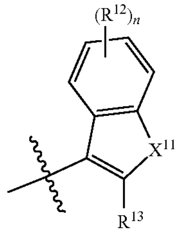

$X^1$, $X^2$, $X^3$, $X^4$, $X^5$, $X^6$, $X^7$, $X^8$, $X^9$ and $X^{10}$ are each independently N or $CR^7$;

provided that no more than 4 of $X^1$, $X^2$, $X^3$, $X^4$, $X^5$, $X^6$, $X^7$, $X^8$, $X^9$ and $X^{10}$ are N;

$X^{11}$ is O, S or $NR^9$; or $X^{11}$ is —$C(R^{10})$—$C(R^{11})$—, wherein the carbon atom bonded to $R^{10}$ is also bonded to the carbon atom bonded to $R^{13}$, and the carbon atom bonded to $R^{11}$ is also bonded to the phenyl ring moiety in Formula 1;

Y is O, S or $NR^8$;

$Y^1$ is O, S, NR or $CR^{7a}R^{7b}$;

each $R^7$ is independently H, halogen, cyano, nitro, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl;

$R^{7a}$ is H, halogen, —CN, nitro, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl;

$R^{7b}$ is H, halogen, —CN, nitro, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl; or $R^{7a}$ and $R^{7b}$ are taken together as =O; or $R^{7a}$ and $R^{7b}$ are taken together with the carbon atom to which they are bonded to form an optionally substituted 3- to 7-membered carbocyclic ring;

$R^8$ is H, $C_1$-$C_3$ alkyl or $C_1$-$C_3$ haloalkyl;

$R^9$ is H, $C_1$-$C_3$ alkyl or $C_1$-$C_3$ haloalkyl;

$R^{10}$ and $R^{11}$ are independently H, halogen, nitro, —CN, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl;

each $R^{12}$ is independently halogen, —CN, nitro, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_5$ haloalkylthio or $C_2$-$C_5$ alkoxycarbonyl;

$R^{13}$ is H, halogen, nitro, —CN, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl;

$R^{14}$ is H; and n is 0, 1, 2, 3 or 4.

2. The compound of claim 1 wherein

A is A-11;

$R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

$R^2$ is H, halogen, cyano, formyl, $C_1$-$C_7$ alkyl, $C_3$-$C_8$ alkylcarbonylalkyl, $C_3$-$C_8$ alkoxycarbonylalkyl, $C_2$-$C_4$ alkylcarbonyl, $C_2$-$C_7$ alkylcarbonyloxy, $C_4$-$C_7$ alkylcycloalkyl, $C_3$-$C_7$ alkenyl, $C_3$-$C_7$ alkynyl, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_1$-$C_7$ alkoxy, $C_1$-$C_5$ alkylthio or $C_2$-$C_3$ alkoxycarbonyl;

$R^3$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

$R^4$ is H, $C_1$-$C_7$ alkyl, $C_3$-$C_8$ alkylcarbonylalkyl, $C_3$-$C_8$ alkoxycarbonylalkyl, $C_4C4$-$C_7$ alkylcycloalkyl, $C_3$-$C_7$ alkenyl, $C_3$-$C_7$ alkynyl, $C_3$-$C_7$ cycloalkyl, —$C_1$-$C_7$ cycloalkylalkyl, $C_2$-$C_3$ cyanoalkyl, $C_1$-$C_4$ nitroalkyl, $C_2$-$C_7$-haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy, $(CH_2CH_2O)_rR^5$; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

each $R^{12}$ is independently halogen, —CN, $C_1$-$C_3$ alkyl, $C_2$-$C_4$ alkenyl, $C_2$-$C_4$ alkynyl, $C_3$-$C_4$ cycloalkyl, $C_1$-$C_3$ haloalkyl, $C_1$-$C_3$ alkoxy, $C_1$-$C_2$ haloalkoxy, $C_1$-$C_2$ alkylthio or $C_1$-$C_2$ haloalkylthio;

$R^{13}$ is halogen, —CN, $C_1$-$C_3$ alkyl, $C_2$-$C_4$ alkenyl, $C_2$-$C_4$ alkynyl, $C_3$-$C_4$ cycloalkyl, $C_1$-$C_3$ haloalkyl, $C_1$-$C_3$ alkoxy, $C_1$-$C_2$ haloalkoxy, $C_1$-$C_2$ alkylthio or $C_1$-$C_2$ haloalkylthio.

3. The compound of claim 2 wherein $R^1$ is $C_1$-$C_4$ alkyl, $C_3$-$C_4$ alkenyl, $C_3$-$C_4$ alkynyl, $C_3$-$C_4$ cycloalkyl, $C_2$-$C_3$ cyanoalkyl, $C_1$-$C_3$ haloalkyl or $C_2$-$C_4$ alkoxyalkyl;

$R^2$ is H, halogen, —CN, $C_1$-$C_4$ alkyl, $C_3$-$C_5$ cycloalkyl, $C_1$-$C_3$ haloalkyl, $C_2$-$C_4$ alkoxyalkyl or $C_1$-$C_3$ alkoxy;

$R^3$ is H, $C_1$-$C_4$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ cycloalkyl, $C_4$-$C_7$ cycloalkylalkyl, $C_2$-$C_3$ cyanoalkyl, $C_1$-$C_7$ haloalkyl, $C_2$-$C_7$ alkoxyalkyl or $C_1$-$C_7$ alkoxy;

$R^4$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl or $C_1$-$C_7$ alkoxy;

$R^{12}$ is independently halogen, —CN, methyl, ethyl, methoxy or ethoxy; and $R^{13}$ is halogen, —CN, methyl, ethyl, $—CH═CH_2$, —C≡CH, cyclopropyl, $CF_3$, methoxy or ethoxy.

4. The compound of claim 3 wherein $R^1$ is $C_1$-$C_3$ alkyl, allyl, propargyl, $CH_2CH_2CN$, $C_1$-$C_2$ haloalkyl or 2-methoxyethyl;

$R^2$ is H, halogen, $C_1$-$C_3$ alkyl, cyclopropyl, $C_1$-$C_2$ haloalkyl, methoxy or ethoxy;

$R^3$ is H, $C_1$-$C_4$ alkyl, $C_3$-$C_7$ cycloalkyl, $C_4$-$C_7$ cycloalkylalkyl or $C_1$-$C_7$ alkoxy;

$R^4$ is H, $C_1$-$C_4$ alkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl or $C_1$-$C_7$ alkoxy;

each $R^{12}$ is independently F, Cl, Br, methyl, ethyl or methoxy; and n is 0, 1 or 2.

5. The compound of claim 4 wherein $R^1$ is methyl, ethyl, n-propyl or 2-methoxyethyl;

$R^2$ is H, F, Cl, methyl, ethyl, n-propyl, $CF_3$ or methoxy;

$R^3$ is H or methyl;

$R^4$ is H, $C_1$-$C_4$ alkyl, $C_4$-$C_7$ cycloalkylalkyl or $C_1$-$C_7$ alkoxy;

$X^{11}$ is $—C(R^{10})═C(R^{11})—$; and independently, $R^{10}$ and $R^{11}$ are H, halogen or $C_1$-$C_2$ alkyl.

6. The compound of claim 5 wherein $R^1$ is methyl;

$R^2$ is Me or Cl;

$R^3$ is H;

$R^4$ is H, methyl, ethyl, cyclopropyl, cyclobutyl, cyclopentyl, cyclohexyl, methoxy or ethoxy; and $R^{10}$ is H and $R^{11}$ is H, or $R^{10}$ is H and $R^{11}$ is $CH_3$, or $R^6$ is $CH_3$ and $R^7$ is H.

7. The compound of claim 4 wherein $R^1$ is methyl, ethyl, n-propyl or 2-methoxyethyl;

$R^2$ is H, F, Cl, methyl, ethyl, n-propyl, $CF_3$ or methoxy;

$R^3$ is H or methyl;

$R^4$ is H, $C_1$-$C_4$ alkyl, $C_4$-$C_7$ cycloalkylalkyl, or $C_1$-$C_7$ alkoxy;

$X^{11}$ is O.

8. The compound of claim 4 wherein $R^1$ is methyl, ethyl, n-propyl or 2-methoxyethyl;

$R^2$ is H, F, Cl, methyl, ethyl, n-propyl, $CF_3$ or methoxy;

$R^3$ is H or methyl;

$R^4$ is H, $C_1$-$C_4$ alkyl, $C_4$-$C_7$ cycloalkylalkyl, or $C_1$-$C_7$ alkoxy;

$X^{11}$ is S.

9. The compound of claim 4 wherein

X is a direct bond or O.

10. The compound of claim 1 wherein

A is selected from A-1, A-4 and A-6;

$R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

$R^2$ is H, halogen, cyano, formyl, $C_1$-$C_7$ alkyl, $C_3$-$C_8$ alkylcarbonylalkyl, $C_3$-$C_8$ alkoxycarbonylalkyl, $C_2$-$C_4$ alkylcarbonyl, $C_2$-$C_7$ alkylcarbonyloxy, $C_4$-$C_7$ alkylcycloalkyl, $C_3$-$C_7$ alkenyl, $C_3$-$C_7$ alkynyl, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_1$-$C_7$ alkoxy, $C_1$-$C_5$ alkylthio or $C_2$-$C_3$ alkoxycarbonyl;

$R^3$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

$R^4$ is H, $C_1$-$C_7$ alkyl, $C_3$-$C_8$ alkylcarbonylalkyl, $C_3$-$C_8$ alkoxycarbonylalkyl, C4-$C_7$ alkylcycloalkyl, $C_3$-$C_7$ alkenyl, $C_3$-$C_7$ alkynyl, $C_3$-$C_7$ cycloalkyl, C4-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy, $(CH_2CH_2O)_tR^5$; or benzyl or phenyl, the ring in said benzyl or phenyl group optionally substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy.

11. The compound of claim 10 wherein

A is A-1;

$R^1$ is H, $C_1$-$C_7$ alkyl, $C_3$-$C_8$ alkoxycarbonylalkyl, $C_4$-$C_7$ alkylcycloalkyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_2$-$C_7$ alkoxyalkyl, $C_3$-$C_7$ alkylthioalkyl, $C_1$-$C_7$ alkoxy or benzyl;

$R^2$ is H, halogen, —CN, $C_1$-$C_4$ alkyl, $C_3$-$C_5$ cycloalkyl, $C_1$-$C_3$ haloalkyl, $C_2$-$C_4$ alkoxyalkyl or $C_1$-$C_3$ alkoxy;

$R^3$ is H, $C_1$-$C_4$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ cycloalkyl, $C_4$-$C_7$ cycloalkylalkyl, $C_2$-$C_3$ cyanoalkyl, $C_1$-$C_7$ haloalkyl, $C_2$-$C_7$ alkoxyalkyl or $C_1$-$C_7$ alkoxy;

$R^4$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl or $C_1$-$C_7$ alkoxy;

each $X^1$, $X^2$, $X^3$, $X^4$, $X^5$, $X^6$, $X^7$, $X^8$ and $X^9$ is $CR^7$;

each $R^7$ is independently H, halogen, $C_1$-$C_3$ alkyl, $C_3$-$C_4$ cycloalkyl, $C_1$-$C_3$ haloalkyl or $C_1$-$C_3$ alkoxy;

X is a direct bond or O.

12. The compound of claim 11 wherein $R^1$ is $C_1$-$C_4$ alkyl, $C_3$-$C_4$ alkenyl, $C_3$-$C_4$ alkynyl, $C_3$-$C_4$ cycloalkyl, $C_2$-$C_3$ cyanoalkyl, $C_1$-$C_3$ haloalkyl or $C_2$-$C_4$ alkoxyalkyl;

$R^2$ is H, halogen, $C_1$-$C_3$ alkyl, cyclopropyl, $C_1$-$C_2$ haloalkyl, methoxy or ethoxy;

$R^3$ is H, $C_1$-$C_4$ alkyl, $C_3$-$C_7$ cycloalkyl, $C_4$-$C_7$ cycloalkylalkyl or $C_1$-$C_7$ alkoxy;

each $R^7$ is independently H, halogen, $C_1$-$C_2$ alkyl, cyclopropyl or $C_1$-$C_2$ haloalkyl.

13. The compound of claim 12 wherein $R^1$ is methyl, ethyl, n-propyl or 2-methoxyethyl;

$R^2$ is H, F, Cl, methyl, ethyl, n-propyl, $CF_3$ or methoxy; and each $R^7$ is independently H, halogen, methyl, ethyl or $CF_3$.

14. The compound of claim 1 selected from the group consisting of

5-[(acetyloxy)methoxy]-6-chloro-4-(2,7-dimethyl-1-naphthalenyl)-2-methyl-3(2H)-pyridazinone;

5-[(acetyloxy)methoxy]-4-(2-bromo-5-fluorobenzo[b]thien-3-yl)-2,6-dimethyl-3(2H)-pyridazinone;

[[5-(2-fluoro-7-methyl-9-anthracenyl)-1,6-dihydro-1,3-dimethyl-6-oxo-4-pyridazinyl]oxy]methyl methyl carbonate;

5-[(acetyloxy)methoxy]-6-chloro-2-methyl-4-(2-methyl-1-naphthalenyl)-3(2H)-pyridazinone; and 5-[(acetyloxy)methoxy]-4-(2-fluoro-7-methyl-9-anthracenyl)-2,6-dimethyl-3(2H)-pyridazinone.

15. A herbicidal composition comprising a compound of claim 1 and at least one component selected from the group consisting of surfactants, solid diluents and liquid diluents.

16. A herbicidal composition comprising a compound of claim 1, at least one additional active ingredient selected from the group consisting of other herbicides and herbicide safeners, and at least one component selected from the group consisting of surfactants, solid diluents and liquid diluents.

17. A herbicidal mixture comprising (a) a compound of claim 1, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solanesyltransferase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, hydantocidin, metam, methyldymron, oleic acid, oxaziclomefone, pelargonic acid and pyributicarb, (b16) herbicide safeners, and salts of compounds of (b1) through (b16).

18. A method for controlling the growth of undesired vegetation comprising contacting the vegetation or its environment with a herbicidally effective amount of a compound of claim 1.

* * * * *